United States Patent
Evans et al.

(10) Patent No.: US 6,468,265 B1
(45) Date of Patent: Oct. 22, 2002

(54) PERFORMING CARDIAC SURGERY WITHOUT CARDIOPLEGIA

(75) Inventors: Philip C. Evans, Portola Valley, CA (US); Frederic H. Moll, Woodside, CA (US); Gary S. Guthart, Foster City, CA (US); William C. Nowlin, Los Altos, CA (US); Rand P. Pendleton, Palo Alto, CA (US); Christopher P. Wilson, La Honda, CA (US); Andris D. Ramans, Mountain View, CA (US); David J. Rosa, San Jose, CA (US); Volkmar Falk, Woodside, CA (US); Robert G. Younge, Portola Valley, CA (US)

(73) Assignee: Intuitive Surgical, Inc., Mountain View, CA (US)

( * ) Notice: Subject to any disclaimer, the term of this patent is extended or adjusted under 35 U.S.C. 154(b) by 0 days.

(21) Appl. No.: 09/436,982

(22) Filed: Nov. 9, 1999

Related U.S. Application Data

(60) Provisional application No. 60/109,359, filed on Nov. 20, 1998, provisional application No. 60/109,301, filed on Nov. 20, 1998, provisional application No. 60/109,303, filed on Nov. 20, 1998, and provisional application No. 60/150,145, filed on Aug. 20, 1999.

(51) Int. Cl.$^7$ .............................................. A61B 17/00
(52) U.S. Cl. ............................ 606/1; 600/103; 600/229
(58) Field of Search ................................. 600/103, 109, 600/111, 227–231, 102, 407, 595; 606/241, 1, 130; 700/245; 901/2, 30

(56) References Cited

U.S. PATENT DOCUMENTS 4,101,961 A  7/1978  Reiber (List continued on next page.)

FOREIGN PATENT DOCUMENTS

WO  WO 95/01757  1/1995

OTHER PUBLICATIONS

Askew et al., "Ground control testbed for space station freedom robot manipulators" IEEE (1993) pp. 69–75.

(List continued on next page.)

Primary Examiner—Shawna J. Shaw
(74) Attorney, Agent, or Firm—Townsend and Townsend and Crew LLP

(57) ABSTRACT

A surgical system or assembly for performing cardiac surgery includes a surgical instrument; a servo-mechanical system engaged to the surgical instrument for operating the surgical instrument; and an attachment assembly for removing at least one degree of movement from a moving surgical cardiac worksite to produce a resultant surgical cardiac worksite. The surgical system or assembly also includes a motion tracking system for gathering movement information on a resultant surgical cardiac worksite. A control computer is engaged to the attachment assembly and to the motion tracking system and to the servo-mechanical system for controlling movement of the attachment assembly and for feeding gathered information to the servo-mechanical system for moving the surgical instrument in unison with the resultant surgical cardiac worksite such that a relative position of the moving surgical instrument with respect to the resultant surgical cardiac worksite is generally constant. A video monitor is coupled to the control computer; and an input system is coupled to the servo-mechanical system and to the control computer for providing a movement of the surgical instrument. The video monitor displays movement of the surgical instrument while the resultant surgical cardiac worksite appears substantially stationary, and while a relative position of the surgical instrument moving in unison with the resultant surgical cardiac worksite, as a result from the movement information gathered by the motion tracking system, remains generally constant. A method of performing cardiac surgery without cardioplegia comprising removing at least one degree of movement freedom from a moving surgical cardiac worksite to produce at least a partially stationary surgical cardiac worksite while allowing a residual heart section, generally separate from the at least partially stationary surgical cardiac worksite, to move as a residual moving heart part. Cardiac surgery is performed on the at least partially stationary cardiac worksite with a surgical instrument such as needle drivers, forceps, blades and scissors.

75 Claims, 56 Drawing Sheets

U.S. PATENT DOCUMENTS

| | | | | |
|---|---|---|---|---|
| 4,182,311 | A | 1/1980 | Seppi et al. | |
| 4,649,930 | A | 3/1987 | Groch et al. | |
| 4,764,944 | A | 8/1988 | Finlayson | |
| 4,891,767 | A | 1/1990 | Rzasa et al. | |
| 4,942,538 | A | 7/1990 | Yuan et al. | |
| 4,942,539 | A | 7/1990 | McGee et al. | |
| 5,036,463 | A | 7/1991 | Abela et al. | |
| 5,098,426 | A | 3/1992 | Sklar et al. | |
| 5,119,817 | A | 6/1992 | Allen | |
| 5,142,930 | A | 9/1992 | Allen et al. | |
| 5,175,694 | A | 12/1992 | Amato | |
| 5,196,688 | A | 3/1993 | Hesse et al. | |
| 5,222,499 | A | 6/1993 | Allen et al. | |
| 5,230,338 | A | 7/1993 | Allen et al. | |
| 5,233,516 | A | 8/1993 | LeRoux | |
| 5,236,432 | A | 8/1993 | Matsen, III et al. | |
| 5,240,011 | A | 8/1993 | Assa | |
| 5,251,127 | A | 10/1993 | Raab | |
| 5,251,128 | A | 10/1993 | Crawford | |
| 5,279,309 | A | 1/1994 | Taylor et al. | |
| 5,321,353 | A | 6/1994 | Furness | |
| 5,403,319 | A | 4/1995 | Mattsen, III et al. | |
| 5,417,210 | A | 5/1995 | Funda et al. | |
| 5,464,410 | A | 11/1995 | Skeens et al. | |
| 5,572,999 | A | 11/1996 | Funda et al. | |
| 5,631,973 | A | 5/1997 | Green | |
| 5,676,673 | A | 10/1997 | Ferre et al. | |
| 5,695,500 | A | 12/1997 | Taylor et al. | |
| 5,762,458 | A | 6/1998 | Wang et al. | |
| 5,808,665 | A | 9/1998 | Green | |
| 5,876,325 | A | 3/1999 | Mizuno et al. | |
| 5,894,843 | A | 4/1999 | Benetti et al. | |
| 5,923,770 | A | 7/1999 | O'Donnell et al. | |
| 5,971,976 | A | 10/1999 | Wang et al. | |
| 6,210,323 | B1 * | 4/2001 | Gilhuly et al. | 600/210 |
| 6,231,585 | B1 * | 5/2001 | Takahashi et al. | 606/191 |
| 6,368,332 | B1 * | 4/2002 | Salcudean et al. | 606/130 |
| 2001/0023311 | A1 * | 9/2001 | Snow | 600/37 |
| 2002/0045888 | A1 * | 4/2002 | Ramans et al. | 606/1 |

OTHER PUBLICATIONS

Dolan et al., "A robot in an operating room: a bull in a china shop?" IEEE Ninth Annual Conference of the Engineering in Medicine and Biology Society, (1987) pp. 1096–1097.

Finlay, "Orthosista™ An active surgical localiser for assisting orthopaedic fracture fixation38 , Second Annual International Symposium on medical Robotics and Computer Assisted Surgery" (Nov. 4–7, 1995) pp. 203–207.

Galloway et al., "A new device for interactive, image–guided surgery" Proceedings The International Society of Optical Engineering SPIE, Medical Imaging V: Image Capture, Formatting, and Display, Kim, Y., Ed., (1991) vol. 1444, pp. 9–18.

Lazarevic, "Feasibility of a stewart platform with fixed actuators as a platform for CABG surgery device" Master's Thesis as posted at http://www.cs.columbia.edu/~laza/Stewart/thesis/, Columbia University, Department of Bioengineering, (1997) 29 pages total.

Moravec, H.P. "Obsticle avoidance and navigation in the real world by a seeing robot rover" Ph.D. Dissertation, Stanford University, (1980) Chapter 3, pp. 13–18.

Smith et al., "Correction of distortion in endoscope images" IEEE Transactions on Medical Imaging (1992) 11(1):117–122.

Taubes et al., "Surgery in cyberspace" Discover (1994) pp. 85–92.

Tendick et al., "Comparison of laproscopic imaging systems and conditions using a knot tying task" Second Annual International Symposium on Medical Robotics and Computer Assisted Surgery (Nov. 4–7–, 1995), Marriot Inner Harbor Hotel, Baltimore, Maryland, USA.

Trevelyan et al., "Motion control for a sheep shearing robot" Chapter 2, pp. 175–190.

Trinder et al., "A close range digital photogrammetry system" SPIE (1990) vol. 1395, pp. 440–447.

Tsai, "A versatile camera calibration technique for high–accuracy 3D machine vision metrology using off–the–shelf TV cameras and lenses" IEEE Journal of Robotics and Automation (1987) vol. RA–3, No. 4, pp. 323–344.

* cited by examiner

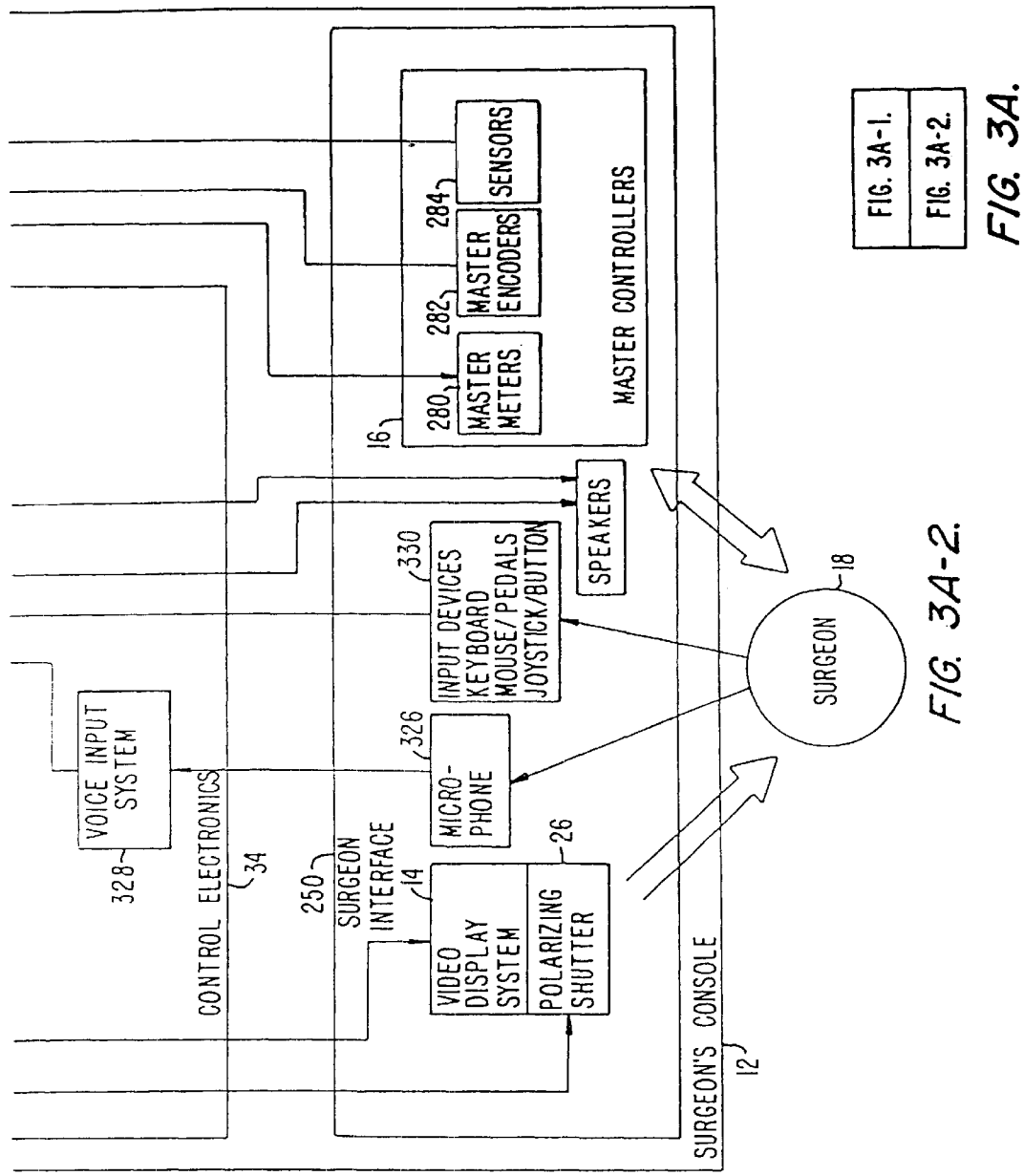

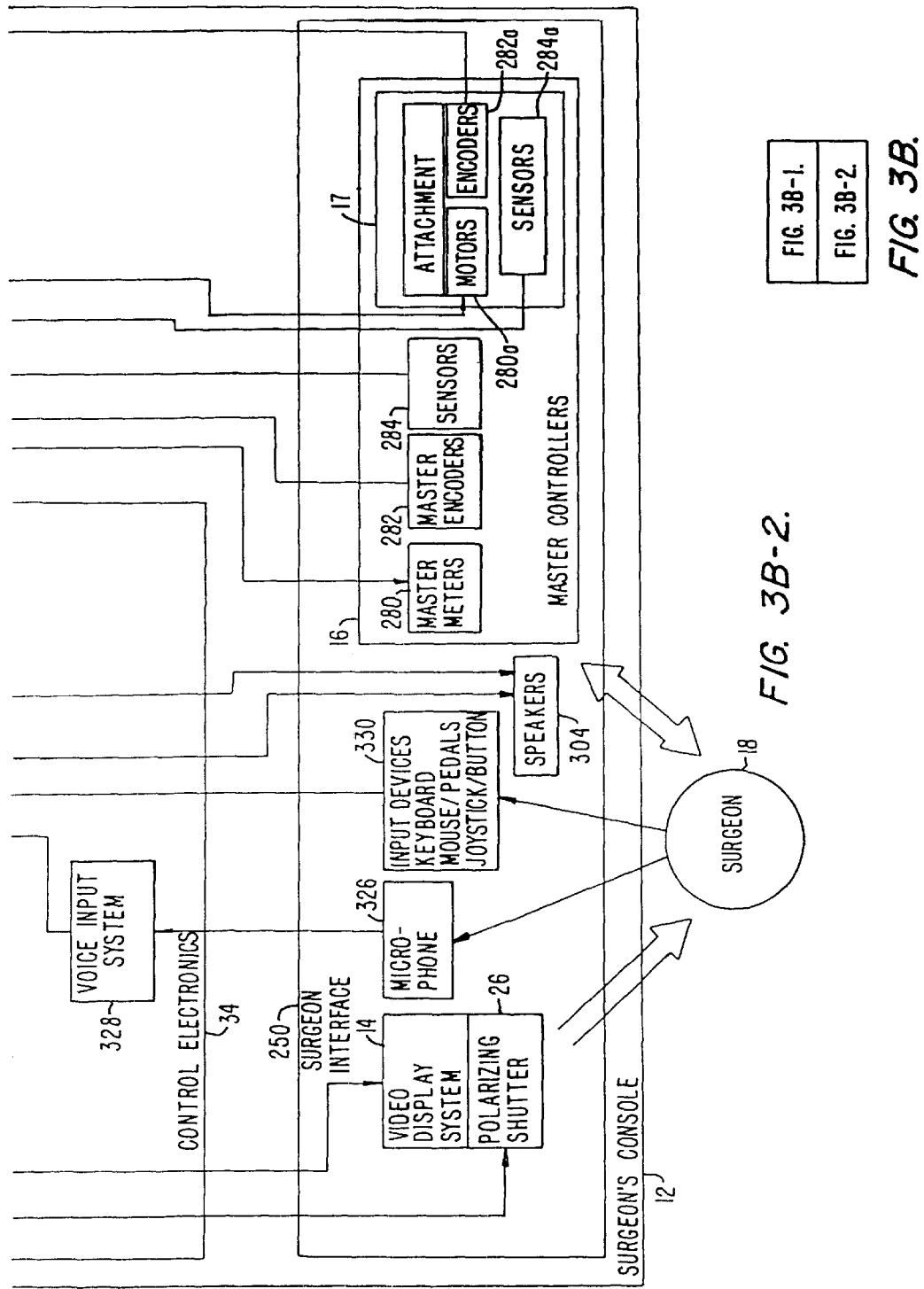

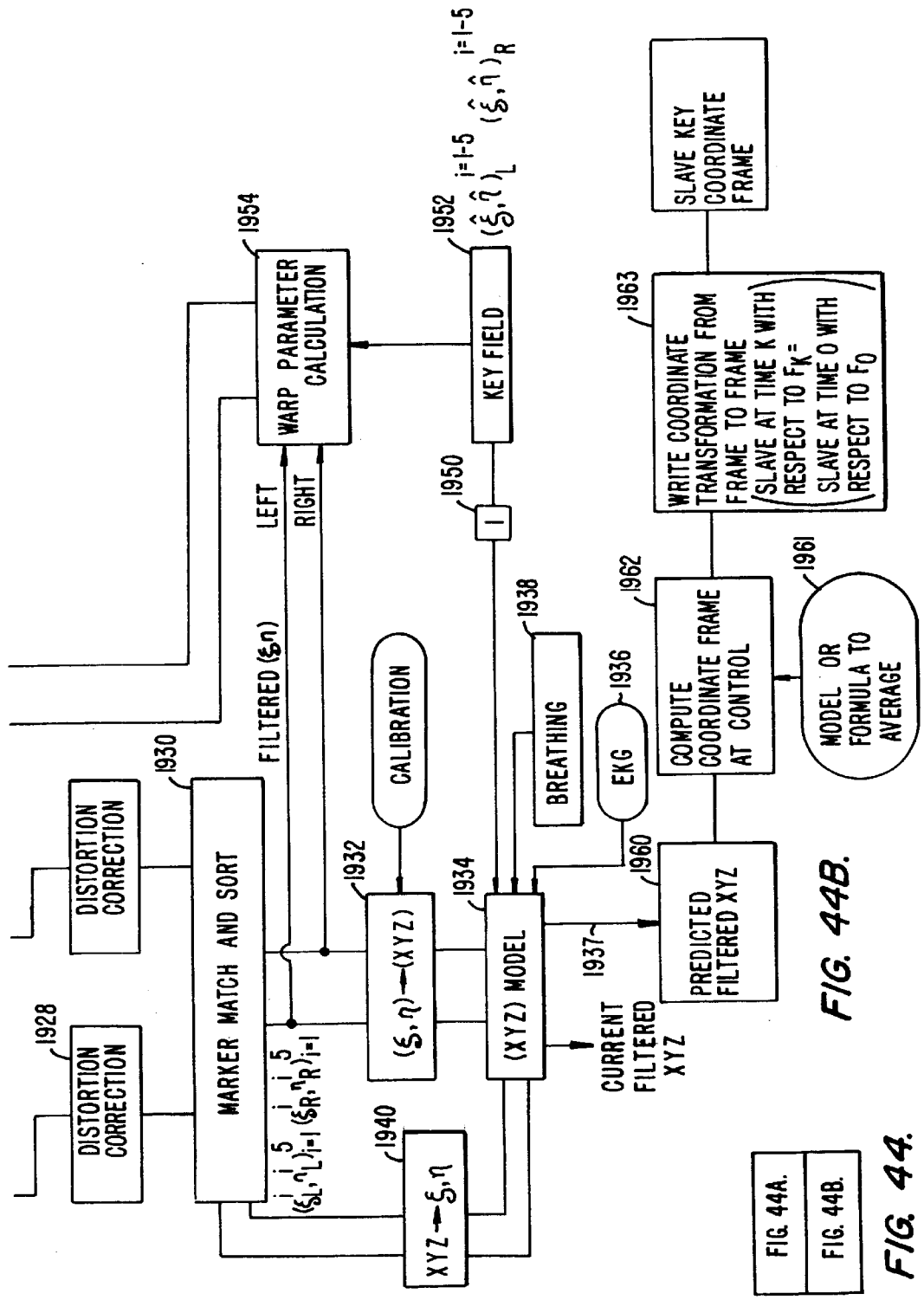

PERFORMING CARDIAC SURGERY WITHOUT CARDIOPLEGIA

CROSS-REFERENCES TO RELATED APPLICATIONS

The present application claims priority from U.S. Provisional Patent Application No. 60/109,359, filed Nov. 20, 1998; U.S. Provisional Patent Application No. 60/109,301, filed Nov. 20, 1998; U.S. Provisional Patent Application No. 60/109,303, filed Nov. 20, 1998; U.S. application Ser. No. 09/374,643, filed Aug. 16, 1999 and abandoned Jun. 29, 2000; U.S. Provisional Application No. 60/150,145, filed Aug. 20, 1999; U.S. patent application Ser. No. 09/399,457, filed Sep. 17, 1999 and abandoned Dec. 19, 2000, and U.S. application Ser. No. 09/433,120, filed Nov. 3, 1999, entitled "Cooperative Minimally Invasive Telesurgical System", the complete disclosures of which are incorporated herein by reference.

BACKGROUND OF THE INVENTION

1. Field of the Invention

This invention relates generally to cardiac surgery. More specifically, this invention provides methods for enhancing the performance of cardiac surgery. In particular, this invention relates to systems and methods which use servomechanisms under surgeon control to augment a surgeon's ability to perform surgical procedures on a beating heart.

2. Description of the Prior Art

Coronary artery disease remains the leading cause of morbidity and mortality in Western societies. Coronary artery disease is manifested in a number of ways. For example, disease of the coronary arteries can lead to insufficient blood flow resulting in the discomfort and risks of angina and ischemia. In severe cases, acute blockage of coronary blood flow can result in myocardial infarction, leading to immediate death or damage to the myocardial tissue. A number of approaches have been developed for treating coronary artery disease. In less severe cases, it is often sufficient to treat the symptoms with pharmaceuticals and lifestyle modification to lessen the underlying causes of disease. In more severe cases, the coronary blockages can often be treated endovascularly using techniques such as balloon angioplasty, atherectomy, laser ablation, stents, hot tip probes, and the like. In cases where pharmaceutical treatment and/or endovascular approaches have failed, or are likely to fail, it is often necessary to perform a coronary artery bypass graft (CABG) procedure.

CABG procedures are commonly performed using open-heart techniques. Such techniques require that the patient's sternum be divided and the chest be spread apart to provide access to the heart. The patient is then placed on a heart/lung machine which oxygenates the patient's blood and pumps it through the circulatory system during the CABG procedure. After the patient is placed on cardiopulmonary bypass, drugs are administered to temporarily stop the patient's heart (cardioplegia) to allow the CABG procedure to be performed. In the CABG procedure, a source of arterial blood (graft) is connected to a coronary artery downstream from an occlusion thus bypassing the occlusion. The source of blood is often the left or right internal mammary artery, and the target coronary artery can be the left anterior descending artery or any other coronary artery which might be narrowed or occluded. Conventional open surgical procedures for performing coronary artery bypass grafting are described in Kirklin & Barratt Boyes', Cardiac Surgery, John Wiley & Sons, Inc., N.Y., 1993 (2nd Ed.), fully incorporated herein by reference as if repeated verbatim immediately hereinafter.

While very effective in many cases, the use of open surgery to perform coronary artery bypass grafting is highly traumatic to the patient. The procedure often requires immediate post-operative care in an intensive care unit, a total period of hospitalization of seven to ten days, and a recovery period that can be as long as six to eight weeks. Thus, minimally invasive medical techniques for performing CABG procedures and other cardiac surgery have recently been proposed.

Minimally invasive surgical techniques are generally aimed at reducing the amount of extraneous tissue which is damaged during diagnostic or surgical procedures, thereby reducing the patient's recovery time, discomfort, and deleterious side effects. The common feature of minimally invasive surgical techniques is that a surgeon can visualize a surgical worksite within the human body and pass specially designed surgical instruments through natural orifices or small incisions to the worksite to manipulate human tissues. Minimally invasive surgical techniques (MIS) include endoscopy, laparoscopy, thoracoscopy, arthroscopy, retroperitoneoscopy, pelviscopy, nephroscopy, cystoscopy, cisternoscopy, sinoscopy, hysteroscopy and urethroscopy.

MIS techniques for cardiac surgery avoid the need to divide the sternum and open a large incision in the patient's chest. Typically, MIS techniques access the thoracic cavity through one or more small ports placed between the patient's ribs. Some access techniques involve removing a rib to gain access to the thoracic cavity. Other access techniques involve making small incisions across the sternum or adjacent the sternum. The heart and coronary arteries are typically visualized directly through the port or visualized with the use of an endoscope, thoracoscope, surgical telescope or video camera, or the like. Conventional thoracoscopic techniques are described in Landrenea et al., Ann Thorac. Surg. 54:80 (1992) p. 807, fully incorporated herein by reference as if repeated verbatim immediately hereinafter. In addition, further description of MIS cardiac techniques is provided by U.S. Pat. No. 5,458,574, fully incorporated herein by reference thereto as if repeated verbatim immediately hereinafter.

MIS techniques are less traumatic than open-heart surgery techniques for performing coronary artery bypass grafts (CABG). The MIS techniques have the potential for decreasing morbidity and mortality, surgical cost, and recovery time, when compared to conventional open surgical coronary bypass procedures. However, one of the most significant causes of patient morbidity during a cardiac procedure is the need for cardioplegia and cardiopulmonary bypass. First, the heart-lung machine requires a large blood transfusion to prime the system. Second, the heart-lung machine causes damage to the blood cells and other blood constituents resulting typically in severe post-operative swelling in the patient. Finally, there is a danger that the heart cannot be restarted after the procedure.

Present MIS techniques for cardiac surgery do not obviate the need for cardiopulmonary bypass or cardioplegia. Indeed, the constraints imposed by small access ports and specialized surgical instruments increase the difficulty of the required surgery. Because the difficulty of the surgery is increased, the need for the heart to be stationary and thus the need for cardiopulmonary bypass and cardioplegia may also be increased.

Mechanically-assisted surgical systems have been developed which augment a surgeon's ability to perform surgery. Such systems include servo-assisted surgical manipulators which operate surgical instruments to manipulate human tissues at the surgical worksite. The surgical manipulators support and control the surgical instruments after they have been introduced directly into an open surgical site or through trocar sleeves, or the like, into a body cavity, such as the patient's abdomen. During the operation, each surgical manipulator typically can provide mechanical actuation and control of a variety of different surgical instruments, such as medical cameras, tissue graspers, needle drivers, and the like. These surgical instruments can typically perform various different functions, such as holding or driving a needle, grasping a blood vessel, dissecting tissue, and the like. The surgical manipulators are typically controlled by the surgeon at a remote operator control station. An overview of the state of the art in computer-assisted and servo-assisted surgical instruments can be found in *Computer-Integrated Surgery: Technology and Clinical Applications* (MIT Press, 1986), fully incorporated herein by reference as if repeated verbatim immediately hereinafter. Exemplary embodiments of systems for manipulating surgical instruments can be found in U.S. Pat. Nos. 5,402,801; 5,417,210; 5,524,180; 5,515,478; 5,817,084; and 5,808,665, all of which are fully incorporated herein by reference as if repeated verbatim immediately hereinafter.

It is an object of this invention to provide systems and methods which augment a surgeon's ability to perform cardiac surgery and minimally invasive cardiac surgery through the use of servo-mechanical surgical manipulators and without cardiopulmonary bypass or cardioplegia. It is a further object of this invention to provide systems and methods which augment a surgeon's control of surgical instruments so as to enhance the performance of beating-heart surgery using MIS techniques.

It is also an object of this invention to provide systems and methods for augmenting a surgeon's ability to perform cardiac surgery through the use of servo-mechanical surgical manipulators.

It is also an object of this invention to provide systems and methods for augmenting a surgeon's ability to perform minimally invasive cardiac surgery through the use of servo-mechanical surgical manipulators.

It is a further object of this invention to provide systems and methods for enabling a surgeon to perform cardiac surgery without cardiopulmonary bypass or cardioplegia.

It is another object of this invention to provide systems and methods for enabling a surgeon to perform minimally invasive cardiac surgery without cardiopulmonary bypass or cardioplegia.

It is also another object of this invention to augment a surgeon's control of surgical instruments so as to facilitate beating-heart surgery using MIS techniques by allowing a surgeon to utilize the same or a similar level of dexterity in the control of surgical instruments as is available using open-heart techniques.

It is a further object of this invention to provide apparatus and methods for tracking and controlling cardiac motion during cardiac surgery without cardioplegia.

SUMMARY OF THE INVENTION

According to one aspect of the invention, there is provided a method of performing a surgical procedure on a beating heart of a patient. The method includes positioning an end effector in close proximity to a surgical site on the heart at which site a surgical procedure is to be performed, the end effector being mounted on a robotically controlled arm. The method further includes monitoring motion of the surgical site, computing tracking command signals in response to monitored motion of the surgical site and forwarding the tracking command signals to actuators operatively associated with the robotically controlled arm to cause the arm to move the end effector generally to track motion of the surgical site. The method yet further includes inputting an end effector movement command signal and forwarding the end effector movement command signal to the actuators to cause the end effector to move relative to the surgical site so as to perform the surgical procedure on the surgical site.

According to another aspect of the invention, there is provided a method of performing a surgical procedure on a beating heart of a patient, the method including positioning an end effector in close proximity to a surgical site on the heart at which site a surgical procedure is to be performed, the end effector being mounted on a robotically controlled arm. The method further includes bracing the beating heart with a brace member to at least reduce motion of the surgical site, inputting an end effector movement command signal, and forwarding the end effector movement command signal to actuators operatively associated with the robotically controlled arm to cause the end effector to move relative to the surgical site so as to perform the surgical procedure on the surgical site.

According to a further aspect of the invention, there is provided a method of performing a surgical procedure on a beating heart of a patient, the method including positioning an end effector in close proximity to a surgical site on the heart at which site a surgical procedure is to be performed, the end effector being mounted on a robotically controlled arm. The method may further include monitoring motion of the surgical site, using monitored motion history of the surgical site to compute predictive tracking command signals in response to monitored motion of the surgical site and forwarding the predictive tracking command signals to actuators operatively associated with the robotically controlled arm to cause the end effector generally to track motion of the surgical site. The method may further include inputting an end effector movement command signal and forwarding the end effector movement command signal to the actuators to cause the end effector to move relative to the surgical site so as to perform the surgical procedure on the surgical site.

According to yet a further aspect of the invention, a robotically controlled surgical system for performing a surgical procedure on a beating heart of a patient is provided. The system includes a robotically controlled arm, an end effector mounted on the arm and arranged to perform the surgical procedure on a surgical site on the heart, a plurality of actuators operatively associated with the arm so as to move the arm in response to the actuators receiving actuator command signals, a motion tracking system for monitoring motion of the surgical site and a master input device through which an operator can selectively input end effector movement commands. The system may further include a control system in which the robotically controlled arm, the motion tracking system and the master input device are operatively connected, the control system being arranged to compute a first set of actuator command signals, in response to information received from the motion tracking system, arranged to cause the actuators to move the end effector generally to track surgical site motion, and a second set of actuator command signals, in response to input from the master input device, arranged to move the end effector relative to the surgical site so as to perform the surgical procedure.

In accordance with another aspect of the invention, there is provided a surgical system which includes a motion tracking system for gathering movement information of a moving surgical site on an anatomical part, such as a beating heart, of a patient's body; a plurality of surgical manipulators for manipulating surgical instruments under surgeon control, master controllers operatively associated with the surgical manipulators so as to permit the surgeon to control the surgical manipulators by means of the master controllers, and a control computer for receiving inputs from the master controllers and the motion tracking system so as to generate output command signals for controlling motors associated with the master controllers and motors associated with the surgical manipulators.

The surgical system may include a video camera and a video display system for providing the surgeon with an image of the surgical worksite and the surgical instruments. The surgical system may also include an image processing system for processing an image of the surgical worksite for display to the surgeon. The surgical instruments may include a medical camera, such as an endoscope, or the like, which may be manipulated by the surgical manipulators. In a particular embodiment, the video camera can be a stereo video camera, or stereo endoscope, which, in addition to being coupled to the video display system for viewing by the surgeon, can form a component of the motion tracking system. The surgical instruments may be any surgical instrument or apparatus, such as a surgical instrument selected from the group consisting of medical cameras, needle drivers, forceps, blades, scissors, cauterizers, and the like.

According to yet a further aspect of the invention, there is provided a robotically controlled surgical system for performing a surgical procedure on a beating heart of a patient body, the system comprising a robotically controlled arm, a brace member operatively mounted on the robotically controlled arm, the brace member being arranged to brace, or stabilize, a beating heart so as at least to reduce motion of a surgical site on the beating heart, at which site a surgical procedure is to be performed, at least one other robotically controlled arm, a surgically end effector operatively mounted on the other robotically controlled arm, the surgical end effector being arranged to perform at least part of the surgical procedure on the surgical site, at least one master control input device and a control system in which the robotically controlled arms, the brace member, the end effector and the master control input device are operatively connected, so as to enable movement of the robotically controlled arms, the brace member, and the end effector to be remotely controlled in response to input through the master control input device.

In accordance with another aspect of the invention, a method for performing cardiac surgery including the steps of: (a) providing a surgical system comprising a video display system and a servo-mechanism-operated surgical instrument coupled by a control computer to a motion input device and to a motion tracking system; (b) displaying a moving image of a heart on the video display system; (c) identifying on the moving image of the heart a surgical worksite in motion; (d) operating the motion tracking system to determine the motion of the surgical worksite; (e) moving the surgical instrument to track or follow motion of the surgical worksite such that the surgical instrument generally tracks motion to the surgical worksite; (f) displaying on the video display system an image of the heart in which the surgical worksite is made to be generally stationary or still; (g) operating the motion input device to direct motion of the surgical instrument; and (h) moving the surgical instrument relative to the surgical worksite.

In accordance with yet another aspect of the invention, there is provided a method of performing cardiac surgery without cardioplegia comprising the steps of: (a) providing a surgical system comprising a control assembly coupled to a motion input device, a video display system coupled to the control assembly, and a servo-mechanism-operated surgical instrument coupled to the control assembly; (b) displaying on the video display system a moving image of a heart within a human body; (c) identifying on the moving image of the heart a moving surgical worksite; (d) generally immobilizing the moving surgical worksite to produce an essentially stationary surgical worksite while allowing a residual heart section, generally separate from the essentially stationary surgical worksite, to move as a residual moving heart part; (e) displaying on the video display system the essentially stationary surgical worksite; and (f) operating the motion input device to move the servo-mechanism-operated surgical instrument relative to the essentially stationary surgical worksite of the heart to perform cardiac surgery on the essentially stationary surgical worksite without cardioplegia while the residual moving heart part moves. The generally immobilizing step (d) may comprise providing a servo-mechanism-operated manipulator arm coupled to the control assembly and having an attachment member secured thereto and including a motor for receiving a control function from the control assembly for moving the servo-mechanism-operated manipulator arm including the attachment member with six degrees of freedom, and at least one encoder means for informing the control assembly of the position of the attachment member; affixing (e.g., by releasably securing) the attachment member to the heart in proximity to the moving surgical worksite on the heart; and signaling the control assembly for imparting a control function on the motor to move the servo-mechanism-operated manipulator arm and cause the attachment member to apply a force against the moving surgical worksite to generally immobilize the moving surgical worksite.

In accordance with another aspect of the invention, there is provided a method of performing cardiac surgery without cardioplegia, the method comprising the steps of: (a) providing a surgical system comprising a control assembly coupled to a motion input device, a video display system coupled to the control assembly, and a servo-mechanism-operated surgical instrument coupled to the control assembly; (b) displaying on the video display system a moving image of a heart within a human body; (c) identifying on the moving image of the heart a moving surgical worksite moving in six degrees of movement; (d) restricting at least one degree of movement of the moving surgical worksite while allowing a residual heart section, generally separate from the surgical worksite, to move as a residual moving heart part; (e) displaying on the video display system the surgical worksite; and (f) operating the motion input device so as to move the servo-mechanism-operated surgical instrument relative to the surgical worksite of the heart to perform cardiac surgery on the surgical worksite without cardioplegia while the residual moving heart part moves. If the surgical worksite has any residual movement after the at least one degree of movement has been restricted, the method may additionally comprise operating a motion tracking system to determine the residual movement of the surgical worksite and moving the servo-mechanism-operated surgical instrument in response to the determined residual movement so as to cause the surgical instrument generally to track the residual movement of the surgical worksite.

In accordance with yet another aspect of the present invention, there is provided an apparatus for manipulating a moving surgical instrument in a surgical procedure, the apparatus comprising: motion tracking means for obtaining a motion pattern of a moving surgical worksite on a beating heart of a patient; means, coupled to the motion tracking means, for moving a surgical instrument in the same motion pattern as the moving surgical worksite; means, coupled to the motion tracking means, for providing a generally still image of the moving surgical worksite on an image display; and means, coupled to the means for moving, for adding a second motion pattern to the surgical instrument to cause the instrument to move relative to the surgical site. Accordingly, the apparatus is for manipulating a surgical instrument relative to a moving anatomical part of a patient's body in a surgical procedure and includes motion tracking means for gathering movement information on a moving anatomical part of a patient's body; a surgical instrument; and manipulator means coupled to the surgical instrument, for manipulating the surgical instrument. The apparatus also includes control means, coupled to the means for gathering and to the manipulator means, for feeding gathered movement information to the manipulator means so as to manipulate the surgical instrument such that the surgical instrument generally tracks the moving anatomical part; a video display system coupled to the control means so as to display a generally still image of the surgical site; and master controller means, operatively associated with the surgical instrument so as to provide the surgical instrument with an incremental movement differing from the tracking movement so as to move the surgical instrument relative to the surgical site.

In accordance with another aspect of the invention, there is provided a surgical system for performing cardiac surgery without cardioplegia, the surgical system comprising a surgical instrument; a servo-mechanical system engaged to the surgical instrument for operating the surgical instrument; and a motion tracking system for gathering movement information of a moving surgical worksite on a heart of a patient. A control computer may be provided that is engaged to the motion tracking system and to the servo-mechanical system so as to feed gathered movement information to the servo-mechanical system thereby to move the surgical instrument generally to track the moving surgical worksite. The surgical system can further include a video display system coupled to the control computer so as to provide a generally still image of the moving surgical site on an image display of the video display system; and an input system coupled to the control computer and arranged to cause movement of the surgical instrument that may be seen on the video display system while the moving surgical worksite on the heart appears substantially stationary, and while a position of the surgical instrument moves relative to the surgical site. The surgical instrument may be a surgical instrument selected from the group consisting of endoscopic cameras, needle drivers, forceps, blades, scissors, and the like. The motion tracking system may comprise a camera device coupled to the video display system and to the control computer, and/or a motion tracking device coupled to the control computer.

In accordance with yet a further aspect of the invention, there is provided an apparatus for controlling cardiac motion and for manipulating a surgical instrument relative to a cardiac worksite, the apparatus comprising: an attachment means for restricting at least one degree of movement of a moving surgical cardiac worksite so as to define a resultant surgical cardiac worksite in motion within at least one residual degree of movement; a motion tracking means for gathering movement information on the resultant surgical cardiac worksite; a surgical instrument; and a manipulator means, coupled to the surgical instrument, for manipulating the surgical instrument. The apparatus may further comprise control means, coupled to the attachment means and to the motion tracking means and to the manipulator means, for controlling movement of the attachment means and for feeding gathered movement information to the manipulator means for manipulating the surgical instrument such that the surgical instrument generally tracks the resultant surgical cardiac worksite; a video display system coupled to the control means; and a master controller means, coupled to the control means, for providing the surgical instrument with an incremental movement differing from the tracking movement such that the incremental movement can be detected on the video display system while an image of the resultant cardiac worksite on the video display system appears generally stationary. Stated alternatively and more particularly, the apparatus for controlling cardiac motion and for manipulating a surgical instrument relative to a cardiac worksite includes a surgical system for performing cardiac surgery without cardioplegia, the system comprising a surgical instrument; a servo-mechanical system engaged to the surgical instrument for controlling movement of the surgical instrument; and an attachment assembly for restricting at least one degree of movement of a moving surgical cardiac worksite to define a resultant surgical cardiac worksite. The surgical system may further comprise a motion tracking system for gathering movement information on the resultant surgical cardiac worksite; and a control computer, engaged to the attachment assembly and to the motion tracking system and to the servo-mechanical system, for controlling movement of the attachment assembly and for feeding gathered information to the servo-mechanical system for moving the surgical instrument in sympathy with the resultant surgical cardiac worksite such that a relative position of the moving surgical instrument with respect to the resultant surgical cardiac worksite is generally constant. A video display system may be coupled to the control computer; and an input system may also be coupled to the control computer for providing a movement to the surgical instrument that may be seen on the video display system while the resultant surgical cardiac worksite appears substantially stationary, and while a relative position of the surgical instrument moving in unison with the resultant surgical cardiac worksite, as a result of the movement information gathered by the motion tracking system, remains generally constant.

BRIEF DESCRIPTION OF THE DRAWINGS

These, together with the various ancillary objects and features which will become apparent to those possessing ordinary skill in the art as the following description proceeds, are attained by the novel apparatus, systems and surgical methods for performing cardiac surgery, in accordance with the invention, preferred embodiments of which are shown with reference to the accompanying drawings, by way of example only, wherein.

DESCRIPTION OF THE SPECIFIC EMBODIMENTS

This application is related to the following patents and patent applications, the full disclosures of which are incorporated herein by reference: PCT International Application No. PCT/US98/19508, filed on Sep. 18, 1998; U.S. Provisional Patent Application No. 60/111,713, filed on Dec. 8, 1998; U.S. Provisional Patent Application No. 60/111,711, filed on Dec. 8, 1998; U.S. Provisional Patent Application No. 60/111,714, filed on Dec. 8, 1998; U.S. Provisional Patent Application No. 60/111,710, filed on Dec. 8, 1998; U.S. Provisional Patent Application No. 60/116,891, filed on Jan. 22, 1999; U.S. patent application Ser. No. 09/378,173, filed on Aug. 20, 1999; U.S. patent application Ser. No. 09/398,507, filed on Sep. 17, 1999; U.S. patent application Ser. No. 09/399,457, filed on Sep. 17, 1999 and abandoned Dec. 19, 2000; U.S. patent application Ser. No. 09/418,726, filed on Oct. 15, 1999, now U.S. Pat. No. 6,331,181, issued Dec. 18, 2001; and U.S. patent application Ser. No. 08/709,965, filed Sep. 9, 1996 now U.S. Pat. No. 5,808,665 issued Sep. 15, 1998.

Mechanically assisted surgical systems have been developed which augment a surgeon's ability to perform surgery. Such systems include servo-assisted surgical manipulators which operate surgical instruments to manipulate human tissues at a surgical worksite. The surgical manipulator supports and controls the surgical instruments that are typically introduced directly into an open surgical site or through trocar sleeves, or the like, into a body cavity, such as the patient's abdomen. During the operation, the surgical manipulator provides mechanical actuation and control of a variety of surgical instruments, such as medical cameras, tissue graspers, needle drivers, etc. These surgical instruments may perform various functions for the surgeon, such as holding or driving a needle, grasping a blood vessel or dissection of tissue. The surgical manipulators are typically controlled by the surgeon at a remote operator control station.

Figure 1:
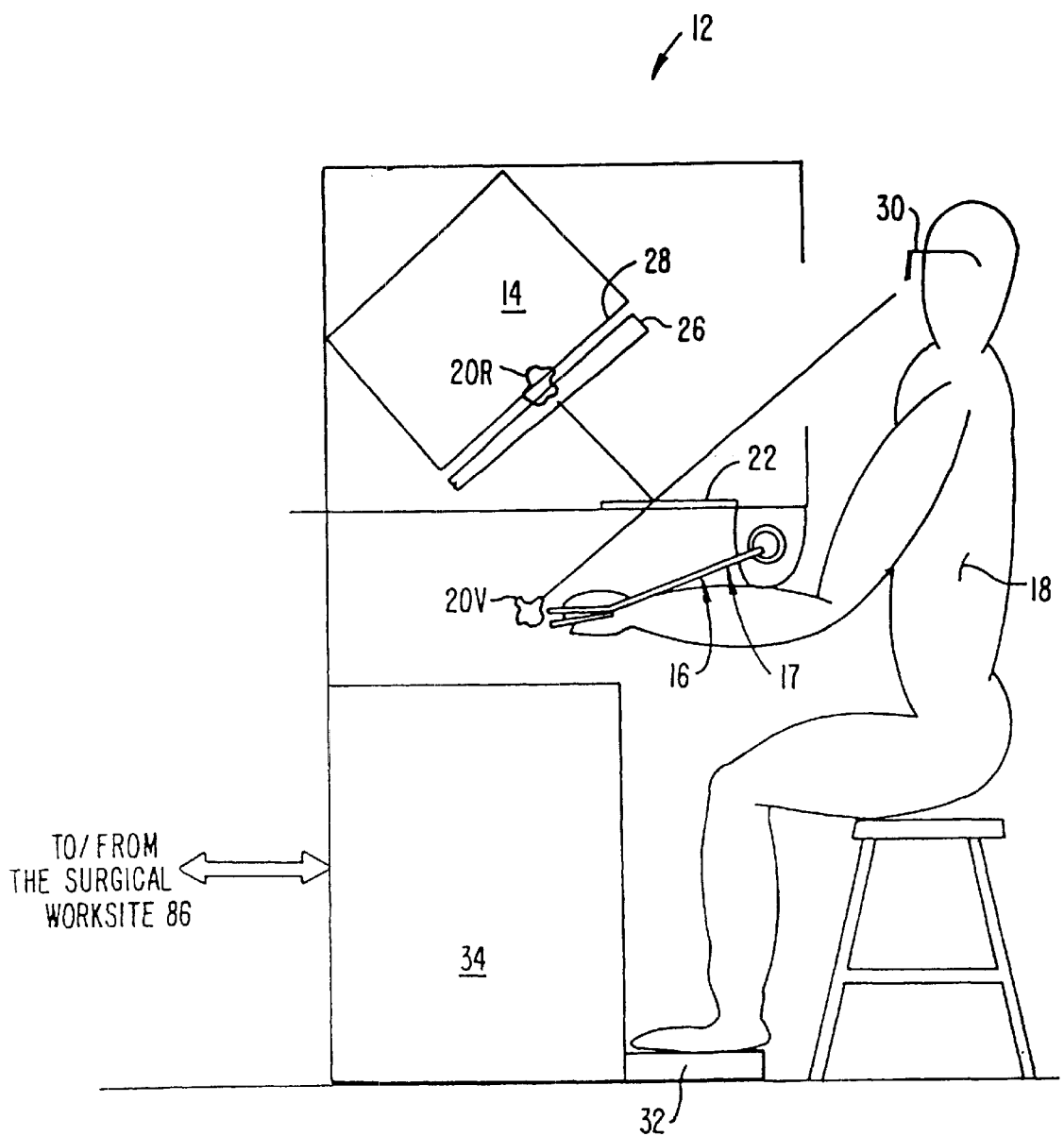
FIG. 1 shows a schematic side view of a surgeon sitting at a console of a surgical system or assembly of the present invention performing a Minimally Invasive Surgery (MIS) coronary procedure, by means of the system, on an anatomical worksite on a patient.
Figure 2A:
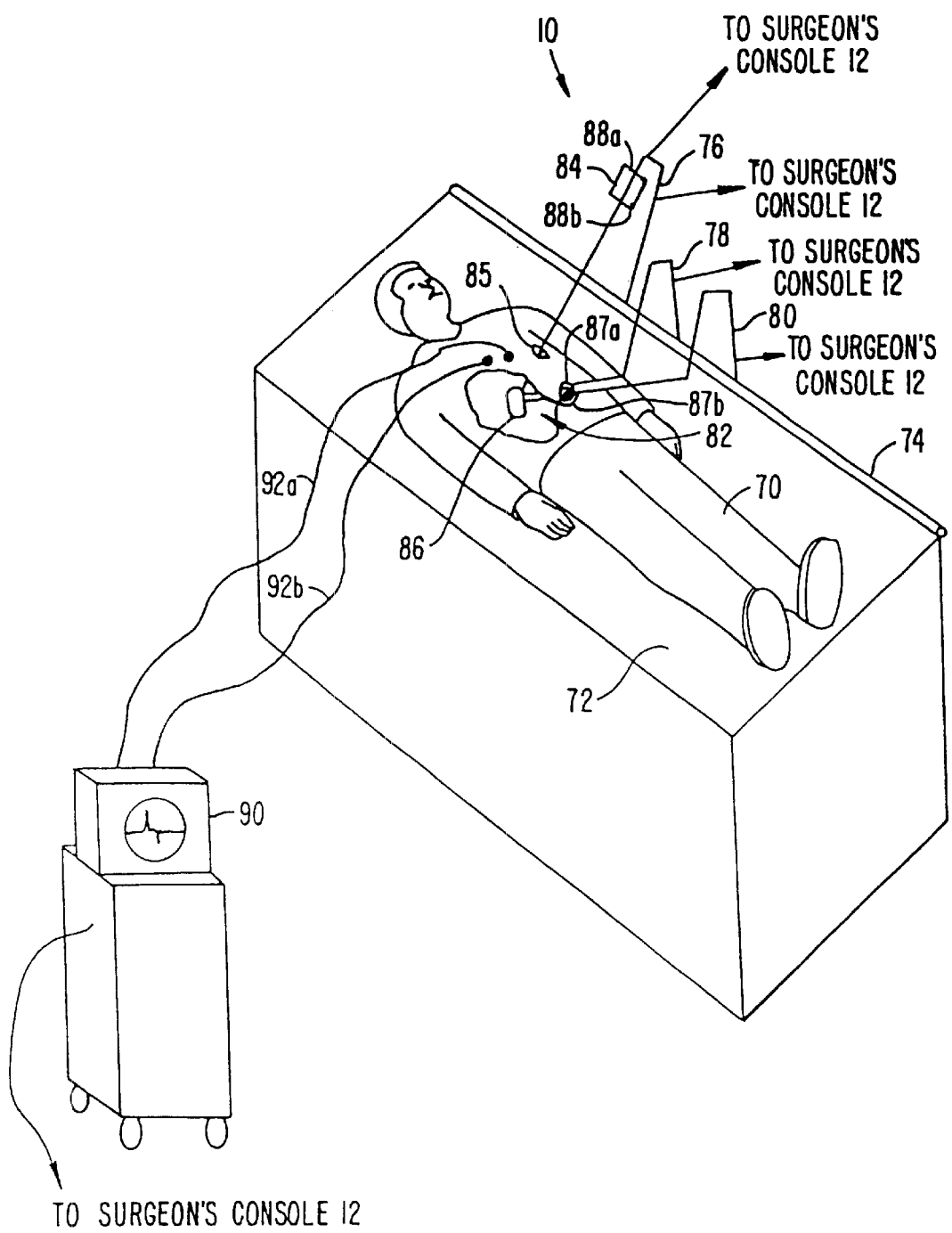
FIG. 2A shows a schematic perspective view of a patient on an operating room table during the performance of a MIS coronary procedure using the surgical system of the invention.

Referring in detail now to the drawings wherein similar parts of the present invention are identified by like reference numerals, there is seen a surgical system, assembly or apparatus, generally illustrated as 10 in FIG. 2A, for performing surgery. The surgical system 10 of the present invention is particularly suited for performing cardiac surgery. In a preferred embodiment of the present invention and as best shown in FIG. 1, the surgical system 10 comprises a surgeon's console 12 having a video display system 14 and master controllers 16 operated by an operator or surgeon 18. The master controllers 16 include master motors 280, master encoders 282 and master sensors 284, as can best be seen in FIGS. 3A and 3B of the drawings. At the surgeon's console 12, the surgeon 18 is presented with a virtual image 20V, of a surgical worksite 86 in a patient 70, as can best be seen with reference to FIGS. 2A–2C of the drawings. The virtual image 20V is provided by a mirror 22 which reflects the real image 20R displayed by the video display system 14.

The virtual image 20V of the surgical worksite 86 is provided at a position adjacent to the master controllers 16, such that the surgeon 18 manipulating the master controllers 16 is provided with the sensation that he/she is working inside the virtual image 20V. The master controllers 16 function as a means for providing an incremental movement to surgical manipulators 76, 78, and 80 (see FIG. 2A for surgical manipulator 76, and FIGS. 2A–2C for surgical manipulators 78 and 80) which manipulate the surgical instruments 82 (see FIGS. 2A–2C). Embodiments of typical surgical manipulators and surgical instruments are described in greater detail herein below. The master controllers 16 of the present invention may be any suitable computer interface that is capable of feeding instrument control information from the surgeon 18 to a control computer 310 (see FIGS. 3A and 3B). It is also desirable that the master controllers 16 be capable of feeding haptic information back to the surgeon (force feedback). Master controllers 16 suitable for use in the present invention may be purchased commercially under the trademarks/tradenames: Phantom from SensAble Devices, Inc. of Cambridge, Mass., Freedom-6 or Freedom 7 from MPB Technologies, Inc. of Quebec, ONT. (Canada) and CyberImpact from Cybernet Systems Corp. of Ann Arbor, Mich. Embodiments of another master controller are described in greater detail below.

Figures 1, 3A:
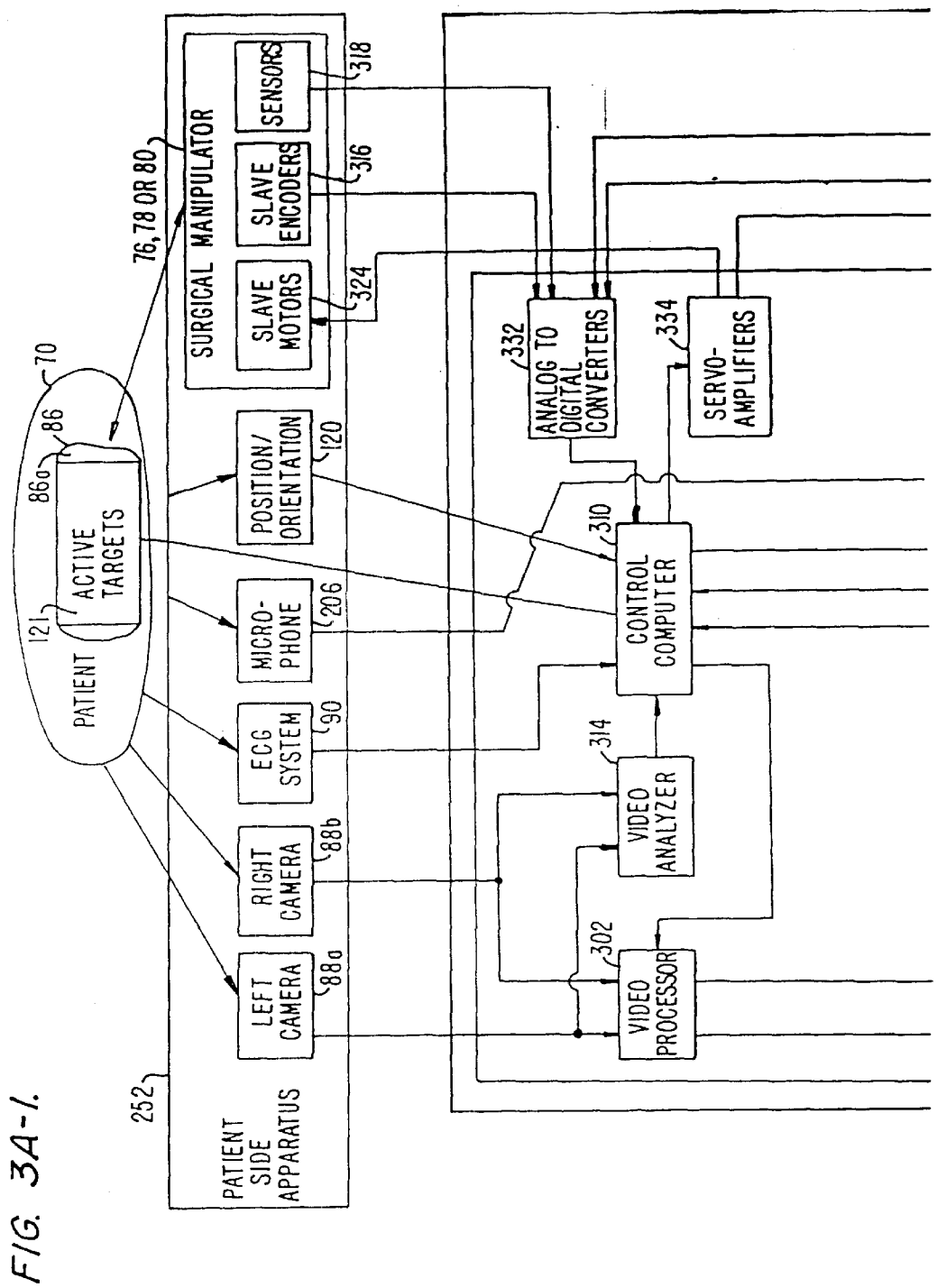
FIG. 3A shows a schematic diagram of part of the surgical system of the invention illustrating the relationship between certain components and the interaction of such components with the surgeon and the patient.
Figures 1, 3B:
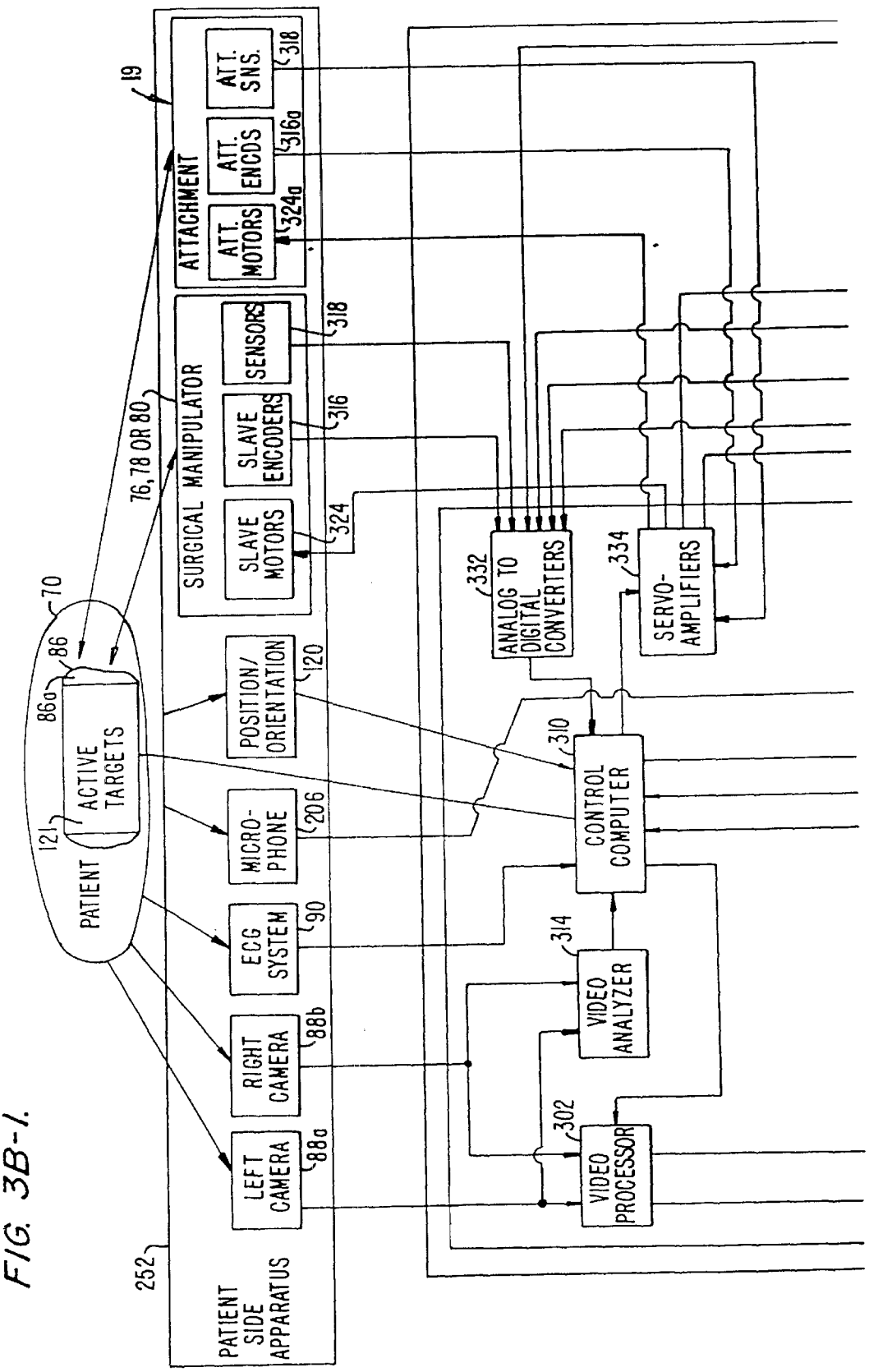
FIG. 3B shows a schematic diagram of part of another surgical system of the present invention illustrating the relationship between certain components, including an attachment assembly, and the interaction of such components with the surgeon and the patient.
Figure 16:
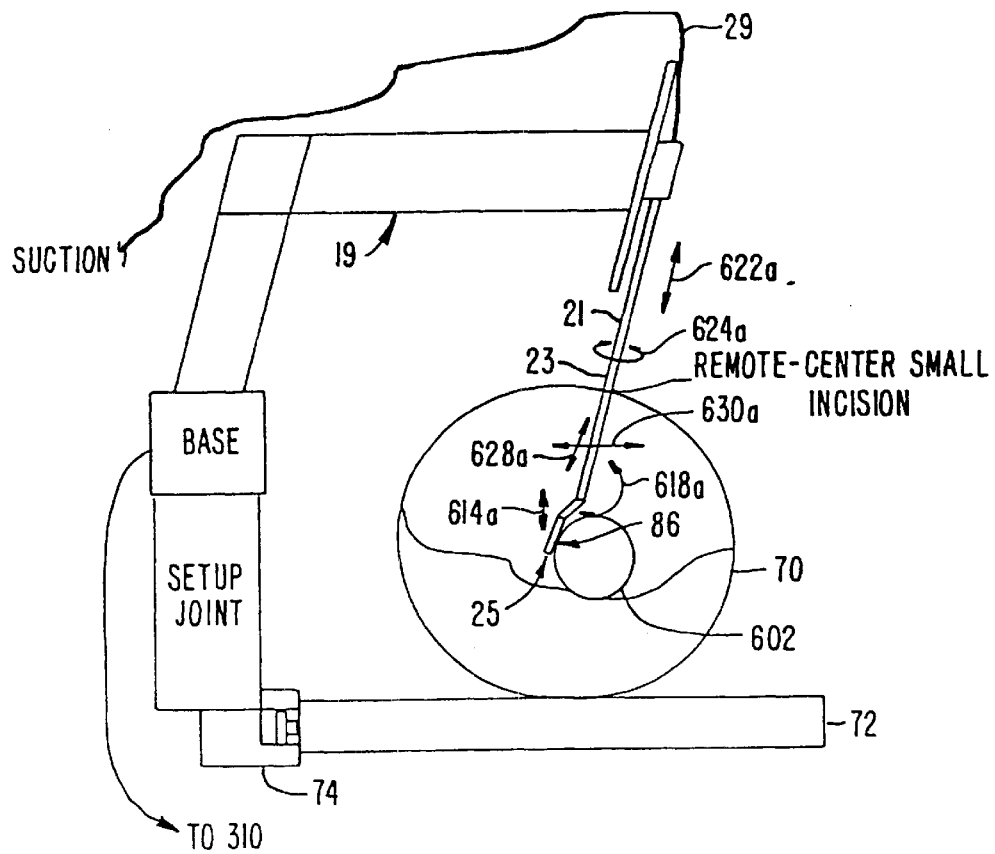
FIG. 16 shows a schematic side view of a servo-mechanism-operated manipulator arm assembly coupled to a control computer of a control assembly for use in conjunction with MIS beating heart telepresence surgery systems, with the servo-mechanism-operated manipulator arm assembly having an attachment member secured thereto and including a motor for receiving a control function from the control assembly for moving the servo-mechanism-operated manipulator arm assembly including the attachment member in a desired direction with six degrees of freedom.
Figure 17:
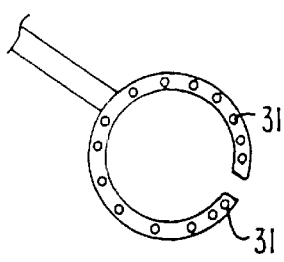
FIG. 17 shows a schematic bottom plan view of an attachment member having a plurality of openings through which air is sucked to releasably connect the attachment member to a heart.

For the embodiment of the invention illustrated in FIGS. 3B and 16–17, the master controllers 16 include an attachment control assembly, generally illustrated as 17 in FIG. 3B. The attachment control assembly 17 includes master attachment motors 280a, master attachment encoders 282a and master attachment sensors 284a. For this embodiment of the present invention, the master controllers 16 (including the attachment control assembly 17) also function as a means for providing an incremental movement to attachment manipulators 19 (see FIGS. 3B and 16) which manipulate attachment assemblies, each generally illustrated as 21 (see FIGS. 16–28). Each attachment assembly 21 includes an attachment arm, generally illustrated as 23, having secured thereto an attachment member, generally illustrated as 25 (FIGS. 16–28 again). As will be further explained hereinafter, the attachment assembly 21 of the present invention may be employed in the following three modes: tracking, stabilization, or a combination of tracking and stabilization.

Preferably, as shown in FIG. 1, the video display system 14 is a stereo video system capable of displaying 3-dimensional (3-D) images. One possible embodiment of such a system displays left and right image frames sequentially in video display system 14. A polarizing shutter 26 placed in front of the screen 28 is synchronized with the video display system 14 and has two polarization modes. The surgeon 18 wears a pair of glasses 30 which have left and right lenses with opposite polarization. The polarizing shutter 26 is operated such that the polarization of the shutter and the left eye lens are the same when the left side image is displayed, and the polarization of the shutter and the right eye lens are the same when the right side image is displayed. In this way the right and left eyes see the correct right and left images and a stereo image is produced. As an alternative display device, a head-mounted display which has a separate LCD or CRT display device for each eye can be provided. Another embodiment of a video display system can include two display areas guided separately to the operator's eyes, as described in greater detail in Applicants' co-pending U.S. patent application Ser. No. 09/378,173, filed Aug. 20, 1999, the full disclosure of which is incorporated herein by reference as if repeated verbatim herein below.

The surgeon's console 12 is additionally provided with a number of auxiliary input devices 330 (see FIG. 3A and FIG. 3B) to permit the surgeon 18 to control the surgical procedure. For example, foot-operated switches 32 (FIG. 1) may be provided which allow the surgeon 18 to input commands without removing his/her hands from the master controllers 16. Instead or in addition, a microphone 326 (see FIG. 3A and FIG. 3B) can be provided to allow the surgeon 18 to input voice commands for controlling the surgical procedure. Furthermore, additional hand-operated switches, keypads, joysticks or a mouse (not shown) can be provided as required to allow the surgeon 18 to enter commands and data for controlling the surgical manipulators 76, 78, 80, and the attachment manipulators 19, or designating a surgical worksite (see FIGS. 2A–2C).

The surgeon's console 12 also preferably contains the control electronics 34. In an alternative embodiment, not shown, the control electronics 34 may be located outside the surgeon's console 12. The control electronics 34 operate as the interface between the surgeon-controlled input devices, such as the master controllers 16 and the foot-operated switches 32, and the patient-side apparatuses 252 (see FIG. 3A and FIG. 3B) located near the patient 70 (see FIG. 3A). A detailed diagram of the control electronics 34 is provided in FIGS. 3A and 3B and is described in greater detail herein below.

Figure 2B:
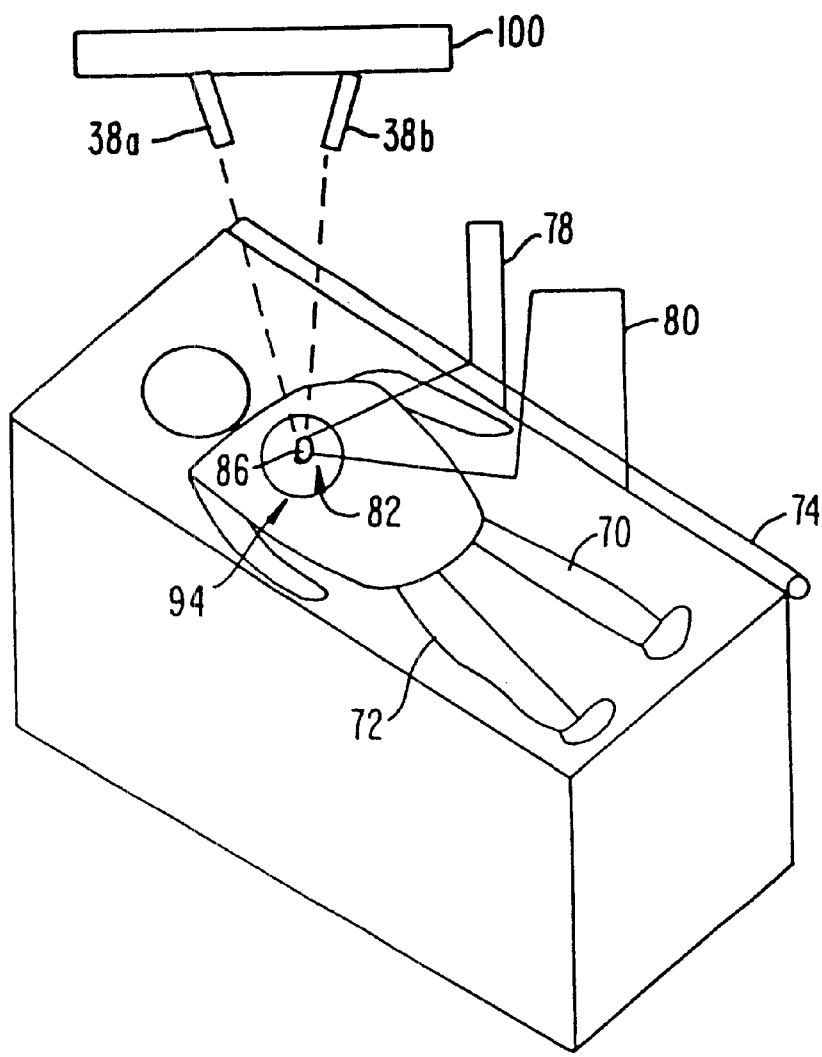
FIG. 2B shows a schematic perspective view of a patient on an operating room table during the performance of an open coronary procedure using the surgical system of the invention.
Figure 2C:
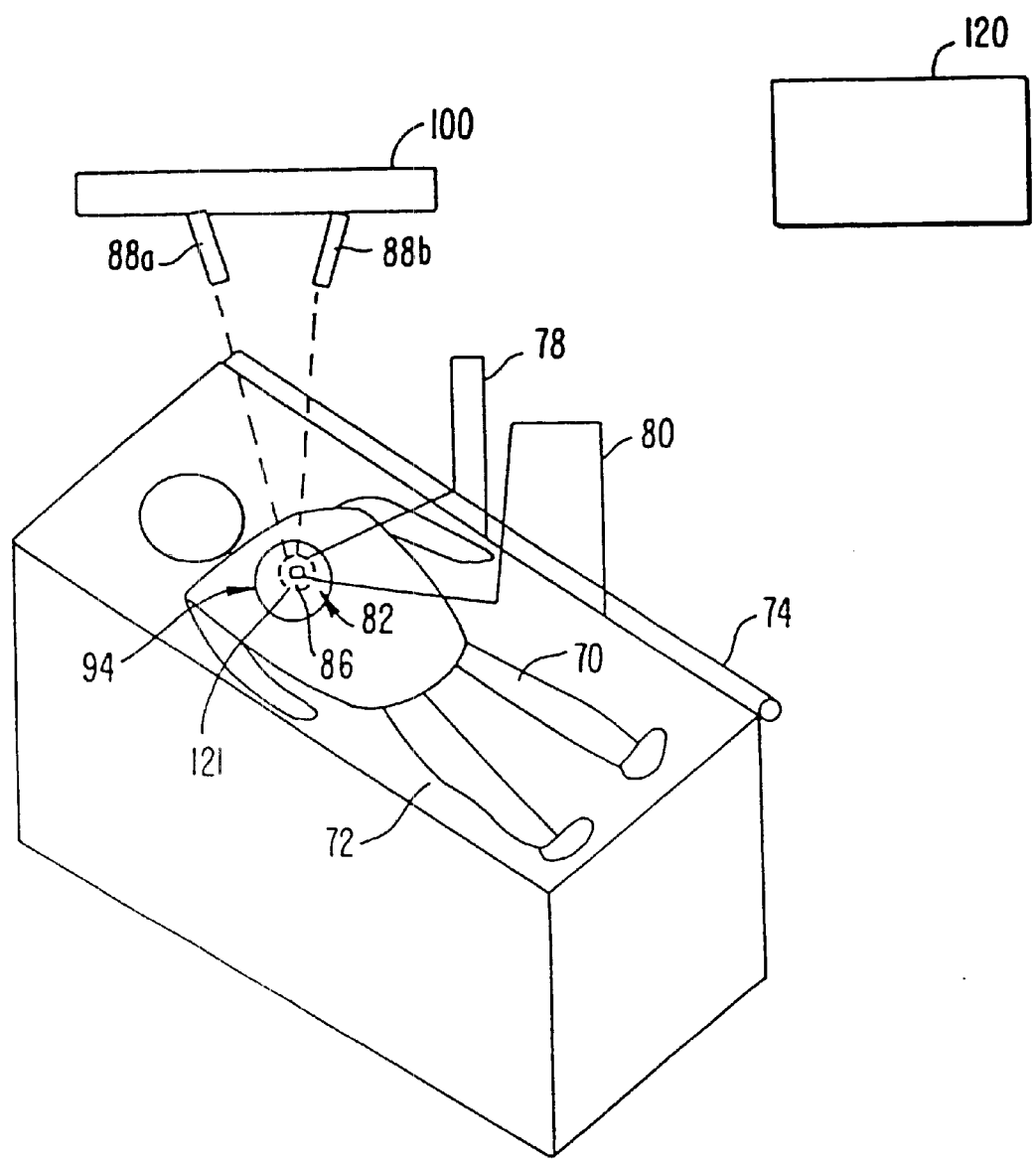
FIG. 2C shows a schematic perspective view of a patient on an operating room table during the performance of an open coronary procedure using another embodiment of the surgical system of the invention.

Typically, the surgeon's console 12 is located in the same operating room as the patient 70 (see FIGS. 2A–2C). In such a situation, the surgeon's console 12 and the control electronics 34 can be directly connected to the patient-side apparatuses 252 (see FIG. 3A) adjacent to the patient 70 (see FIG. 3A). However, the surgeon's console 12 can be located outside of the operating room, for example, where direct contact with the patient is either inappropriate or not possible, due to biohazard or large separation distances, and/or the like.

Reference is now made to FIGS. 2A–2C which show different embodiments of the patient-side apparatuses located adjacent the patient 70. Referring to FIG. 2A, the patient 70 is shown located on an operating room table 72. Attached to a rail 74 of the table 72 are the three surgical manipulators or robotic arms 76, 78 and 80. Each surgical manipulator 76, 78 or 80, is typically a robot-type arm comprising stiff links connected by flexible joints. The movement of the surgical manipulators 76, 78, and 80 is driven by a plurality of slave motors 324 and detected by a plurality of slave encoders 316 (see FIG. 3A). The surgical manipulators 76, 78 and 80 may be provided with additional sensors 318 (see FIG. 3A) such as: potentiometers to detect the orientation of links relative to each other; inclinometers to measure the orientation of links relative to vertical; force sensors to measure forces applied to the links, and/or the like.

The surgical manipulator 76 engages and controls a stereoscopic endoscope medical camera 84 which is typically inserted into a small incision 85 for viewing the surgical worksite 86 inside the patient 70. Similarly, the surgical manipulators 78 and 80 which engage the surgical instruments 82 are typically inserted through small incisions 87a and 87b for performing a surgical procedure at the surgical site inside the patient.

Referring now to FIGS. 16–17, there is seen attached to the rail 74 (see FIG. 16) of the table 72 an attachment manipulator 19 which is in the form of a robot-type arm comprising stiff links connected together by flexible joints. The movement of the attachment manipulator 19 is driven by a plurality of slave attachment motors 324a and detected by a plurality of slave attachment encoders 316a (see FIG. 3B). The attachment manipulator 19 may be provided with additional attachment sensors 318a such as: potentiometers to detect the orientation of links relative to each other; inclinometers to measure the orientation of links relative to vertical; force sensors to measure forces applied to the links, and/or the like.

The attachment manipulator 19 engages and controls the attachment arm 23 of the attachment assembly 21. The attachment arm 23 is typically inserted through a small incision 85a (see FIGS. 23–27) in order to position the attachment member 25 at a desired location on a surgical worksite. It will be appreciated that more than one attachment manipulator 19 can be provided.

The attachment manipulator 19 can be caused to move by control of currents driven by a control computer 310 to the slave attachment motors 324a by means of a servo-amplifier 334 (see FIG. 3B). By utilizing the slave attachment encoders 316a and the additional attachment sensors 318a, each attachment manipulator 19 feeds back data about the motion, position, orientation and forces exerted on its associated attachment assembly 21 (including the attachment arm 23 and the attachment members 25) to the control computer 310. The number of attachment manipulators 19 used in the present invention can be increased or decreased, depending on the particular surgical procedure. In the embodiment of the invention illustrated in FIGS. 24 and 27, two attachment manipulators 19—19 are employed for operating a pair of attachment assemblies 21—21.

Figure 23:
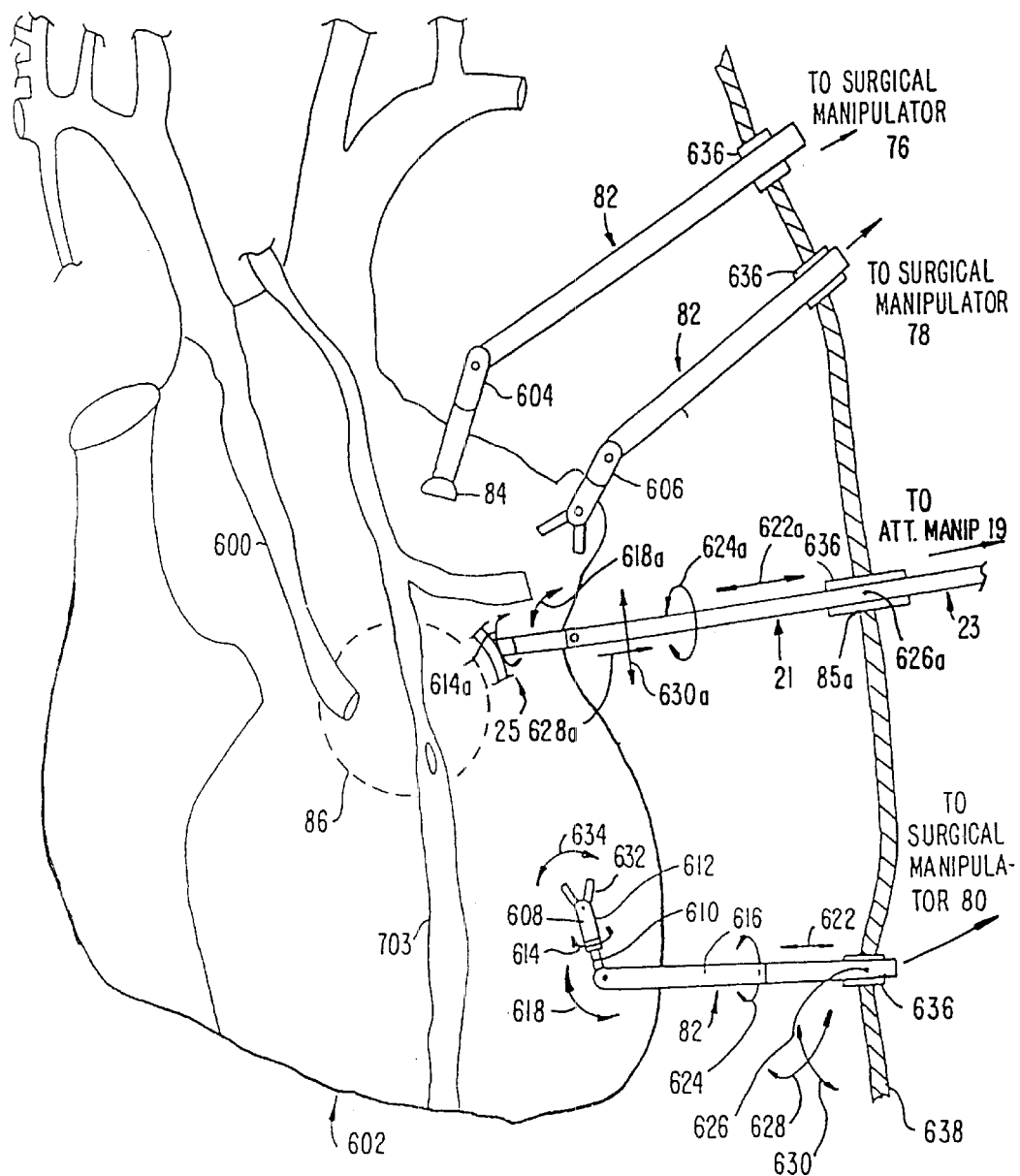
FIG. 23 shows a schematic view of a surgical cardiac worksite illustrating an arrangement of end effectors of surgical manipulators, an endoscope for producing a telepresence effect, and an attachment assembly comprising a servo-mechanism-operated manipulator arm including an attachment member, with six degrees of freedom of movement, for generally immobilizing, a moving cardiac worksite.
Figure 24:
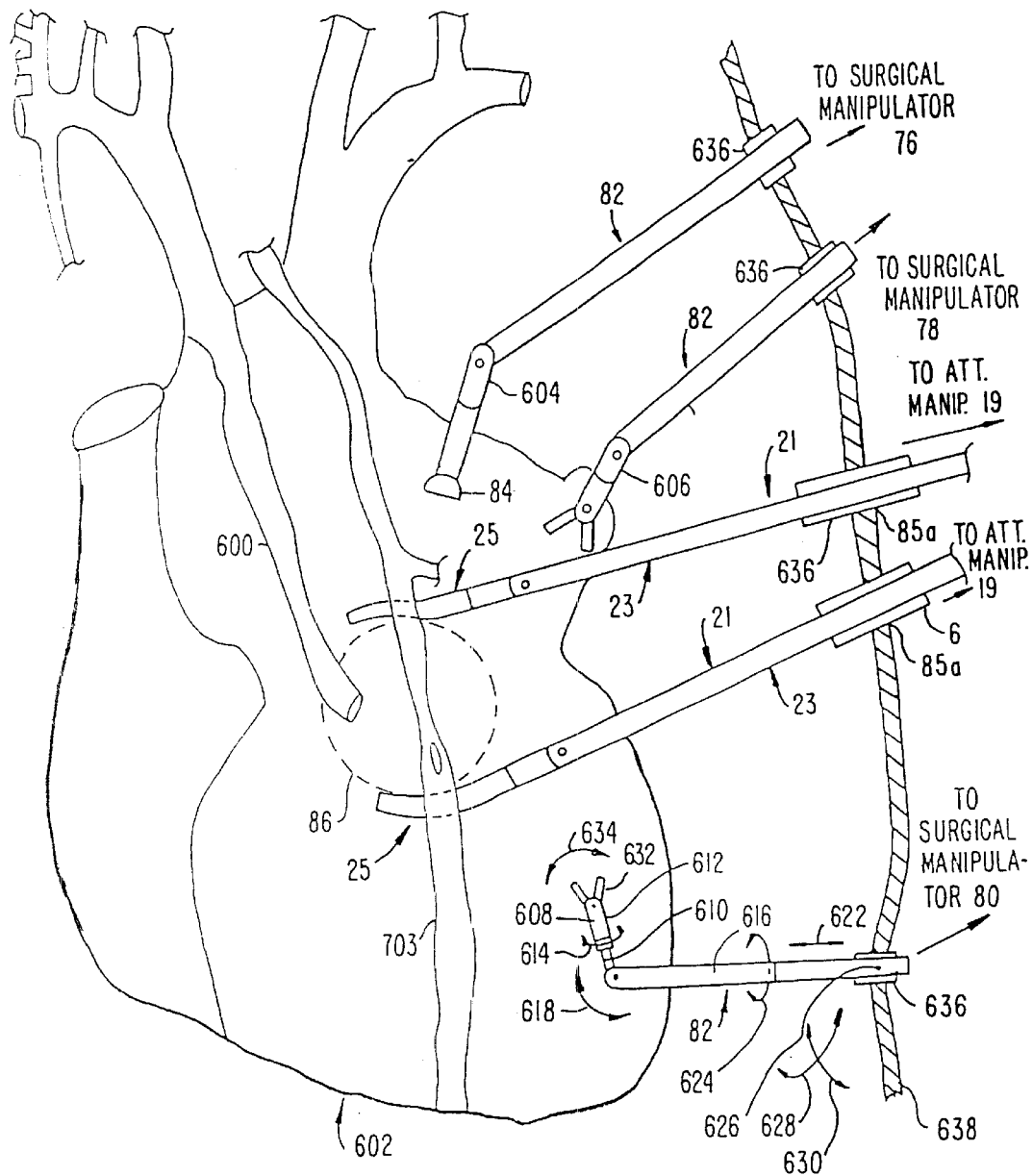
FIG. 24 shows a schematic view of a surgical cardiac worksite illustrating an arrangement of end effectors of surgical manipulators, an endoscope for producing a telepresence effect, and an attachment assembly comprising a pair of servo-mechanism-operated manipulator arms including two attachment members, each with six degrees of freedom of movement, for generally immobilizing a moving cardiac worksite.
Figure 25:
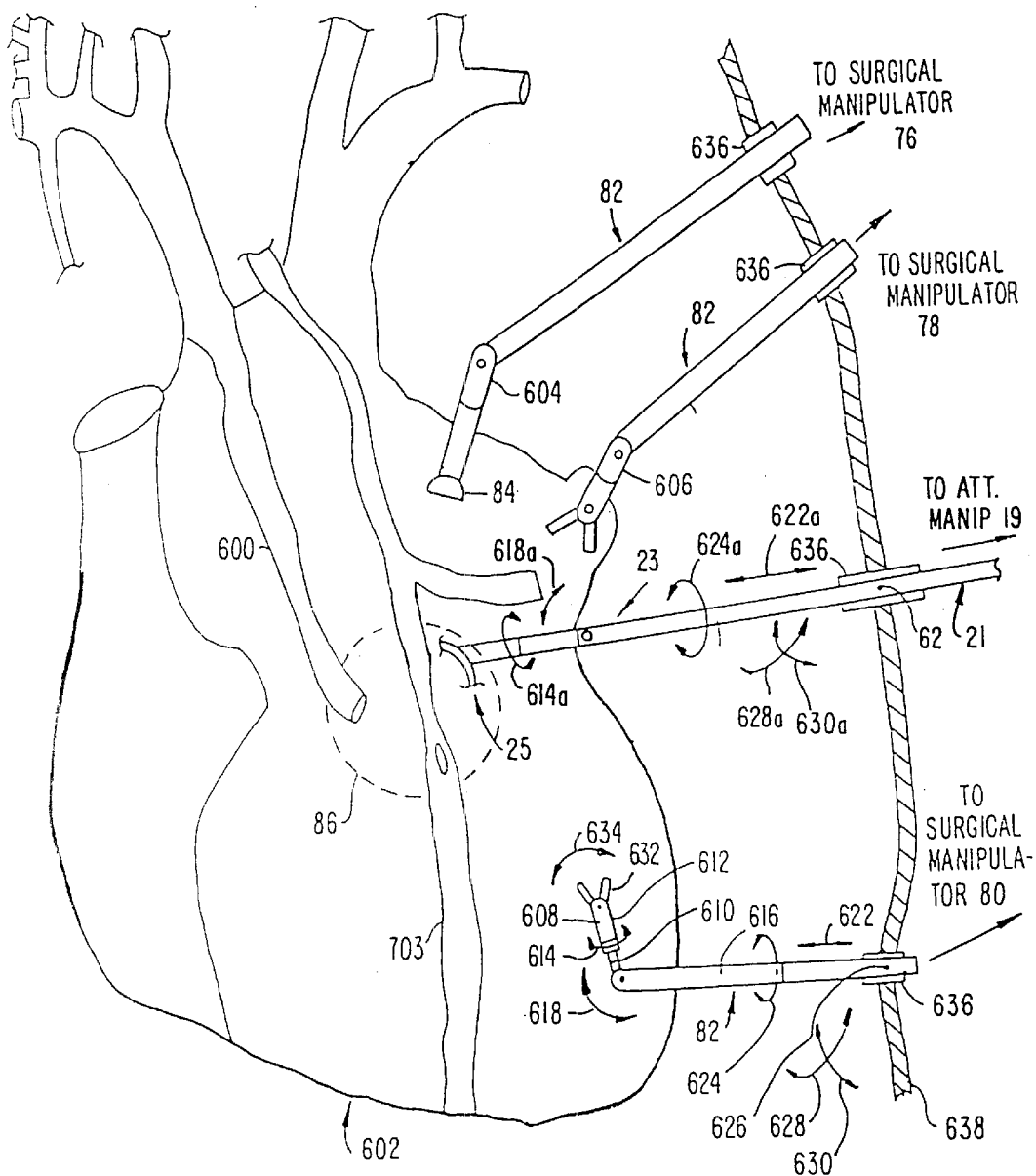
FIG. 25 shows a schematic view of a surgical cardiac worksite illustrating an arrangement of end effectors of surgical manipulators, an endoscope for producing a telepresence effect, and an attachment assembly comprising a servo-mechanism-operated manipulator arm including an attachment member, with six degrees of freedom of movement, for tracking a moving cardiac worksite.

Each of the attachment manipulators 19 may be adapted to support, orient and actuate a specially adapted attachment assembly 21, including a specially adapted attachment arm 23 and a specially adapted attachment member 25. The attachment arm 23 may be coupled to the attachment manipulator 29 in any suitable manner. Likewise, the attachment member 25 may be coupled to the attachment arm 23 in any suitable manner. The attachment member 25 can be any suitable type of apparatus or device that is capable of tracking the surgical worksite 86, as best shown in FIG. 25; or restricting motion of the surgical worksite 86, as best shown in FIGS. 23 and 24; or at least partially immobilizing (i.e., restricting at least one degree of movement) of the surgical worksite 86, leaving a resultant surgical worksite 86a (see FIG. 26) in motion with at least one residual degree of movement, and subsequently tracking the motion of the at least one residual degree of movement of the resultant surgical worksite 86a, as best shown in FIG. 27. The attachment member(s) 25 may be releasably attached to the surgical worksite 86 in any suitable manner, such as, and by way of example only: mechanically (e.g., by clamping); adhesively (e.g., by use of any dissolvable adhesives); suture(s) (e.g., by use of removable suture(s)); suction; and/or the like.

Figure 18:
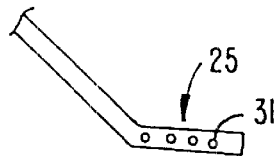
FIG. 18 shows a schematic bottom plan view of another attachment member which has a plurality of openings through which air is sucked to releasably connect the attachment member to a heart.
Figure 19:
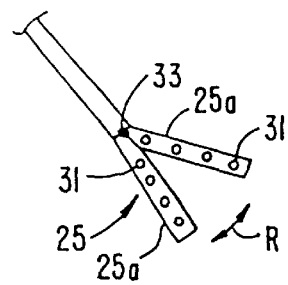
FIG. 19 shows a schematic bottom plan view of a bifurcated forceps (i.e., pincers or tongs) attachment member having a pair of pivotally secured arms, each arm having a plurality of openings through which air is sucked to releasably connect the attachment member to a heart.
Figure 20:
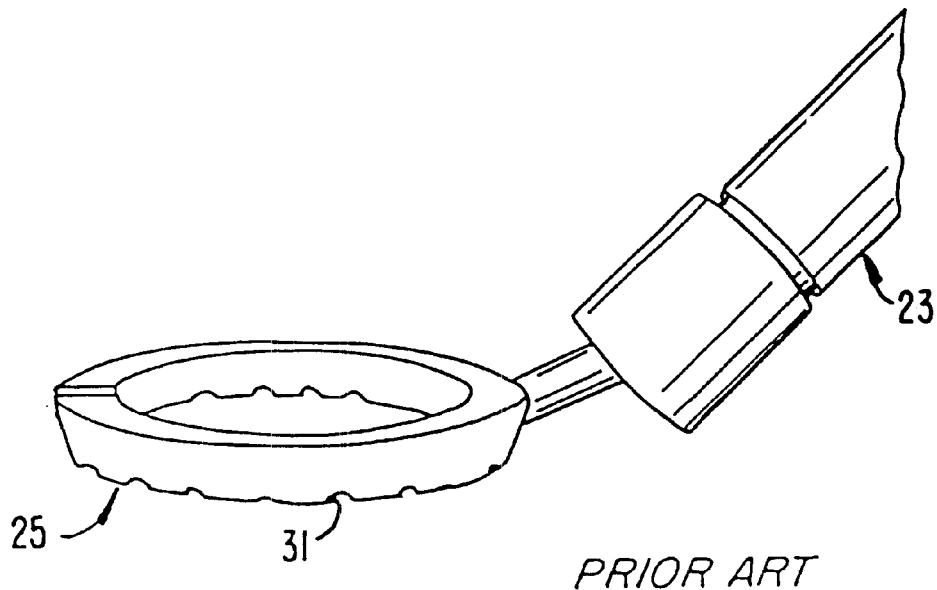
FIG. 20 shows a schematic perspective view of the attachment member of FIG. 17.

Referring now to FIGS. 17–22, there is seen a number of suction-type attachment members 25, all of which are releasably held by a conduit-type attachment arm 23 which is connectable to and in communication with a suction hose 29 (see FIG. 16) that communicates with a vacuum or suction source (not shown). In FIGS. 17 and 20 there is seen a circular design attachment member 25 having a plurality of openings 31 wherethrough suction occurs to releasably attach or engage this circular design attachment member 25 to the surgical worksite 86.

Figure 21:
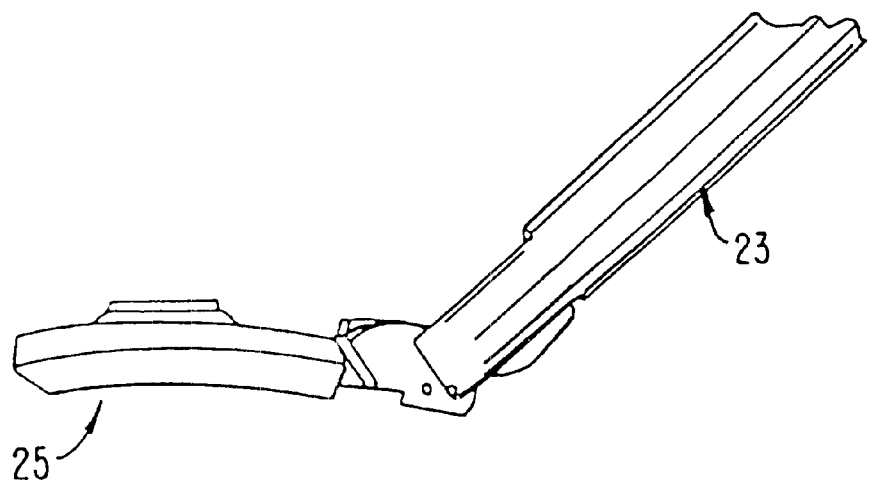
FIG. 21 shows a schematic perspective view of the attachment member of FIG. 18.
Figure 22:
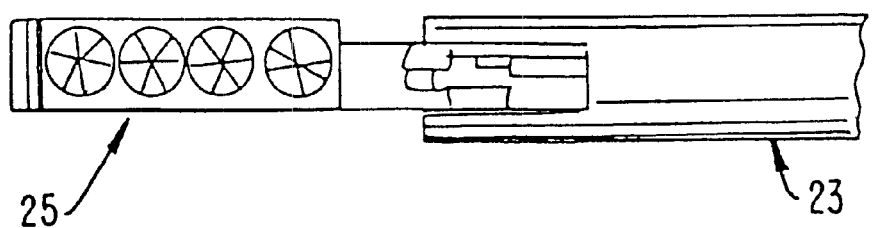
FIG. 22 shows a schematic bottom plan view of the attachment member of FIG. 21.

In FIGS. 18, 21 and 22 there is seen a linear design attachment member 25 having a plurality of openings 31 wherethrough a suction occurs to releasably engage the linear design attachment member 25 to the surgical worksite 86. The linear design attachment member 25 of FIGS. 18, 21 and 22 may be introduced through a cannula. Typically, when the linear design attachment member 25 of FIGS. 18, 21 and 22 is employed, at least two attachment manipulators 19—19 (along with at least two associated attachment assemblies 21—21) are employed in order to stabilize or monitor the surgical worksite 86 as best shown in FIG. 24. A preferred embodiment of an attachment member is disclosed in Applicants' co-pending U.S. patent application Ser. No. 09/399,457, filed Sep. 17, 1999 now abandoned Dec. 19, 2000, the full disclosure of which is fully incorporated herein by reference as if forming part of this specification.

Figure 26:
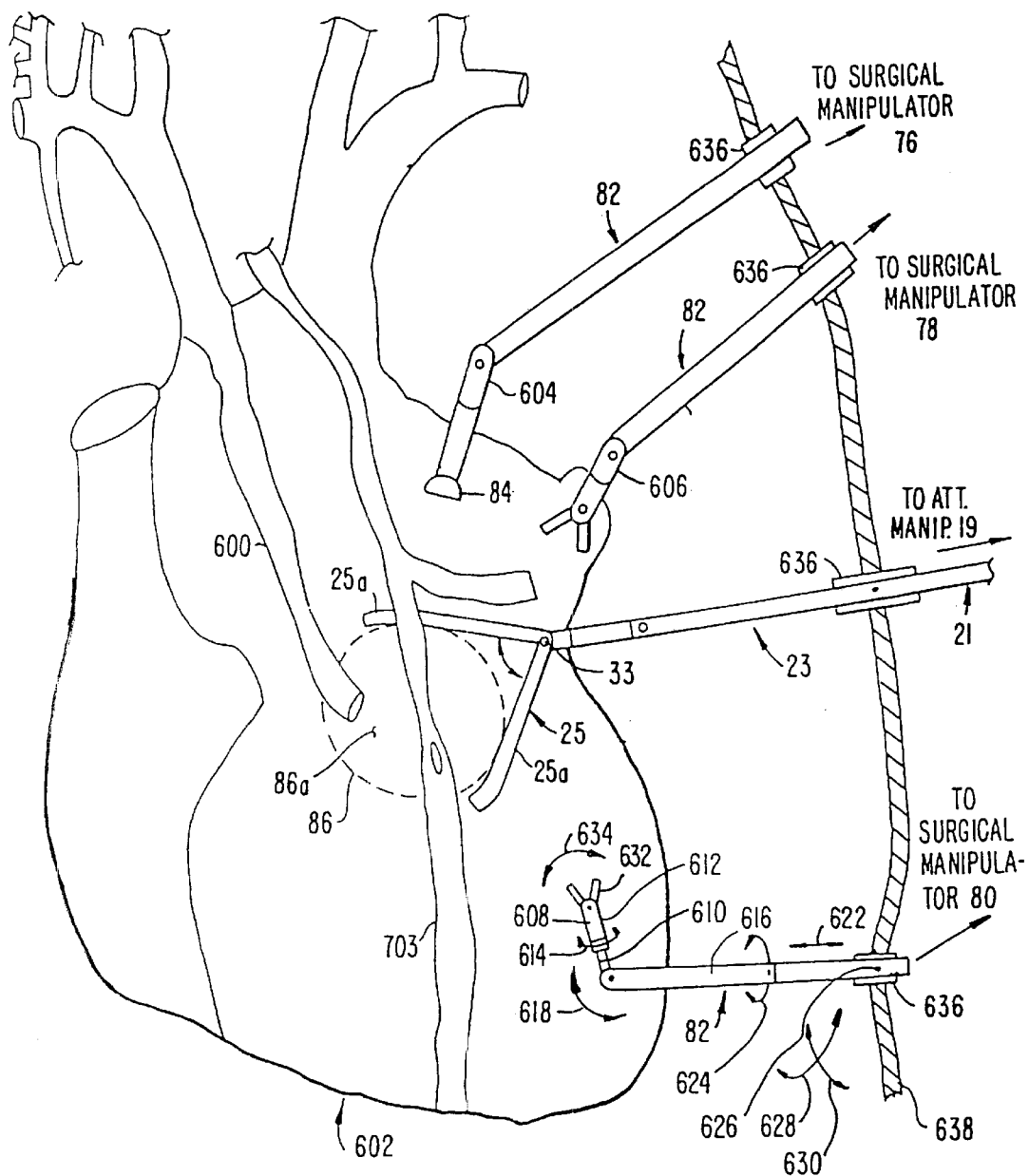
FIG. 26 shows a schematic view of a surgical cardiac worksite illustrating an arrangement of end effectors of surgical manipulators, an endoscope for producing a telepresence effect, and an attachment assembly comprising a servo-mechanism-operated manipulator arm including a bifurcated attachment member, with six degrees of freedom of movement, for generally partially immobilizing movement of the cardiac worksite.
Figure 27:
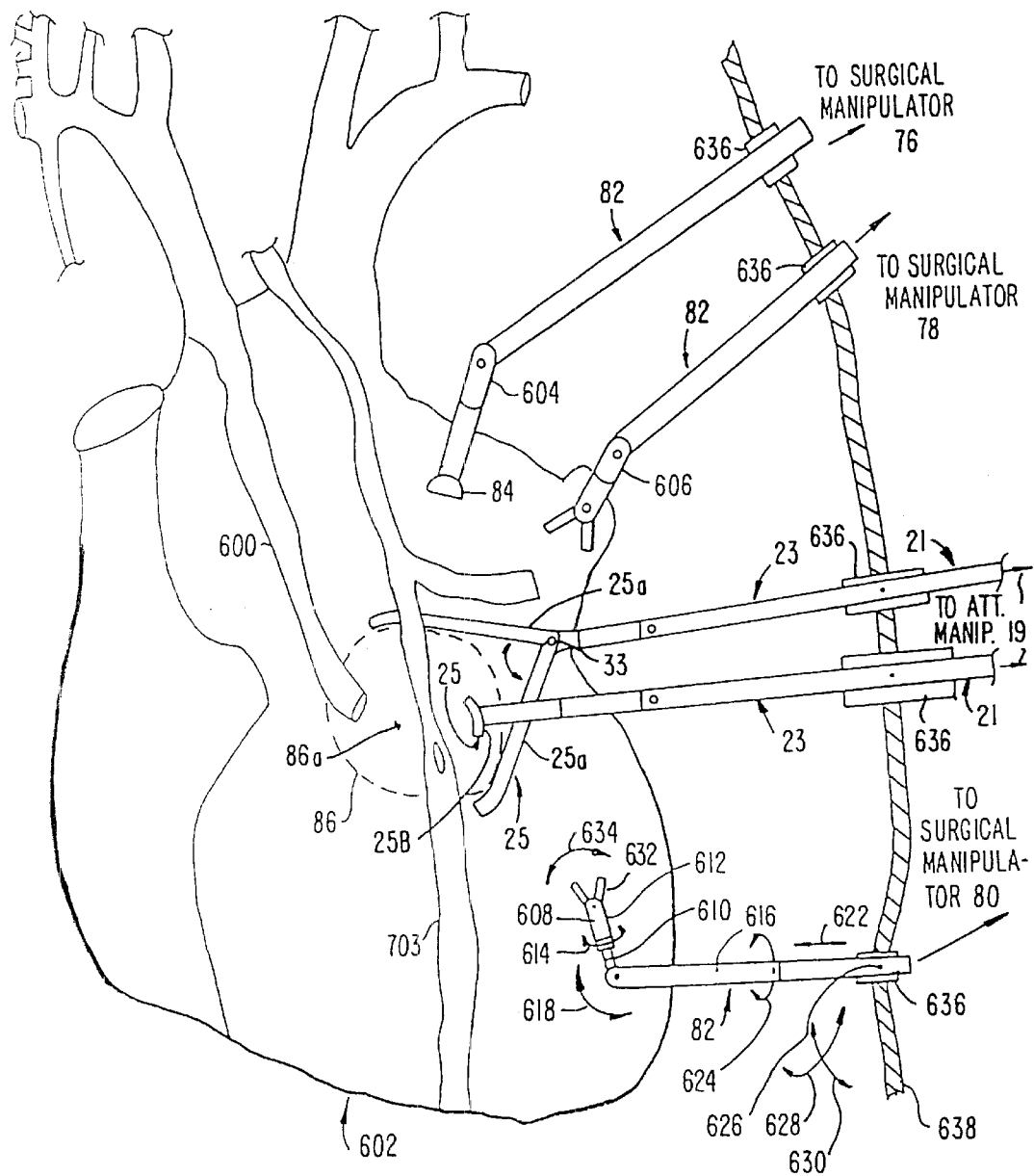
FIG. 27 shows a schematic view of a surgical cardiac worksite illustrating an arrangement of end effectors of surgical manipulators, an endoscope for producing a telepresence effect, and a bifurcated attachment assembly comprising a servo-mechanism-operated manipulator arm including a bifurcated attachment member, with six degrees of freedom of movement, for generally partially immobilizing movement of the cardiac worksite, and another attachment assembly including a servo-mechanism-operated manipulator arm having an attachment member, with six degrees of freedom of movement, for tracking the partially immobilized moving cardiac worksite.

In FIGS. 19, 26 and 27, there is seen a V-shaped design attachment member 25 which is capable of being introduced through a cannula (identified as "636" below) while in a collapsed condition and of being deployed to surround the surgical worksite 86 as best shown in FIGS. 26 and 27 after having passed through the cannula. The V-shaped design attachment member 25 includes a pair of attachment jaws 25a—25a which are capable of pivoting at pivot 33. Each attachment jaw 25a preferably includes a plurality of openings 31 wherethrough suction occurs to releasably engage the V-shaped design attachment member 25 around the surgical worksite 86. The jaws 25a—25a may be spring-loaded to move in a direction as indicated by arrows R in FIG. 19, but are preferably directly controlled by an actuator motor which is not shown but could be comparable to the motor identified as "end effector drive motor 182" in U.S. Pat. No. 5,808,665, fully incorporated herein by reference thereto as if repeated verbatim immediately hereinafter.

Figure 22A:
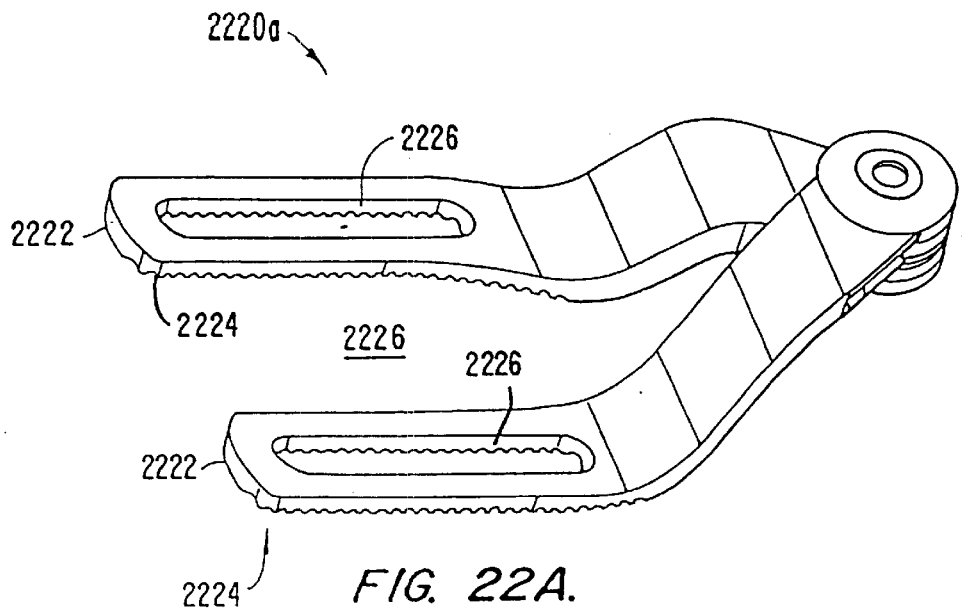
FIGS. 22A to 22C illustrate alternative end effectors having surfaces for stabilizing and/or retracting tissue.
Figure 22B:
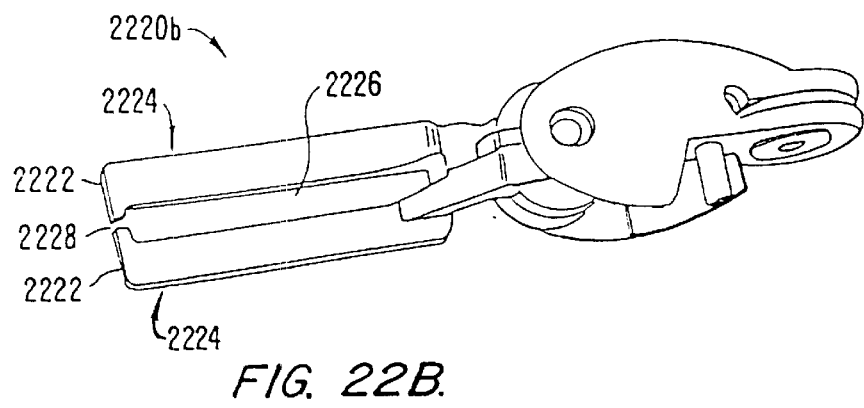
Figure 22C:
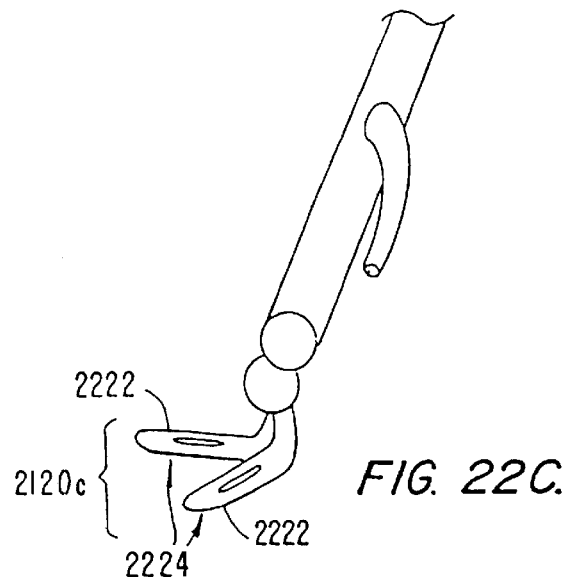

Referring now to FIGS. 22A to 22C, tissue stabilizer end effectors, or attachment members, 2220a, 2220b, and 2220c are referred to generally as tissue stabilizers, or brace members, 2220. The tissue stabilizer 2220 may have one or two end effector elements 2222. The elements 2222 are preferably pivotally attached to a distal end of a shaft, or wrist, of a surgical instrument and are typically movable relative to each other. The elements 2222 preferably define tissue-engaging surfaces 2224. The tissue-engaging surfaces can define protrusions, ridges, vacuum ports, or other features arranged so as to inhibit movement between tissue, engaged by the surfaces 2224, and the stabilizer 2220. This can typically be achieved by means of pressing the surfaces 2224 against tissue, or by passing air through the vacuum ports to cause the surfaces 2224 to attach to the tissue by suction, or a combination of the application of pressure and vacuum, or the like. Ideally, the tissue-engaging surfaces 2224 will constrain and/or reduce motion of the engaged tissue in two lateral axes directed along the tissue-engaging surfaces 2224. In use, the stabilizer 2220 at least partially reduces tissue motion in a direction normal to the surfaces 2224 when the stabilizers 2220 are attached, or engaged, to the moving tissue. Although this is a preferred stabilizer, other types of stabilizers are known in the art, such as those referred to as the Octopus II from Medtronic, Inc. and those available from Heartport, Inc. and Cardiothoracic Systems. These stabilizers include stabilizers having multi-pronged and donut-type configurations. When such a stabilizer, or the preferred stabilizer as described above, is engaged to moving tissue, such as a beating heart, tissue adjacent the stabilizer, typically where a surgical procedure is to be performed, is braced to at least reduce movement of the surgical site.

To facilitate performing a procedure on a surgical site stabilized by means of the tissue stabilizer 2220, an opening 2226 can be formed in an individual stabilizer element 2222, and/or between independently movable end effector elements. As illustrated in FIG. 22B, stabilizer 2220b includes cooperating tissue grasping surfaces 2228 disposed between stabilizer end effector elements 2222. This permits the stabilizer 2220b to engage tissue, so as to provide a dual function of both stabilizing the tissue at the surgical site as well as to grasp, or hold, tissue on which a surgical procedure is to be performed. Stabilizer 2220b can be used, for example, as a grasper, or a holder, for harvesting and/or preparing an internal memory artery (IMA) so as to perform a coronary artery bypass graft (CABG) procedure, and/or to hold the IMA during the formation of an anastomosis on the stabilized beating heart.

Figure 22D:
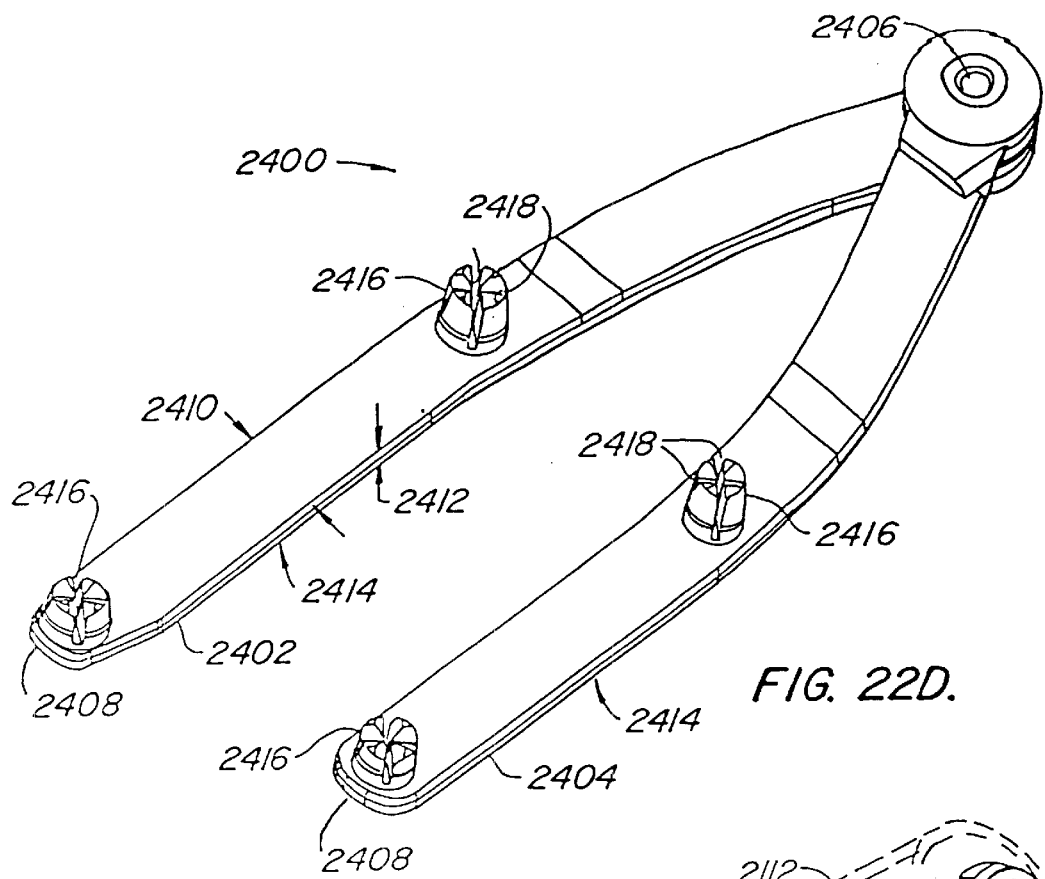
FIG. 22D shows a perspective view of an exemplary tissue stabilizer end effector having two pivotally coupled finger formations each having anchors for securing tensionable elongate flexible members thereto.
Figure 22E:
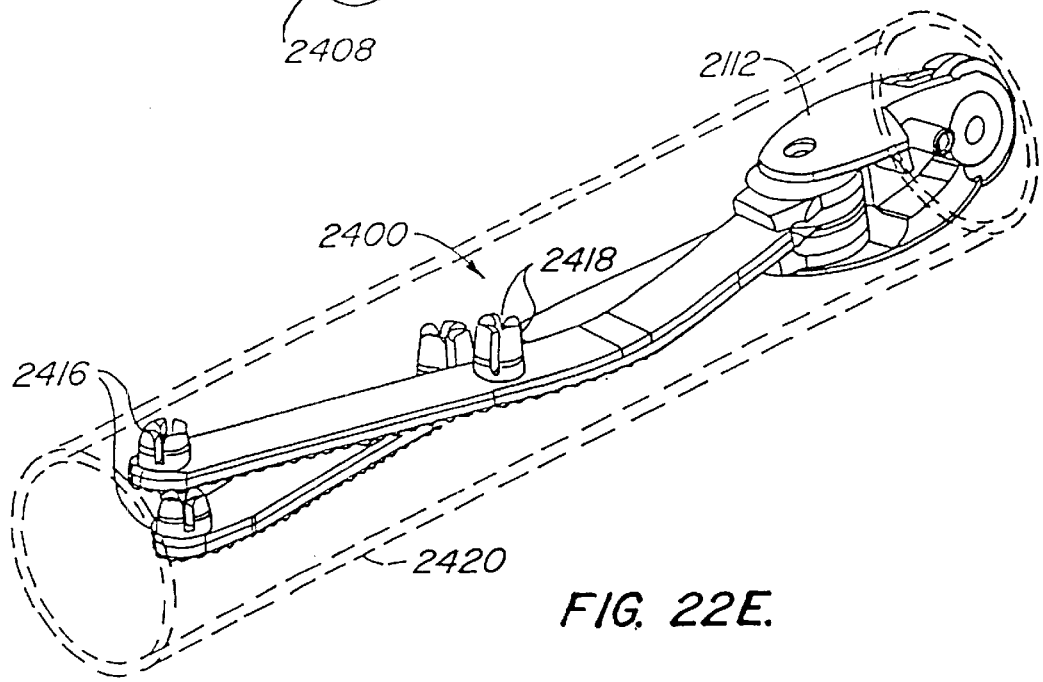
FIGS. 22E to 22H illustrate the stabilizer of FIG. 22D in a collapsed condition to enable it to be inserted through a relatively small aperture, such as an aperture defined by a cannula, to be introduced to an internal surgical site.

An exemplary stabilizer end effector, or brace member, or attachment member, 2400 is illustrated in FIG. 22D. Preferred stabilizer 2400 generally comprises a bifurcated structure having first and second bodies, or members, 2402, 2404 operatively connected to each other and to an associated tool shaft, wrist, wrist member, or the like, at a stabilizer pivot 2406.

Figure 22F:
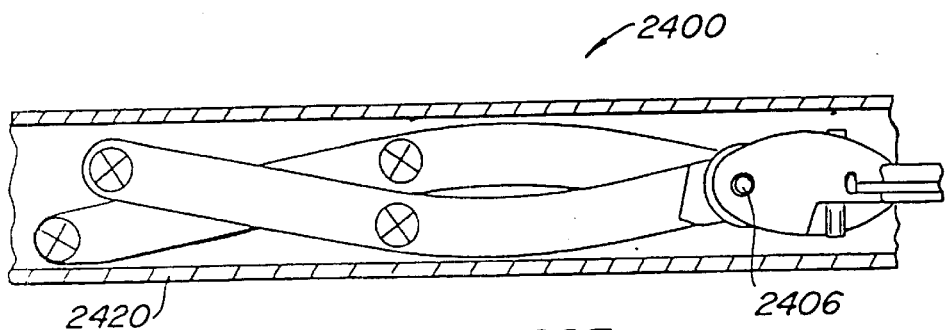
Figure 22G:
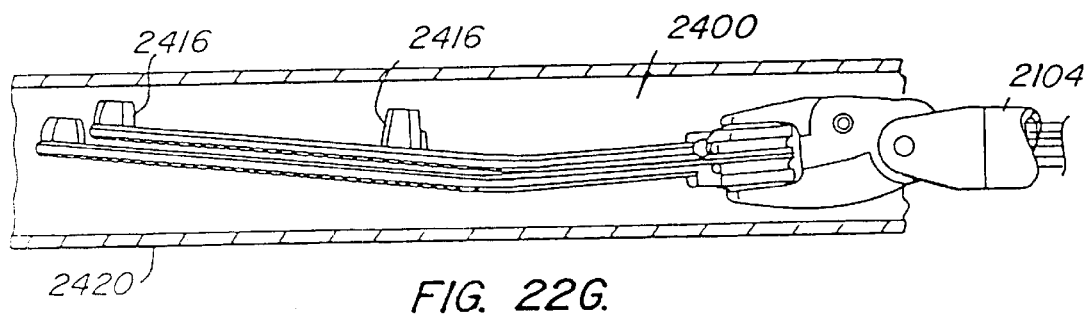
Figure 22H:
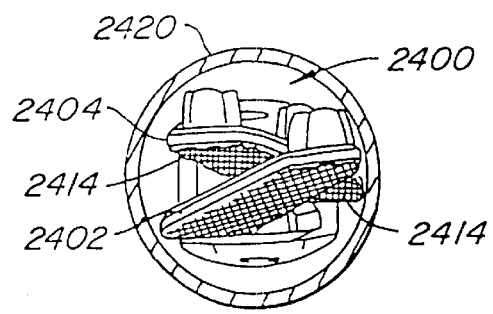

Each of the stabilizer bodies 2402, 2404 comprises an elongate plate-like structure extending away from the pivot 2406 to an opposed end 2408. Each plate generally has a width 2410 which is less than its length, and a thickness 2412 less than its width. As can best be seen with reference to FIGS. 22F and 22G, each plate bends laterally relative to its length in the direction of its width (so that bodies 2402, 2404 cross distally of pivot 2406 when the stabilizer is in a small profile or collapsed condition) and in the direction of its thickness (as shown in FIG. 22G) so that tissue stabilizing surfaces 2414 of the bodies can engage a tissue surface without interference from the pivot at 2406. Pivot 2406 maintains alignment between tissue-engaging surfaces 2414, and these tissue-engaging surfaces will generally be adapted to inhibit relative motion between tissue engaged by the stabilizer and the stabilizer itself Engagement with the tissue can be enhanced by providing a textured, knurled, roughened, or other frictional formation, or the like, at 2414. Instead, or in addition, engagement can be enhanced by means of one or more suction ports, by providing a high friction material, coating, and/or adhesive, or the like.

As can be seen in FIGS. 22D to 22H, protruding anchors or cleats 2416 extend away from the tissue engaging surfaces 2414. The cleats typically have channels, or slits, 2418 for laterally receiving an elongate flexible member such as a suture, tape, silastic tubing, or the like, and for attaching the flexible member to the body 2402, 2404 of stabilizer 2400. As illustrated in FIG. 22D, channels, or slits, 2418 are preferably orientated at about 45° relative to the adjacent edge of the bodies 2402, 2404. Channels 2418 in each anchor 2416 can be of different sizes to permit different types of flexible members having different lateral dimensions, to be used. More than two slots can be provided in each anchor. Anchors 2416 and the channels 2418 therein, may be generally hour-glass-like in shape, to facilitate tying off the flexible member to the anchor. Bodies 2402, 2404 and anchors 2416 may be of metal such as 17-4 stainless steel, or a polymer, or the like. The anchors 2416 may optionally be deformable to anchor the flexible members in the slits 2418. When a high strength material, such as metal, in the form of stainless steel for example, is used, anchors 2416 will preferably be electropolished to smooth any rough edges and avoid cutting of the flexible member.

Referring now to FIGS. 22E to 22H, stabilizer 2400 can be selectively displaceable between a collapsed and a deployed condition. In a collapsed condition, the stabilizer 2400 has a generally small profile configuration to enable it to be inserted through a cannula 2420 so as to be introduced to an internal surgical site in a minimally invasive manner. Preferably, cannula 2420 defines an internal aperture having a diameter of less than 0.5 inch, advantageously having an inner diameter of less than 0.4 inch, and ideally having an internal diameter which tapers slightly from about 0.383 inches to about 0.34 inches distally. First body 2402 may be longer than the second body 2404 so as to permit the distal ends 2408 of the bodies to cross, or overlap, without interference from the cleats 2416. Stabilizer 2404 may have an overall length from pivot 2406 to distal end 2408 falling in the range between about 0.75 inches to about 3.5 inches. Preferably, the length falls in the range between about 1 inch to about 2.5 inches. The plates from which the bodies are formed may have thicknesses of about 0.035 inch, while anchors 2416 may protrude by a distance falling in the range between about 0.03 inches to about 0.15 inches with the distal anchors optionally protruding less than the proximal anchors to enhance clearance between the stabilizer and the surrounding cannula 2420.

As shown in FIGS. 23–24, the attachment assembly/assemblies 21, as well as surgical instruments 82, are shown as extending through cannula(s) 636 in a chest wall 638 of the patient 70. Where appropriate, when reference is made to attachment assembly/assemblies 21, it is to be understood that the attachment assembly/assemblies can include either of the members 25, 2220 or 2400, in the description which follows.

Each surgical manipulator 76, 78 or 80 can be caused to move independently by control of currents driven by the control computer 310 to the slave motors 324 by means of the servo-amplifier 334 (see FIG. 3A). By utilizing the slave encoders 316 and the additional sensors 318, each surgical manipulator 76, 78 or 80 feeds back data about the motion, position, orientation and forces exerted on the surgical instrument (e.g., stereoscopic endoscope medical camera 84, surgical instruments 82, etc.) to the control computer 310 (see FIG. 3A). The number of surgical manipulators used in the present invention can be increased or decreased, depending on the particular surgical procedure to be performed.

Figure 7:
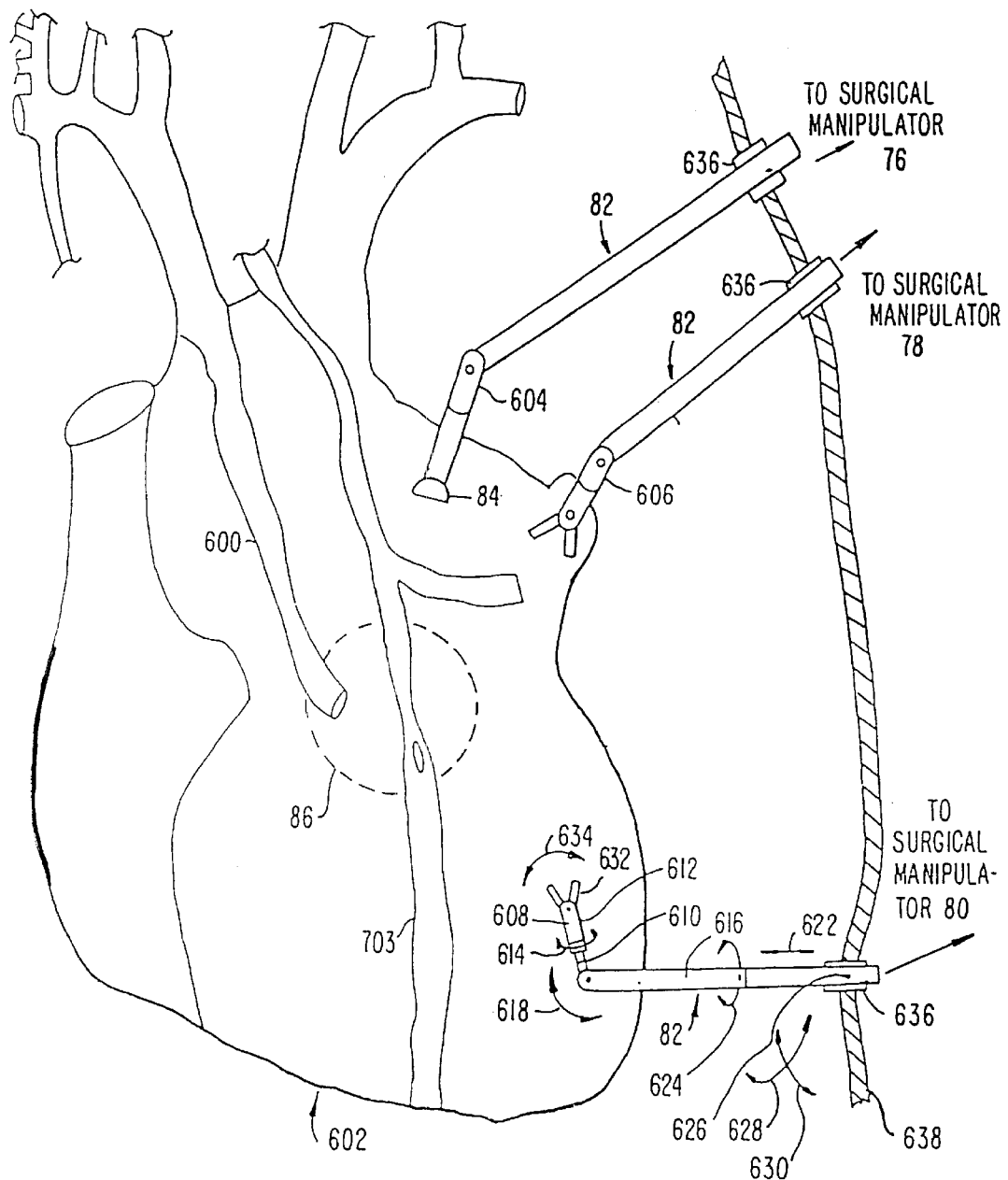
FIG. 7 shows a schematic view of an anatomical worksite on a beating heart and illustrates an arrangement of end effectors of surgical manipulators of the surgical system of the invention.

Each surgical manipulator 76, 78 or 80 may be adapted to support, orient and actuate a specially adapted surgical instrument. The surgical instruments 82 may be engaged to the surgical manipulators 76, 78 and 80 in any suitable fashion. The surgical instruments 82 can include any instrument that may be employed in any surgical procedure, such as, by way of example only, a stereoscopic endoscope medical camera 84 (see FIG. 2A), and any of the following surgical implements not shown in the drawings: forceps, blades, scissors, needle drivers, electrocautery devices, and the like. For example, the stereoscopic endoscope medical camera 84 (see FIG. 2A) may be attached to the surgical manipulator 76, while forceps, blades, scissors, needle drivers or any other surgical tool may be attached to the surgical manipulators 78 and 80. The surgical manipulators 76, 78 and 80 may engage and control any of the surgical instruments 82 and may be arranged and moved with respect to the surgical worksite 86 in any desired manner to accomplish a desired surgical procedure. For example, and as best illustrated in FIG. 7 where a saphenous or internal mammary artery graft 600 is being applied to the surgical worksite 86 of a heart 602, the surgical manipulator 76 engages and controls the stereoscopic endoscope medical camera 84. Similarly, the surgical manipulators 78 and 80 engage and control surgical instruments 82 which include end effectors 604 and 606 (see FIG. 7) for engaging the human tissues at the surgical worksite 86 (see FIGS. 2A–2C). The engagement may be in the form of gripping, grasping, cutting, driving, or performing other functions during surgery and the end effectors may comprise the tips of standard open surgical or endoscopic instruments such as forceps, scissors, graspers, needle drivers, electrocautery instruments, and/or the like.

The surgical manipulators 76, 78 and 80 may manipulate the surgical instruments 82 with various degrees of freedom, as described in U.S. Pat. Nos. 5,808,665 and 5,817,084, fully incorporated herein by reference as if repeated verbatim immediately hereinafter. In some embodiments, the surgical manipulators manipulate the surgical instruments with six degrees of freedom for orientation and position of the end effector and one degree of freedom for actuation of the end effector. Similarly, the attachment manipulators 19 may manipulate the attachment assembly/assemblies 21 (including attachment arm(s) 23) with the same various degrees of freedom. More specifically, and in one embodiment of the invention, the attachment manipulator(s) 19 manipulates the attachment assembly/assemblies 21 (including the attachment arms 23) with six degrees of freedom for orientation and position of the attachment member 25 and one degree of freedom for actuation of the attachment member 25.

As best illustrated in FIG. 7, the surgical instrument 82, for example, has a wrist 608 which comprises an axially aligned inner link 610 and an outer link 612. The outer link 612 is rotatable about its longitudinal axis relative to the inner link 610 by the slave motors 324 of manipulator 80 (see FIG. 3A) in the direction of the double-headed arrow 614 in response to control signals from the control computer 310 (see FIG. 3A). The inner link 610 is pivotally attached to a forearm 616 of the surgical instrument 82 and may be operated by manipulator 80 for pivotal movement or pitch movement in the direction of the double-headed arrow 618 in response to control signals from the control computer 310 (see FIG. 3A). The forearm 616 of surgical instrument 82 may be moved by manipulator 80 longitudinally in the direction of the double-headed arrow 622 in response to control signals from the control computer 310 (see FIG. 3A). The forearm 616 may also be rotated by manipulator 80 about its longitudinal axis in the direction of the double-headed arrow 624 in response to control signals from the control computer 310 (see FIG. 3A). Additionally, the forearm 616 may be pivoted by manipulator 80 about a pivot point or fulcrum 626 in the directions of the double-headed arrows 628 and 630 in response to control signals from the control computer 310 (see FIG. 3A). For biomedical use, such as laparoscopic surgery, the pivot point 626 is substantially located at the level of the chest wall 638 through which the surgical instrument 82 extends. In FIG. 7, the surgical manipulator 80 is shown as extending through the cannula 636 which penetrates the chest wall 638.

The surgical instrument 82 has an end effector comprising a pair of movable jaws 632 for manipulating tissues or gripping a needle or suture. The movable jaws 632 can move in the directions of the double headed arrows 634 for gripping. The movable jaws 632 can be in the form of standard surgical instruments such as forceps, needle drivers, scissors, graspers and electrocautery instruments depending upon the surgical actions desired.

Therefore, operation of the manipulator 80 to move the forearm 616 and the wrist 608 permits the end effector to be positioned and orientated with six degrees of freedom. Similarly, the surgical manipulators 76 and 78 may each manipulate surgical instruments with six degrees of freedom of position and orientation and a seventh degree of freedom for actuation of the end effector. The surgical instruments engaged by manipulators 76, 78 and 80 may be any suitable surgical instruments such as endoscopic cameras, forceps, needle drivers, scissors, graspers and electrocautery instruments depending upon the surgical actions desired.

Figure 28:
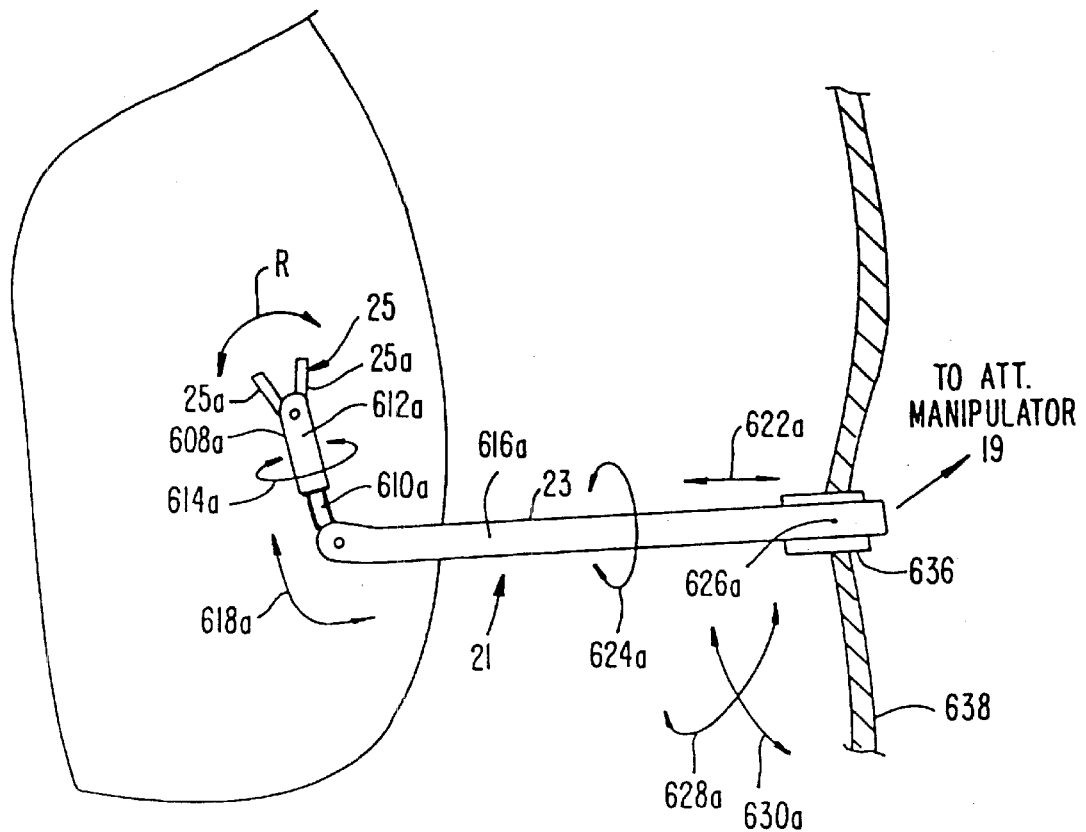
FIG. 28 shows a schematic view of another embodiment of an attachment assembly of the present invention.

Referring now to FIG. 28 there is seen another embodiment of the attachment assembly 21 including the attachment arm 23. In FIG. 28, the attachment assembly 21 has a wrist 608a which comprises an axially aligned inner link 610a and an outer link 612a. The outer link 612a is rotatable about its longitudinal axis relative to the inner link 610a by the slave attachment motors 324a of attachment manipulator 19 (see FIG. 3B) in the direction of the double-headed arrow 614a in response to control signals from the control computer 310 (see FIG. 3B). The inner link 610a is pivotally attached to the forearm 616a of the attachment arm 23 and may be operated by attachment manipulator 19 for pivotal movement or pitch movement in direction of the double-headed arrow 618a in response to control signals from the control computer 310 (see FIG. 3B). The forearm 616a of the attachment arm 23 may be moved by attachment manipulator 19 longitudinally in the direction of the double-headed arrow 622a in response to control signals from the control computer 310 (see FIG. 3B). The forearm 616a may also be rotated by attachment manipulator 19 about its longitudinal axis in the direction of the double-headed arrow 624a in response to control signals from the control computer 310 (see FIG. 3B). Additionally, the forearm 616a may be pivoted by attachment manipulator 19 about the pivot point 626a in the directions of the double-headed arrows 628a and 630a in response to control signals from the control computer 310 (see FIG. 3B). For biomedical use, such as laparoscopic surgery, the pivot point 626a is substantially located at the level of the chest wall 638 through which the attachment arm 23 extends.

As was previously mentioned, the attachment member 25 may be in the form of the V-shaped design of FIG. 19 having a pair of actuated jaws 25a—25a which may be moved in the direction of the double-headed arrow R in FIGS. 19 and 28. Therefore, operation of the attachment manipulator 19 to move the forearm 616a, the wrist 608a and the inner link 610a (all of the attachment arm 23) permits the attachment member 25 to be positioned and orientated with six degrees of freedom. Similarly, the attachment manipulator 19 may manipulate the components (i.e., forearm 616a, wrist 600a, inner link 610a) of the attachment arm 23 with six degrees of freedom of position and orientation and a seventh degree of freedom for actuation of the attachment member 25. As also previously mentioned, the attachment member 25 engaged by attachment manipulator 19 may be any suitable attachment member 25, such as those illustrated in FIGS. 17, 18 and 19, for example.

The actuators for the surgical manipulators 76, 78, and 80 are shown as the slave motors 324 in FIG. 3A and may be any suitable servo motor that can be coupled to the control computer 310 (see FIG. 3A). The slave motors 324 (see FIG. 3A) are capable of actuating the surgical manipulators 76, 78 and 80. Suitable servo motors with integral encoders can be purchased commercially from the Hewlett-Packard Company. The surgical manipulators may use alternative mechanical actuators, such as, piezoelectric motors, stepper motors, electrostrictive materials, pneumatic or hydraulic systems, and/or the like, for example.

The actuators for the attachment manipulators 19 are shown as the slave attachment motors 324a in FIG. 3B and may be any suitable servo motor that can be coupled to the control computer 310a (see FIG. 3B). The slave attachment motors 324a (see FIG. 3B) are capable of actuating the attachment manipulators 19. As was previously indicated for the surgical manipulators 76, 78, and 80, suitable servo motors with integral encoders for the attachment manipulators 19 can be purchased commercially from the Hewlett-Packard Company. The attachment manipulators 19 may use alternative mechanical actuators, such as, piezoelectric motors, stepper motors, electrostrictive materials, pneumatic or hydraulic systems, and/or the like, for example.

Referring again to FIG. 2A, the stereoscopic endoscope medical camera 84 functions as a means for observing the surgical worksite 86 in the patient 70. The stereoscopic endoscope 84 may incorporate two independent lens systems (shown as left and right cameras 88a and 88b) or optical fibers (not shown), and may be capable of transmitting two simultaneous images from the body of the patient 70. The independent images provided by left camera 88a and the right camera 88b are separated by a small known distance and are thus able to provide a stereoscopic image. The stereoscopic video images may be used for two purposes: display to the surgeon; and, in addition, for motion tracking of the surgical worksite in accordance with one embodiment of the invention described in greater detail herein below. The stereo endoscope medical camera 84 may alternatively be replaced by two video cameras or two endoscopes. For example, in another embodiment (not shown) two monocular endoscopes may be attached to the end of the surgical manipulator 76 or to other surgical manipulators (not shown) in place of stereo endoscope 84.

Also shown in FIG. 2A is an optional electrocardiograph (ECG) system 90 coupled to the patient 70 by the ECG leads 92a and 92b. The optional ECG system 90 may be used to monitor the electrical activity of the patient's heart during the procedure. The ECG data can be provided to the control electronics 34 (see FIG. 1) of the surgeon's console 12 to augment motion tracking of the surgical worksite 86. By correlating the ECG data with the position of the surgical worksite over time, the system can be arranged to predict the position of the worksite from the ECG data. The predicted position can be used, for example, to augment, verify, or substitute the position determined by the motion tracking system, and/or to compensate for system lag, and/or the like.

FIG. 2B illustrates a second embodiment of the present invention adapted for open surgical procedures, such as open coronary surgical procedures. As in FIG. 2A, the surgical manipulators 78 and 80 operate the surgical instruments 82 at the surgical worksite 86 of the patient 70 whilst lying on the operating room table 72. The surgical instruments 82 are inserted through the surgical opening 94 in the patient 70 for performing the surgical procedure. However, because the procedure is an open procedure, the endoscopic camera can be replaced with another viewing system. This embodiment of the invention includes a viewing system 100, which is preferably employed during an open-chest surgical procedure. The viewing system 100 includes a left camera 88a and a right camera 88b that are located outside the body of the patient 70 during the open-chest surgical procedure. The left and right cameras 88a and 88b of the viewing system 100 can be used to provide optical data for motion tracking of the surgical worksite 86 and may also be used to provide magnified stereo video images of the surgical worksite 86 of the patient 70 to the surgeon.

FIG. 2C illustrates a third embodiment of the present invention which includes a position/orientation device 120 in addition to the left and right cameras 88a and 88b. The position/orientation device 120 is a dedicated motion tracking sensor that tracks the motion of targets 121, examples of which are described in greater detail herein below, which are attached to the surgical worksite 86. The position/orientation device 120 may comprise an electromagnetic sensing device which detects the position and orientation of the targets 121, which may be in the form of, for example, active transmitters, or receivers, or the like. Suitable position/orientation devices 120 are available commercially from Polhemus, Incorporated. Further description of a suitable position/orientation device 120 is provided by U.S. Pat. No. 5,453,686 entitled "Pulsed-DC Position And Orientation Measurement System," which is fully incorporated herein by reference as if repeated verbatim immediately hereinafter. The position/orientation device 120 may be used to augment or replace the optical motion tracking performed by the left and right cameras 88a and 88b or other cameras (not shown) in either MIS or open surgical procedures.

The attachment assembly 21 of the present invention may be employed not only for stabilization, but also for tracking (see FIG. 25) or for a combination of tracking and stabilization (see FIGS. 26 and 27). For tracking purposes, the attachment member 25 becomes (or includes) the position/orientation device 120, which is a dedicated motion tracking sensor for tracking motion of the surgical worksite 86. When the attachment member 25 performs the functions of the position/orientation device 120, the attachment member 25 can include an electromagnetic sensing device (e.g., active transmitters or receivers, etc.) for detecting the position and orientation of the surgical worksite 86, or for detecting the position and orientation of a resultant worksite 86a as described in greater detail herein below with reference to FIG. 27. As further shown in FIG. 27, if the mode of operation is for both tracking and stabilization, two attachment assemblies 21—21 respectively having attachment members 25A and 25B would be employed such that attachment member 25A would be used to partially immobilize the surgical worksite 86, leaving the resultant surgical worksite 86a in motion, and attachment member 25B would be employed for tracking the motion of the resultant surgical worksite 86a. As previously indicated, attachment members 25 which could function as tracking devices (i.e., position/orientation devices 120) are available commercially from Polhemus, Incorporated. Further description of suitable attachment members 25 which could function as tracking devices, such as position/orientation devices 120, is provided by the previously mentioned U.S. Pat. No. 5,453,686 entitled "Pulsed-DC Position And Orientation Measurement System."

Reference is now made to FIGS. 3A and 3B which are schematic diagrams showing components of the surgical system of the invention and the interaction of the components with the surgeon 18, the patient 70 and each other. The components of the surgical system can be divided into three main groups, for the sake of ease of description, namely: patient-side apparatus 252 which comprises the apparatus which performs procedures upon and gathers data from the patient 70; surgeon's interface 250 which comprises the apparatus for displaying information about the progress of the procedure to the surgeon and for allowing the surgeon to control the procedure; and control electronics 34 which couples the surgeon's interface 250 to the patient-side apparatus 252. The surgeon's interface 250 and control electronics 34 are preferably located within the surgeon's console 12.

The surgeon interface 250 provides the surgeon with information about the progress of the surgical procedure in various ways. First, visual information is provided on display 14 about the surgical worksite 86. The visual information of the surgical worksite 86 is obtained by the left and right cameras 88a and 88b located at the surgical worksite of patient 70. The visual information is processed by the video processor 302 of the control electronics 34. The video display 14 receives the visual information from the video processor 302 and displays it to the surgeon 18 so that the surgeon can observe the surgical worksite 86. In the embodiment shown, images from the left and right cameras 88a and 88b are displayed sequentially on video display 14. The polarizing shutter 26 is controlled by the video processor to synchronize with the sequential display of the images such that the image from the left camera is displayed only to the left eye of the surgeon and the image from the right camera is displayed only to the right eye of the surgeon.

The surgeon 18 can also be provided with audio information in the form of sounds or voice instructions through speakers 304. The sound or voice instructions can originate from a microphone 206 located at the surgical worksite. Alternatively, or in addition, the sound or voice instructions can originate from the control computer 310. For example, the control computer 310 can provide warning or timing "beeps" or synthesized voice through the speakers 304. Haptic and/or tactile information, including force feedback, may also be provided to the surgeon 18 through the master controllers 16 from the slave encoders 316 and sensors 318 and/or from the slave attachment encoders 316a and attachment sensors 318a.

The surgeon may control the surgical system 10 of this invention through the surgeon interface 250 in various ways. First, the surgeon 18 may manipulate the master controllers 16 to drive the movement of a surgical manipulator 76, 78 or 80 and/or the attachment manipulator 19 (see FIG. 3B). Second, the surgeon 18 may input voice commands through the microphone 326, which is coupled by the voice input system 328 to the control computer 310. Third, the surgeon 18 may also use the optional input devices 330 that are coupled to the control computer 310. The optional input devices 330 can include, for example, the foot operated switches 32 (see FIG. 1), buttons, switches, dials, joysticks, keyboards, mice, touch screens, and/or the like.

Continuing to refer to FIGS. 3A and 3B, the control computer 310 couples the surgeon interface 250 to the patient-side apparatus 252. The control computer 310 controls the movements of the surgical manipulators 76, 78 and 80 and the attachment manipulator 19 in response to input signals from the surgeon interface 250 thus allowing the surgeon 18 to perform the medical procedure. The control computer 310 also receives input signals from the left and right cameras 88a and 88b (via the video analyzer 314), the ECG system 90, the position/orientation device 120, and the slave encoders 316, slave attachment encoders 316a, sensors 318 and attachment sensors 318a (via the analog-to-digital converters 332). The video analyzer 314 may be a hardware element that is coupled to the control computer 310, or may form part of the control computer 310 as application software. The control computer 310 sends output control signals, via the servo-amplifier 334, to master motors 280 and slave motors 324 for controlling the movement of surgical manipulators 76, 78 or 80. The control computer 310 may also send output control signals, via the servo-amplifier 334, to master attachment motors 280a and slave attachment motors 324a for controlling movement of attachment manipulator 19. By generating the output signals in response to the input signals, the control computer 310 can control the attachment manipulators 19 and/or the surgical manipulators 76, 78 or 80 to track the moving surgical worksite 86.

The control computer 310 of the present invention may be any suitable computer that is capable of calculating the desired motions of the surgical manipulators 76, 78 and 80 and/or of the attachment manipulators 19 based on various inputs from the surgeon's console 12 and from the patient-side apparatus 252. After calculating the desired motions of the manipulators, the control computer 310 provides control signals to the slave motors 324, to the master motors 280, and/or to the slave attachment motors 324a and the master attachment motors 280a. Control computer 310 should be capable of receiving data from a large number of data input channels, performing calculations and transformations on that data and outputting commands to the servo amplifier 334 in real time. This task may typically require parallel execution. The control computer 310 may have a DSP architecture. A suitable control computer 310 may be purchased commercially under the tradename dSPACE from Digital Signal Processing and Control GmbH of Germany.

Figure 4A:
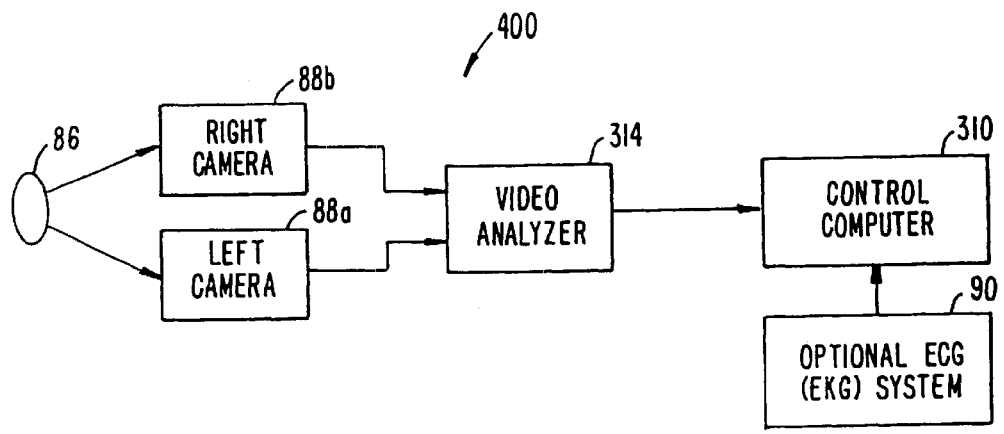
FIG. 4A shows a schematic diagram of one embodiment of a motion tracking system of the invention.
Figure 4B:
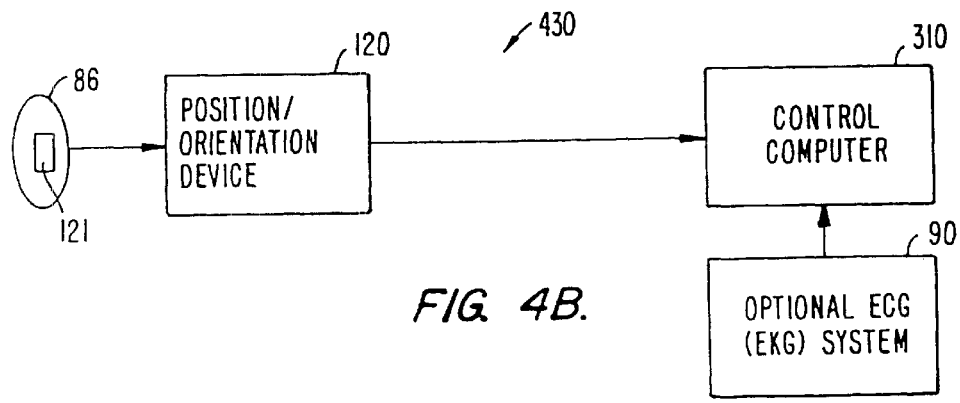
FIG. 4B shows a schematic diagram of another motion tracking system of the invention.
Figure 4C:
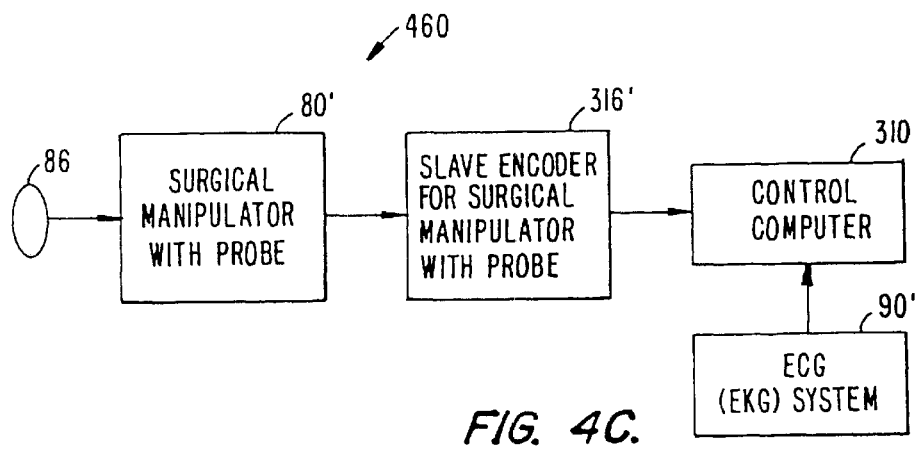
FIG. 4C shows a schematic diagram of yet another motion tracking system of the invention.

FIGS. 4A–4C are various embodiments of motion tracking systems which comprise various components of the patient-side apparatus 252 and the control electronics 34. The motion tracking systems track the movement of the surgical worksite 86 and may control the manipulators 76, 78 and 80 to move in unison with, or track, the surgical worksite 86. In FIG. 4A, the motion tracking system 400 includes the left and right cameras 88a and 88b for obtaining optical information of the surgical worksite 86. The left and right cameras 88a and 88b feed the visual information of the surgical worksite 86 into the video analyzer 314. The video analyzer 314 then feeds the visual information into the control computer 310. The control computer 310 processes the visual information from the video analyzer 314 for providing control currents to the slave motors 324 (see FIG. 3) and to the master motors 280 (see FIG. 3). The optional ECG system 90 can be coupled to the control computer 310 to augment the motion tracking of the surgical worksite 86.

The motion tracking system 400 in FIG. 4A can be used in the MIS procedure of FIG. 2A and the open surgical procedure of FIG. 2B. For a MIS procedure, the left and right cameras 88a and 88b of motion tracking system 400 can be attached to the one of the surgical manipulators 76, 78 or 80 (see FIG. 2A). For the open surgical procedure, the left and right cameras 88a and 88b of the motion tracking system 400 can be attached to the visual system 100 (FIGS. 2B and 2C). The motion tracking system 400 tracks the movement of the surgical worksite 86 during real time (i.e., during the surgical procedure).

The motion tracking system 430 of FIG. 4B includes the position/orientation device 120 coupled to the control computer 310. The position/orientation device 120 detects the movements of the targets 121 (see FIG. 2C) which are attached to the surgical worksite 86, and feeds signals based on the movements of the targets 121 into the control computer 310. For the embodiment of the invention illustrated in FIG. 27, the attachment assembly 21 including the attachment arm 25B functions as the position/orientation device 120 for feeding signals based on movements of the target 121 (e.g., the resultant surgical worksite 86a). The targets may be active or passive targets depending upon the motion tracking technology used. The control computer 310 then sends control currents to the slave motors 324 (see FIG. 3A) and optionally to the master motors 280 (see FIG. 3A) for manipulating the surgical manipulators 76, 78 or 80 (see FIG. 3A). For the embodiment of the invention illustrated in FIGS. 3B and 16–28, the control computer 310 sends control currents to the slave attachment motors 324a and optionally the master attachment motors 280a for manipulating the attachment manipulators 19.

The optional ECG system 90 can also be coupled to the control computer 310 to augment the motion tracking of the surgical worksite 86. In addition, the motion tracking system 430 may be used during the MIS procedure or during an open surgical procedure as shown in FIG. 2C for tracking the movement of the surgical worksite 86 and/or of the resultant surgical worksite 86a. The motion tracking system 430 tracks the motion of the surgical worksite 86 and/or of the resultant surgical worksite 86a during real time (i.e., during the surgical procedure). It is to be understood that the resultant surgical worksite 86a (see FIG. 27) may be tracked not only with one of the attachment assemblies 21 of the present invention, but instead, or in addition, with any other tracking devices and/or systems disclosed herein.

The motion tracking system 460 shown in FIG. 4C includes a surgical manipulator with probe (probed surgical manipulator) 80'. The slave encoder 316' attached to the probed surgical manipulator 80' records the position or motion of the surgical worksite 86 based on the ECG correlation method to be described below. The output of the ECG systems 90' and of the slave encoder 316' for the probed surgical manipulator 80' are processed by the control computer 310 so as to track the motion of the surgical worksite 86.

Figure 11:
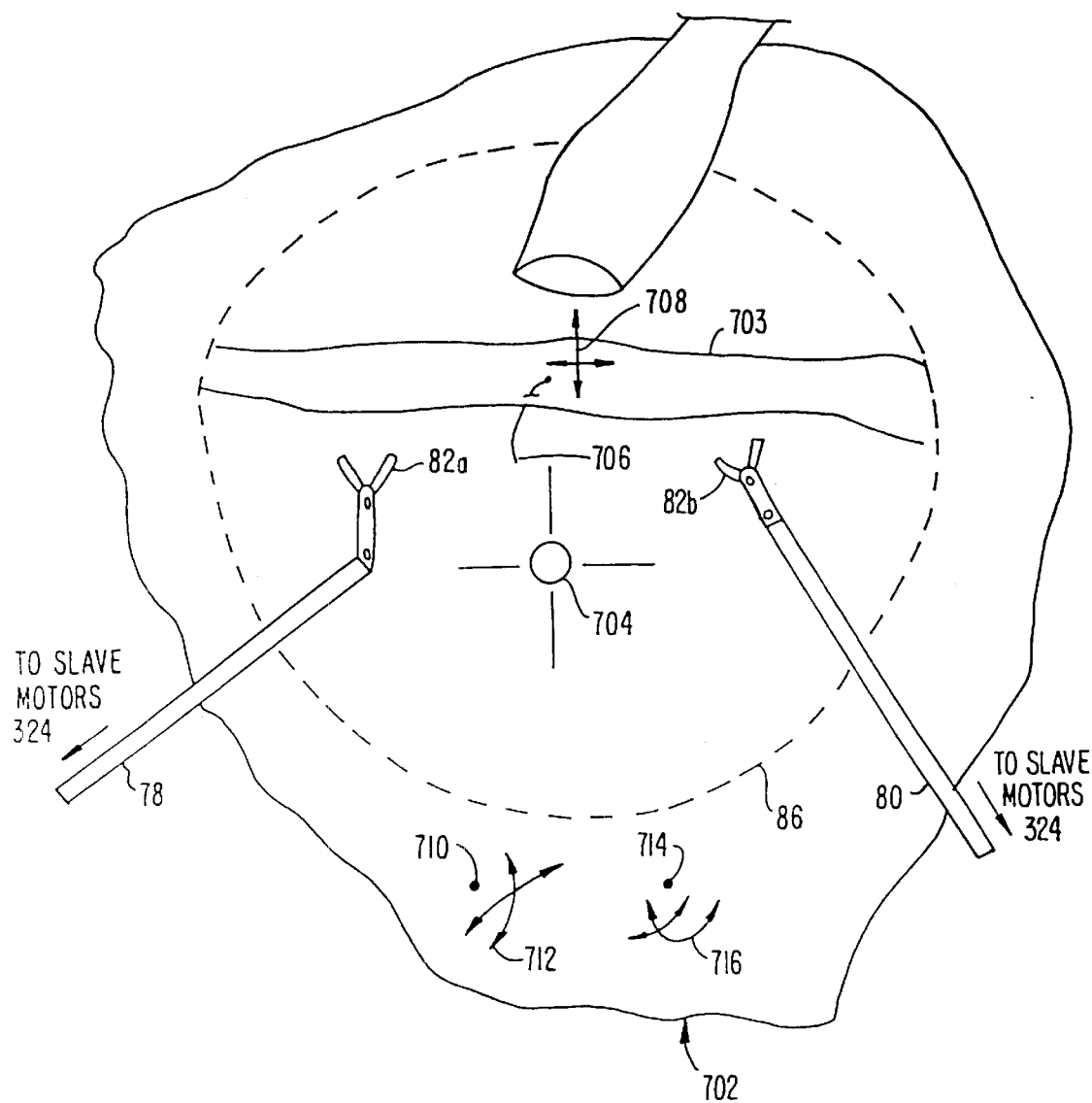
FIG. 11 shows a schematic view illustrating a surgical worksite on a heart, the surgical worksite moving in various directions.

As best shown in FIG. 11 which illustrates details of a heart area 702 prior to anastomosis, a cursor 704, which may be provided by the left and right cameras 88a and 88b (see FIG. 3A), is used as a guide for tracking a moving point 706 in surgical worksite 86. The point 706, moving in the direction of the arrows 708 or in any other free direction of movement, may be representative of the motion of the surgical worksite 86 if the surgical worksite 86 is sufficiently small in area. Since the heart is not a rigid body, the motion of the point 706 may, however, differ from a point 710, which moves in the direction of arrows 712, or a point 714 which moves in the direction of the arrows 716.

Information from images taken from the left and right cameras 88a and 88b (see FIGS. 3A and 3B) which are located at desired vantage points, is fed to the surgeon's console 12 (see FIGS. 3A and 3B) to provide precise position and orientation information to assist in using the surgical instruments 82 (see FIGS. 2A–2C) precisely on the desired portion of the patient's anatomy. It is desired that the three translations and three rotations of the surgical worksite, namely the six degrees of movement of the surgical site (i.e., position and orientation) in space, be measured in order to accurately describe its motion.

In some instances, the motion of a single point 706 in the surgical worksite 86, or in the resultant surgical worksite 86a (see FIG. 27), may not be sufficiently representative of the motion of the surgical worksite 86 or of the resultant surgical worksite 86a. Accordingly, it can be difficult to extract sufficient information from a single point to determine the motion of the surgical site within a sufficient degree of accuracy, where, for example, the surgical site has a relatively large angular motion away from a plane generally perpendicular to the viewing axis of each camera. Furthermore, it may be inconvenient to extract sufficient information about the motion of the surgical site from only a single point. Therefore, a plurality of points (not shown) on the surgical worksite 86 or on the resultant surgical worksite 86a that are in motion independently of each other may respectively be chosen or selected to determine the movement of the surgical worksite 86 or of the resultant surgical worksite 86a. The motion of the surgical worksite 86 or of the resultant surgical worksite 86a can be determined, for example, by processing all the motions of the chosen plurality of points on the surgical worksite 86 or on the resultant surgical worksite 86a. Other methods may be used to extrapolate the representative movement of the surgical worksite 86 or of the resultant surgical worksite 86a. For example, the "average motion" of the selected plurality of points may be computed by processing all the motions.

After the point 706, which is to represent the movement of the surgical worksite 86, or of the resultant surgical worksite 86a, has been determined, the motion of the point 706 is monitored for tracking purposes. Referring back to FIGS. 4A–4C, the motion tracking systems 400 and 430 of FIG. 4A and FIG. 4B, respectively, track the motion of the point 706 in real time (for example, during or shortly prior to suturing). If an MIS procedure is being performed, the motion tracking system 400 may use the stereoscopic endoscope medical camera 84 (see FIG. 2A) or another camera (not shown) to track the point 706. If an open-chest surgery is being performed, the motion tracking system 400 may use the visual system 100 (see FIG. 2B or 2C) to track the point 706.

In addition to, or as an alternative to, using the stereoscopic endoscope medical camera 84 (see FIG. 2A), the motion tracking system 400 or 430 may track the point 706 by correlating the position of the point 706 over a time period (for example, 10 seconds or 20 heartbeats) with an electrocardiogram (ECG) signal (see FIG. 5) from the optional ECG system 90 (see FIGS. 4A and 4B). Two methods can be used to correlate the position of the point 706 with the ECG trace 502. The first method can be performed in real time and involves recording the position of the point 706 visually with the left and right cameras 88a and 88b (see FIG. 4A) over a time period, and comparing the recorded positions of the point 706 with the ECG trace 502 (see FIG. 5). These correlated date are stored and can be updated every 10 seconds, for example. It will be appreciated that, instead, this can be accomplished in a "quasi-continuous" fashion, by adapting the correlation incrementally every computer cycle or at predetermined cycles which are spaced apart by a predetermined number of cycles, in accordance with conventional techniques, in similar fashion to LMS adaptive filtering, for example. These data allow the control computer to predict the particular position of the point 706 based on the ECG trace 502 (see FIG. 5).

An alternative method for correlating the position of the point 706 with the ECG trace 502 (see FIG. 5) involves determining the position of the point 706 by contacting the tip of the probed surgical manipulator 80' with the point 706.

The position of the probed surgical manipulator with probe 80' then moves in sympathy with point 706 and its motion is recorded over time by the encoder 316' (see FIG. 4C). The position over time of the tip of the probed surgical manipulator 80' is then. correlated with the ECG trace 502 (see FIG. 5). The method above can be performed. in non-real time (for example, prior to suturing). Other alternative and more intrusive methods may be used to correlate the position of point 706 with the ECG trace 502. For example, various probes or other instruments may be used prior to, or during, the surgical procedure to track the motion of the point 706 so as to correlate it with the ECG trace 502. The motion tracking systems 460 (see FIG. 4C) uses the ECG correlation method above as the primary method for tracking the surgical worksite 86.

The system of this invention is shown for purposes of illustration only and is not intended to be limiting. It is intended that the disclosed invention could be used with any master-slave manipulator system. Preferably, the system of this invention would be light and stiff with high bandwidth, low backlash and good force feedback. Additionally, the surgical manipulators 76, 78 and 80 and attachment manipulator 19 should preferably have a minimum of six degrees of freedom of movement in addition to end effector actuation and the attachment member 25 actuation in order to provide the surgeon 18 with sufficient dexterity, such as for suturing in the case of the surgical manipulators 76, 78 and 80, or for tracking and or immobilizing in the case of the attachment manipulator 19.

Figure 5:
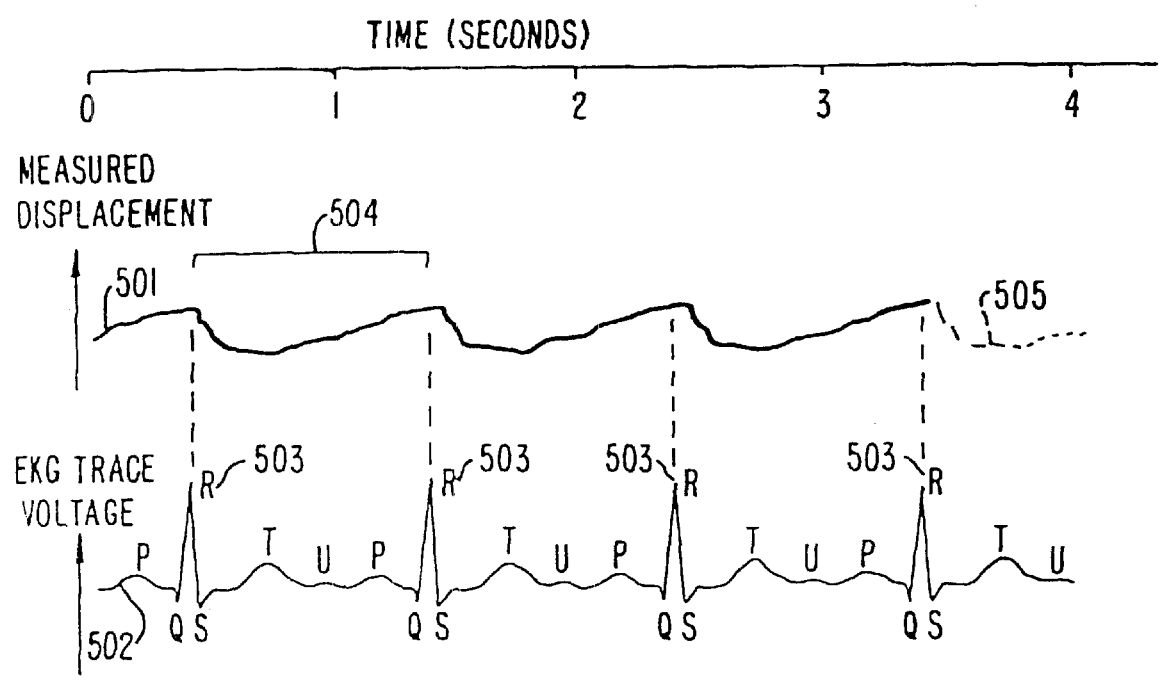
FIG. 5 shows an exemplary ECG graph produced by an ECG system by sampling a beating heart or surgical anatomical worksite during a surgical procedure performed by the surgical system of the invention.

FIG. 5 illustrates the manner in which the ECG system can be used to augment the motion tracking system of the present invention. ECG trace 502 is the standard output of an ECG system. The ECG trace can be compared over time to the measured displacement of the worksite. Trace 501 illustrates a typical displacement cycle in one dimension for a portion of the cardiac surface. The amplitude of the displacement has been measured as 1–2 cm. Although the displacement cycle is not necessarily completely repeatable, correlation between the ECG trace 502 and the displacement motion trace 501 can be derived by the computer control system. This correlation can be used to predict cardiac worksite motion. For example, the R wave 503 typically precedes by a few microseconds a phase of rapid displacement of the cardiac worksite indicated as 504. Thus, the computer control system can, by detecting R wave 503, anticipate the future contraction of the cardiac muscle and consequent displacement. For example, after detecting an R wave the computer control system could predict the displacement indicated by dashed line 505. This predicted motion of the cardiac worksite could be used to enhance the accuracy of the detected motion of the cardiac worksite, or to substitute for detected position when the motion tracking system is intermittently unable to track the surgical worksite, or to compensate for system lag, and/or the like.

Figure 6:
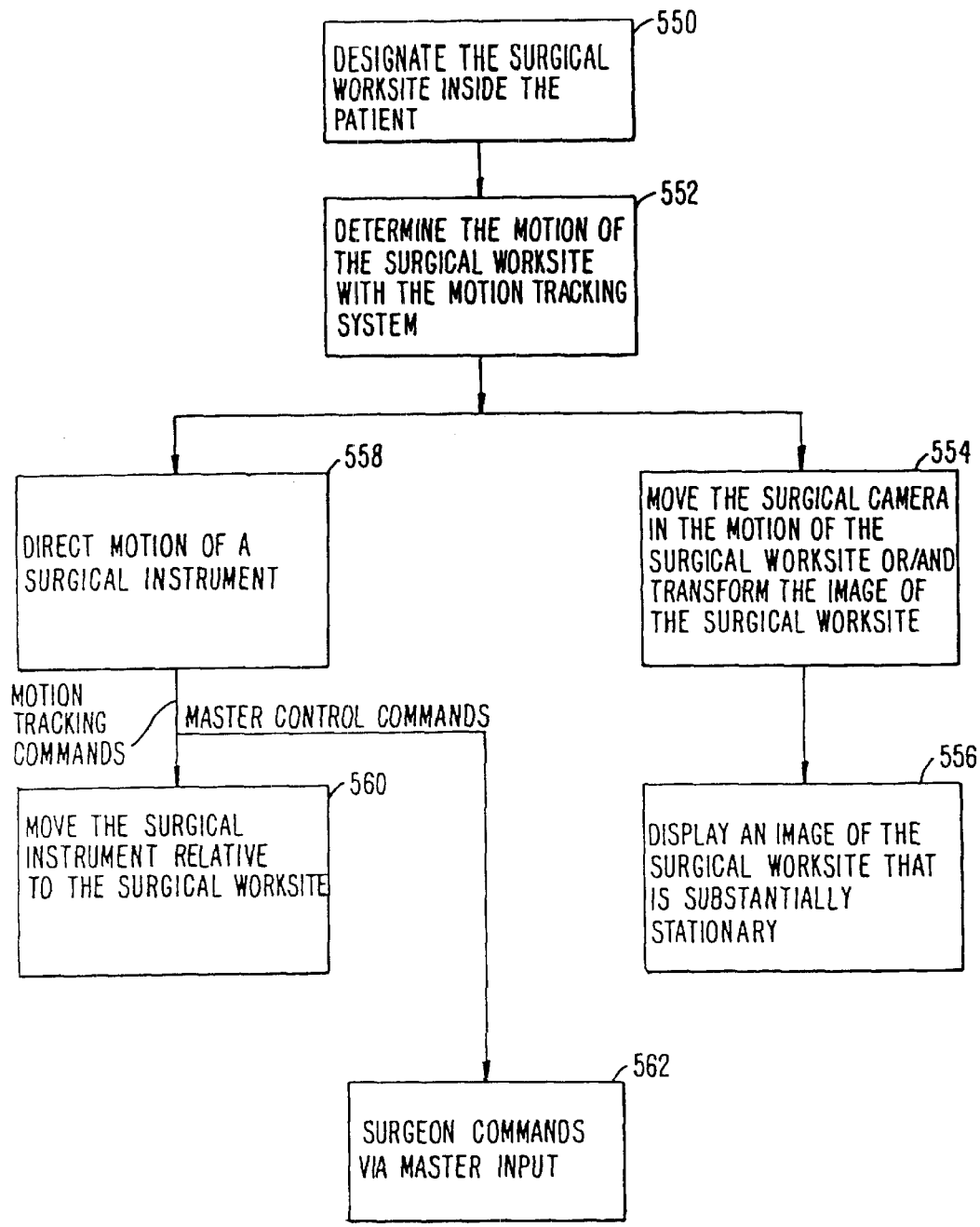
FIG. 6 shows a flowchart describing a method of the invention.

FIG. 6 is a block diagram illustrating steps of a method as described above. Block 550 represents the step of designating the surgical worksite 86 inside the patient 70 (see FIGS. 3A and 3B). The surgical worksite 86 is typically in the form of a small area on the surface of an anatomical structure on which a surgical procedure is to be performed. For CABG procedures the surgical worksite 86 will typically comprise a portion of a coronary artery.

The surgical worksite 86 may be designated in any suitable manner, such as by manipulating a graphical object (not shown), such as a cursor, on the video display system 14 at the surgeon's console 12 (see FIG. 1), until the graphical object is coincident with the surgical worksite 86 (see FIGS. 3A and 3B) which has been designated for surgery. The cursor may be in the form of a 3-D stereoscopic object superimposed on the image of the surgical worksite 86 (see FIGS. 3A and 3B). Any appropriate input methods (such as voice commands, use of foot pedals, a mouse or joystick) can be used to specify the desired motion of the graphical object within the stereoscopic volume of the image of the surgical worksite 86 (see FIGS. 3A and 3B). Alternatively, a tip of a surgical tool (for example, the tip of the probed surgical manipulator 80' in FIG. 4C) may be used to designate the surgical worksite 86 (see FIGS. 3A and 3B). When the tip of the probed surgical manipulator 80' (see FIG. 4C) has designated the surgical worksite 86, the system is informed of the designation, for example, by a voice command, or by pressing a button, or other mechanical action in the surgeon's console 12, or the like (see FIG. 1).

In an alternative method, the target worksite may be designated by surrounding the worksite with a plurality of spaced apart markers placed on the heart. In such a case, the system may be commanded to automatically stabilize a point corresponding to a computed centroid of an area, which contains the surgical site, and which extends between the markers. Thus, the surgical worksite 86 would be designated by the surgeon when the markers were placed on the heart.

After the surgical worksite 86 (see FIGS. 3A and 3B) has been designated, the motion or movement of the surgical worksite 86 or of the resultant surgical worksite 86a is determined as represented by block 552 in FIG. 6. This is preferably achieved by using the motion tracking system 400, 430 or 460 (see FIGS. 4A, 4B or 4C, respectively). As was previously mentioned, the attachment assemblies 21 may be used to assist in determining the motion or movement of the surgical worksite 86 (see FIG. 25) or of the resultant surgical worksite 86a (see FIG. 27). Following the step of determining the motion or movement of the surgical worksite 86 (see FIGS. 3A and 3B), or of the resultant surgical worksite 86a, a stationary or substantially stationary image of the surgical worksite 86 or of the resultant surgical worksite 86a is obtained and displayed on the video display system 14 (see FIG. 1) in accordance with a step represented by block 556. A number of different methods, as indicated at 554, can be employed to generate such a stationary or still image. In accordance with one method, the left and right cameras 88a and 88b (see FIGS. 3A and 3B), or the stereoscopic endoscope medical camera 84, can be moved so as to maintain a substantially fixed relationship in position and/or orientation with respect to the surgical worksite 86 (see FIGS. 3A and 3B) or as the resultant surgical worksite 86a, by manipulating the surgical manipulator 76 (see FIG. 2A) to which the left and right cameras 88a and 88b are attached or to which the stereoscopic endoscope medical camera 84 is attached. In such a case, the video cameras, such as the cameras of a stereo endoscope, are maintained substantially stationary relative to the surgical worksite 86, or the resultant surgical worksite 86a (see FIGS. 3A and 3B), and thus the image of the surgical worksite 86, or the resultant surgical worksite 86a, provided by the video cameras is substantially stationary and can be displayed directly on the video display system 14 (see FIG. 1).

In accordance with another method, the endoscope camera 84, or left and right cameras 88a and 88b (see FIGS. 3A and 3B), are not maintained substantially stationary relative to the surgical worksite 86, or the resultant surgical worksite 86a (see FIGS. 3A and 3B). Instead, the moving image of the surgical worksite 86, or of the resultant surgical worksite 86a (see FIGS. 3A and 3B), relative to the cameras 88a and 88b is manipulated or processed by the video processor 302

(see FIGS. 3A and 3B) and transformed into a stationary or generally still image. This can be accomplished by using video or image processing techniques as described in greater detail herein below.

In accordance with yet another method, a combination of the above techniques may be used to stabilize or still the display image of the surgical worksite 86 or of the resultant surgical worksite 86a. In such a case, for example, the left and right cameras 88a and 88b, or the stereoscopic endoscope medical camera 84, are moved to track part of the motion of the surgical worksite 86, or of the resultant surgical worksite 86a, and image processing is used to still a remaining part of the motion of the surgical worksite 86, or of the resultant surgical worksite 86a.

Block 556 represents the step of displaying to the surgeon 18 (see FIGS. 1 and 3A) the stationary or substantially stationary image of the surgical worksite 86, or of the resultant surgical worksite 86a. The image of the surgical worksite 86, or of the resultant surgical worksite 86a, may be the real image 20R (see FIG. 1) provided directly by the video display system 14 (see FIG. 1), or the virtual image 20V (see FIG. 1) reflected in the mirror 22 (see FIG. 1). The image of the surgical worksite 86, or of the resultant surgical worksite 86a, is preferably a stereoscopic image. At substantially the same time as step 556, the motion of one or more of the surgical instruments 82 (see FIGS. 2A–2C) attached to the surgical manipulators 76, 78 or 80 (see FIG. 2A) may be regulated, as represented by the step in block 558, to track motion of the surgical worksite 86 (see FIGS. 2A–2C), or the resultant surgical worksite 86a, so as to maintain a generally fixed relationship between the two. The surgeon commands 562 input at the master controls are then superimposed onto the computed motion commands from 558 to form a total surgical instrument motion at step 560. Therefore, in the absence of surgeon commands 562, the surgical instruments 82 will be rendered stationary or substantially stationary relative to the surgical worksite 86, or the resultant surgical worksite 86a. To the surgeon viewing the real image 20R or the virtual image 20V (see FIG. 1), it will appear as if the surgical worksite 86, or the resultant surgical worksite 86a (see FIGS. 2A–2C), is substantially stationary even though the surgical worksite 86, or the resultant surgical worksite 86a, and the surgical instruments 82, are moving.

Typically, the surgeon 18 (see FIG. 1) moves the surgical instruments 82 (see FIGS. 2A–2C) so as to perform surgical procedures by using the master controllers 16 (see FIG. 1) located at the surgeon's console 12 (see FIG. 1). The motion of the master controllers 16 (see FIG. 1) relative to a fixed reference point on the surgeon's console 12 (see FIG. 1) is used to control motion of the surgical manipulators 76, 78 and 80 (see FIGS. 2A–2C) and the surgical instruments 82 (see FIGS. 2A–2C) relative to the motion of the surgical worksite 86 (see FIGS. 2A–2C), or of the resultant surgical worksite 86a. This is typically accomplished by superimposing the surgeon commands 562 onto the computed motion commands at 558 to form a combined surgical instrument motion command at 560. To the surgeon viewing the real image 20R (see FIG. 1), or the virtual image 20V (see FIG. 1), it will appear generally as if the surgical instruments 82 are responding solely to the surgeon commands 562 and both the surgical worksite 86, or the resultant surgical worksite 86a (see FIGS. 2A–2C), are substantially stationary, even though the surgical worksite 86, or the resultant surgical worksite 86a, and the surgical instruments 82, are moving.

As shown in FIGS. 3A and 3B, the video analyzer 314 receives visual information from the left and right cameras 88a and 88b, or from the stereoscopic endoscope medical camera 84. The visual information is then input by the video analyzer 314 into the control computer 310. The control computer 310 then typically transforms the visual information into a vector $\theta H$, which corresponds to a vector of motion (translation and rotation) of the surgical worksite 86, or of the resultant surgical worksite 86a. It will be appreciated that this corresponds to "joint space", and that corresponding values relative to a coordinate reference frame can be determined and used instead. In such a case, use can typically be made of Cartesian reference coordinates and/or associated transforms, or the like, as is described in greater detail herein below. It will be appreciated further that the equations described below for joint space may work only approximately to track motions that are small relative to the joint range of motion and/or have a relatively small rotational component. The slave encoders 316 and sensors 318 also input motion information of the surgical manipulator 76, 78 or 80 into the control computer 310 via the analog-to-digital converters 332. The control computer 310 can then transform the motion information from the slave encoders 316 and the sensors 318 into a position and orientation vector $\theta Sact$, which corresponds to the "actual" joint position of the slave. The master encoders 282 and the sensors 284 also input motion information of the master controllers 16 into the control computer 310 via the analog-to-digital converters 332. The control computer 310 then transforms the motion information from the master encoders 282 and the sensors 284 into a vector $\theta Mact$ which corresponds to the "actual" joint position of the master.

The desired position of the surgical manipulator 76, 78 or 80 is given by the equation: $\theta Sdes = \theta Mact + \theta H$, where $\theta Sdes$ corresponds to the "desired" joint position for the slave. Thus, the control computer 310 calculates a joint position "error signal" for the slave, indicated by $\theta Serr$ as follows: $\theta Serr = \theta Sact - \theta Sdes = \theta Sact - \theta Mact - \theta H$. Based on the foregoing error signal, the control computer 310 generates a control current through servo amplifier 334 to the slave motors 324, thereby driving the surgical manipulator 76, 78 or 80 toward the desired position. In the force feedback master-slave system of FIGS. 3A and 3B, the desired position of the master controllers 16 is given by the equation: $\theta Mdes = \theta Sact - \theta H$, where $\theta Mdes$ corresponds to the "desired" joint position for the master. Thus, the control computer 310 also calculates a second error signal, indicated by $\theta Merr$, as follows: $\theta Merr = \theta Mact - \theta Mdes = \theta Mact - \theta Sact + \theta H$. Based on the second error signal, the control computer 310 generates a control current through the servo amplifier 334 to the master motors 280 in order to provide the required force feedback. It will be appreciated that these equations can be extended to other forms or representations (other than joint space). Cartesian reference control equations, for example, are possible and are described in greater detail below. It will be appreciated further that the method of providing force feedback may be replaced, or augmented, by other methods, for example, by using force sensors, or the like.

In FIGS. 3B and FIGS. 16–28, the surgical worksite 86 may be generally immobilized with the attachment assembly 21 as illustrated in FIG. 23, or with a pair of attachment assemblies 21—21 as illustrated in FIG. 24. If the surgical worksite 86 is generally immobilized, essentially all of the degrees of freedom of movement are removed from the surgical worksite 86 and no tracking may be necessary, since the surgical worksite 86 would appear essentially stationary to the surgeon 18, as viewed by the cameras 88a and 88b, or by endoscope 84, and displayed on the video display system 14. Thus, the master controllers 16 may now be moved by the surgeon 18 to effect movement of the surgical manipulators 76, 78 or 80 including the surgical instruments 82 to perform a surgical procedure without causing the surgical instruments 82 to track the surgical worksite 86, since the surgical worksite 86 is generally stationary since its motion has been generally immobilized.

Motion of the attachment control assembly 17 of the master controllers 16 (see FIG. 1) relative to a fixed reference point on the surgeon's console 12 (see FIG. 1) typically can be used to control motion of the attachment manipulators 19, including the attachment assemblies 21, relative to the motion of the surgical worksite 86 (see FIGS. 2A–2C), or of the resultant surgical worksite 86$a$. It is further possible that attachment manipulators 19 may not require attachment masters for control. For example, they may be controlled by an assistant on the patient's side, or they may obtain their command signal from force sensors used to maintain a particular force against the beating heart.

As previously indicated, the video analyzer 314 receives visual information from the left and right cameras 88$a$ and 88$b$, or from the stereoscopic endoscope medical camera 84. The visual information is input by the video analyzer 314 into the control computer 310. The control computer 310 then transforms the visual information into a vector $\theta H$, which corresponds to a vector of motion (translation and rotation) of the surgical worksite 86, or of the resultant surgical worksite 86$a$. The slave attachment encoders 316$a$ and attachment sensors 318$a$ also input motion information of the attachment manipulators 19 into the control computer 310 via the analog-to-digital converters 332. The control computer 310 then transforms the motion information from the slave attachment encoders 316$a$ and the attachment sensors 318$a$ into a position and orientation attachment vector $\theta ASact$, which corresponds to "actual" joint position for the attachment slave. The master attachment encoders 282$a$ and the attachment sensors 284$a$ also input motion information of the attachment control assembly 17 of the master controllers 16 into the control computer 310 via the analog-to-digital converters 332. The control computer 310 then transforms the motion information from the master attachment encoders 282$a$ and the attachment sensors 284$a$ into a vector $\theta AMact$, which corresponds to "actual" joint position for the attachment master.

The desired position of the attachment manipulators 19 is given by the equation: $\theta ASdes = \theta AMact + \theta H$, where $\theta ASdes$ corresponds to "desired" joint position for the attachment slave. Thus, the control computer 310 calculates a joint position "error signal" for the attachment slave, indicated by $\theta ASerr$ as follows: $\theta ASerr = \theta ASact - \theta ASdes = \theta ASact - \theta AMact - \theta H$. Based on the foregoing error signal, the control computer 310 generates a control current through servo amplifier 334 to the slave attachment motors 324$a$, thereby driving the attachment manipulators 19 toward the desired position. In the force attachment feedback master-slave system of FIG. 3B, the desired position of the attachment control assembly 17 of the master controllers 16 is given by the equation: $\theta AMdes = \theta ASact - \theta H$, where $\theta AMdes$ corresponds to "desired" joint position for the attachment master. Thus, the control computer 310 also calculates a second joint "error signal" for the attachment master, indicated by $\theta AMerr$ as follows: $\theta AMerr = \theta AMact - \theta AMdes = \theta AMact - \theta ASact + \theta H$. Based on the second error signal, the control computer 310 generates a control current through the servo amplifier 334 to the master attachment motors 280$a$ in order to provide the required force attachment feedback. It will be appreciated that these equations can be extended to other forms or representations (other than joint space). It will be appreciated further that the method of providing force feedback may be replaced, or augmented, by other methods, for example, by using force sensors, or the like.

Figure 8:
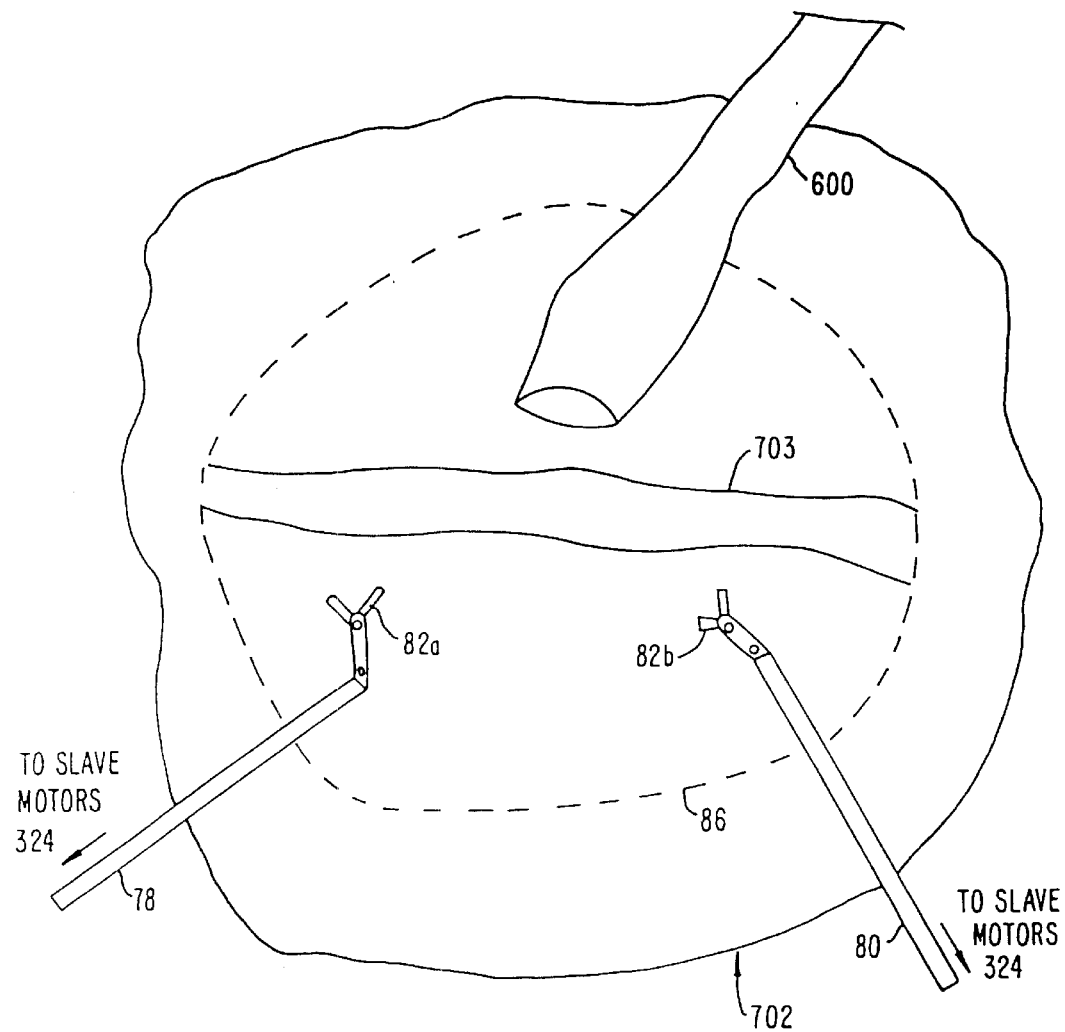
FIG. 8 shows a schematic view of an image of a surgical worksite taken by a medical camera.

Referring now to FIG. 8, a heart area 702 is shown as including the surgical worksite 86 as viewed from one of the left and right cameras 88$a$ and 88$b$ of the stereoscopic endoscope medical camera 84 (see FIG. 2A), or of the viewing system 100 (see FIGS. 2B and 2C). The left and right cameras 88$a$ and 88$b$ detect the three-dimensional (3-D) features and motion of the heart area 702 based on the natural features of the heart, such as the coronary artery 703 or other distinctive features on the surface of the heart. Techniques for extracting information about surface shape and movement from stereo video images are described in greater detail herein below.

Figure 9:
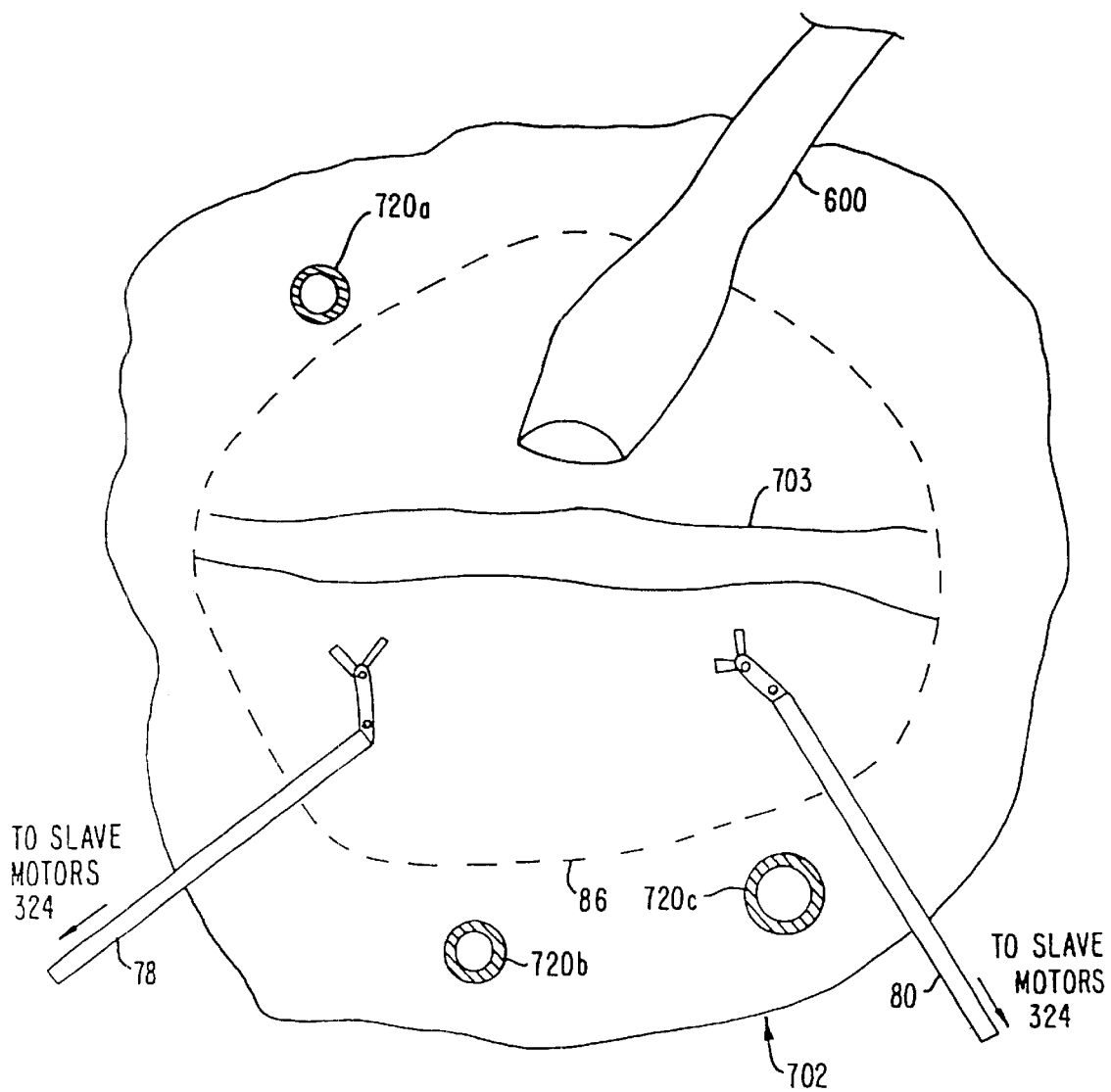
FIG. 9 shows a schematic view of a surgical worksite surrounded by passive artificial visual targets used to determine 3-D motion information of the surgical worksite.

In addition to, or as an alternative to, relying on the natural features of the heart to detect 3-D motion information, passive elements (artificial visual targets) 720$a$, 720$b$ and 720$c$ may be attached to the heart area 702 to surround the surgical worksite 86, as shown in FIG. 9. The passive elements 720$a$, 720$b$ and 720$c$ may also be used to detect 3-D motion of the resultant surgical worksite 86$a$. The passive elements 720$a$, 720$b$, and 720$c$ can include, but are not limited to, one or more passive devices having a distinctive appearance, such as a blue or patterned marker, e.g. a spherical or circular marker, or the like, or an IR reflector, or the like.

Figure 10:
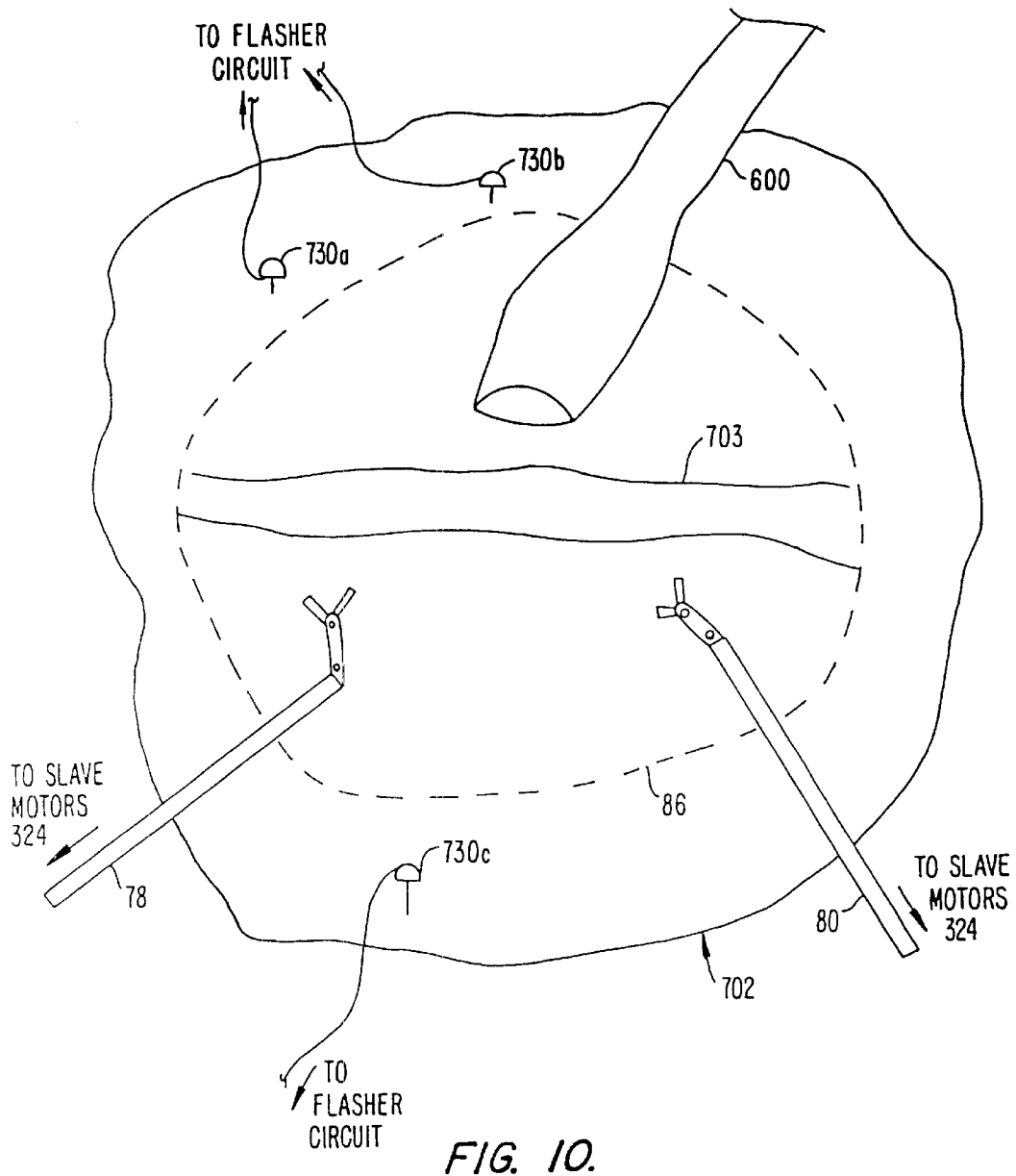
FIG. 10 shows a schematic view illustrating a surgical worksite surrounded by active artificial visual targets used to determine 3-D motion information of the surgical anatomical worksite.

In FIG. 10, another alternative to detect 3-D motion information is shown. Active elements 730$a$–730$c$, such as light emitting diodes (LEDs) coupled to a flasher circuit (not shown), are attached to the heart area 702. The active elements 730$a$–730$c$ can instead be infrared emitting diodes (IREDS) which are detectable by an infrared detector (not shown), or the like. The passive elements 720$a$–$c$ and the active elements 730$a$–730$c$ discussed above could augment extraction of 3-D motion information of the surgical worksite 86, or of the resultant surgical worksite 86$a$.

As previously mentioned, FIG. 11 is a view of the heart area 702 with the surgical worksite 86 moving in various directions. To obtain a substantially stationary image of the surgical worksite 86 in the video display system 14 (see FIG. 1), the stereoscopic endoscope medical camera 84 (see FIG. 2A), or the viewing system 100 (see FIGS. 2B and 2C), can be moved in sympathy with motion of the surgical worksite 86. Thus, the relative position of the stereoscopic endoscope medical camera 84 (see FIG. 2A), or the viewing system 100 (see FIGS. 2B and 2C), to the surgical worksite 86 can be caused to remain generally the same.

Figure 12:
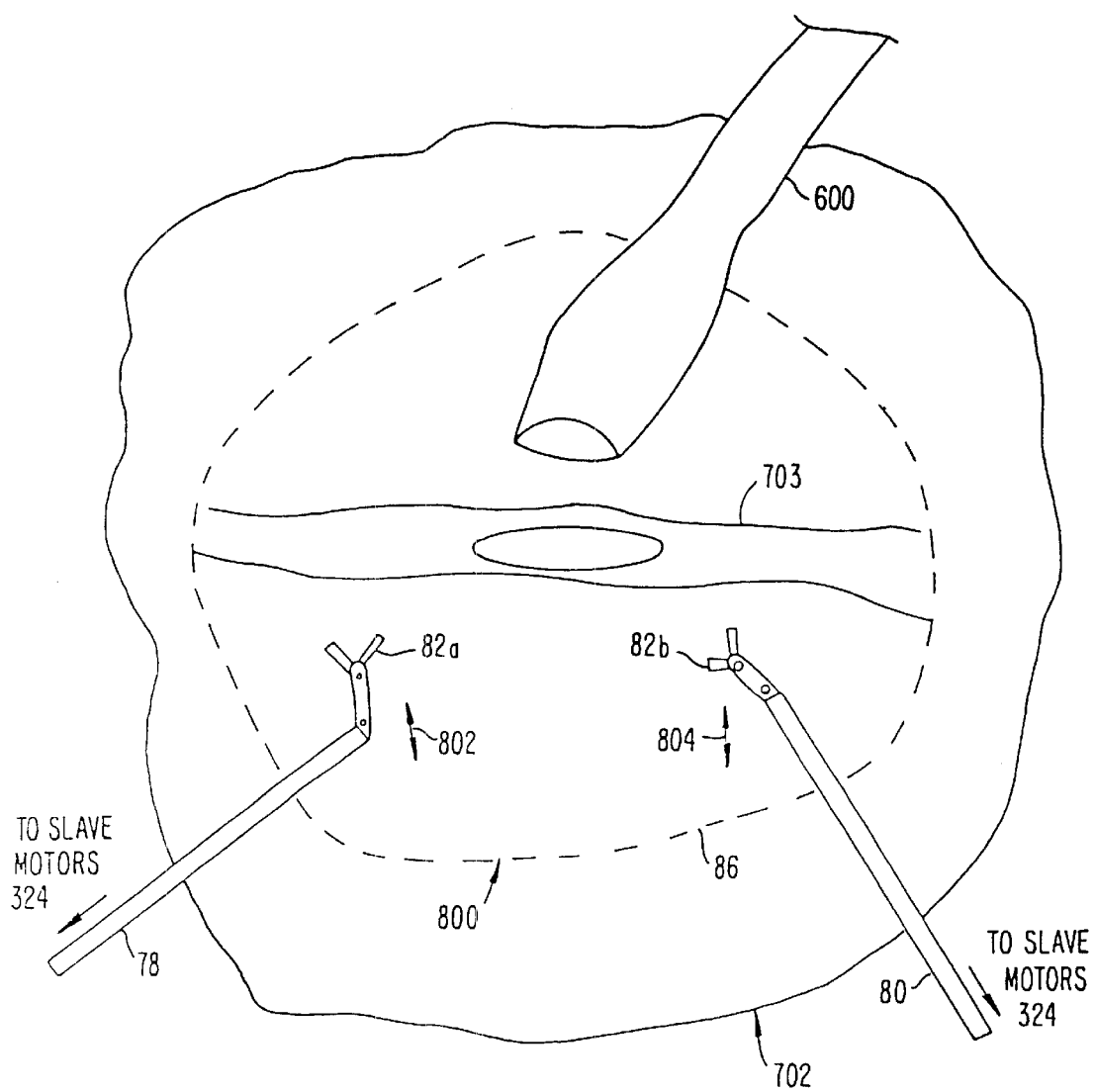
FIG. 12 shows a schematic view of a stationary image from a video of a surgical worksite, prior to stabilizing surgical tools.

FIG. 12 shows a view from one of the left or the right cameras 88$a$ and 88$b$ (see FIG. 3A) after the motion of the surgical worksite 86 has been tracked by the motion tracking system 400, 430 or 460 (see FIGS. 4A, 4B or 4C, respectively) and processed by the control computer 310 (see steps 554 and 556 of FIG. 6) but without generating motion compensation commands fed to the control computer 310, that is, omitting steps 558 and 560. The control computer 310 (see FIG. 3A) sends control signals or commands to the slave motors 324 (see FIG. 3A) and the master motors 280 (see FIG. 3A) for controlling the movement of the surgical manipulators 76, 78 and 80 (see FIG. 3A) but these commands are typically independent of the motion of the surgical worksite 86 (except for commands for the left and right cameras 88$a$ and 88$b$ in some cases). In FIG. 12, a stationary or substantially stationary image 800 of the surgical worksite 86 is seen by the surgeon in the video display system 14 (see FIG. 1). Note that in FIG. 12, although the image of surgical worksite 86 has been stabilized, surgical worksite 86 is still moving relative to surgical instruments 82a and 82b. This relative motion of surgical instruments 82a and 82b compared to surgical worksite 86 is illustrated in FIG. 12 by arrows 802 and 804, respectively. For the embodiment of the invention shown in FIG. 27, although the image of the resultant surgical worksite 86a would be stabilized, the resultant surgical worksite 86a would still be moving relative to the surgical instruments 82.

The left and right cameras 88a and 88b (see FIG. 3A) may be in a fixed vision system or have fewer than 6 degrees of freedom, particularly if the open-chest procedure shown in FIGS. 2B or 2C is being performed. It will be appreciated that to obtain a substantially stationary or still image 800 of the surgical worksite 86 or of the resultant surgical worksite 86a, video or image processing techniques and systems can be used by the video processor 302 (see FIG. 3A) to transform the moving image of the surgical worksite 86 or of the resultant surgical worksite 86a into a generally still image, as described in greater detail herein below. For example, video processing techniques and systems can be used to correct for zoom, lateral translation and rotation of the surgical worksite 86, or of the resultant surgical worksite 86a, so that the surgeon is able to observe a stationary or substantially stationary image 800 of the surgical worksite 86, or of the resultant surgical worksite 86a. An advantage of using video processing techniques is that the left and right cameras 88a and 88b in the vision system 100 (see FIGS. 2B and 2C) need then not be moved. If the medical cameras do not have a remote center positioner as described in U.S. Pat. No. 5,817,084, fully incorporated herein by reference as if repeated verbatim immediately hereinafter, then video processing equipment may be coupled to the left and right cameras 88a and 88b (see FIG. 3A) to correct for zoom, lateral translation and rotation of the image of the surgical worksite 86, or of the resultant surgical worksite 86a, to obtain a substantially stationary image 800. A disadvantage of using such processing techniques is the potential for creating artifacts in the image of the surgical worksite 86 or of the resultant surgical worksite 86a. However, such artifacts can be corrected for, as described in greater detail herein below.

After the motion of the surgical worksite 86, or of the resultant surgical worksite 86a has been determined by the motion tracking system 400, 430 or 460 (see FIGS. 4A, 4B or 4C, respectively), a stationary or substantially stationary image 800 of the surgical worksite 86, or of the resultant surgical worksite 86a, will be produced, as shown in FIG. 12. Ideally, the stationary image 800 of surgical worksite 86, or of the resultant surgical worksite 86a, will have little or no apparent motion that is noticeable to the surgeon.

Figure 13:
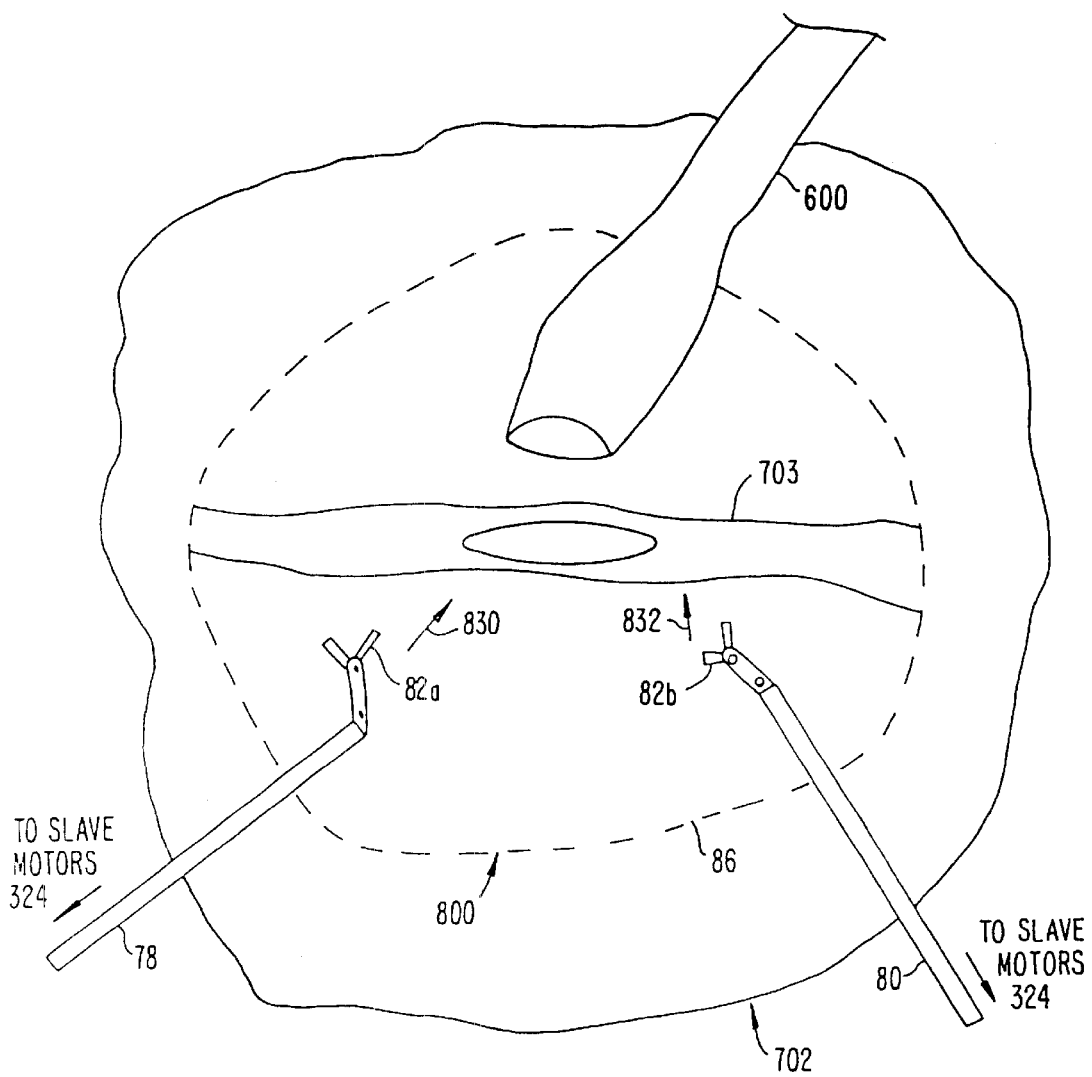
FIG. 13 shows a schematic view of a stationary image from a video of a surgical worksite and surgical tools, prior to suturing.

FIG. 13 shows a view from one of the left and right cameras 88a and 88b (see FIG. 3A) after the six degrees of freedom movement data of the surgical worksite 86 is fed to the control computer 310 (see FIG. 3A) so that surgical manipulators 78 and 80 are tracking the surgical worksite 86 (refer to steps 558 and 560 in FIG. 6). Since the surgical manipulators 78 and 80 remain substantially stationary relative to the surgical worksite 86, the surgeon is able to observe an image wherein the surgical manipulators 78 and 80 (with the surgical instruments 82a and 82b) and the surgical worksite 86 are stationary or substantially stationary. The surgeon can then observe movement that he/she provides to the surgical instruments 82a and 82b (refer to step 562 in FIG. 6) in the directions of the arrows 830 and 832, respectively, while continuing to view the surgical worksite 86 as a stationary image 800. In this manner, cardiac surgery can be performed without cardioplegia. The foregoing would also be true for the embodiment of the invention producing the resultant surgical worksite 86a (see FIG. 27).

As previously mentioned, the surgical worksite 86 (see FIGS. 2A–2C and 3A) may be designated by a number of methods. The surgical worksite 86 (see FIGS. 2A–2C and 3A) may be designated by manipulating a 3-D stereoscopic graphical object (not shown), such as a cursor, on the stereoscopic display 14 (see FIG. 1) in the surgeon's console 12 (see FIG. 1), until the graphical object is coincident with the surgical worksite 86 which has been designated for surgery.

Any appropriate input method (such as voice commands, or use of a mouse, or the like) can be used to specify the desired motion of the graphical object within the stereoscopic volume of the image. Alternatively, and as indicated above, a tip of the probed surgical manipulator 80' (see FIG. 4C) may be used to designate the surgical worksite 86 (see FIGS. 2A–2C and 3A). When the tip of the probed surgical manipulator 80' (see FIG. 4C) has designated the surgical worksite 86 (see FIGS. 2A–2C and 3A), the surgical system of the present invention is informed of the designation by voice command or by pressing the foot switches 32 (see FIG. 1) or other mechanical action at the surgeon's console 12 (see FIG. 1).

After the surgical worksite 86 has been designated, the motion or movement of the surgical worksite 86 is determined, preferably by using the motion tracking system 400, 430 or 460 (see FIGS. 4A, 4B or 4C, respectively). First, the 3-D features and motion of the surgical worksite 86 are identified by viewing the natural features of the heart 602 (see FIG. 7), such as the coronary artery 703 (see FIG. 7) or other distinctive features on a surface of the heart 602, preferably with the stereoscopic endoscope medical camera 84 (see FIG. 2A). In addition to, or as an alternative to, relying on natural features of the heart to detect 3-D motion information, the passive devices or artificial visual targets 720a–720c may be attached to the area surrounding the surgical worksite 86, as shown in FIG. 9. These targets can include, but are not limited to, one or more passive devices having a distinctive appearance, such as a blue or patterned dot or distinctive reflective characteristics such as IR reflectors. The active devices 730a–730c (see FIG. 10), such as light emitting diodes (LEDs) coupled to a flasher circuit (not shown), may also be attached to the heart area 702 (see FIG. 10) to extract 3-D information. The active elements 730a–730c may also be infrared emitting diodes (IREDS) which are detectable by an infrared detector (not shown).

For the embodiment of the invention illustrated in FIGS. 3B and 16–28, after the worksite 86 has been designated, the attachment assemblies 21 may be used generally to immobilize the surgical worksite 86 (see FIGS. 23 and 24) such that no tracking is necessary since the surgical worksite 86 would then be generally stationary. The attachment assemblies 21 may instead be used to remove at least one degree of movement freedom from the surgical worksite 86, leaving the resultant surgical worksite 86a in motion with at least one residual degree of movement.

Thereafter, and as was previously mentioned above, the motion of the surgical worksite 86, or of the resultant surgical worksite 86a (see FIGS. 2A–2C and 3A and 3B), can be tracked using the motion tracking system 400, 430 or 460 (see FIGS. 4A, 4B or 4C, respectively) The motion tracking system 400, 430 or 460 (see FIGS. 4A, 4B or 4C respectively) functions as a means for tracking the motion of the surgical worksite 86, or of the resultant surgical worksite 86*a* (see FIGS. 2A–2C and 3A and 3B), in real time and/or for gathering movement information over a period of time (from 1 second to about 10 seconds) on a moving anatomical part, such as the surgical worksite 86, or of the resultant surgical worksite 86*a* (see FIGS. 2A–2C and 3A and 3B). As was previously mentioned, the attachment assembly 21 of FIGS. 16 and 25 may be used for assisting in tracking the surgical worksite 86 (see FIG. 25) or for tracking the resultant surgical worksite 86*a*.

The point 706 (see FIG. 11), moving in the direction of the arrows 708 (see FIG. 11) or in any other free direction of movement, may be representative of the motion of the surgical worksite 86 (see FIG. 11) if the surgical worksite 86 is sufficiently small in area. The movement of the point 706 (see FIG. 11) is then typically consistent and nonvarying. If the motion of a single point 706 (see FIG. 11) in the surgical worksite 86 (see FIG. 11) is not representative of the motion of the surgical worksite 86, a plurality of points (not shown) in the surgical worksite 86 that are in motion independent from each other may be chosen to represent the movement of the surgical worksite 86. In such instances, the motion of the surgical worksite 86 (see FIG. 11) may be determined by computing, for example, an average motion of the selected plurality of points in the surgical worksite 86, or by making use of an appropriate model to map, for example, a plane to the marker positions and attaching a frame to the plane as described in greater detail herein below, or by using any other appropriate computational model or method. The foregoing may apply for the point 706 being on the resultant surgical worksite 86*a* (see FIG. 27). It will be appreciated that a single point will normally not provide information relating to orientation change. Typically, a plurality of points is used when rotation of the surgical site should be taken into account.

After the point 706 (see FIG. 11) which represents the movement of surgical worksite 86 (see FIG. 11), or of the resultant surgical worksite 86*a* (see FIG. 27), has been determined, the next step can be to track the motion of the point 706 with the motion tracking system 400, 430 or 460 (see FIGS. 4A, 4B or 4C, respectively). If an MIS procedure is being performed, the motion tracking system may use the stereoscopic endoscope medical camera 84 (see FIG. 2A) or another camera (not shown) to track the point 706 (see FIG. 11). If an open-chest surgery is being performed as illustrated in FIGS. 2B and 2C, the motion tracking system may employ the vision system 100 to track the point 706 (see FIG. 11). In addition to the stereoscopic endoscope medical camera 84 or the vision system 100, the motion tracking system may track the point 706 (see FIG. 11) by correlating the position of the point 706 over a time period with an ECG signal 502 (see FIG. 5) in the optional ECG system 90. Alternatively, primarily the ECG system 90' (see FIG. 4C) may perform the motion tracking of the point 706 (see FIG. 11).

At least two methods are available for correlating the position of the point 706 (see FIG. 11) with the ECG systems 90 or 90'. One method can be performed in real time and involves recording the position of the point 706 (see FIG. 11) visually with the stereoscopic endoscope medical camera 84 (see FIG. 2A) or the vision system 100 (see FIGS. 2B and 2C) over a time period, and comparing the recorded positions of the point 706 with the ECG trace 502 (see FIG. 5). These correlated data can be stored and can be updated at regular intervals or "quasi-continuously". These corre-lated data allow the surgeon to predict the particular position of the point 706 (see FIG. 11) based on the ECG trace 502 (see FIG. 5). An alternative method for correlating the position of the point 706 (see FIG. 11) with the ECG trace 502 (see FIG. 5) involves determining the position of the point 706 by contacting the tip of the probed surgical manipulator 80' (see FIG. 4C) with the point 706. The position of the tip of the probed surgical manipulator 80' moves with the point 706 (see FIG. 11) can be recorded over time by the probed surgical manipulator encoder 316' (see FIG. 4C). The position over time of the tip of the probed surgical manipulator 80' is then correlated with the ECG trace 502 (see FIG. 5) to predict or enhance tracking of the motion of the point 706 (see FIG. 11). As previously indicated, the method above can be performed in non-real time (for example, prior to suturing).

The motion tracking systems 400 and 430 (see FIGS. 4A and 4B) can use the ECG correlation method above as a secondary (backup) method for tracking the movement of the surgical worksite 86 (see FIGS. 4A and 4B) or of the resultant surgical worksite 86*a*. The motion tracking system 460 (see FIG. 4C) uses the ECG correlation method above as the primary motion tracking method. Other methods may be used by the motion tracking systems 400, 430 and 460 (see FIGS. 4A–4C) to track the movement of the surgical worksite 86 (see FIGS. 4A–4C), or of the resultant surgical worksite 86*a*.

Following the step of determining the motion or movement of the surgical worksite 86, or of the resultant surgical worksite 86*a*, a stationary or substantially stationary image 800 (see FIG. 12) of the surgical worksite 86 (see FIG. 12), or of the resultant surgical worksite 86*a*, is obtained and displayed on the video display system 14 (see FIG. 1) by moving a surgical camera, such as the stereoscopic endoscope medical camera 84 (see FIG. 2A), in the same motion as the surgical worksite 86, or the resultant surgical worksite 86*a*, and/or by transforming the moving image of the surgical worksite 86, or of the resultant surgical worksite 86*a*, into a stationary or substantially still image 800 by making use of video or image processing techniques performed by the video processor 302 (see FIG. 3A). The surgeon then typically sees a virtual image 20V (see FIG. 1) or a real image 20R (see FIG. 1), on the video display system 14 (see FIG. 1) of the stationary or substantially stationary image 800, (see FIG. 12) of the surgical worksite 86 (see FIG. 12), or of the resultant surgical worksite 86*a*.

After, or while, the stationary image 800 (see FIG. 12) of the surgical worksite 86 (see FIG. 12), or of the resultant surgical worksite 86*a* is displayed, one or more surgical instruments 82 (see FIGS. 2A–2C) attached to the surgical manipulators 76, 78 or 80 (for example, see FIG. 2A) can be commanded to track the motion of the surgical worksite 86 (see FIG. 12), or the resultant surgical worksite 86*a*, such that the image of the surgical instruments 82 and the surgical worksite 86, or the resultant surgical worksite 86*a*, appear stationary or substantially stationary to the surgeon who is viewing the video display system 14 (see FIG. 1). The surgeon can then cause the surgical instruments 82 (see FIGS. 2A–2C) to perform surgical procedures from the surgeon's console 12 (see FIG. 1). The surgeon can then observe movement that he/she provides to the surgical instruments 82*a* and 82*b* (see FIG. 13) in the directions of the arrows 830 and 832 (see FIG. 13), respectively, while continuing to view the surgical worksite 86 (see FIG. 13) or the resultant surgical worksite 86*a* as a stationary image or substantially stationary image 800 (see FIG. 13).

The present invention is particularly useful in performing coronary artery bypass graft (CABG) procedures without cardioplegia. Conventional CABG procedures are described in U.S. Pat. No. 5,452,733 which is fully incorporated herein by reference as if repeated verbatim immediately hereinafter. Conventional CABG procedures often require that a source of arterial blood be prepared for subsequent bypass connection to the narrowed coronary artery at a location beyond the narrowing. Such arterial blood sources are typically of two types. First, existing arteries can be dissected from their natural attachments and transected to provide upstream and downstream free ends. The upstream free end, which is the arterial blood source, can be secured to the coronary artery at a location distal to the narrowing, thus providing the desired bypass blood flow. Second, artificial arterial shunts may be prepared by attaching a natural or synthetic blood vessel, typically a length obtained from a leg vein, at one end to the proximal ascending aorta and at the other end to the target location on a coronary artery. The use of transected arteries is generally preferable since they tend to remain patent for long periods and typically require only one anastomosis.

The arterial blood source is typically the left or right internal mammary artery. It is also possible to use the gastroepiploic artery in the abdomen. Access to the gastroepiploic artery can be obtained laparoscopically, with the artery being brought into the thorax from the abdominal cavity via a window through the diaphragm. When necessary, it can be possible to prepare free grafts from the aorta. Such free grafts can be formed from veins or arteries harvested from other locations in a patient's body, or may comprise synthetic graft materials. The free graft may be passed into the thorax through either an access trocar sheath or through the aorta (by punching a hole therethrough). The free grafts thus located are typically attached at one end to the proximal ascending aorta (to provide the arterial blood supply) and at the other end to the target location on the coronary artery.

The left internal mammary artery is suitable as an arterial source for target locations on the left anterior descending coronary artery, the diagonal coronary artery, the circumflex artery/obtuse marginal artery, and the ramus intermedius coronary artery.

The right internal mammary artery is typically available for connection to all of the same target locations, as well as the right coronary artery and the posterior descending artery. The gastroepiploic artery and free grafts from the aorta are typically available for all target locations.

In transecting the left internal mammary artery, the left lung is often deflated and a length of the internal mammary artery is dissected from the inner thoracic all. The side branches of the internal mammary artery are typically sealed.

Figure 14:
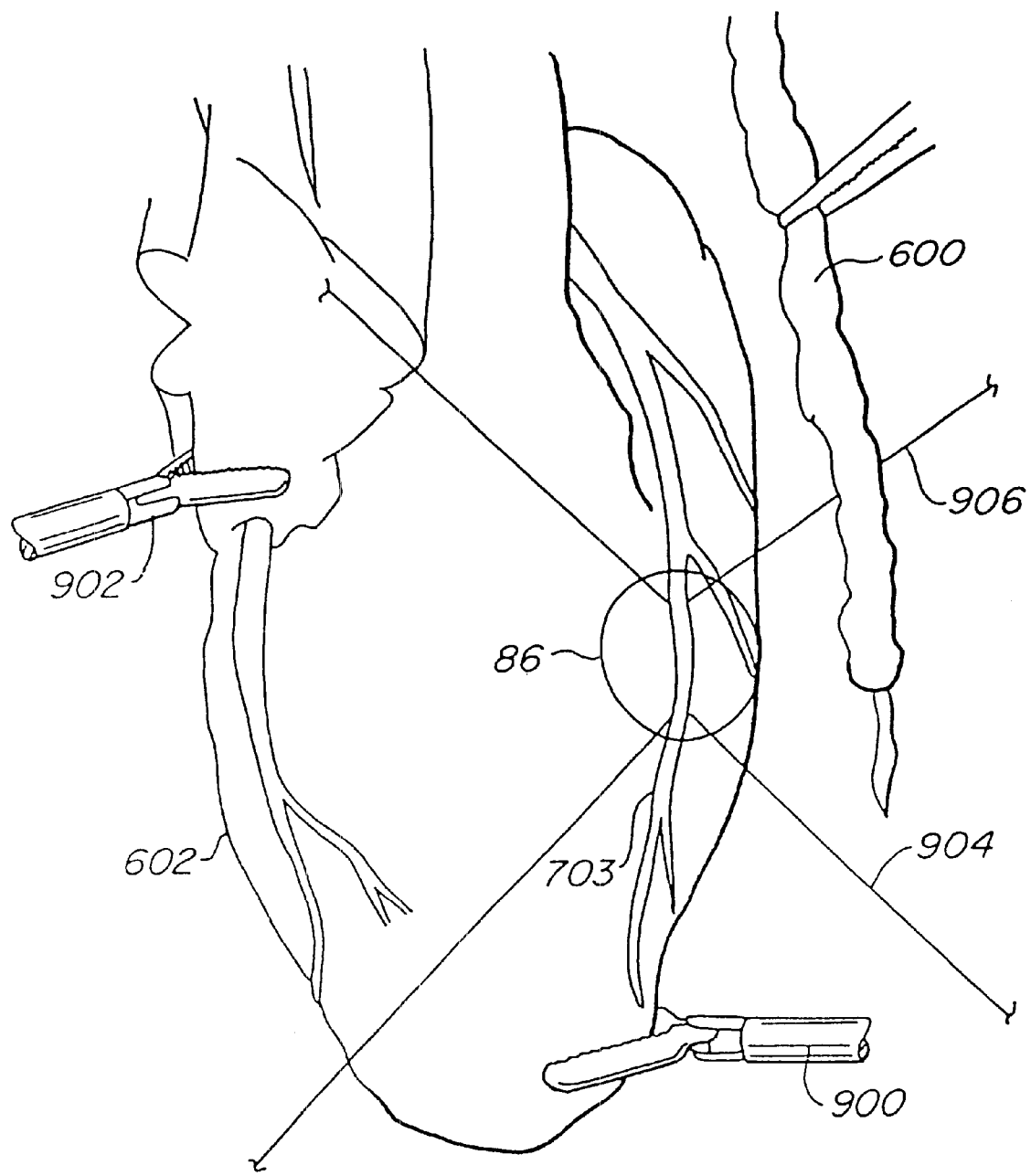
FIG. 14 shows a schematic view of a surgical worksite on a heart prior to a coronary artery bypass graft procedure.

As shown in FIG. 14, the heart 602 is repositioned using suitable instruments in order to better expose the coronary artery 703 which is the target for anastomosis in the surgical worksite 86. Suitable instruments include hooks, suction catheters, grasping rods, pushing rods, and the like. Gravity can also be used to help position the heart 602 if the patient can be turned appropriately. As illustrated in FIG. 14, a pair of graspers 900 and 902 can be used to secure opposite sides of the heart 602 and permit turning of the heart 602 as desired. Optionally, trocar sheaths (not shown) may be introduced at other sites to provide thoracic access. For example, one or more parasternal punctures, one or more punctures in the midclavicular line, and/or a subxyphoid puncture may be introduced. The elastic members 904 and 906, which are introduced through appropriately positioned trocar sheaths (not shown), place axial tension on the surgical worksite 86 in the coronary artery 703 which is to be prepared for anastomosis. In addition, they provide a bloodless lumen, permitting good visualization. As illustrated in FIG. 14, the coronary artery 703 is first pulled upward from the surface of the heart 602 and stretched using the pair of elastic members 904 and 906. The surgical worksite 86 in the coronary artery 703 is designated for anastomosis.

The motion of the surgical worksite 86 is then determined and tracked by the motion tracking system 400, 430 or 460 (see FIGS. 4A, 4B or 4C, respectively). The foregoing procedure could be applied to the resultant surgical worksite 86a. It will be appreciated that if the surgical site does not have excessive residual motion, tracking may be optional, or unnecessary.

Figure 14A:
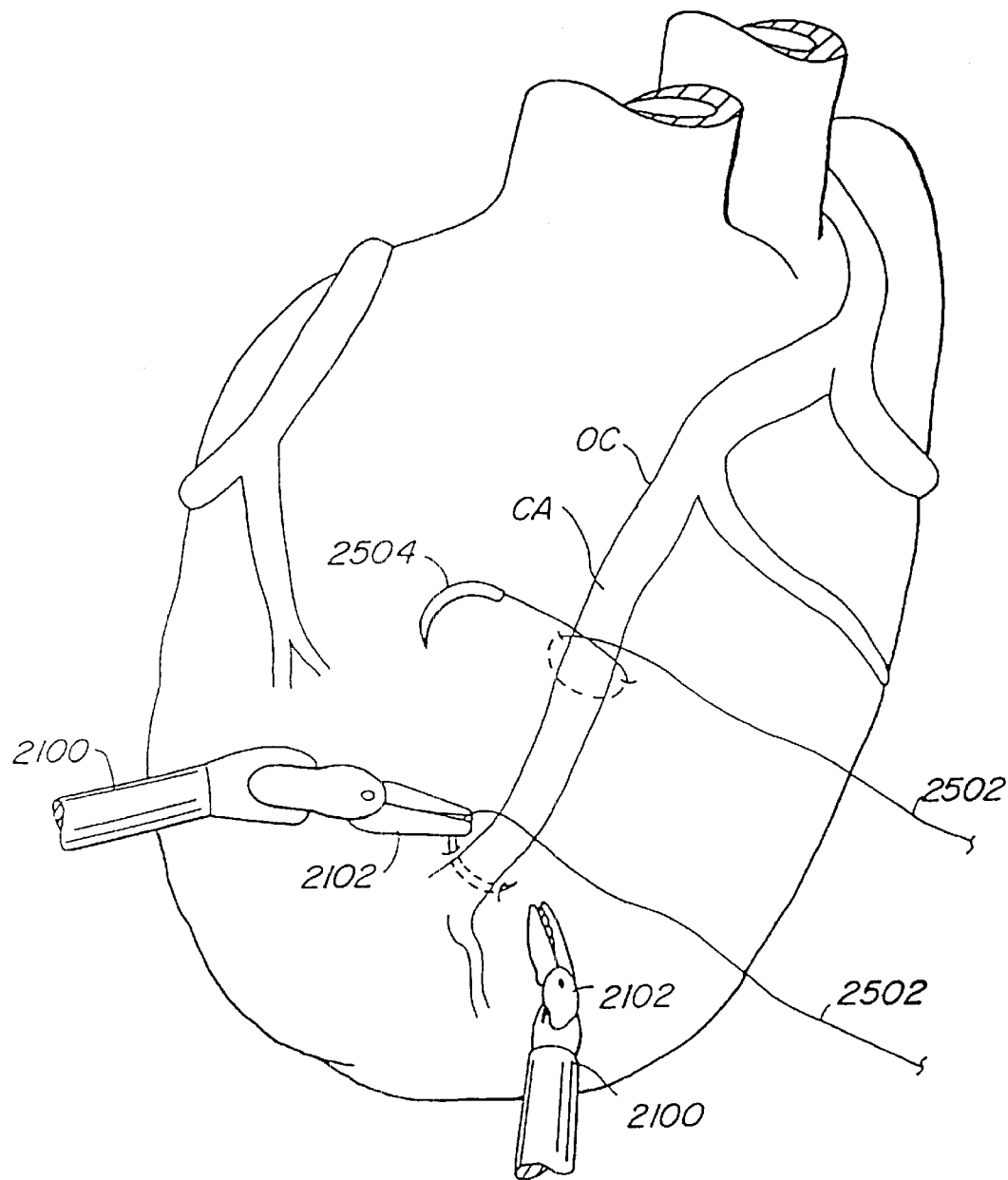
FIGS. 14A and 14B illustrate a method for using a stabilizer shown in FIGS. 22D to H to stabilize a target region of the heart and also to isolate a target region of a coronary artery for anastomosis.
Figure 14B:
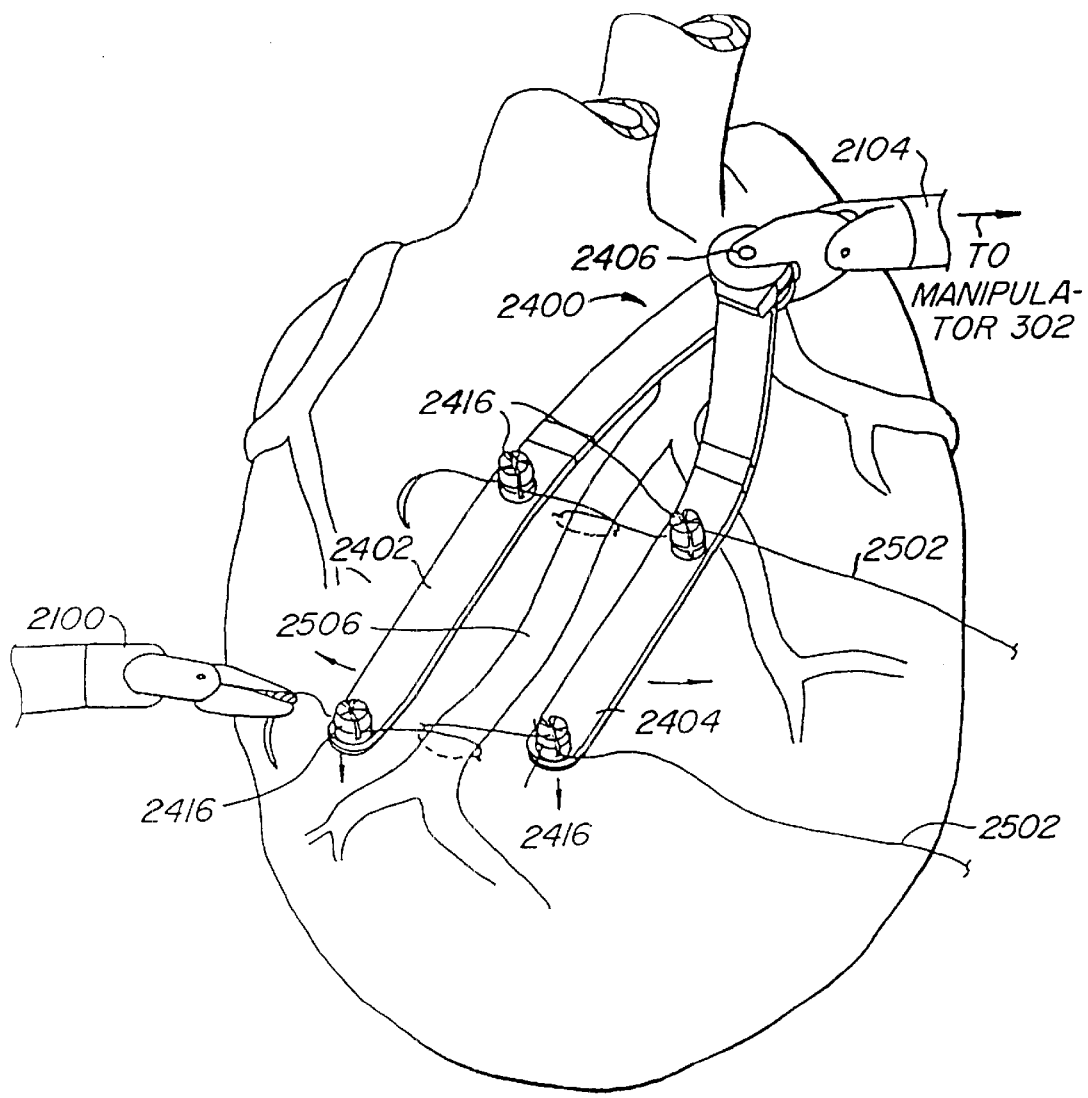

A method for isolating a coronary artery CA downstream of an occlusion OC using preferably stabilizer 2400, as indicated in FIG. 22D, will now be described with reference to FIGS. 14A and 14B. Rather than straightening and tensioning the coronary artery CA by tensioning elastic flexible members extending through the chest wall, a flexible member 2502 is passed under the coronary artery CA using end effectors 2102 of tools 2100 as illustrated in FIG. 14A. As indicated in FIG. 14B, the stabilizer 2400 is positioned against the heart with the first and second bodies 2402, 2404 of the stabilizer being positioned on either side of the coronary artery CA so as to inhibit motion of the surgical worksite. A target region 2506 of the coronary artery CA is isolated from upstream and downstream blood flow by tensioning flexible members 2502 and tying the tensioned flexible members to the opposed anchors 2416 of the stabilizer 2400. This is typically achieved by looping the flexible members 2502 around the coronary artery at opposed positions, as shown. In this manner, not only is the coronary artery held by means of the stabilizer 2400, but the surgical site is also stabilized, or braced, to at least reduce its motion so as to ease the task of surgically working on the coronary artery CA.

Advantageously, the flexible members 2502 are comprised of silastic tubing, the tubing preferably being large enough to catch in the channels of the anchors 2416 but not so large so as to cause large penetrations about the vessel, or to be ineffective in occluding the vessel. For the exemplary anchors 2416 having a channel with a width of about 0.010 inches, a preferred silastic tubing will have an outer diameter of about 0.050 inches and an inner diameter of about 0.030 inches. Such silastic tubing is available from QUEST MEDICAL of Allen, Tex., under the product "Retract-O-Tape." These methods and devices are more fully described in U.S. patent application Ser. No. 09/436,524, filed Nov. 9, 1999, entitled "Stabilizer for Robotic Beating-Heart Surgery", filed concurrently herewith, the full disclosure of which is incorporated herein by reference. Alternatively, elastic and/or inelastic flexible members can be used. Flexible member 2502 is tied off on the anchors 2416 using tools 2100 by means of a totally endoscopic procedure, while the heart is beating and without a thoracotomy or a minithoracotomy.

Figure 14C:
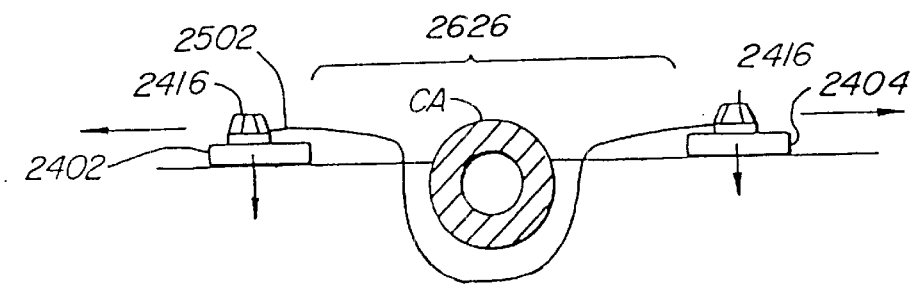
FIG. 14C schematically illustrates an alternative arrangement of fixable members anchored to bifurcated stabilizer bodies to isolate the target region of a coronary artery in the method as shown in FIGS. 14A and 14B.

Referring now to FIG. 14C, an alternative arrangement for occluding the coronary artery CA using preferred stabilizer 2400 will now be described. It will be understood that tensioning of flexible member 2502 may be effected by moving first body 2402 away from second body 2404 about pivot 2406, or the flexible member may simply be tied with tension to the pre-positioned anchor of the stabilizer using tools 2100. Regardless, tension of flexible member 2502 will preferably substantially occlude the lumen of the coronary artery CA, when the loop is tightened, and the tension may also aid to inhibit movement of the coronary tissues between first and second bodies 2402, 2404.

Figure 15A:
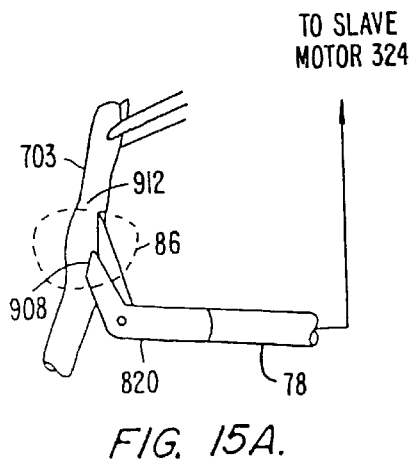
FIGS. 15A to 15D show schematic views illustrating the use of surgical manipulators of the present invention to suture an anastomosis on a beating heart.
Figure 15B:
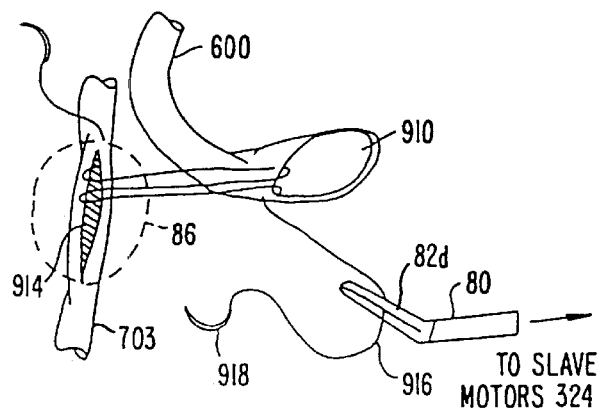
Figure 15C:
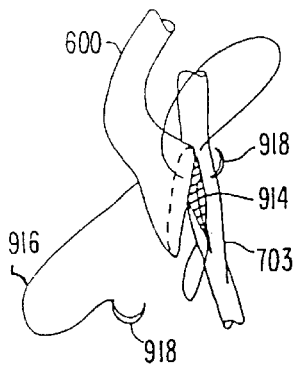
Figure 15D:
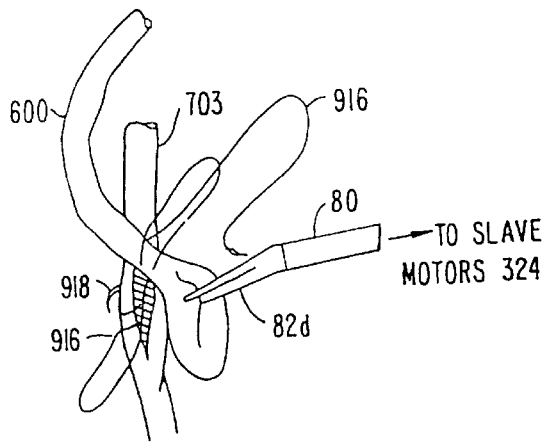

Referring now to FIG. 15A, the surgical worksite 86 is seen as a stationary or substantially stationary or still image. An incision 908 is made in the wall of the coronary artery 703, where the incision 908 has dimensions selected to match those of the upstream free end 910 (see FIG. 15B) of the internal mammary artery 600 graft. The incision 908 is made by first piercing the arterial wall 912 using the tip of a scalpel (not illustrated). A surgical instrument 82c, such as a scissor, is attached to the surgical manipulator 78. The surgical tool 82c is introduced through the incision 908 to axially extend the incision 908, as illustrated at 914 in FIG. 15B. The movement of surgical instrument 82c is directed by the surgeon from the surgeon interface 250 (see FIG. 3A).

The internal mammary artery can be joined to the extended incision 914 in the coronary artery 703 by a variety of conventional techniques, including suturing, laser welding, microstapling, and/or the like. It can be preferable to use conventional suturing techniques as illustrated in FIGS. 15A–D. A length of suture 916 (see FIGS. 15A–D) has needles 918 at either end. The needles can be manipulated using forceps 82d attached to the surgical manipulator 80 to join the free upstream end 910 of the internal mammary artery 600 graft to the opening created by extended incision 914 in the coronary artery 703. It is to be understood that the foregoing procedures described with reference to FIGS. 15A–D and with respect to the surgical worksite 86 is also applicable to the resultant surgical worksite 86a of FIG. 27.

After the suturing is complete, the internal mammary artery 600 is joined to the coronary artery 703. It is noted that prior to suturing, temporary clips (not shown) are placed upstream and downstream of the region of the internal mammary artery to be transected. After suturing, the temporary clips are removed to permit blood flow into the coronary artery 703, thus bypassing the previous blockage in the coronary artery 703. The downstream free end of the internal mammary artery typically remains clipped. Following completion of the coronary anastomosis, all heart manipulating devices (not shown) are removed from the patient, and the heart is permitted to return to its natural orientation.

Figure 15E:
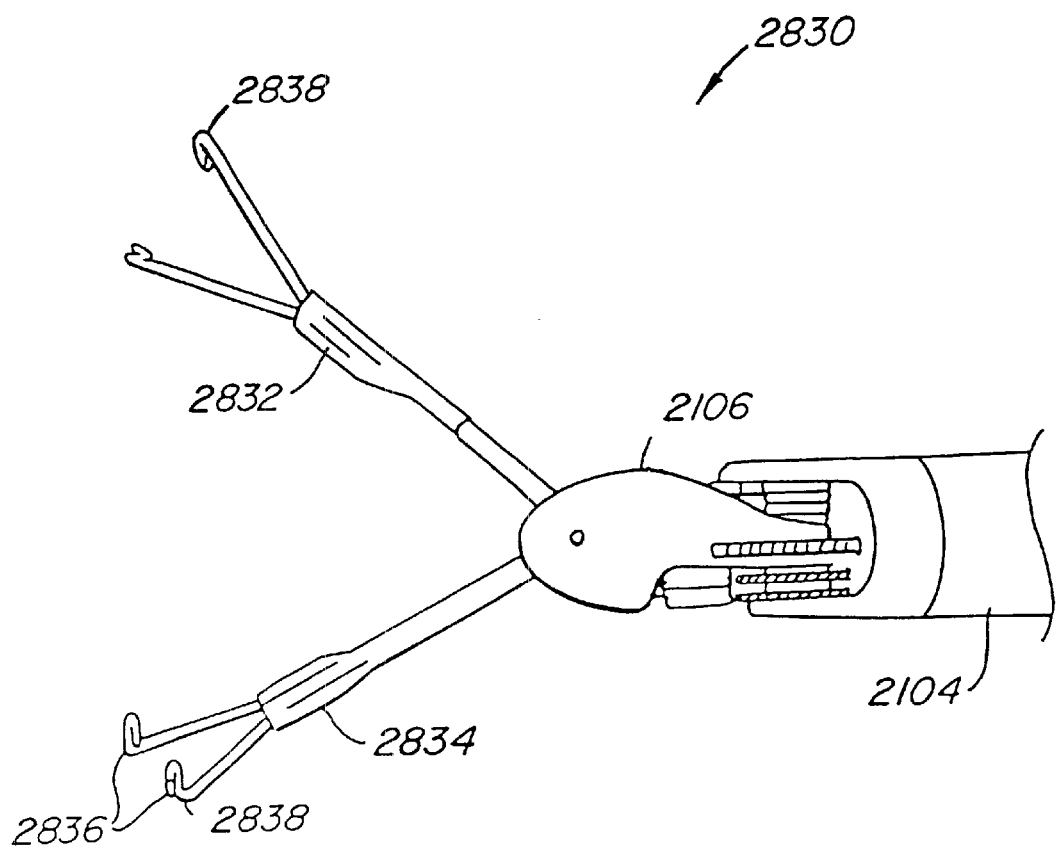
FIGS. 15E and 15F show a retractor used to at least partially stabilize a surgical site on the beating heart.
Figure 15F:
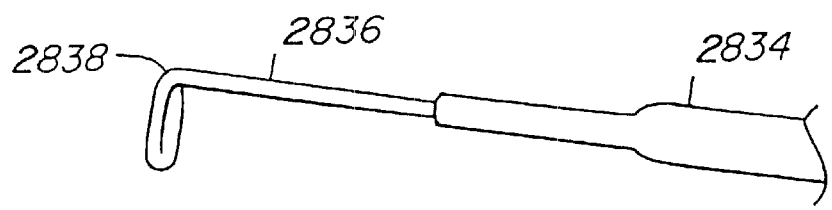

FIGS. 15E and 15F illustrate a robotic tissue retractor 2830 for use with the system of FIG. 1. The retractor 2830 includes first and second retractor elements 2832, 2834 which can be independently articulated, as described above. Each retractor element has at least one arm 2836 and a bend 2838 so that the arms can each pull and/or push tissue normal to the retractor element. Preferably, two or more arms are provided on each element, with the tool typically having one, two, or more retractor elements.

In use, retractor elements 2832, 2834 can be spread apart and used to retract tissue from an internal surgical site as described. The arms 2836 of a first retractor element 2832 may extend distally beyond bends 2838 of the second retractor element 2834 to avoid interference when the elements are aligned in a small profile or collapsed configuration for insertion and removal. The exemplary retractor elements comprise flattened hypotube crimped and glued around formed wire, such as 0, 021 diameter stainless steel. The proximal ends of the hypotube may similarly be crimped and glued to end effector elements of a microforceps or the like. Alternative retractor elements may comprise structures similar to those described in U.S. Pat. No. 5,613,937, the full disclosure of which is incorporated herein by reference.

Thus, the practice of the present invention provides apparatuses 10 (i.e., surgical systems 10 or assemblies) and methods for performing surgery, preferably cardiac surgery without cardioplegia. The patient 70 (see FIGS. 2A–2C and 3A and 3B) first consults a physician such as the surgeon 18 (see FIG. 1). If surgery is required, the present invention allows the surgeon 18 (see FIG. 1) to designate the surgical worksite 86 (see FIGS. 2A–2C and 3A and 3B) and to subsequently operate on the surgical worksite 86 of the patient 70 (see FIGS. 2A–2C and 3A and 3B) from the surgeon's console 12 (see FIG. 1). From the video display system 14 (see FIG. 1), the surgeon 18 first observes the surgical worksite 86, such as a surgical site on a beating heart (see FIGS. 2A–2C and 3A and 3B) in movement. A stationary or substantially stationary image 800 (see FIG. 12) of the beating heart is then displayed on the video display system 14 (see FIG. 1). The surgeon 18 then observes a real image 20R (see FIG. 1) or a virtual image 20V (see FIG. 1) of a stationary or substantially stationary image of the surgical site and the tools 82 (see FIGS. 2A–2C) which are attached to the surgical manipulators 78 and 80 (see FIGS. 2A–2C). From the surgeon's console 12 (see FIG. 1), the surgeon 18 inputs control commands so as to move the surgical instruments 82 (see FIGS. 2A–2C) via the master controllers 16 (see FIG. 1). The system 10 continues to provide the stationary image of the surgical worksite 86 and tools 82 and provides an image of the surgical instruments' movements relative to the surgical site in response to the surgeon 18 (see FIG. 1) input at the surgeon's console 12 (see FIG. 1). Consequently, the surgeon 18 (see FIG. 1) views a generally stationary image of the beating surgical worksite 86 (see FIGS. 2A–2C and 3A and 3B) and can perform cardiac surgery without cardioplegia.

The practice of the present invention also provides attachment assemblies 21 including attachment arms 23 and attachment members 25. The attachment members 25 may be affixed to the heart in a region adjacent to or surrounding the surgical worksite 86. Each attachment assembly 21 is connected to a servo-mechanism-operated slave attachment manipulator 19. The attachment manipulator 19 includes slave motors 324a which can move the associated attachment assembly 21 with six degrees of freedom (i.e., three linear degrees of freedom and three rotational degrees of freedom). Associated with each motion axis of the attachment assembly 21 are one or more attachment encoders 316a (or potentiometers) which inform the control computer 310 of the position of the attachment assembly 21. The attachment members 25 may be releasably attached to the heart by one or more of the following methods: mechanical, adhesive, suture, suction, and/or the like.

The attachment assemblies 21 may be used in one of the following modes: tracking, stabilization, or a combination of tracking and stabilization. In the tracking mode, the attachment member 25 is releasably engaged or attached to the heart and the attachment motors 324a apply essentially no net force to the attachment assembly 21 after the attachment member 25 has been releasably connected to the heart. The attachment encoders 316a (and potentiometers) of the attachment manipulator 19 can detect the position of the attachment assembly 21 and the attachment member 25. The relative motion of the surgical worksite 86, or of the resultant surgical worksite 86a and the attachment assembly 21 is small. Therefore, movement information of the attachment arm 23 and the attachment member 25 can be used to provide reference information to the cameras 88a and 88b or endoscope 84 and the surgical instruments 82 to stabilize the image of the surgical instruments 82 relative to the moving surgical worksite 86, or the resultant surgical worksite 86a, and to cause the surgical instruments to track the site 86 or 86a.

In the stabilization mode, the attachment motors 324a apply force to the attachment assembly 21 including the attachment arm 23 and the attachment member 25 such that the force upon the attachment member 25 will prevent the surgical worksite 86 from moving in the region of attachment. In the stabilization mode, the surgical worksite 86 is kept as stationary as possible. Therefore, the surgical instruments 82 and the cameras (cameras 88a and 88b and/or endoscope 84) may not need to track the surgical worksite 86. The servo-mechanism-operated attachment manipulator 19 has the following advantages over a simple rigid clamp arm with respect to generally immobilizing a moving anatomical part, such as a moving heart: (1) the position of the attachment assembly 21 may be easily adjusted; and (2) the attachment manipulator 19 may be able to use active/predictive controls to reduce as opposed to preventing actual motion of the heart or the surgical worksite 86 compared to a simple rigid clamp arm, for example.

When the attachment assemblies 21 operate in a combination mode, the attachment motors 324a apply some force to the attachment assemblies 21 including the attachment arm 23 and the attachment member 25 in an attempt to reduce motion of the surgical worksite 86, producing the resultant surgical worksite 86a. The forces applied by the attachment motors 324a can be applied selectively to control motions; that is, some motions in some axes may be controlled more than some motions in other axes. For example, the attachment assemblies 21 can be controlled by the attachment manipulator 19 to allow motion only in one axis, or the attachment assemblies 21 can be controlled by the attachment manipulator 19 to reduce motions in all axes (i.e., a dampening action), or the attachment assemblies 21 can be controlled by the attachment manipulator 19 to allow only linear motions and no rotational motions of the surgical worksite 86. Preferably, the forces applied by the attachment motors 324a are in such a manner that any remaining motion of the surgical worksite 86 (i.e., the resultant surgical worksite 86a) can be easily tracked by the cameras 88a and 88b or the endoscope 84 or by another attachment assembly 21 (see FIG. 27) or other surgical instruments 82. The advantage of the combination mode over a stabilization mode, or a rigid clamping mode, is that smaller forces may be applied to the surgical worksite 86; thus, less trauma would be caused to the heart. Additionally, the heart may be tolerant of reduced motion of the surgical worksite 86 compared to no motion at all which would result from the stabilization mode or the rigid clamping mode. The remaining motion of the attachment assembly 21 including its associated attachment arm 23 and attachment member 25 (see attachment member 25A in FIG. 27) may be measured and used to control the tracking cameras 88a and 88b or the endoscope 84 and the surgical instruments 82 as in the tracking mode. Accordingly, the remaining motions of the resultant surgical worksite 86a may be measured and tracked by the cameras 88a and 88b or the endoscope 84 or another attachment assembly 21 (see attachment member 25B in FIG. 27) and the surgical instruments 82.

Figure 29:
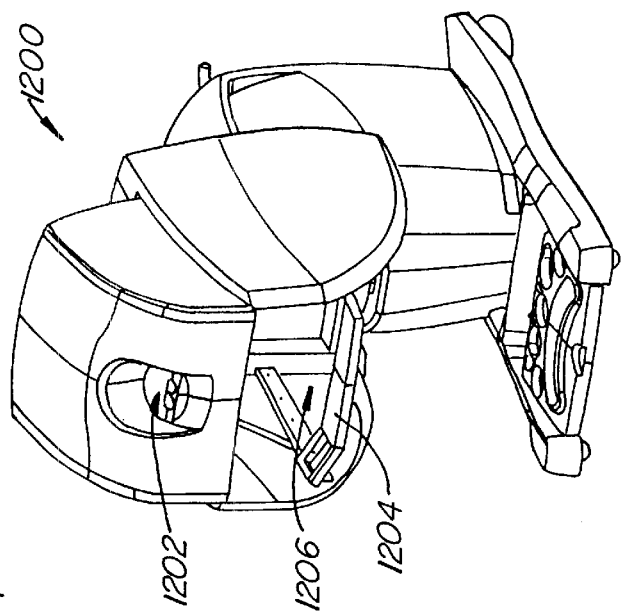
FIG. 29 shows a three-dimensional view of an operator station of another telesurgical system in accordance with the invention.

Another telesurgical/surgical system in accordance with the invention will now be described with reference to FIGS. 29 to 38 of the drawings. In FIG. 29, an operator station or surgeon's console of this telesurgical system in accordance with the invention is generally indicated by reference numeral 1200. The station 1200 includes a viewer 1202 where an image of a surgical site is displayed in use. A support 1204 is provided on which an operator, typically a surgeon, can rest his or her forearms while gripping two master controls (refer to FIG. 35), one in each hand. The master controls are positioned in a space 1206 inwardly beyond the support 1204. When using the control station 1200, the surgeon typically sits in a chair in front of the control station 1200, positions his or her eyes in front of the viewer 1202 and grips the master controls one in each hand while resting his or her forearms on the support 1204.

Figure 30:
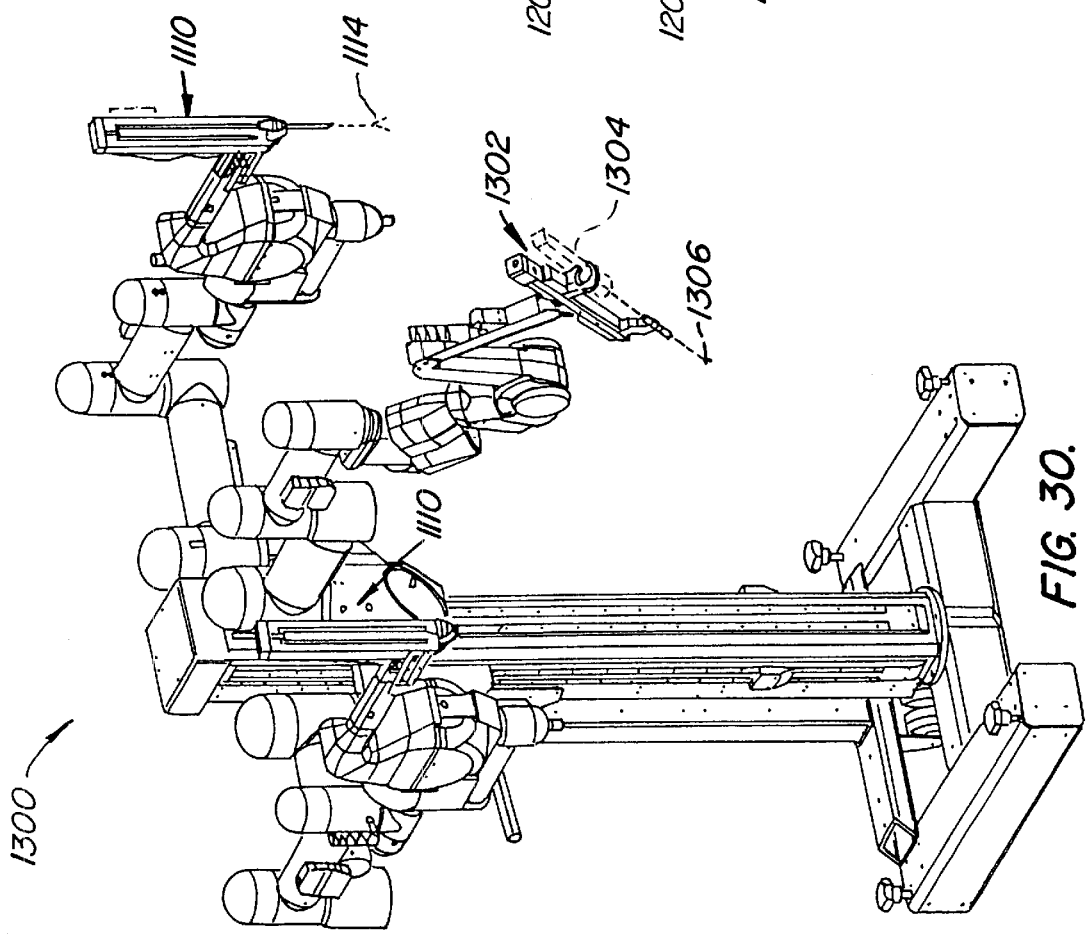
FIG. 30 shows a three-dimensional view of a cart or surgical station of the other telesurgical system, the cart carrying three robotically controlled arms, the movement of the arms being remotely controllable from the operator station shown in FIG. 29.

In FIG. 30 of the drawings, a cart or surgical station of the telesurgical system is generally indicated by reference numeral 1300. In use, the cart 1300 is positioned close to a patient requiring surgery and is then normally caused to remain stationary until a surgical procedure to be performed has been completed. The cart 1300 typically has wheels or castors to render it mobile. The station 1200 is typically positioned remote from the cart 1300 and can be separated from the cart 1300 by a great distance, even miles away, but will typically be used within an operating room with the cart 1300.

The cart 1300 typically carries at least three robotic arm assemblies. One of the robotic arm assemblies, indicated by reference numeral 1302, is arranged to hold an image capturing device 1304, e.g., an endoscope, or the like. Each of the two other arm assemblies 1110, 1110 respectively, includes a surgical instrument 1114. The endoscope 1304 has an object viewing end 1306 at a remote end of an elongate shaft thereof. It will be appreciated that the endoscope 1304 has an elongate shaft to permit its viewing end 1306 to be inserted through an entry port in a patient's body so as to access an internal surgical site. The endoscope 1304 is operatively connected to the viewer 1202 to display an image captured at its viewing end 1306 on the viewer 1202. Each robotic arm assembly 1110, 1110 is normally operatively connected to one of the master controls. Thus, the movement of the robotic arm assemblies 1110, 1110 is controlled by manipulation of the master controls. The instruments 1114 of the robotic arm assemblies 1110, 1110 have end effectors which are mounted on wrist members which are pivotally mounted on distal ends of elongate shafts of the instruments 1114. It will be appreciated that the instruments 1114 have elongate shafts to permit the end effectors to be inserted through entry ports in a patient's body so as to access an internal surgical site. Movement of the end effectors relative to the ends of the shafts of the instruments 1114 is also controlled by the master controls. Thus, in this embodiment of the invention, the robotic arms which carry the surgical instruments and the endoscope are not mounted on an operating table, but on a mobile cart. When a surgical procedure is to be performed, the cart carrying the robotic arms is wheeled to the patient and is normally maintained in a stationary position relative to the patient during the surgical procedure.

Figure 31:
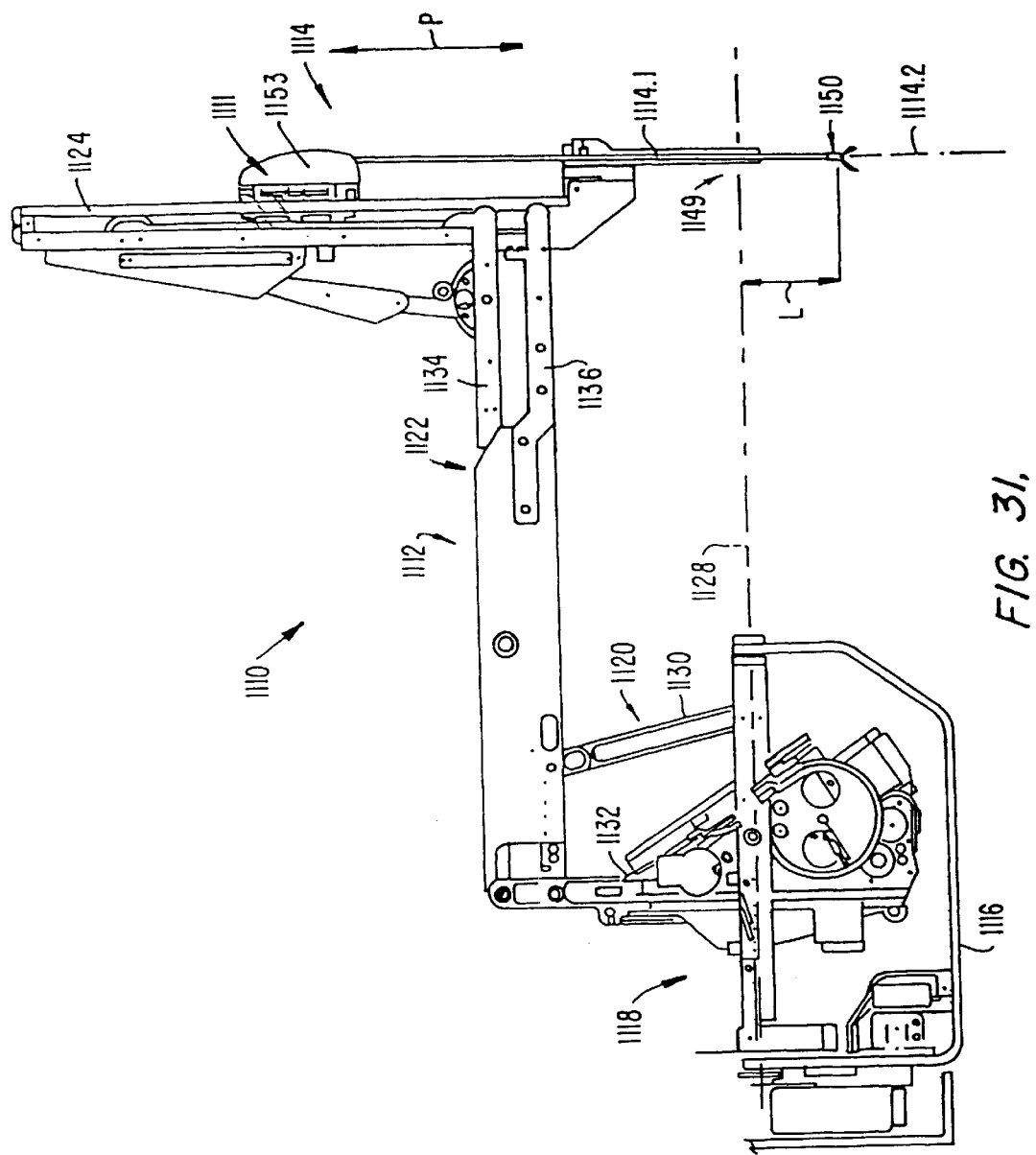
FIG. 31 shows a side view of a robotic arm and surgical instrument assembly of the other telesurgical system.
Figure 32:
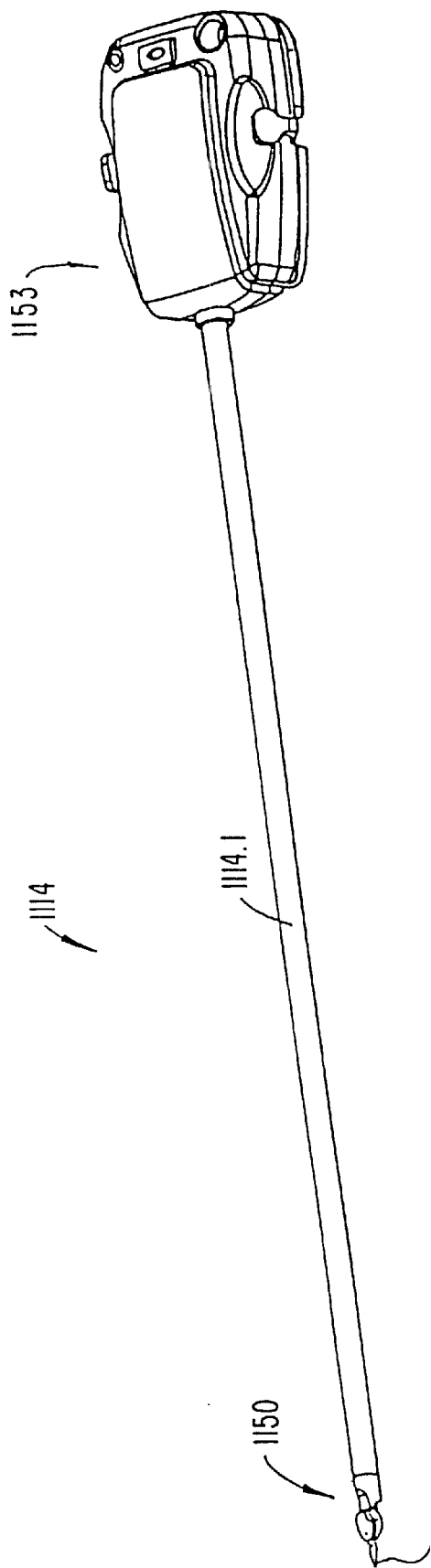
FIG. 32 shows a three-dimensional view of a typical surgical instrument of the other telesurgical system.

In FIG. 31 of the drawings, one of the robotic arm assemblies 1110 is shown in greater detail. Each assembly 1110 includes an articulated robotic arm 1112, and a surgical instrument, schematically and generally indicated by reference numeral 1114, mounted thereon. FIG. 32 indicates the general appearance of a typical surgical instrument 1114 in greater detail.

The surgical instrument 1114 includes an elongate shaft 1114.1. The wrist-like mechanism, generally indicated by reference numeral 1150, is located at a working end of the shaft 1114.1. A housing 1153, arranged releasably to couple the instrument 1114 to the robotic arm 1112, is located at an opposed end of the shaft 1114.1. In FIG. 31, and when the instrument 1114 is coupled or mounted on the robotic arm 1112, the shaft 1114.1 extends along an axis indicated at 1114.2. The instrument 1114 is typically releasably mounted on a carriage 1111, which can be driven to translate along a linear guide formation 1124 of the arm 1112 in the direction of arrows P.

The robotic arm 1112 includes a cradle, generally indicated at 1118, an upper arm portion 1120, a forearm portion 1122 and the guide formation 1124. The cradle 1118 is pivotally mounted on a plate 1116 in a gimbaled fashion to permit rocking movement of the cradle 1118 about a pivot axis 1128. The upper arm portion 1120 includes link members 1130, 1132 and the forearm portion 1122 includes link members 1134, 1136. The link members 1130, 1132 are pivotally mounted on the cradle 1118 and are pivotally connected to the link members 1134, 1136. The link members 1134, 1136 are pivotally connected to the guide formation 1124. The pivotal connections between the link members 1130, 1132, 1134, 1136, the cradle 1118, and the guide formation 1124 are arranged to constrain the robotic arm 1112 to move in a specific manner. The movement of the robotic arm 1112 is illustrated schematically in FIG. 33.

Figure 33:
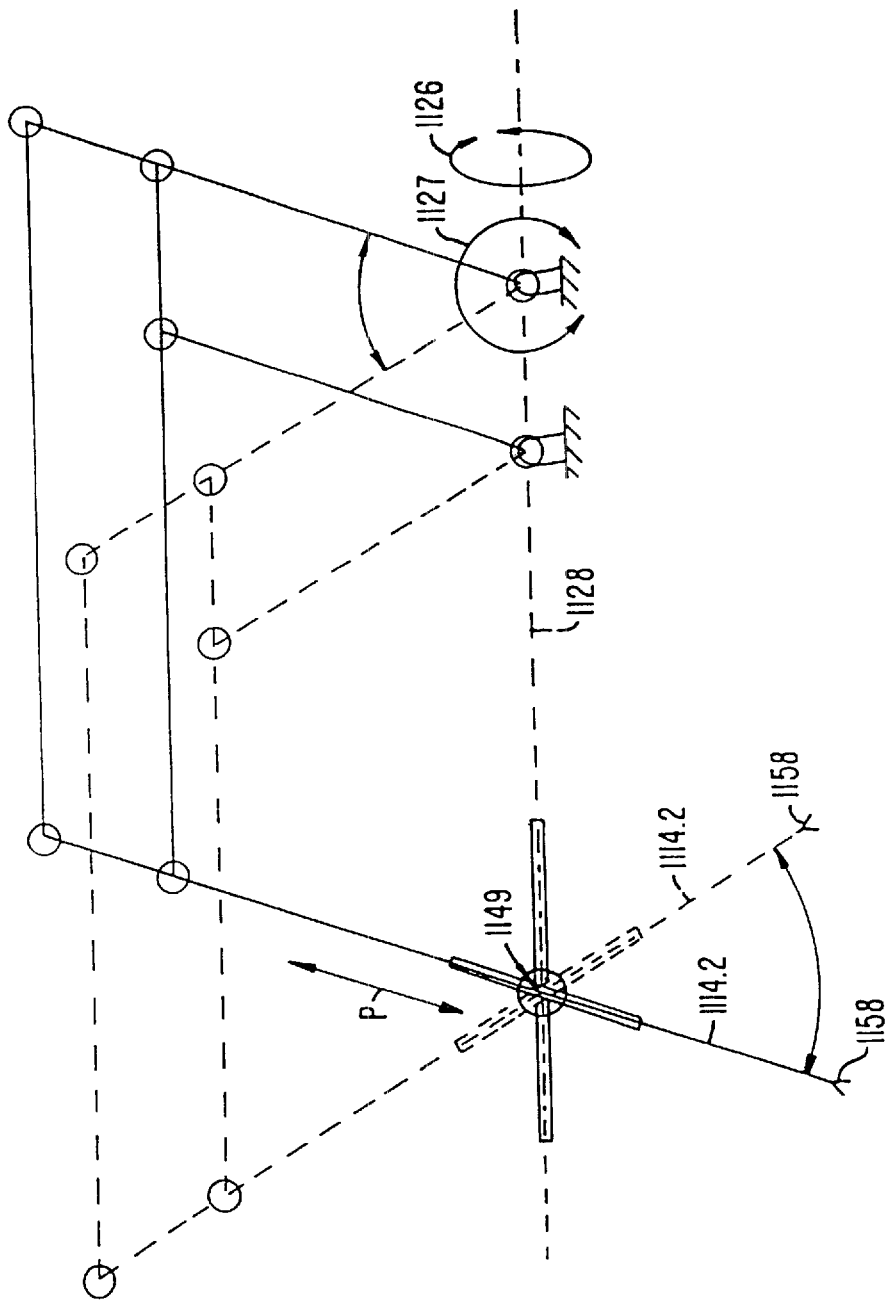
FIG. 33 shows a schematic kinematic diagram corresponding to the side view of the robotic arm shown in FIG. 31, and indicates the arm having been displaced from one position into another position.

With reference to FIG. 33, the solid lines schematically indicate one position of the robotic arm 1112 and the dashed lines indicate another possible position into which the arm can be displaced from the position indicated in solid lines.

It will be understood that the axis 1114.2 along which the shaft 1114.1 of the instrument 1114 extends when mounted on the robotic arm 1112 pivots about a pivot center or fulcrum 1149. Thus, irrespective of the movement of the robotic arm 1112, the pivot center 1149 normally remains in the same position relative to the stationary cart 1300 on which the arm 1112 is mounted. In use, the pivot center 1149 is positioned at a port of entry into a patient's body when an internal surgical procedure is to be performed. It will be appreciated that the shaft 1114.1 extends through such a port of entry, the wrist-like mechanism 1150 then being positioned inside the patient's body. Thus, the general position of the mechanism 1150 relative to the surgical site in a patient's body can be changed by movement of the arm 1112. Since the pivot center 1149 is coincident with the port of entry, such movement of the arm does not excessively effect the surrounding tissue at the port of entry.

As can best be seen with reference to FIG. 33, the robotic arm 1112 provides three degrees of freedom of movement to the surgical instrument 1114 when mounted thereon. These degrees of freedom of movement are firstly the gimbaled motion indicated by arrows 1126, pivoting or pitching movement as indicated by arrows 1127 and the linear displacement in the direction of arrows P. Movement of the arm as indicated by arrows 126, 127 and P is controlled by appropriately positioned actuators, e.g., electrical motors, or the like, which respond to inputs from an associated master control to drive the arm 1112 to a required position as dictated by movement of the master control. Appropriately positioned sensors, e.g., potentiometers, encoders, or the like, are provided on the arm to enable a control system of the telesurgical system to determine joint positions, as described in greater detail herein below. It will be appreciated that whenever "sensors" are referred to in this specification, the term is to be interpreted widely to include any appropriate sensors such as positional sensors, velocity sensors, or the like. It will be appreciated that by causing the robotic arm 1112 selectively to displace from one position to another, the general position of the wrist-like mechanism 1150 relative to the surgical site can be varied during the performance of a surgical procedure.

Figure 34:
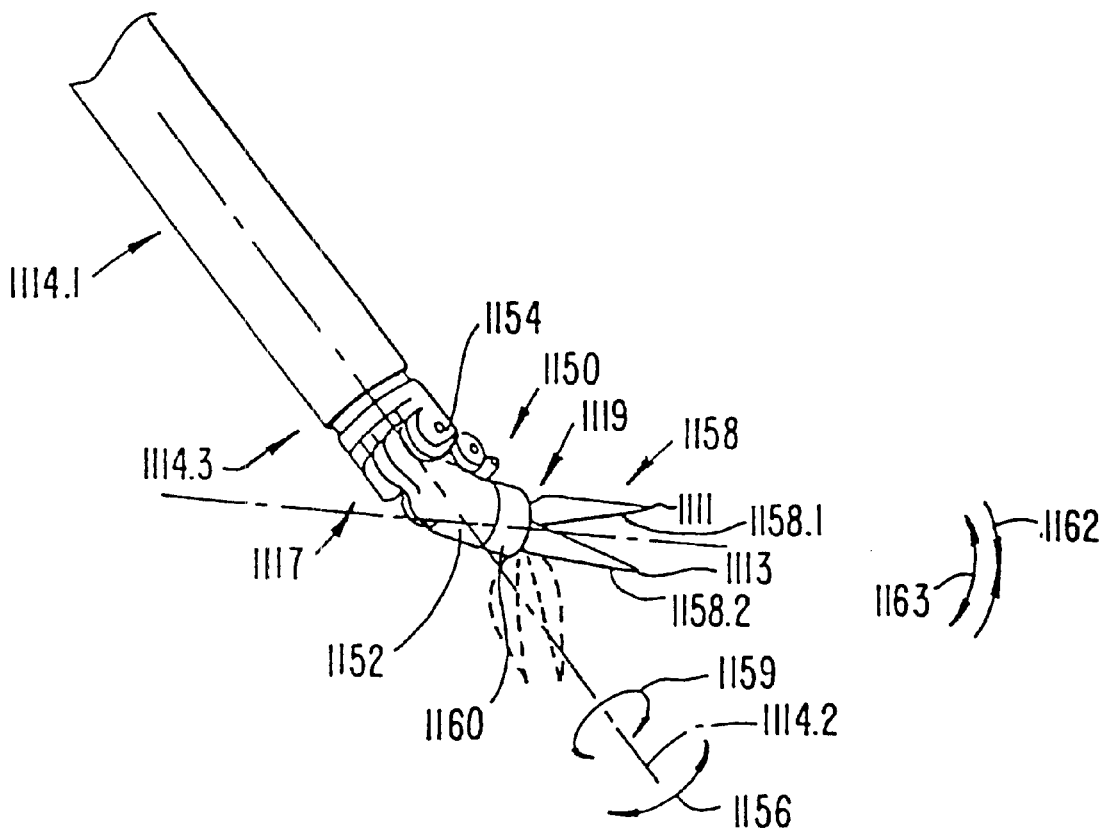
FIG. 34 shows, at an enlarged scale, a wrist member and end effector of the surgical instrument shown in FIG. 32, the wrist member and end effector being movably mounted on a working end of a shaft of the surgical instrument.

Referring now to FIG. 34 of the drawings, the wrist-like mechanism 1150 will now be described in greater detail. In FIG. 34, the working end of the shaft 1114.1 is indicated at 1114.3. The wrist-like mechanism 1150 includes a wrist member 1152. One end portion of the wrist member 1152 is pivotally mounted in a clevis, generally indicated at 1117, on the end 1114.3 of the shaft 1114.1 by means of a pivotal connection 1154. The wrist member 1152 can pivot in the direction of arrows 1156 about the pivotal connection 1154. An end effector, generally indicated by reference numeral 1158, is pivotally mounted on an opposed end of the wrist member 1152. The end effector 1158 is in the form of, e.g., a clip applier for anchoring clips during a surgical procedure. Accordingly, the end effector 1158 has two parts 1158.1, 1158.2 together defining a jaw-like arrangement.

It will be appreciated that the end effector can be in the form of any desired surgical tool, e.g., having two members or fingers which pivot relative to each other, such as scissors, pliers for use as needle drivers, or the like. Instead, it can include a single working member, e.g., a scalpel, cautery electrode, or the like. When a tool other than a clip applier is required during the surgical procedure, the tool 1114 is simply removed from its associated arm and replaced with an instrument bearing the required end effector, e.g., a scissors, or pliers, or the like.

The end effector 1158 is pivotally mounted in a clevis, generally indicated by reference numeral 1119, on an opposed end of the wrist member 1152, by means of a pivotal connection 1160. It will be appreciated that free ends 1111, 1113 of the parts 1158.1, 1158.2 are angularly displaceable about the pivotal connection 1160 toward and away from each other as indicated by arrows 1162, 1163. It will further be appreciated that the members 1158.1, 1158.2 can be displaced angularly about the pivotal connection 1160 to change the orientation of the end effector 1158 as a whole, relative to the wrist member 1152. Thus, each part 1158.1, 1158.2 is angularly displaceable about the pivotal connection 1160 independently of the other, so that the end effector 1158, as a whole, is angularly displaceable about the pivotal connection 1160 as indicated in dashed lines in FIG. 34. Furthermore, the shaft 1114.1 is rotatably mounted on the housing 1153 for rotation as indicated by the arrows 1159. Thus, the end effector 1158 has three degrees of freedom of movement relative to the arm 1112, namely, rotation about the axis 1114.2 as indicated by arrows 1159, angular displacement as a whole about the pivot 1160 and angular displacement about the pivot 1154 as indicated by arrows 1156. By moving the end effector within its three degrees of freedom of movement, its orientation relative to the end 1114.3 of the shaft 1114.1 can selectively be varied. It will be appreciated that movement of the end effector relative to the end 1114.3 of the shaft 1114.1 is controlled by appropriately positioned actuators, e.g., electrical motors, or the like, which respond to inputs from the associated master control to drive the end effector 1158 to a required orientation as dictated by movement of the master control. Furthermore, appropriately positioned sensors, e.g., encoders, or potentiometers, or the like, are provided to permit the control system of the telesurgical system to determine joint positions as described in greater detail herein below.

Figure 35:
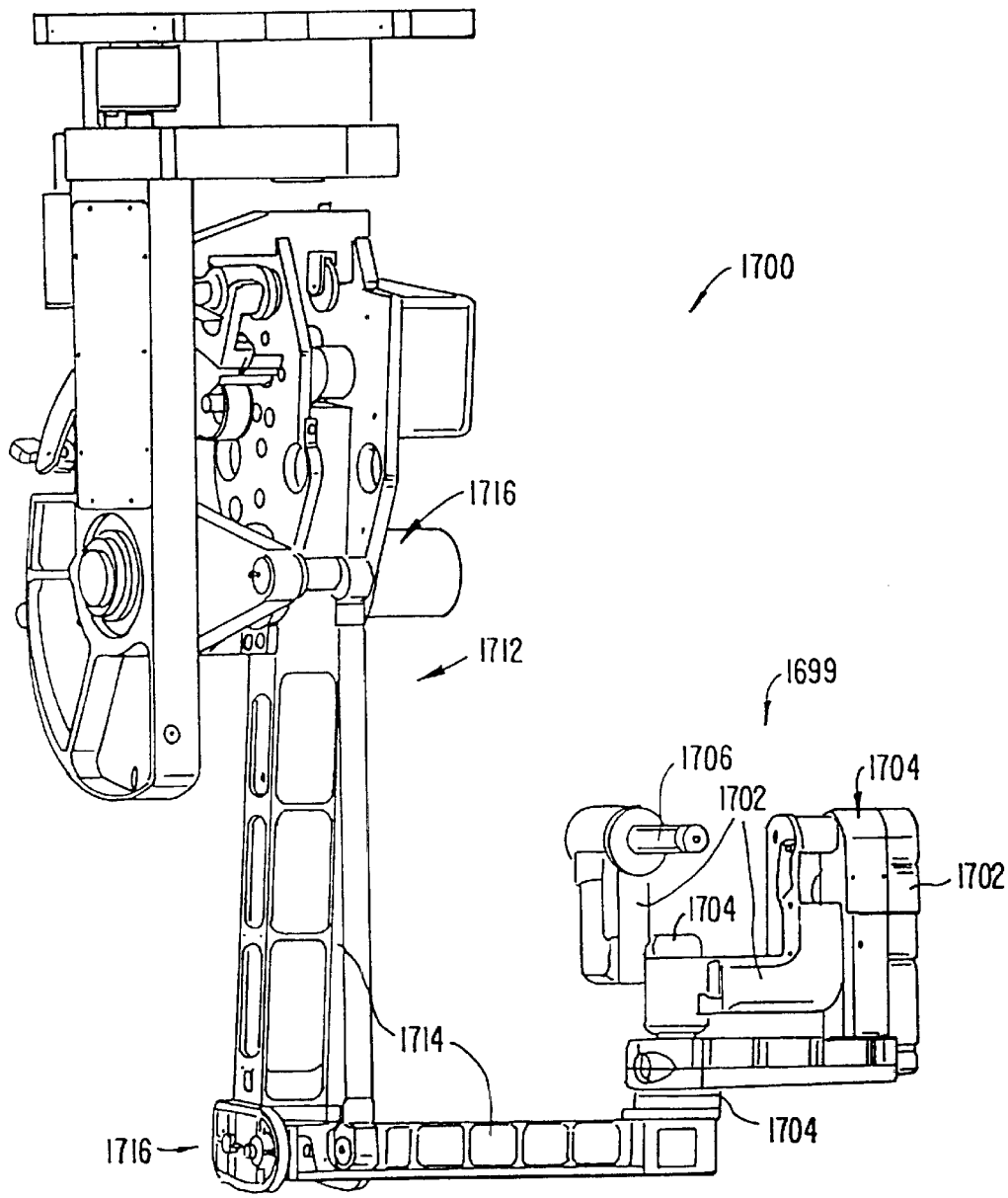
FIG. 35 shows a three-dimensional view of a master control device.

One of the master controls is indicated generally in FIG. 35 by reference numeral 1700. A hand held part or wrist gimbal of the master control 1700 is generally indicated by reference numeral 1699. Part 1699 has an articulated arm portion including a plurality of members or links 1702 connected together by pivotal connections or joints 1704. The surgeon grips the part 1699 by positioning his or her thumb and index finger over a pincher formation 1706. When the pincher formation 1706 is squeezed between the thumb and index finger, the fingers or end effector elements of the end effector 1158 close. When the thumb and index finger are moved apart the fingers of the end effector 1158 move apart in sympathy with the moving apart of the pincher formation 1706. The joints 1704 of the part 1699 are operatively connected to actuators, e.g., electric motors, or the like, to provide for, e.g., force feedback, gravity compensation, and/or the like. Furthermore, appropriately positioned sensors, e.g., encoders, or potentiometers, or the like, are positioned on each joint 1704 of the part 1699, so as to enable joint positions of the part 1699 to be determined by the control system.

The part 1699 is typically mounted on an articulated arm 1712. The articulated arm 1712 includes a plurality of links 1714 connected together at pivotal connections or joints 1716. It will be appreciated that also the articulated arm 1712 has appropriately positioned actuators, e.g., electric motors, or the like, to provide for, e.g., force feedback, gravity compensation, and/or the like. Furthermore, appropriately positioned sensors, e.g., encoders, or potentiometers, or the like, are positioned on the joints 1716 so as to enable joint positions of the articulated arm 1712 to be determined by the control system as described in greater detail herein below.

To move the orientation of the end effector 1158 and/or its position along a translational path, the surgeon simply moves the pincher formation 1706 to cause the end effector 1158 to move to where he wants the end effector 1158 to be in the image viewed in the viewer 1202. Thus, the end effector position and/or orientation is caused to follow that of the pincher formation 1706.

The actuators and sensors associated with the robotic arms 1112 and the surgical instruments 1114 mounted thereon, and the actuators and sensors associated with the master control devices 1700 are operatively linked in a control system. The control system typically includes at least one processor, typically a plurality of processors, for effecting control between master control device input and responsive robotic arm and surgical instrument output and for effecting control between robotic arm and surgical instrument input and responsive master control output in the case of, e.g., force feedback, or the like.

Figure 36:
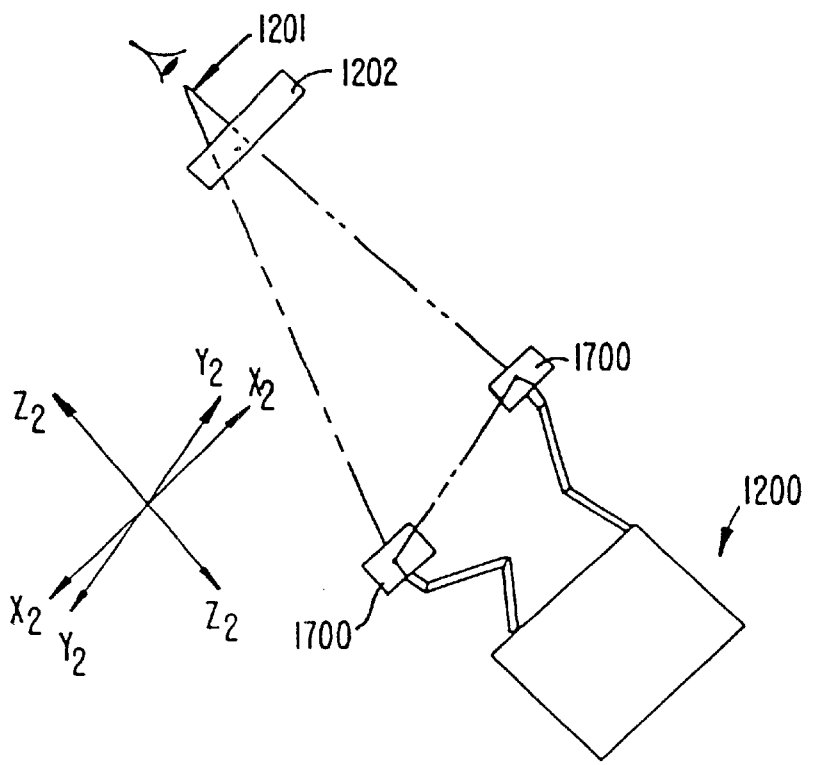
FIG. 36 shows a schematic three-dimensional drawing indicating positions of end effectors relative to a viewing end of an endoscope and the corresponding positions of master control devices relative to the eyes of an operator, typically a surgeon.
Figure 36:
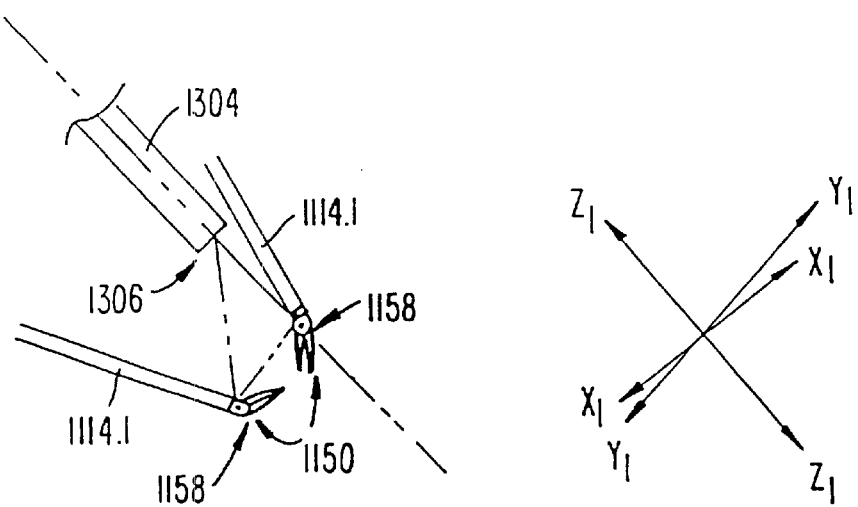

In use, and as schematically indicated in FIG. 36 of the drawings, the surgeon views the surgical site through the viewer 1202. The end effector 1158 carried on each arm 1112 is caused to perform positional and orientational movements in response to movement and action inputs on its associated master control. The master controls are indicated schematically at 1700, 1700. It will be appreciated that during a surgical procedure images of the end effectors 1158 are captured by the endoscope 1304 together with the surgical site and are displayed on the viewer 1202 so that the surgeon sees the responsive movements and actions of the end effectors 1158 as he or she controls such movements and actions by means of the master control devices 1700, 1700. The control system is arranged automatically to cause end effector orientational and positional movement as viewed in the image at the viewer 1202 to be mapped onto orientational and positional movement of the pincher formation 1706 of the master control as will be described in greater detail herein below.

The operation of the control system of the surgical apparatus will now be described. In the description which follows, the control system will be described with reference to a single master control 1700 and its associated robotic arm 1112 and surgical instrument 1114. The master control 1700 will be referred to simply as "master" and its associated robotic arm 1112 and surgical instrument 1114 will be referred to simply as "slave."

Figure 37:
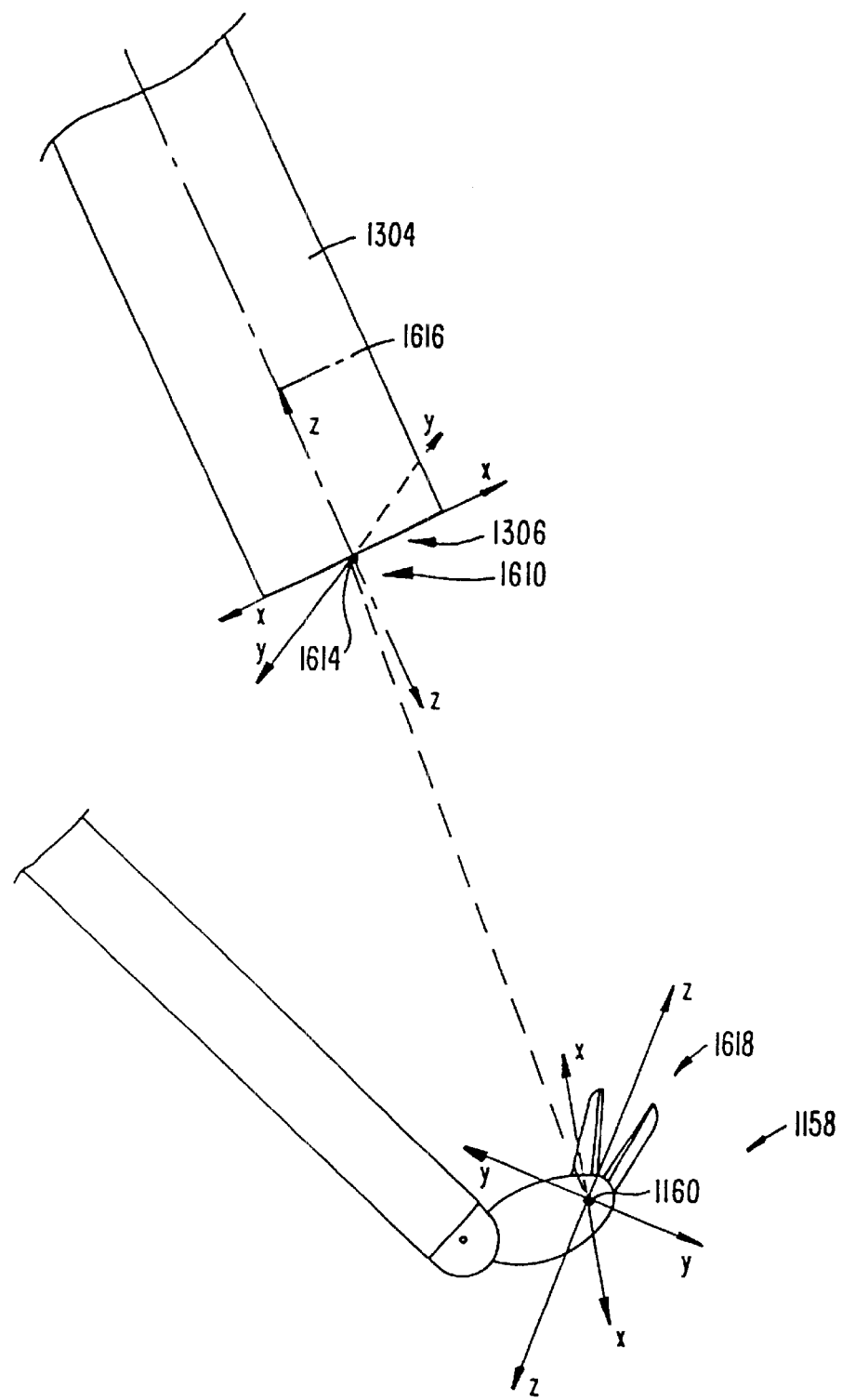
FIG. 37 shows a schematic three-dimensional view indicating the position and orientation of an end effector relative to a camera Cartesian coordinate reference system.

The method whereby control between master movement and corresponding slave movement is achieved by the control system of the surgical apparatus will now be described with reference to FIGS. 36 to 39 of the drawings in overview fashion. For a more detailed description of control between master movement and corresponding slave movement refer to Applicants' co-pending U.S. patent application Ser. No. 09/373,678, filed Aug. 13, 1999, which is fully incorporated herein by reference as if part of this specification. Control between master and slave movement is achieved by comparing master position and orientation in an eye Cartesian coordinate reference system with slave position and orientation in a camera Cartesian coordinate reference system. For ease of understanding and economy of words, the term "Cartesian coordinate reference system" will simply be referred to as "frame" in the rest of this specification. It is to be appreciated that the term "frame" should not be confused with a video signal frame when referred to in this specification. Accordingly, when the master is stationary, the slave position and orientation within the camera frame is compared with the master position and orientation in the eye frame, and should the position and/or orientation of the slave in the camera frame not correspond with the position and/or orientation of the master in the eye frame, the slave is caused to move to a position and/or orientation in the camera frame at which its position and/or orientation in the camera frame does correspond with the position and/or orientation of the master in the eye frame. In FIG. 37, the camera frame is generally indicated by reference numeral 1610 and the eye frame is generally indicated by reference numeral 1612 in FIG. 38.

When the master is moved into a new position and/or orientation in the eye frame 1612, the new master position and/or orientation does not correspond with the previously corresponding slave position and/or orientation in the camera frame 1610. The control system then causes the slave to move into a new position and/or orientation in the camera frame 1610 at which new position and/or orientation, its position and orientation in the camera frame 1610 does correspond with the new position and/or orientation of the master in the eye frame 1612.

It will be appreciated that the control system includes at least one, and typically a plurality, of processors which compute new corresponding positions and orientations of the slave in response to master movement input commands on a continual basis at a rate corresponding to the processing cycle rate of the control system. A typical processing cycle rate of the control system is about 1300 Hz. Thus, when the master is moved from one position to a next position, the corresponding movement of the slave to respond is computed at about 1300 Hz. Naturally, the control system can have any appropriate processing cycle rate depending on the processor or processors used in the control system.

The camera frame 1610 is typically positioned such that its origin 1614 is at the viewing end 1306 of the endoscope 1304. Conveniently, the z axis of the camera frame 1610 extends axially along a viewing axis 1616 of the endoscope 1304. Although in FIG. 37, the viewing axis 1616 is shown in coaxial alignment with a shaft axis of the endoscope 1304, it is to be appreciated that the viewing axis 1616 can be angled relative thereto. Thus, the endoscope can be in the form of an angled scope. Naturally, the x and y axes are positioned in a plane perpendicular to the z axis. The endoscope is typically angularly displaceable about its shaft axis. The x, y and z axes are fixed relative to the viewing axis of the endoscope 1304 so as to displace angularly about the shaft axis in sympathy with angular displacement of the endoscope 1304 about its shaft axis.

To enable the control system to determine slave position and orientation, a frame is defined on or attached to the end effector 1158. This frame is referred to as an end effector frame or slave tip frame, in the rest of this specification, and is generally indicated by reference numeral 1618. (Conveniently, the end effector frame 1618 has its origin at the pivotal connection 1160. However, depending on the type of end effector used, the origin may be offset relative to such a pivotal connection should an improved or more intuitive response between master input and slave output be achieved thereby). For the end effector as shown in the drawings, one of the axes, e.g. the z axis, of the frame 1618 is defined to extend along an axis of symmetry, or the like, of the end effector 1158. Naturally, the x and y axes then extend perpendicularly to the z axis. It will be appreciated that the orientation of the slave is then defined by the orientation of the frame 1618 having its origin at the pivotal connection 1160, relative to the camera frame 1610. Similarly, the position of the slave is then defined by the position of the origin of the frame at 1160 relative to the camera frame 1610.

Figure 38:
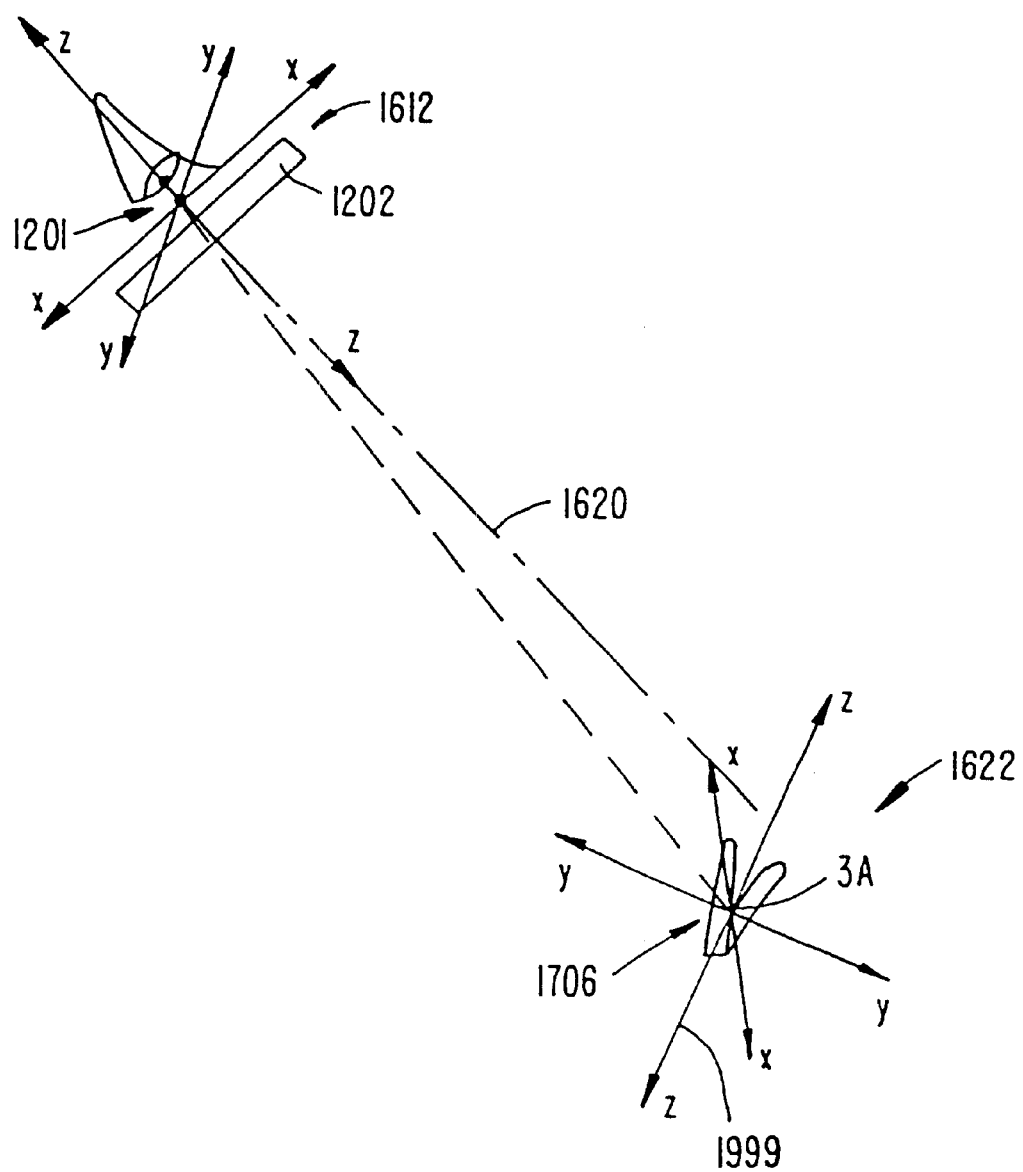
FIG. 38 shows a schematic three-dimensional view indicating the position and orientation of a pincher formation of the master control device relative to an eye Cartesian coordinate reference system.

Referring now to FIG. 38 of the drawings, the eye frame 1612 is typically chosen such that its origin corresponds with a position 1201 where the surgeon's eyes are normally located when he or she is viewing the surgical site at the viewer 1202. The z axis typically extends along a line of sight of the surgeon, indicated by axis 1620, when viewing the surgical site through the viewer 1202. Naturally, the x and y axes extend perpendicularly from the z axis at the origin 1201. Conveniently, they axis is chosen to extend generally vertically relative to the viewer 1202 and the x axis is chosen to extend generally horizontally relative to the viewer 1202.

To enable the control system to determine master position and orientation within the viewer frame 1612, an appropriate point, e.g., point 3A, is chosen on the master to define an origin of a master or master tip frame, indicated by reference numeral 1622. It will be appreciated that the point relative to the master at which the origin of the master frame 1622 is attached is chosen to enhance intuitive response between master and slave and can thus be at any appropriate location relative to the master. Conveniently, the axis of the master frame 1622 on the master extends along an axis of symmetry of the pincher formation 1706 which extends coaxially along a rotational axis 1999. The x and y axes then extend perpendicularly from the rotational axis 1999 at the origin 3A. Accordingly, orientation of the master within the eye frame 1612 is defined by the orientation of the master frame 1622 relative to the eye frame 1612. The position of the master in the eye frame 1612 is defined by the position of the origin 3A relative to the eye frame 1612.

Figure 39:
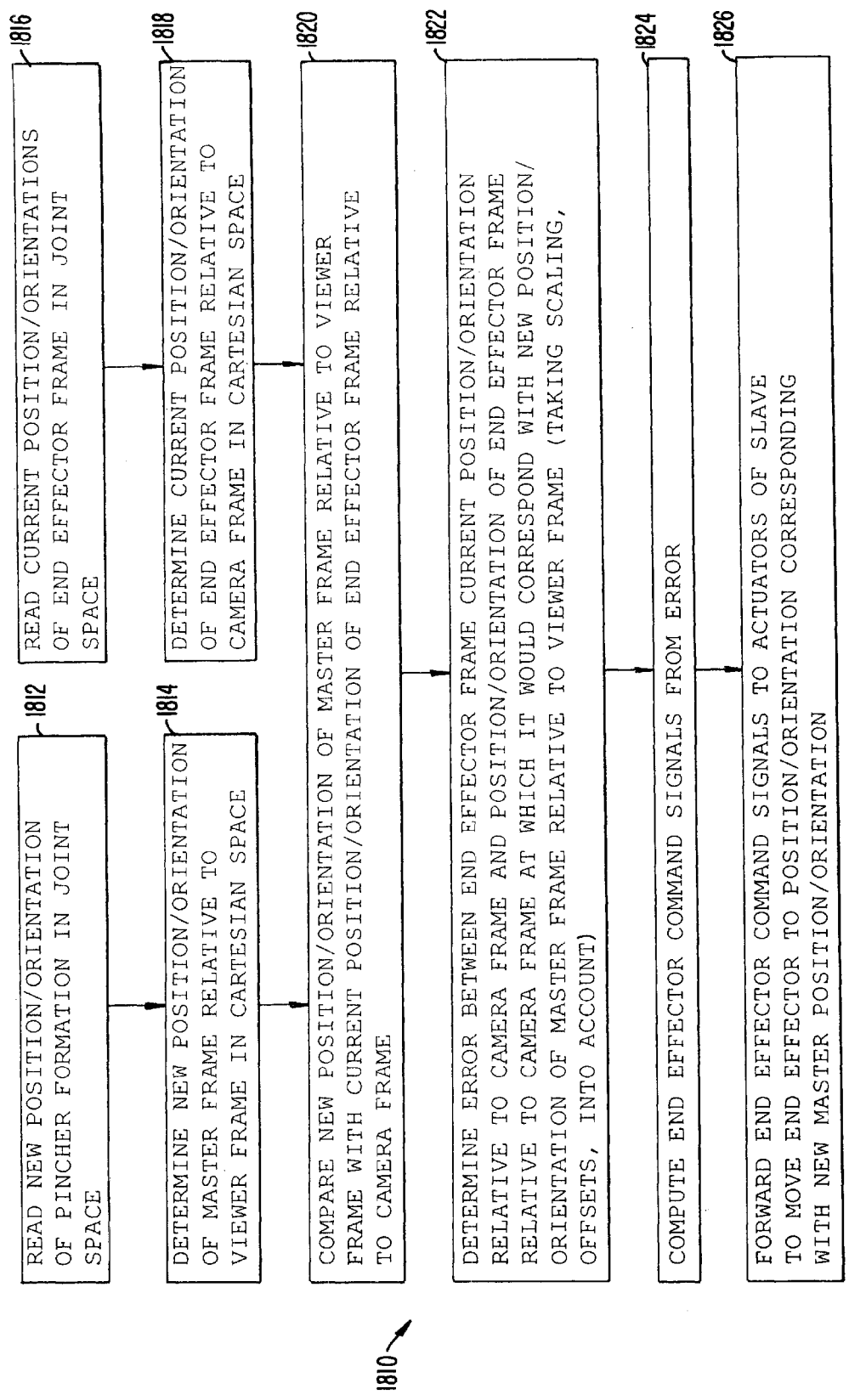
FIG. 39 shows a block diagram indicating control steps of a control system of the surgical system in accordance with the invention, the control system being arranged to effect control between master input and slave output.

Referring now to FIG. 39 of the drawings, a control system employed to cause the slave to track master input is generally and schematically indicated by reference numeral 1810. The control method as indicated by reference numeral 1810 assumes that the master and slave were at corresponding positions and the master has been moved into a new position and orientation. Accordingly, since the new position and orientation of the pincher formation 1706 relative to the camera frame 1610 no longer corresponds with the position and orientation of the end effector 1158 relative to the camera frame 1610, the end effector 1158 is caused to move into a corresponding new position and orientation relative to the camera frame 1610 at which it does correspond with the new position and orientation of the pincher formation 1706 relative to the viewer frame 1612.

The new position and orientation of the pincher formation 1706 is read in joint space as indicated by reference numeral 1812. This is achieved by the processor by means of the sensors operatively associated with the joints on the master. From this joint space information, which determines the joint positions of the master, a corresponding new position and orientation of the master frame 1622 relative to the eye frame 1612 is determined in Cartesian space as indicated by reference numeral 1814. In similar fashion, the current position and orientation of the end effector 1158 in joint space is read as indicated by reference numeral 1816. From this information the current position and orientation of the end effector frame 1618 relative to the camera frame 1610 in Cartesian space is computed, as indicated by reference numeral 1818. The new position and orientation of the master frame 1622 relative to the eye frame 1612 in Cartesian space is then compared with the current position and orientation of the end effector frame 1618 relative to the camera frame 1610 as indicated at 1820. An error between the end effector frame 1618 current position and orientation relative to the camera frame 1610 and the position and orientation of the end effector frame 1618 relative to the camera frame 1610 at which it would correspond with the new position and orientation of the master frame 1622 relative to the eye frame 1612 is then computed, as indicated at 1822.

It will be appreciated that master orientational and positional movement variation need not necessarily correspond proportionally with responsive end effector orientational and positional movement variation. Accordingly, the system is typically arranged to provide for scaling so that the translational movement, for example, of the end effector in response to translational movement input on the master is scaled e.g., at a ratio 1 to 2, or the like.

From the error, corresponding end effector command signals are computed as indicated at 1824. The end effector command signals are then forwarded to the slave actuators to cause them to move the end effector 1158 to a new position and orientation relative to the camera frame 1610 at which it corresponds with the new master position and orientation relative to the eye frame 1612, as indicated at 1826.

It will be appreciated that the control system performs the steps indicated in FIG. 39 on a continual basis generally at the processing cycle rate e.g., 1300 Hz. One method which could be employed to perform a surgical procedure on a beating heart using the telesurgical apparatus described with reference to FIGS. 29 to 39, will now be described with reference to FIGS. 40 to 43 of the drawings.

This method in accordance with the invention uses image processing to derive appropriate command signals to be forwarded to the actuators of the slave so as to cause the actuators to drive the end effector so as generally to. track motion of a surgical site on the beating heart at which it is desired to perform a surgical procedure. Image processing is used also to still an image of the surgical site displayed on the viewer at the operator station, so that an apparently stationary or "still" image is displayed to the surgeon.

Figures 1, 40A:
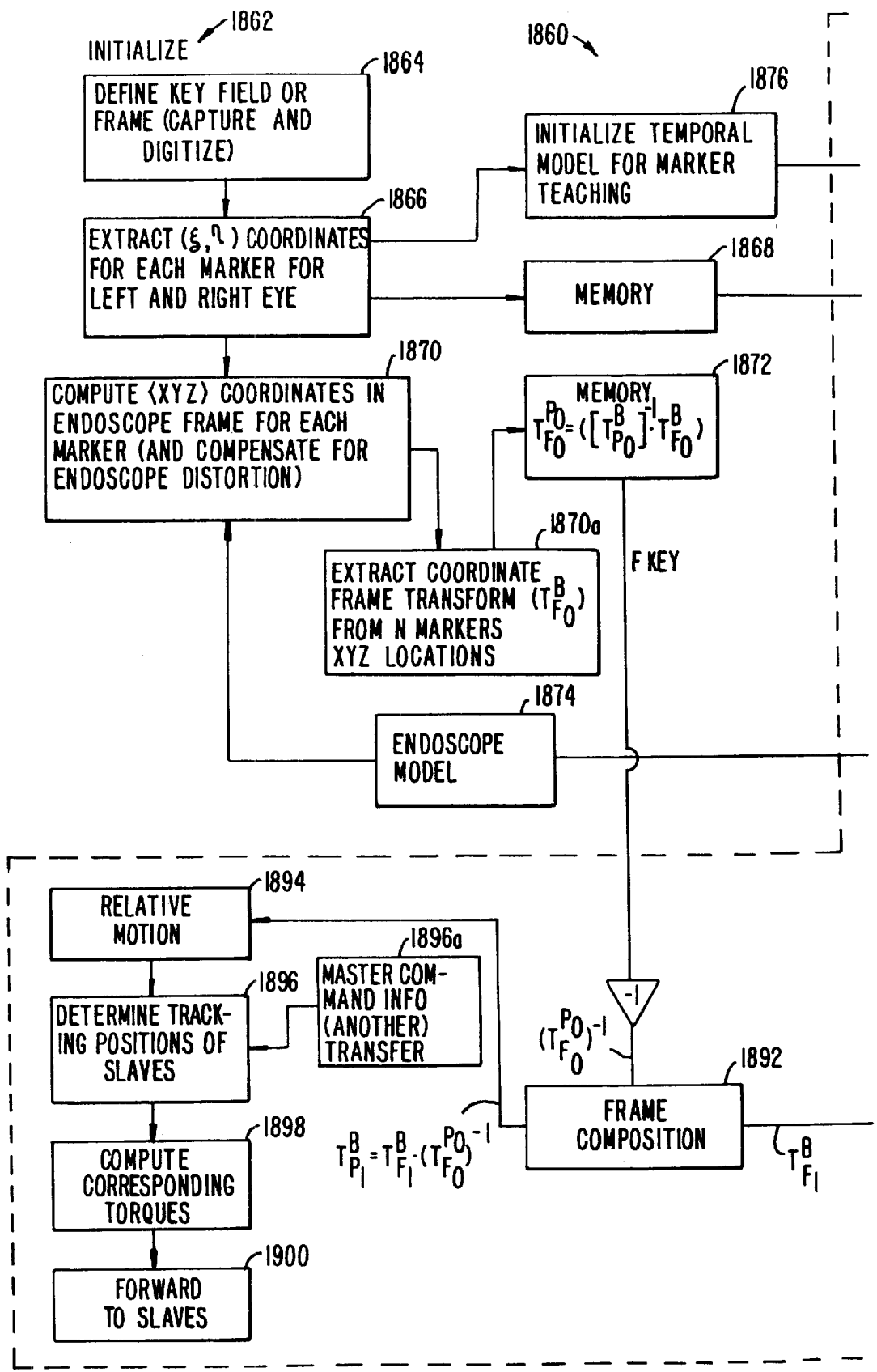
FIG. 40A shows a block diagram indicating control steps of another control system of the surgical system, the control system being arranged to cause end effectors of the surgical system to track motion of a surgical site on a beating heart and to provide a generally "still" image of the moving surgical site at a viewer.
Figures 2, 40A:
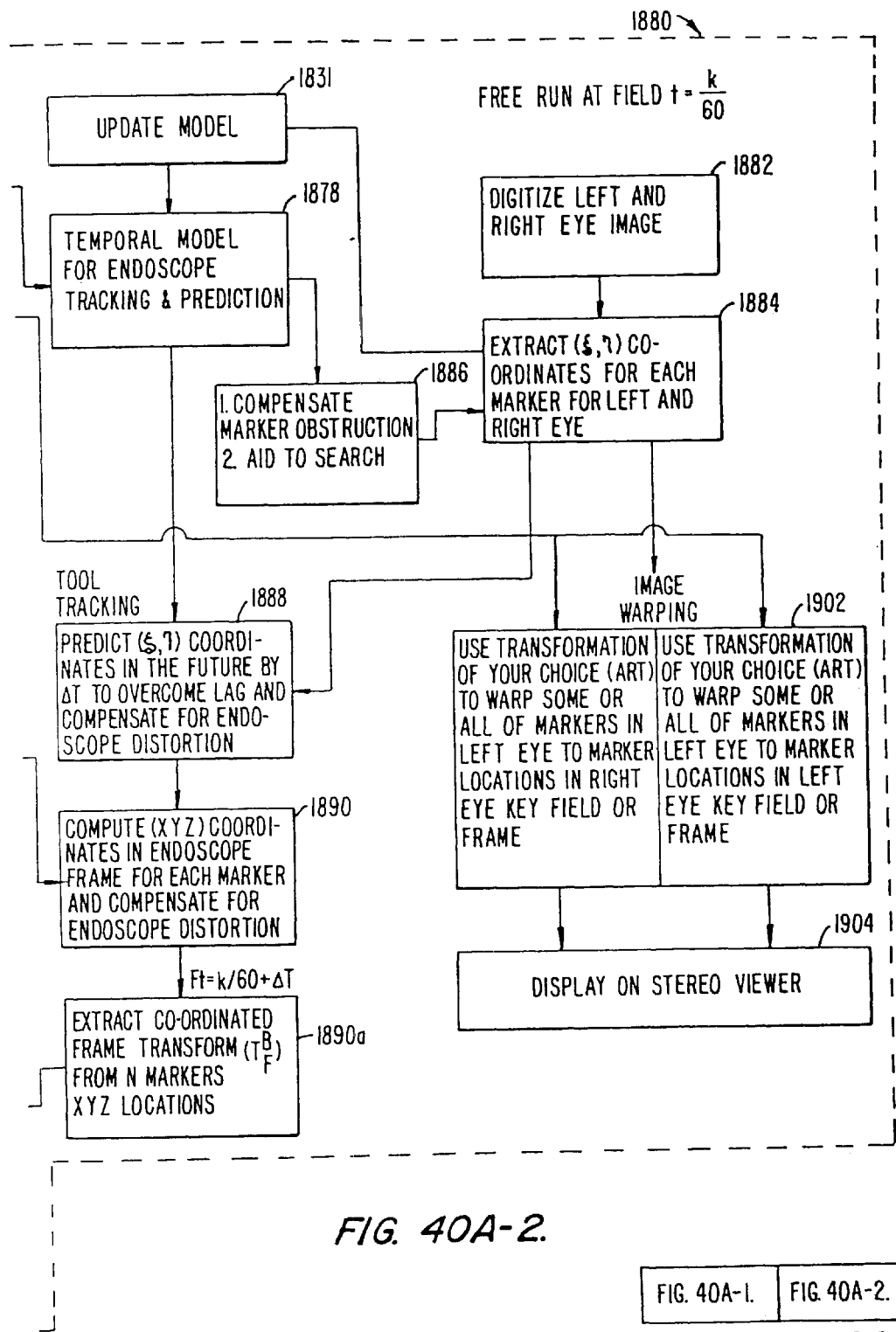
Figure 40B:
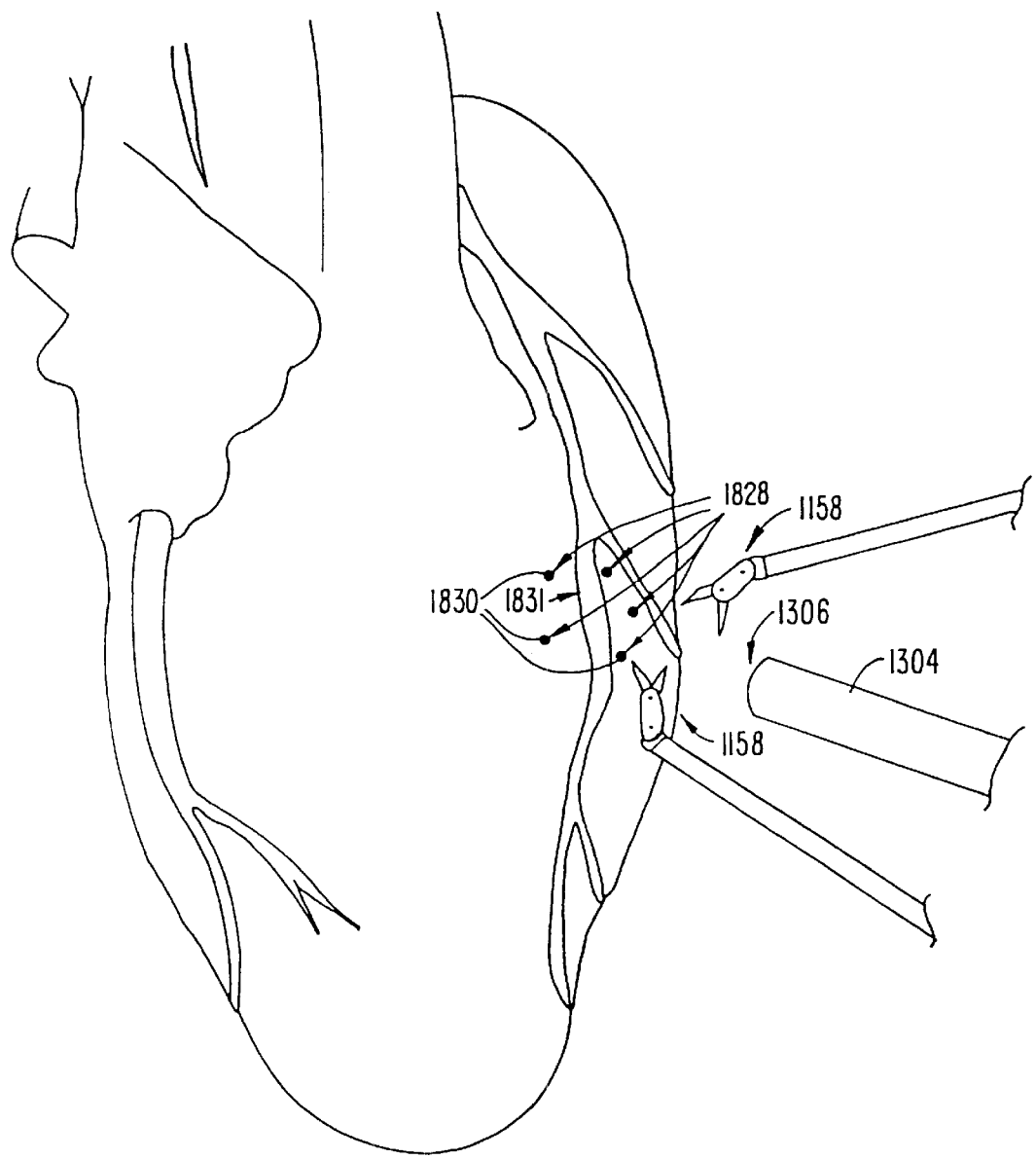
FIG. 40B shows a schematic three-dimensional view of end effectors and an endoscope of the surgical system positioned in close proximity to a moving surgical site on a beating heart.

Referring initially to FIG. 40B, the method for performing a surgical procedure on a beating heart includes identifying an appropriate number, in this case 5, of discrete locations as indicated by reference numeral 1828. Fiducials or markers 1830 are then positioned at the discrete locations 1828 to enhance the system's ability accurately to monitor surgical site movement. Advantageously, the markers 1830 are positioned in a non-uniform arrangement, i.e., they are not equidistantly spaced along a circular circumference. Such a non-uniform positioning of the markers 1830 enhances the ability to determine command signals through image processing especially in the case of rotational shift of the markers in sympathy with surgical site movement. The markers 1830 are typically secured on the heart surface generally to surround the surgical site which is indicated at 1831. Alternatively, for example, the markers may simply be placed on the heart surface and held in place by surface tension due to the presence of fluid on the heart surface. Accordingly, the locations 1828 are chosen so that the surgical site is positioned within a space defined between the markers 1830.

It will be appreciated that this method for performing a surgical procedure on a beating heart need not necessarily involve securing markers at the discrete locations. Instead, readily identifiable locations can be selected which naturally surround the surgical site. However, it has been found that using markers which have a distinctive color so as to stand out relative to the natural occurring color at the surgical site enhances image processing and enables the method to be performed with greater accuracy. The markers are typically spherical in shape and are typically distinctively colored. It has been found that markers which are colored green or yellow provide satisfactory results. Naturally, any appropriate color can be chosen depending on the surrounding color of the surgical site. However, the color should be selected so as to stand out relative to the natural color of the surgical site so as to provide sufficient contrast thereby to enhance image processing. It will be appreciated that for IR reflectors or sources, or the like, color may not be as important as is the case above where passive "visual wavelength" markers are used.

The endoscope 1304 is shown in a position where the viewing end 1306 is directed at the surgical site 1831 so as to capture an image of the surgical site and the fiducials 1830. The endoscope 1304 is typically positioned by passing it through a relatively small incision in the chest of the patient. Similarly, the end effectors 1158 are passed through relatively small incisions in the chest of the patient into positions in close proximity to the surgical site 1831.

Figure 43:
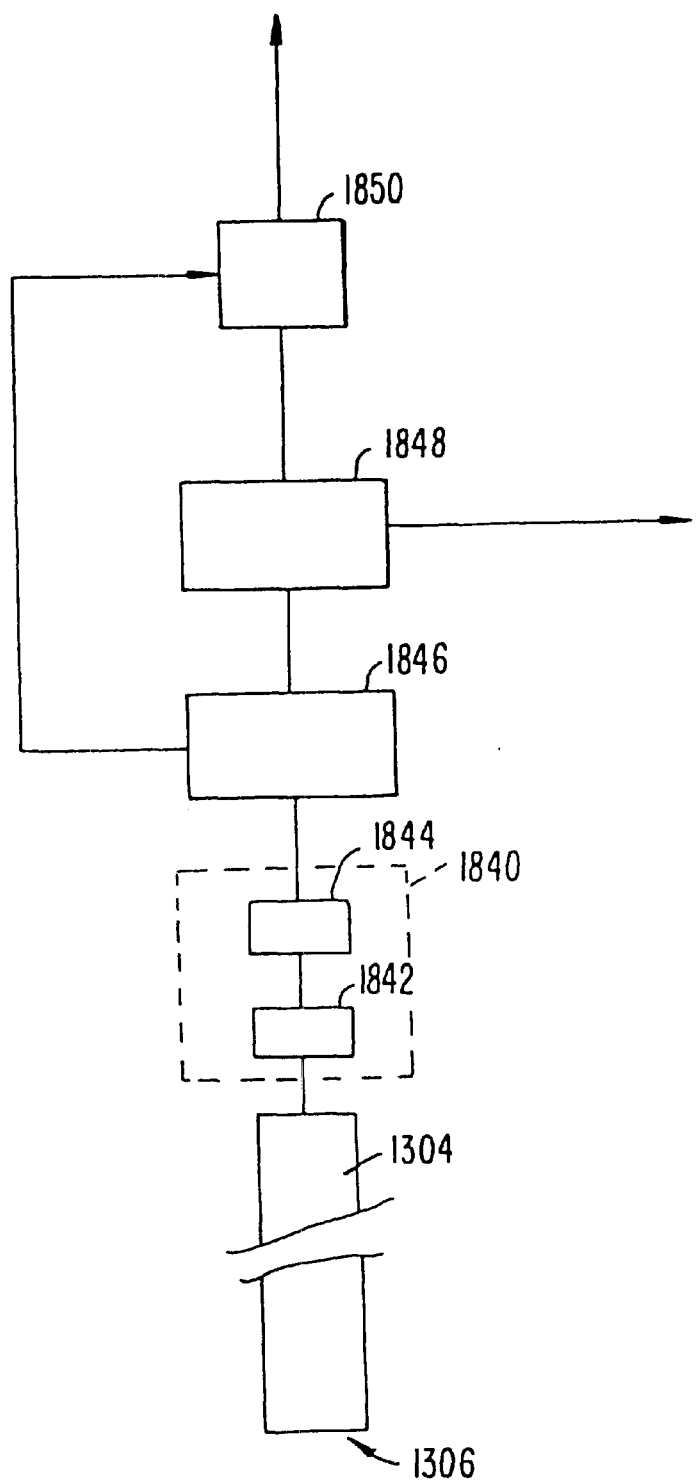
FIG. 43 shows part of an imaging system of the surgical system.

Referring now to FIG. 43 of the drawings, the endoscope, in this case a stereo endoscope 1304, is operatively connected to a camera head 1840. The camera head 1840 typically includes a Charge Couple Device 1842 operatively connected to a Camera Control Unit 1844 for each of a left optical channel and a right optical channel of the endoscope 1304. The camera head 1840 is operatively connected to a digitizer 1846. The digitizer 1846 is operatively connected to a processor at 1848. The processor 1848 is operatively connected to a warp engine 1850.

Referring now to FIG. 40A, a method of performing surgery on a beating heart will now be described in greater detail. A flow diagram showing steps involved in performing a surgical procedure on a surgical site on a beating heart is generally indicated by reference numeral 1860.

In the method indicated by reference numeral 1860 the motion of the surgical site 1831 between the markers 1830 is monitored by image processing techniques. After the endoscope 1304 and the end effectors 1158 have been introduced to the surgical site 1831 defined between the fiducials 1830 as indicated in FIG. 40B, the control system can be initialized so that the desired surgical procedure can be performed at the surgical site 1831 while the heart is beating. When initialized, the system monitors motion of the surgical site and computes associated tracking command signals which are forwarded to the actuators of the slaves so that the end effectors 1158 are driven generally to track surgical site motion. Furthermore, the system provides a generally stationary image at the viewer 1202 so that the operator perceives the surgical site after data associated with the image have been tailored to compensate for motion of the surgical site. In this way, the end effectors 1158 are caused to be generally stationary relatively to the surgical site and the operator is presented with an image of a generally stationary surgical site on the viewer 1202. Thus, when the operator inputs master control commands at the master controls 1700, 1700, while looking at the image of the surgical site at the viewer 1202, the operator is presented with an operating environment simulating an operating environment in which a surgical procedure is performed on a stationary surgical site. It will be appreciated that to move the end effectors 1158, the masters 1700 are moved in the manner as already described above with reference to FIG. 39 save that the end effector command signals input at the master controls 1700, 1700 are super-imposed on the end effector tracking command signals generated in accordance with the method shown in FIG. 40A which is described in greater detail below.

Initially, the control system is initialized by means of any appropriate input. Such an appropriate input can be in the form of a foot pedal, voice command, depressible button, or the like, located at the control console 1200, with reference to FIG. 29, and as indicated by reference numeral 1862 in FIG. 40A. Once the system is initialized, a key field or frame is captured and digitized as indicated at 1864. This is typically performed by the operator at the console 1200 by means of the appropriate input. The operator typically does this by viewing the surgical site whilst in motion as displayed on the viewer 1202 and then actuating the input when the image displayed on the viewer 1202 is appropriate. When the appropriate input has been actuated an image of the surgical site is presented to the operator at the viewer 1202, the image having been changed to compensate for surgical site motion to provide a generally stationary image. If the image displayed at the viewer 1202 after actuation of the appropriate input is inappropriate, the operator can actuate the input again to release the defined key field or frame so as to redefine the key field or frame by reactuating the input. This procedure can be repeated by the operator until the operator is satisfied with the image of the surgical site displayed on the viewer 1202. Instead, or in addition, the system can include an appropriate software routine which automatically centers a centroid between the fiducials 1830 with a generally centrally disposed location on the viewer 1202 upon actuation of the input.

It will be appreciated that when the key field or frame is thus defined, the left and right optical images captured by the endoscope thereafter are passed through the CCDs 1842 and CCUs 1844 and then to the processor 1846. At the processor 1846, coordinates ($\xi$, $\eta$) for each fiducial 1830 for both the left and the right channels are determined, as indicated at 1866. It will be appreciated that these coordinates are determined by the processor 1846. Accordingly, when the key field or frame is defined, associated digital information typically arranged in a digital array for each of the left and right images, is analyzed to determine the location of the digital information corresponding to the fiducials 1830. Once these coordinates (ξ, η) have been determined, they are stored in a memory as indicated at 1868.

Once the coordinates (ξ, η) for each marker for both the left and the right paths have thus been determined, the xyz coordinates for each marker relative to the camera frame 1610, as can best be seen in FIGS. 37 and 38, is computed. This is readily achieved since the endoscope 1304 is a stereo endoscope and since the coordinates (ξ, η) are known for both the left and the right eye channels. Accordingly, using conventional computing techniques and geometric and trigonometric relationships the xyz coordinates for each marker relative to the camera frame 1610 can be computed, as indicated at 1870. Compensation for endoscope distortion can typically be factored into the determination of the xyz co-ordinates from the digital data. Such compensation can involve endoscope alibration as described herein below under the heading "CALIBRATION".

As indicated at 1870*a*, a frame is then extracted or attached relative to the marker locations in xyz, as indicated at 1870*a*. Such a frame can be attached to the marker xyz locations in any appropriate manner. For example, a center or centroid of the markers can be determined and the frame can be attached such that its origin is attached to the centroid. An appropriate axis of the frame, such as the x axis, can then be arranged relative to the marker xyz locations so as to be fixed. For example, the x axis can be attached so as to extend through a specific one of the marker locations. A plane can typically be modeled to the marker xyz locations, the z axis, for example, then extending perpendicularly relative to the plane. A co-ordinate transform associated with the attached frame is then stored in a memory as indicated at 1872.

It will be appreciated that trigonometric and geometric relationships typically used to compute the xyz coordinates of each marker relative to the camera frame 1610 are typically stored in the form of an endoscope model indicated at 1874. Thus, once the (ξ, η) coordinates for each marker in the left and right channel has been determined, the endoscope model 1874 is employed to compute the xyz coordinates for each marker relative to the camera frame 1610.

Once the (ξ, η) coordinates have been determined at 1866, a temporal model for marker tracking is initialized as indicated at 1876. The temporal model is used to record motion history for each marker as discussed in greater detail below. Once the temporal model has been initialized at 1876 the temporal model starts to record actual marker coordinates (ξ, η) for both the left and right channels so as to form data corresponding to marker motion history for both the left and right channel. It will be appreciated that auxiliary information can be used to augment the temporal model at 1878. For example, an ECG can be linked to the temporal model so that data relating to marker coordinates (ξ, η) augmented by ECG information can be obtained. Instead of recording data, the model can be updated continually using information relating to current marker location as indicated at 1831 and as described herein below.

It will be appreciated that the optical information passed through the endoscope is sequentially sampled. The sample rate is typically in the region of 1/60th of a second. Accordingly, the rate used to monitor marker motion is 60 hertz as indicated at 1880. After initialization at 1862 the optical information passing through the endoscope 1304 and as read by the CCD is digitized sequentially at 60 hertz as indicated at 1882. Each time the optical information is digitized, corresponding (ξ, η) coordinates for each marker in each of the left and right eye channels is determined as indicated at 1884. As the coordinates (ξ, η) are sequentially determined, the temporal model at 1878 is continually updated with this information as already mentioned and as indicated at 1831.

In use, typically five fiducials or markers 1830 are used. It will be appreciated that any appropriate number of markers can be used. However, the greater the number of fiducials used, the greater the burden on the processor becomes. It has been found that using three markers can provide adequate results. However, to enable improved image stilling while catering for noise, and possible blocking of markers by the end effectors during the course of a surgical procedure, at least five markers is preferred.

Returning to FIG. 40A, and as indicated at 1886, the temporal model at 1878 is operatively associated with the step 1884 of determining (ξ, η) coordinates for each marker in both the left and the right channel so that such coordinates can be estimated from the temporal model data should one or more of the markers become obstructed or obscured from view, for example. Furthermore, temporal model data derived from the temporal model 1878 is used to assist in the extraction of the coordinates (ξ, η) for both the left and right eye channel. Accordingly, by using the temporal model 1878 the approximate positions of the (ξ, η) coordinates can be estimated so that only a corresponding region needs to be analyzed to determined the actual coordinates (ξ, η). It will be appreciated that this procedure decreases processing time in that not all the digitized data need to be analyzed, but only discrete regions where the digital information relating to the marker coordinates are expected to be.

As indicated at 1888, data associated with actual (ξ, η) coordinates for each marker for both the left and the right eye channel are compared with the temporal model 1878 after the temporal model 1878 has been updated with the current (ξ, η) coordinates so that predictive (ξ, η) coordinates can be determined. Accordingly, at 1888 a future anticipated (ξ, η) coordinate for each of the left and the right eye channels is predicted for a time in the future. Statistical calculations can be performed based on (ξ, η) coordinate history to determined anticipated (ξ, η) coordinates at a lead time interval of time=k/60+ΔT, where k is an integer counter representing consecutive warped fields. The value of ΔT is predetermined and can be derived from system lag or delay factors such as processing time, mechanical inertia of moving components, and the like.

Figure 41A:
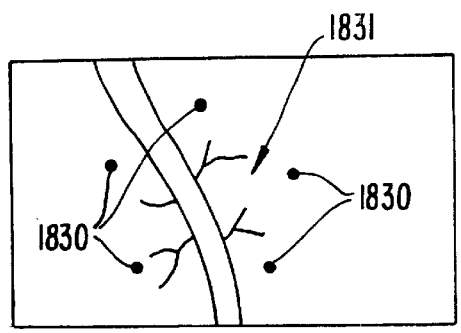
FIGS. 41A to 41D show sequential images of the moving surgical site of FIG. 40B as displayed on a viewer of the surgical system.
Figure 41B:
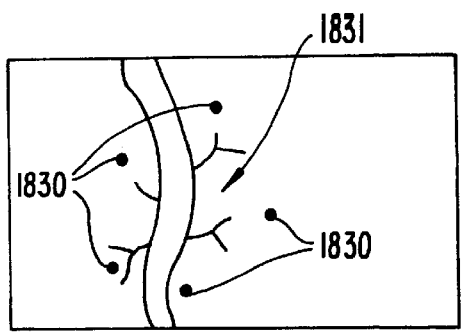
Figure 41C:
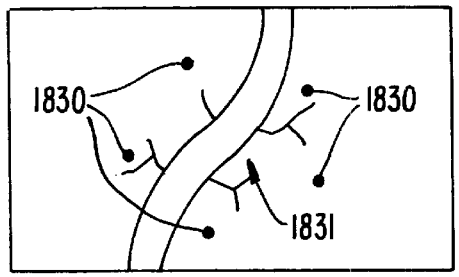
Figure 41D:
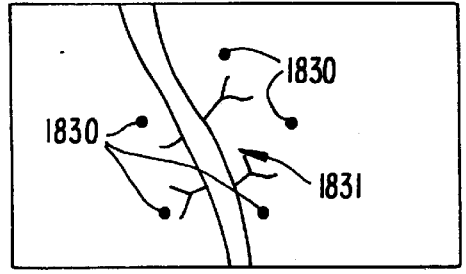

Referring to FIGS. 41A to 41D, four sequential images are shown indicating movement of the surgical site 1831 from a first position in FIG. 41A to a next position shown in FIG. 41D.

Figure 42A:
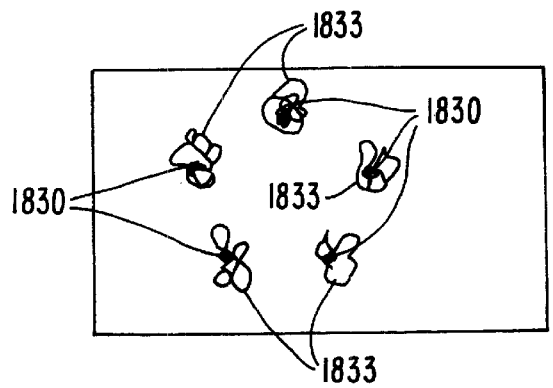
FIG. 42A shows a schematic diagram indicating paths followed by markers or fiducials, positioned around the surgical site of FIGS. 41A to 41D, in response to the moving surgical site.

FIG. 42 schematically shows movement paths, as indicated by reference numeral 1833, of each marker 1831 over time.

Figure 42B:
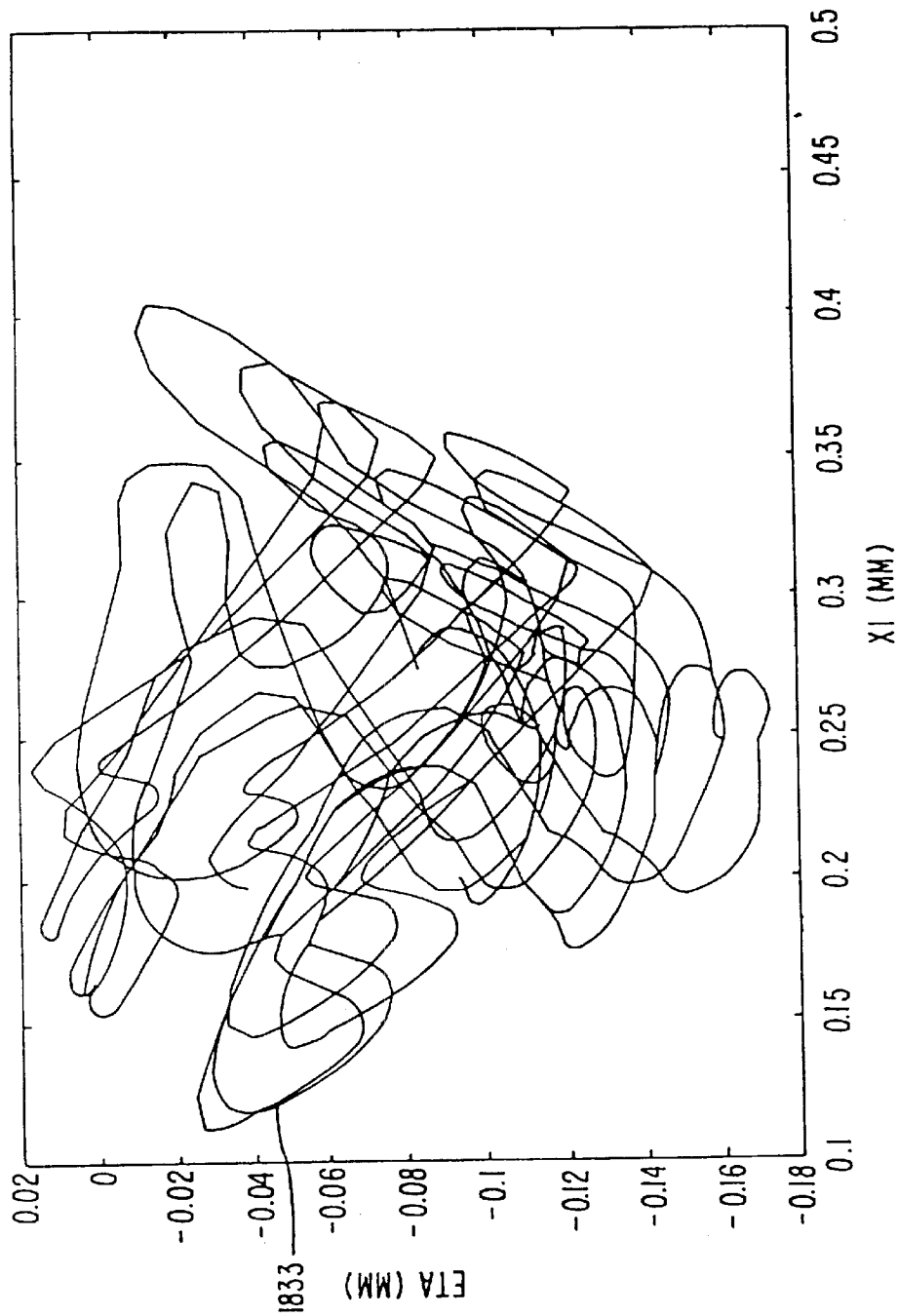
FIG. 42B shows, at an enlarged scale, the path of one of the markers as shown in FIG. 42A.

FIG. 42B shows a typical movement path of a single marker. It will be seen that the movement of the marker is generally periodic and generally follows a similar cyclical path. It will be appreciated that in view of the generally uniform periodic path, estimation of where the marker will be at a certain time=k/60+ΔT in the future, based on current marker position, can be made on a statistical basis, for example.

Once the predicted (ξ, η) coordinates for both the left and the right eye channel have been determined at time=k/60+

ΔT, corresponding xyz coordinates of each marker for the left and right eye channels is computed at 1890 by employing the endoscope model 1874.

Computation of the motion of the end effector relative to the surgical site will now be described.

The predicted xyz coordinates for each marker is derived at 1890. This information is then forwarded to 1890*a* where a co-ordinate frame is extracted from the marker xyz locations, in similar fashion with reference to the step at 1870*a*. An associated transform is thus determined. The transform from 1890*a* is then compared with the transform from 1872 at 1892. The positional and orientational deviation between the two frames can then be computed using the transforms. This typically takes translation as well as rotation into account, as described in greater detail with reference to FIG. 48 herein below. Thus, typically three variables relating to translation, and three variables coded as a 3 by 3 rotation matrix relating to orientation, are computed which are required to bring the one coordinate frame into the position and orientation of the other. In this way, the position and orientation of the coordinate frame corresponding to the predicted xyz coordinates from 1890 can be compared to a frame defined by the xyz coordinates corresponding to the defined key field. The relative position and orientation of the surgical site at time=k/60+ΔT relative to the key field is thus determined by computing a Cartesian error (relative position and orientation). This relative position and orientation is indicated at 1894. From this information the tracking command signals in order to move the end effectors in sympathy with the surgical site is determined at 1896. Corresponding torques are then computed at 1898 which are then forwarded to the slave actuators as indicated at 1900 to cause the actuators to move the end effectors so as to track surgical site motion. As indicated at 1896*a*, master input can be superimposed on the tracking signals to cause the end effector to move relative to the surgical site.

The preceding description described regulating end effector motion to track surgical site motion. Regulation of image information to cause a generally still image to be displayed at the viewer will now be described.

Regulating the digital information relating to the captured images of the surgical site so as to compensate for surgical site motion thereby to provide a relatively "still" image at the viewer is indicated at 1902. At 1902, a transformation is employed to warp some or all of the marker locations in the current left and right channel derived from 1884 respectively to the marker locations defined by the right and left key field or frame locations at 1868. This is typically achieved by means of an appropriate model having free parameters. The free parameters are adjusted so as to move the current $(\xi, \eta)$ coordinates into positions generally conforming to the corresponding co-ordinates in the key-field. This can be achieved using conventional "optimal estimation" techniques. Thus, the monitored current $(\xi, \eta)$ coordinates derived at 1884 are input to the model and compared with the corresponding $(\xi, \eta)$ coordinates of the markers in the selected key field at 1868 to determine a general rule that warps the markers to their key positions.

In solving for free parameters for transformation so that some or all markers are warped, the transformation becomes the rule (map, transformation, function) to warp all pixels to their new locations, i.e., the transformation employs a model that is fit to the data. Because the markers at each subsequent field are typically mapped as closely as possible (within the freedom of the mapping rule) to their locations at the key field, it is apparent that the stereo separation will normally be mapped likewise as a result. Thus, stereo depth perception of the markers should normally be maintained for all fields.

Figure 44A:
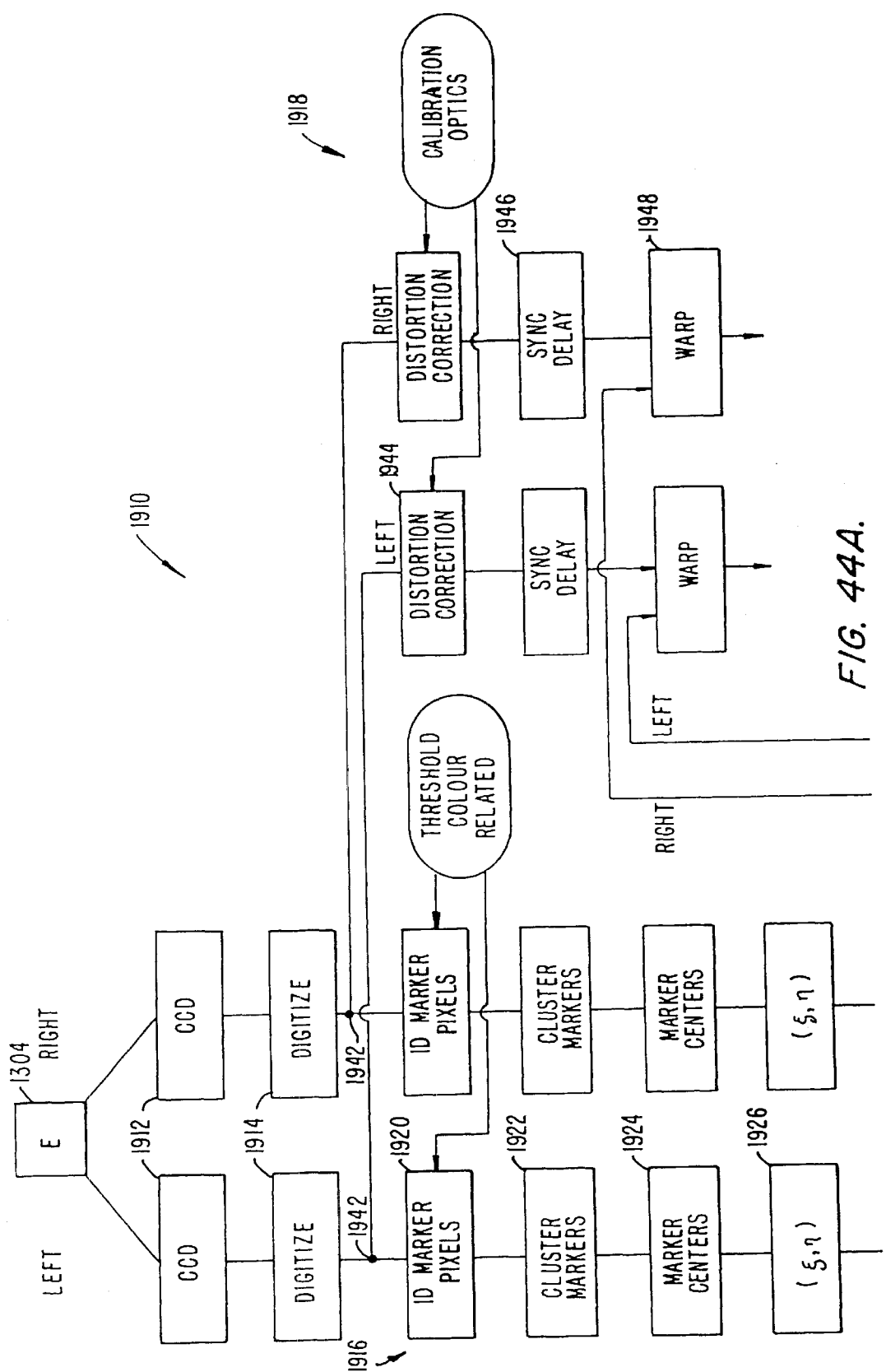
FIG. 44 shows control steps of another control system of the surgical system, the control system being arranged to permit a surgical procedure to be performed on a beating heart.

Referring now to FIG. 44 of the drawings, steps in a system in accordance with the invention whereby a surgical procedure can be performed on a beating heart will now be described. Following the description of the system with reference to FIG. 44, certain of the steps are described in greater detail under separate headings. The system is generally indicated by reference numeral 1910. In FIG. 44 like reference numerals are used to designate similar parts unless otherwise stated.

The endoscope 1304 defines a right and a left optical channel. Optical images pass along the right and the left optical channels to corresponding CCDs 1912. The left and the right optical information captured by the CCDs 1912 are then separately digitized as indicated at 1914. Once the optical information relating to the right and the left optical channels has been digitized at 1914, the digital information is passed along one path indicated at 1916 and another path indicated at 1918. In the path 1916, the digital information for each of the left and the right channels is analyzed to determine general locations of the digital pixels corresponding to the markers. (Refer to FIG. 40B). This can be achieved in accordance with digital processing techniques. Accordingly, the pixel values relating to the distinctively colored markers is searched for using an appropriate threshold value, for example. This step is indicated at 1920. Once the positions of the markers in the digital information relating to the left and the right channels has generally been determined at 1920, the digital information surrounding each marker is clustered as indicated at 1922. Accordingly, a region containing the digital information for each marker is selected. It will be appreciated that only regions including the markers are selected in this fashion so as to decrease processing time since only the digital information in the selected regions is analyzed as opposed to all the digital information relating to the left and the right images, respectively. When the digital information has been clustered at 1922, the digital information in each region is processed to determine the locations of each marker center as indicated at 1924. Accordingly, the marker centers in digital space, namely at coordinates $(\xi, \eta)$, is determined, as indicated at 1926. Thus, at 1926, the centers of each marker in each of the right and left channels relative to the rest of the digital information is determined.

Once the $(\xi, \eta)$ locations have been determined in this fashion, the $(\xi, \eta)$ information is typically corrected to compensate for distortion. It will be appreciated that factors such as, for example, the lack of optical integrity of the endoscope 1304, the alignment of the CCDs with the right and left optical channels, and the like, can cause distortion. The distortion correction step at 1928 is arranged to compensate for such distortion. It will be appreciated that normally even "perfect" optical arrangements often have distortion as a design trade-off. This can typically also be compensated for.

Once the distortion correction has been performed at 1928, the $(\xi, \eta)$ information for both the left and the right channel is forwarded to a marker match and sort block at 1930. At the block 1930, the location of each marker in the one of the left and right channels is paired with the location of its corresponding location in the other of the right and the left optical image.

The $(\xi, \eta)$ coordinates for each marker and for each of the left and the right image channels is then converted to Cartesian space xyz coordinates relative to the camera frame as indicated at 1932. The xyz coordinates are then fed to an xyz model at 1934. The xyz model at 1934 can employ auxiliary information such as information derived from an ECG as indicated at 1936 and optionally from auxiliary information relating to the patient's breathing as indicated at 1938 to augment the model at 1934. It will be appreciated that the model at 1934 records motion history of each marker relative to the camera frame at the end of the endoscope 1304. The input from 1932 causes the model to be continually updated with current xyz information. From the model 1934, the updated xyz information is converted to (ξ, η) space indicated at 1940 which is routed to the marker match and sort step at 1930 to enable the locations of each marker in the one of the left and right channels to be paired with its corresponding location in the other of the left and the right channels.

Figure 47:
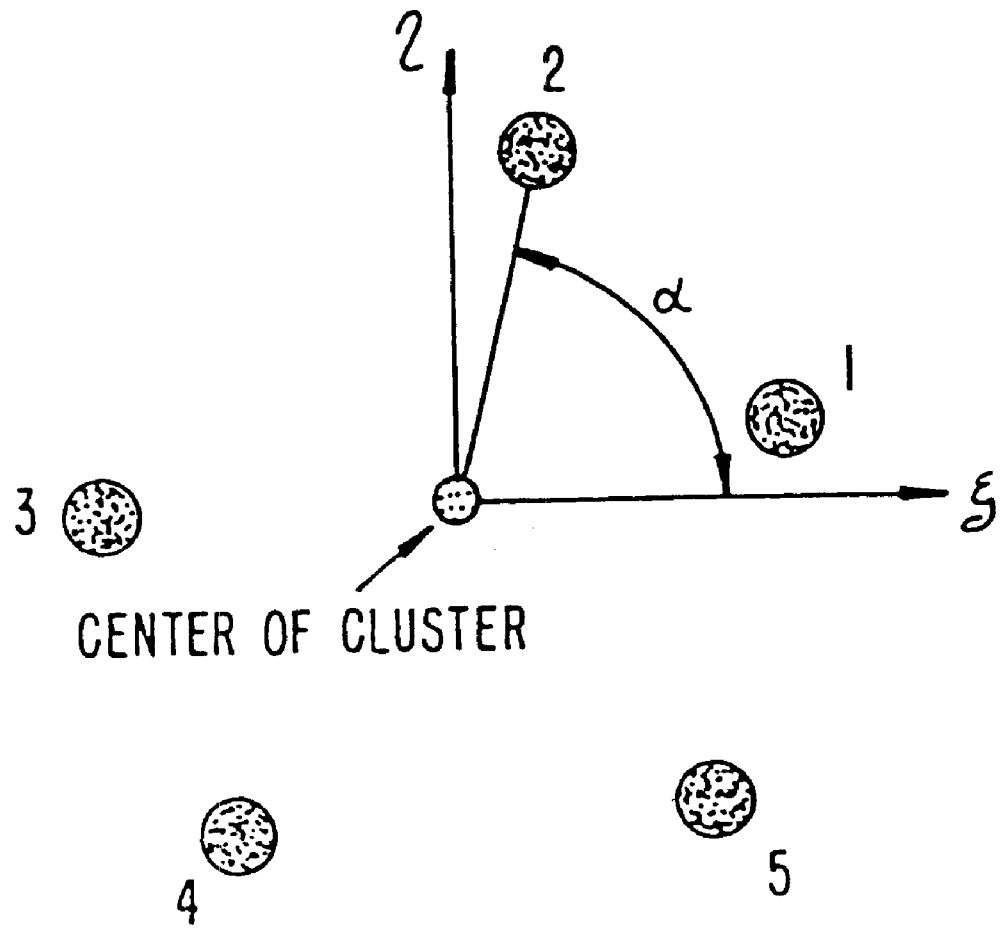
FIG. 47 shows a set of five markers or fiducials, and illustrates some steps whereby marker locations in one image can be matched with marker locations in another image.

In the match and sorting step 1930 an appropriate model can be used to match the marker location of each marker in the one image with its associated location in the other image. It has been found that using the angular positions of the markers relative to a frame having its origin generally at the center of the markers yields satisfactory results. Accordingly, with reference to FIG. 47, the center is indicated at 2110, the angle of one of the markers relative to an ξ axis 2112 of a frame 2114 being indicated at 2116. In similar fashion the angular position of each marker is determined relative to the ξ axis. The underlying assumption can be that the markers do not normally cross in angle, in other words, they do not reorder themselves.

The model at 1934 is updated based on motion history data for each marker in each of the left and right channel. Accordingly, based on the motion history for each marker, the expected position of each marker at some time in the future can be anticipated. The time in the future, namely time=k/60+ΔT, at which the markers are expected to be, is output at 1937 to enable signals to be determined for forwarding to the actuators of the slaves to permit the end effectors to be driven to move generally in sympathy with surgical site motion, while compensating for lag or delay, as described in greater detail herein below. This is typically achieved by extracting model parameters from the marker location history, so as to improve a parameter estimate as time lapses.

It will be appreciated that the path followed as indicated by reference numeral 1916 is followed on a continual basis. Thus, the xyz model at 1934 is continually updated so as to correspond with current xyz coordinates of the markers relative to the camera frame.

The information output from the digitizing steps at 1914, is tapped at 1942 to be fed to distortion correction steps at 1944 in the path 1918. The digital information relating to the left and the right channels is then modified to compensate for distortion as indicated at 1944. This distortion correction corresponds to calibration of the endoscope and CCD system as already described with reference to step 1928. Once the distortion has been corrected at 1944, the digital information is delayed at 1946 to synchronize the information passing along the paths 1916, 1918. The delayed digital information is then forwarded as indicated at 1948, to the viewer. It will be appreciated that, typically, the total delay between when the images are captured by the endoscope and when finally displayed to the surgeon at the viewer, is not readily apparent to the surgeon.

It will be appreciated that the surgical system is not necessarily limited to use in a beating heart application. Accordingly, it can happen that the surgical system is to be used on a surgical site which does not have motion. Naturally, in such a case, it would not be desired to compensate for any surgical site movement. Thus, it is typically only desired to initiate the system for performing a surgical procedure on a surgical site on the beating heart when the surgical procedure is to be performed on a moving surgical site on the beating heart. To initiate the system 1910, the operator typically actuates a suitable input to initialize the system 1910. Such initialization is indicated at 1950 in FIG. 44. Upon such initialization, a key field, indicated at 1952 is selected. Furthermore, the xyz model at 1934 is also initialized upon actuation of the input at 1950. The key field defines the (ξ, η) locations for each of the markers and for each of the left and the right channels. It will be appreciated that the marker locations in (ξ, η) space of the key field corresponds to the marker center locations when initialization was effected at 1950. The (ξ, η) locations of the markers in the key field 1952 are then used by a warp parameter calculation model as indicated at 1954. Together with the key field information derived at 1952, information relating to current (ξ, η) locations for each of the markers in each of the left and the right channels is also input to the warp parameter calculation model 1954 after such current information has been matched and sorted at 1930. The warp parameter calculation model continuously compares current marker location in (ξ, η) space with the corresponding marker locations as set by the key field 1952. Thus, the warp parameter calculation model determines positional deviation between current (ξ, η) locations and set (ξ, η) locations. From this comparison, warping instructions are derived and are input to the warping step at 1948. At 1948, the current digital information relating to the left and the right channels after the sync delay step at 1946 is warped at 1948 in accordance with warping instructions derived from 1954. After the digital information is thus warped, the left and the right channels are fed to typically a left and a right display at the operator station 1200 where the operator views the warped images which together provide a generally still stereo image of the surgical site.

As mentioned earlier, the output from the xyz model 1934, as indicated at 1937, is used to send appropriate signals to the slave actuators to cause them to drive the end effectors generally to track surgical site motion. This will now be described in further detail.

It will be appreciated that the output at 1937 is predicted filtered xyz coordinates of the markers as indicated at 1960, as well as xyz coordinates of the markers in the key field. The predicted xyz locations of the markers was determined by comparing current marker xyz locations with the motion history parameters as extracted by the xyz model so as to anticipate xyz locations of the markers at time=k/60+ΔT in the future to compensate for system delay.

The xyz locations of the markers at ΔT are then used to determine a frame. This can be achieved by determining a center location between the xyz coordinates at ΔT and attaching a frame to the coordinates, the frame having its origin at the center location, as indicated at 1962. This can be achieved by any appropriate model. The model can be arranged to map a plane relative to the xyz locations at time=k/60+ΔT, two of the axes of the frame lying in the plane with the x axis toward a selected marker, for example. Such an appropriate model is indicated at 1961.

In similar fashion, a frame is attached to the xyz coordinates of the key field at 1962.

At 1963 coordinate transformations are written from frame to frame. This will now be described in greater detail.

A symbol $T_b^a$ represents a coordinate transformation which writes basis vectors of the frame b in the new frame a coordinates. Such a transform can be represented by a 3 by 3 matrix R and a 3 by 1 vector c, as in $$T_b^a = (c_b^a; R_b^a).$$

They represent the transformation and orientation of new frame a with respect to old frame b. Frame transformations follow certain mathematical rules, such as:

1) Compositions of Transforms:

$$T_c^a = (T_b^a \cdot T_c^b)$$

Therefore, the transform of c with respect to a equals the composition of b with respect to a and c with respect to b. This is supported by:

$$c_c^a = c_b^a + (R_b^a \cdot c_c^b); \text{ and}$$

$$R_b^a = (R_b^a \cdot R_c^b)$$

2) Inversion of Transformations:

$$T_b^a = inv(T_a^b) = (T_a^b)^{-1}$$

Accordingly, the transform of b with respect to a can be undone by the transform of a with respect to b. This is supported by:

$$c_a^b = -(R_b^a)^T \cdot c_b^a$$

$$R_a^b = (R_b^a)^T$$

$$(T_b^a \cdot T_c^b)^{-1} = (T_c^b)^{-1} \cdot (T_b^a)^{-1}$$

$$T_b^a \cdot (T_b^a)^{-1} = (T_b^a)^{-1} \cdot T_b^a = I$$

(The notation "I" defines the transform from any frame to itself.)

The application of these transforms to the motion tracking of the end effector will now be described with reference to FIG. 48.

Figure 48:
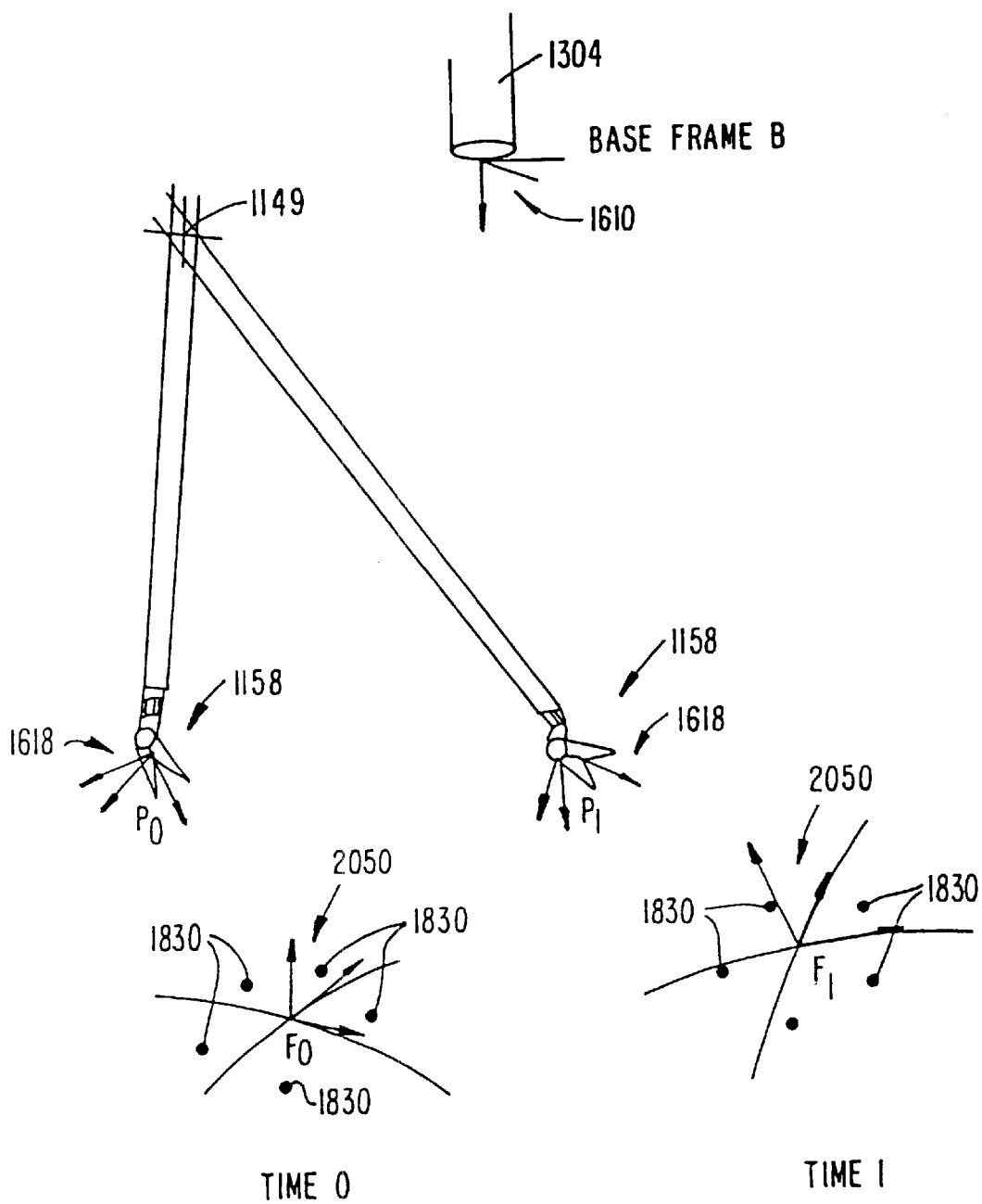
FIG. 48 shows a schematic three-dimensional diagram showing steps involved in a tracking process employed to cause the end effectors to track a moving surgical site on a beating heart.

In FIG. 48, a first position of the end effector relative to the surgical site is indicated at $P_0$ at time=0. A next position is indicated at $P_1$ at time=1 after the end effector has moved to track motion of the surgical site.

The frame attached to the surgical site is indicated by reference numeral 2050. It will be appreciated that this frame at t=0 is determined by the key field. The camera frame is indicated at 1610. At t=1, the surgical site has moved in response to heart motion, and the frame 2050 is now at a different position and orientation relative to the camera frame 1610 than at t=0. What is thus desired is to move the end effector frame 1618 into the same position relative to the frame 2050 at t=1 as it occupied relative to the frame 2050 at t=0. This will now be described.

The following frames are known at time T=0:

B=Base frame at camera tip, namely camera frame 1610;

$F_0$=Frame at center of fiducials on heart surface, relative to camera frame at initialization.

$P_0$=Frame at end effector relative to camera frame at initialization.

Accordingly the following is known:

$T_{P_0}^B$=(Transform writing $P_0$ frame basis vectors in the base frame coordinates, i.e., initial end effector location at initialization.)

$T_{F_0}^B$=(Transform writing $F_0$ frame basis vectors in the base frame coordinates, i.e., initial location of frame 2050 at initialization.)

At t=1, B and $F_1$ are known since the fiducial locations have been determined relative to the camera frame since the movement of the fiducials is monitored continually at 60 Hz for example. Since it is desired to preserve the relationship between $P_0$ and $F_0$ for all time t>0, including t=1, this can be achieved as follows:

$$T_{F_1}^{P_1} = T_{F_0}^{P_0}$$

(This equation typically states that the end effector position and orientation with respect to the frame 2050 on the heart should remain fixed at all times.)

Hence, the initialization equation is typically:

$$T_{F_0}^B = T_{P_0}^B \cdot T_{F_0}^{P_0} \text{ when } T_{F_0}^{P_0} \text{ is desired.}$$

$$\Rightarrow (T_{P_0}^B)^{-1} \cdot T_{F_0}^B = (T_{P_0}^B)^{-1} \cdot T_{P_0}^B \cdot T_{F_0}^{P_0}$$

$$\Rightarrow T_{F_0}^{P_0} = (T_{P_0}^B)^{-1} \cdot T_{F_0}^B$$

Accordingly at T=1:

$$T_{F_1}^B = T_{P_1}^B \cdot T_{F_1}^{P_1}$$

Thus, what is desired is:

$$T_{F_1}^{P_1} = T_{F_0}^{P_0} = (T_{P_0}^B)^{-1} \cdot T_{F_0}^B$$

Therefore:

$$\Rightarrow T_{F_1}^B = T_{P_1}^B \cdot (T_{P_0}^B)^{-1} \cdot T_{F_0}^B$$

To program the end effector movement to follow surgical site movement, $T_{P_1}^B$ is solved as follows:

$$T_{P_1}^B = T_{F_1}^B \cdot ((T_{P_0}^B)^{-1} \cdot T_{F_0}^B)^{-1} = T_{F_1}^B \cdot (T_{F_0}^B)^{-1} \cdot T_{P_0}^B$$

gives the position and orientation of the end effector in the base or camera frame.

Certain steps in FIG. 44 will now be described in further detail under separate headings:

MARKER PIXEL IDENTIFICATION AND CLUSTERING

Identifying the marker pixels and clustering the markers, as indicated in steps 1920, 1922 for each of the left and right optical channels, will now be described in greater detail.

Typically, the system employs Y, Cr, and Cb data format as opposed to the more conventional Red Green Blue format although either format could be used. It will be appreciated that selection of a marker color that is unique in the surgical field, and the signal of which is contained in a single dimension of the data enjoys practical advantages.

In this process, a subset (for example every $4^{th}$ pixel) of the Cr data is searched and, combined with tests on Y, Cr and Cb data, potential marker pixels are identified. The pixel locations are grouped, labeled, and the extent, approximate center, and approximate radius are determined for each marker group. The testing can be performed based on upper and lower threshold values for the Y, Cr, and Cb data thus adapting to different colored markers and adjusting for the camera white balance. In the preferred method all the pixel data are tested and labeled "on the fly" using high speed digital hardware on a pixel by pixel basis, as it comes out of the digitizer, or directly from the camera's digital output.

After the approximate extent of the markers is found in the above process all the data in a region around each marker are extracted from the Cr data. It has been found that using the Cr data, in particular, with a chosen green or cyan marker color, enhances the systems ability to locate the markers in the data stream. This process involves applying a threshold to the Cr data, returning Cr data values that represent markers (within the thresholds) or returning a 0 (outside the thresholds). Because the computational time for this and subsequent processing steps is directly related to the number of pixels in a marker region (the size of the marker in the image), a maximum marker size for the markers in Cr space is typically set initially. This typically sets a minimum distance of about 30 mm for a 2.5 mm diameter marker, for example, where the camera is a camera available from Welch Allyn and having the part number Model 2002. Such amounts can vary depending on, for example, the optics of the camera used. A buffer of 3 pixels can be included around the marker and a region of about 30 by 30 pixels in Cr space can be processed. This Cr gating typically decreases total processing time. It will be appreciated that with a higher capacity processor, this may not be necessary.

DETERMINING MARKER CENTERS

The determination of the marker centers, as indicated by the step 1924, will now be described in greater detail.

Sobel edge detection processing is typically applied to each marker's 30 by 30 data array. This process is used to define the outside or periphery of the marker.

After the Sobel processing is performed on the marker data, the results are thresholded to convert the data to either a "1" for data above the Sobel threshold or a "0" for data below the Sobel threshold. A circle correlation process is then employed to match circles of various radii and shift positions to the thresholded Sobel data. The outputs of this process are the markers' $(\xi, \eta)$ centers to a pixel resolution and the radius in pixels. Using the pixel extracted marker centers and radius determined above, a ring of $(\xi, \eta)$ addresses can be extracted from the thresholded Sobel pixel data, an array for least squares processing can be formed, and the center of the circle can be computed to sub-pixel resolution. The data extraction can involve using pre-computed addresses for an average of about 250 out of 900 possible data points, for example. The processing time scales with the marker size. Adjustments to the ring width can decrease noisy pixel location estimates.

CALIBRATION

The distortion corrective steps 1928, 1944 are derived from calibration of the endoscope. This will now be described in greater detail.

Optical calibration is a process of determining the parameters necessary to define a mathematical transformation from the coordinates of a point in the working space of the endoscope to its coordinates in the left and right camera images, or vice versa. This transformation is typically built around a large number of physical parameters, such as the positions of the lens centers, optical distortion, and orientations of the lenses and CCD video chips. Endoscopes are normally manufactured to tight tolerances. Differences between the two optical systems are thus generally small, but typically not zero, thereby permitting a linearized mathematical model for many of the unknown parameters. Assumptions about symmetry such as that the shaft of the endoscope is a cylinder, its tip face is perpendicular to the cylinder axis, and the pixels in the image lie on a uniform rectangular grid can typically be made. The calibration can be carried out by mounting the endoscope in a test jig, as described in greater detail herein below, and then imaging a test target consisting of an array of dots at known positions. By rotating the endoscope and shifting its distance relative to the target, endoscope characteristics can be separated from jig errors.

The endoscope typically has a long cylindrical body. The endoscope (or object space) coordinates can typically be a right-handed three-dimensional Cartesian coordinate system (x, y, z) describing positions of points in the region being viewed. The endoscope's axis of rotational symmetry can typically be the z axis, pointing from the endoscope out into the object space, and the intersection of this axis with the tip face can define the origin of the endoscope coordinates. The x axis is typically defined as being parallel to a mean orientation of the rows of the two video images pointing right as seen in the images.

Additionally, there are typically Cartesian coordinates in the target plane positioned so that each target spot has (x', y') coordinates that are integer multiples of the constant spot spacing.

Typically, behind each lens of the endoscope, there are image space coordinates $(\xi, \eta, \zeta)$, having an origin at the lens optical center and oriented anti-parallel to (x, y, z). There are typically separate coordinate systems, designed with subscripts $_L$ and $_R$ for the left and right cameras; these typically differ only in their origins. All these coordinates can be defined in units of millimeters.

There are typically also coordinates $(\xi', \eta')$ in the image plane, which can be the active face of the CCD chip, with $\xi'$ along rows and $\eta'$ along columns, for example. They are typically measured in units of pixels, with the origin typically at the upper left corner of the image. Although the CCD's image samples can be located at integer values of $(\xi', \eta')$, these coordinates need not be restricted to integers.

The calibration process preferably includes transforming $(\xi', \eta')$ coordinates into $(\xi, \eta, \zeta)$ coordinates that would be produced by a distortionless lens. One then has the imaging relationships:

$$\frac{\xi}{\zeta} = \frac{x - x_c}{z - z_c}$$
$$\frac{\eta}{\zeta} = \frac{y - y_c}{z - z_c}$$

with $(x_c, y_c, z_c)$ being the coordinates of the lens optical center. These imaging equations typically relate collinear rays, not unique points in space.

Figure 45:
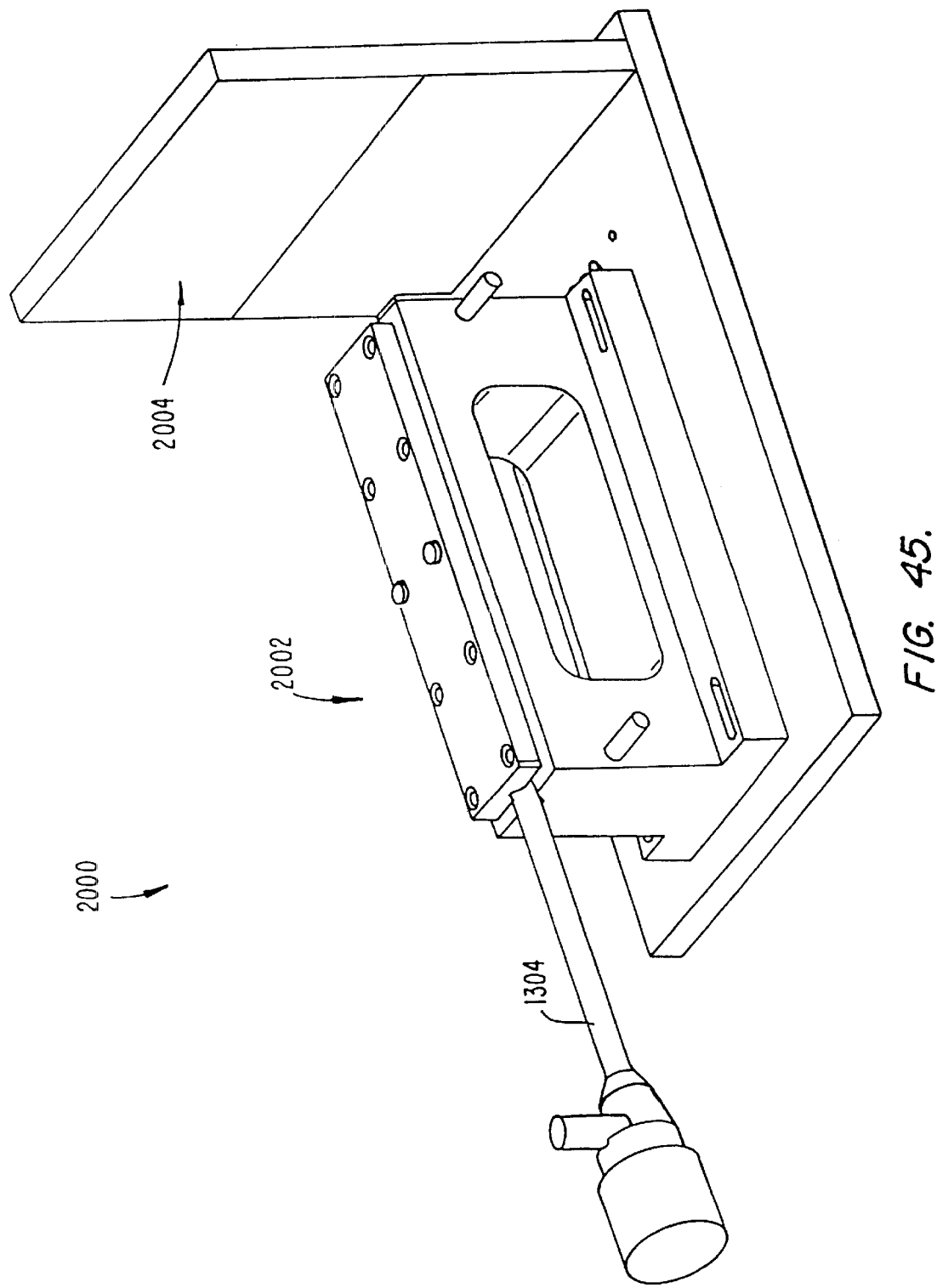
FIG. 45 shows a three-dimensional view of a calibration jig whereby an endoscope of the surgical system can be calibrated.

A diagram of the calibration jig is shown in FIG. 45 as indicated by reference numeral 2000. The shaft of the endoscope 1304 rides in a horizontal V-groove 2005 in a support block 2002, which allows it to slide longitudinally or rotate about z and then be clamped in place. The rotation can be arbitrary, but preferably the endoscope 1304 slides until its tip contacts a flange, so as to provide a known tip position. This permits the z axis and the (x, y, z) origin position to be repeatable after an adjustment, regardless of the diameter of the endoscope being calibrated. A vertical wall 2004 can typically serve to hold a target adhesively, for example. The support block 2002 can be mounted to a base 2009 at various pin-registered locations 2011, each of which provides a carefully measured distance from the tip flange to the target wall.

Figure 46:
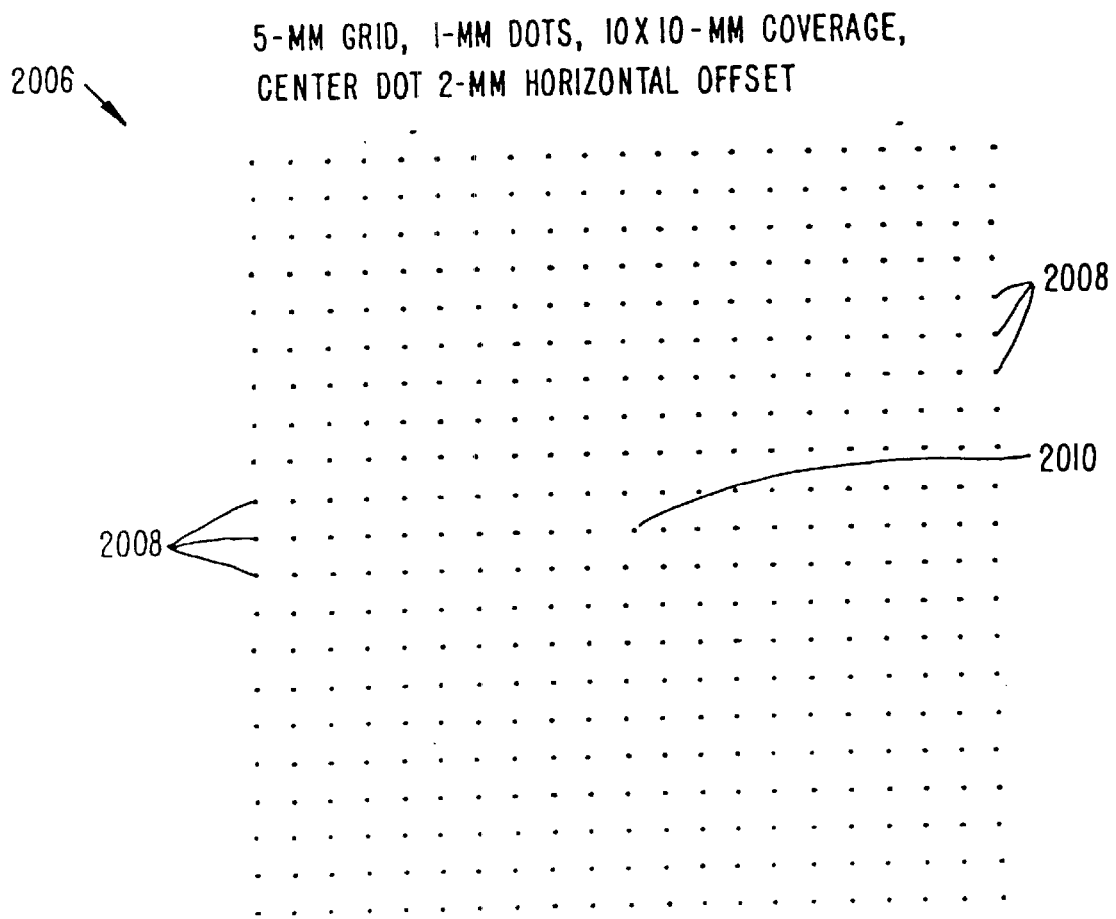
FIG. 46 shows a calibration target grid used with the calibration jig of FIG. 45 so as to calibrate the endoscope.

The calibration target 2006 as indicated in FIG. 46 consists of a square array of circular spots 2008 of known size and spacing printed on a piece of paper by a laser or inkjet printer for example. This could be replaced by a more stable and rugged target, but a paper target can be satisfactory. The spot diameter is typically 1 mm, with a center-to-center spacing of 5 mm. A single spot at the center of the target as indicated by 2010 is offset by 2 mm so that the center and gross orientation of the target are identifiable in an image. Generally, the exact positioning and orientation of the target 2006 are found as part of the calibration process.

The distance of the endoscope tip to the vertical wall 2004 is accurately known so as to enable the scaling of distances in the z direction to be defined. Similarly, the mean spot spacing defines scaling of distances in x and y.

The calibration procedure comprises mounting the endoscope support block 2002 to its base, giving a known z distance from the endoscope tip to the target 2006 secured on the wall 2004. With the endoscope 1304 clamped in the V-groove, a single frame of data can be recorded from each camera. The clamp can then be loosened, the endoscope rotated and re-clamped, and another frame of data can be recorded for each camera. After several rotations, the distance can be changed by remounting the block 2002 in a new pin registered location, and the process repeated. Generally, two rotations at each of two distances can be adequate to perform calibration. However, 12 rotations at three distances can typically be used in order to study the internal consistency of the data collection and analysis procedures.

The first step in processing the data is typically to locate the center of each visible spot in ($\xi'$, $\eta'$). The procedure for this is generally the same as for processing heart marker data as described above under the heading "Determining Marker Centers". Frame, rather than field, data and intensity, rather than color, can be used. Both of these can be done to improve the image resolution.

The result of this step is typically a list of spot centers, typically accurate to about 0.2 pixel, for each image. Some spurious positions may be found which can be edited out by hand or by computer. The number of spots in each image depends on the distance to the target, and can vary from about 50 to 200, for example. At this point the original image can be discarded, as only spot image coordinates are then used.

Rather than throwing all spot centers (about 7000 of them) into one grand least squares solution, the problem can be divided into two parts instead. The first part can be to process the data in a single image to get typically a 13 parameter transformation relating spot center ($\xi'$, $\eta'$) to target position (x', y'). These can then be used to generate four reference points that are generally the equivalent of what would have been measured in the absence of lens distortion. These reduced data sets from each image can then be combined in a least squares solution for the endoscope parameters.

The first step in single image processing can be to determine which target spot corresponds with which measured position. Target spots are typically identified by integer indices in x' and y'. For this, an approximate distortion correction is applied so that the spot locations are approximately along straight (but not necessarily parallel or orthogonal) lines. The spot centers can be used to generate a pseudo-image which can have a spot with Gaussian intensity profile at each measured position. This pseudo-image can be auto-correlated to get the two mean grid spacing vectors, approximately 90° apart and sorted to form a right-handed pair. Another pseudo-image can then be formed with spot spacings given by these grid vectors and cross-correlated with the first pseudo-image. Locating the peak nearest the center can give the mean shift between the two pseudo-images. With these parameters, each distortion corrected spot center can be assigned integer spot indices in (x', y'), although at this time still subject to unknown integer offsets and 90° rotations. This can typically be a starting point for an iterative loop that determines the distortion and perspective parameters and also identifies the central target spot by its residual from the fit. This can permit a generally true assignment of spot indices in subsequent iterations.

Once the spot coordinates have been assigned target indices, and thus known target positions in (x', y'), the least squares fitting can proceed. Typically, the key physical parameters are the lens distortion and the rotations of the target and image planes. In general, mapping one plane into another by straight line projection through a point (the lens center) is described by a perspective transformation, which typically has 8 free parameters. Thus, the fitting models typically accommodate circularly symmetric distortion plus a perspective transformation. This can not only have a physical basis but can also represent the data well with a relatively small number of parameters. Other functions that could be used are general two-dimensional polynomial, which should fit the data well but should typically use a greater number of parameters, and distortion plus an affine transformation, which can typically be perspective with the projection point at infinity. The relevant equations for distortion removal can thus be:

$$\xi'_u = \xi' + (\xi' - \xi'_0) \delta\rho/\rho$$

$$\eta'_u = \eta' + (\eta' - \eta'_0) \delta\rho/\rho$$

$$\delta\rho = d_3 \rho^3 + d_5 \rho^5 + d_7 \rho^7$$

$$\rho = \sqrt{(\xi' - \xi'_0)^2 + (\eta' - \eta'_0)^2}$$

where $\xi'_u$, $\eta'_u$=distortion corrected image coordinates, $\xi'_0$, $\eta'_0$=intersection of the optical axis with the image plane, $d_n$=nth order distortion coefficient, $\rho$=radial distance from the optical axis, $\delta\rho$=radial distortion shift.

There are thus five unknown parameters in the distortion, namely: $\xi'_0$, $\eta'_0$, $d_3$, $d_5$, $d_7$. The perspective transformation is defined as:

$$\begin{bmatrix} wx' \\ wy' \\ w \end{bmatrix} = T \begin{bmatrix} \xi' \\ \eta' \\ 1 \end{bmatrix} \quad (1)$$

where T is a 3×3 matrix with its lower right component equal to 1 and the other eight components are to be determined. An arbitrary scale factor "w" should be normalized out each time the transformation is applied. The eight perspective parameters are similar to specifying the mapping of four non co-linear reference points. After solving for T, it is replaced by pseudo-data representing the distortion-free imaging of points at x'=±10 mm, y'=±10 mm. This can involve inverting (1), which simply means inverting the matrix T.

Because the dependence on $\xi'_0$ and $\eta'_0$ is typically nonlinear, iteration is desired in finding a least squares solution. In addition, only those spots with residuals from a current fit of <0.2 mm, for example, are used for the next iteration. Convergence is typically defined as occurring when all spots included in the solution have residuals <0.2 mm, while all those excluded have residuals >0.2 mm, for example, i.e. a stable set of points has been used. Five to seven iterations are typical. The rms residual can typically be about 0.4 pixel, or about 0.03–0.06 mm, depending on the distance.

After processing each frame independently, the five distortion parameters can be averaged for all the frames from each camera. While holding these distortion parameters fixed, the perspective parameters can be are re-estimated for each frame. At this stage in the processing there are typically four reference points defining the transformation for each frame. Thus, for example, with 12 rotations, three distances, and two cameras, there are typically a total of 228 reference points. Each defines a ray from the target plane, through the lens center, to the image plane. This ray can be described by two direction cosines, but it has been found to be easier to formulate the solution by working with a particular point on the ray. As a result, each reference point can have three associated coordinates, yielding 864 equations in the least squares solution for 348 unknown parameters. These parameters typically are:

The target center $(x'_c, y'_c)$, where the z axis intersects the target plane.

The target plane horizontal and vertical tilts, measured as the deviation of the target plane normal to the z axis.

The left camera lens optical center, $(x_{cL}, y_{cL}, z_{cL})$.

The left camera image center, $(\xi'_{cL}, \eta'_{cL})$, where the $\zeta_L$ axis intersects the image plane.

The left camera CCD pixel spacings, $(\Delta\xi'_L, \Delta\eta'_L)$.

The left image rotation, being the angle between the $\xi'_L$ and x axis.

The left image plane horizontal and vertical tilts, measured as the deviation of the image plane normal from the $\zeta_L$ axis.

The right camera lens optical center, $(x_{cR}, y_{cR}, z_{cR})$.

The right camera image center $(\xi'_{cR}, \eta'_{cR})$, where the $\zeta_R$ axis intersects the image plane.

The right camera CCD pixel spacings, $(\Delta\xi'_R, \Delta\eta'_R)$.

The right image rotation, being the angle between the $\xi'_R$ and x axes.

The right image plane horizontal and vertical tilts, measured as the deviation of the image plane normal from the $\zeta_R$ axis.

The endoscope rotation angle for each image pair (36 unknowns in the case described above).

The distance scale factor for each reference point (288 unknowns), because of treating the measurements as points rather than rays.

Note that $(\xi', \eta')$ coordinates have been distortion corrected, though the same notation is used since these coordinates still lie in the image plane. Typically, there are four parameters relating to the jig, 10 for each of the left and right cameras, plus nine for each image pair. The parameters that define the endoscope calibration are the camera parameters as well as the distortion determined previously, a total of 30 values; all the others are normally irrelevant once the calibration process has been completed.

It will be appreciated that symmetrical inaccuracies which might apply due to manufacturing constraints, for example, can also be taken into account by providing additional constraints to the solution.

The pixel spacings can normally be found only relative to the focal distance, which was set to an assumed value. It may be more physically meaningful to fix the mean of $\Delta\xi'$ and $\Delta\eta'$, which can be established by highly precise manufacturing processes, and then to solve for their ratio and the focal distance. Of course their ratio is also normally precisely controlled, but this value may not be readily determinable; thus it can typically be treated as unknown.

The calibration results, as achieved above, when applied to spot positions measured in the images, give inferred target spot positions with an accuracy that varies with distance. For x and y the rms error is typically about 0.03 mm at 30 mm distance to about 0.06 mm at 70 mm. For z, it is typically about 0.2 mm at 30 mm to about 1.0 mm at 70 mm. The larger values for z are normally consistent with the stereo baseline separation and the working distance. These accuracies refer to high contrast spots measured on a single pair of stereo frames. It has been found that systematic errors, some of which are attributable to the placing of the spots on the target grid, are normally mostly below about 0.1 mm, with occasional values up to about 0.2 mm.

XYZ MODEL

The xyz model as indicated at 1934 will now be described in greater detail.

The function of this model or "tracker" is to use sequential measured positions of a marker in the left and right camera images, form a movement track from these positions, and use the track parameters to predict the marker position at a time $\Delta T$ in the future, of about 50 ms, for example, thereby to compensate for the processing delay, for example.

The tracker that will now be described is an extended Kalman filter. The input data are assumed to be marker positions already corrected for distortion, and already identified as belonging to a specific track. The various markers are tracked independently.

The state of the system is typically a vector containing enough parameters to describe not only the current position of the marker but also its path over time, so that prediction is possible. The state vector is updated with each measurement in a recursive fashion, so that the current best estimate is available. Because the motion of a marker follows a path that is predominantly repetitive, the Cartesian coordinates (x, y, z) are each represented as periodic functions of time with generally slowly varying amplitude, frequency, phase, and waveform.

An important issue is how to describe the waveform. Periodic sampling leads to a time domain representation, while using coefficients of a trigonometric series leads to a frequency domain representation. Other representations are possible and will be evident to those skilled in the art but will not be considered here. The time domain method is complicated by the requirements of fine sampling for easy interpolation to any desired time, as well as a band-limited waveform to control noise. This can lead to an estimation problem in which some type of filtering can be applied at each data update; lower bandwidth normally requires more smoothing and thus normally more computation. In the frequency domain approach the bandwidth is typically set by the number of harmonic coefficients included (lower bandwidth normally means less computation), while the time sampling is typically calculated explicitly each time it is needed. Even though the frequency domain method normally requires many sine and cosine evaluations, it has been found to be of greater simplicity than the time domain method.

There are at least two possible approaches to keeping track of the marker's current position in its cycle. In the first, the evolution of the state is considered to be part of the dynamical process. At each time step each pair of sine and cosine coefficients should be rotated by a phase corresponding to the desired time increment. The position is then typically the sum of the cosine coefficients, since the phase is always zero. The covariance extrapolation step in this approach can be computationally intensive.

The second approach is to leave the waveform coefficients fixed and to shift the phase progressively in time. This puts the state evolution into the measurement process; the dynamical model then normally being trivial. However, there can be an intrinsic ambiguity in this approach that should be recognized. Since the waveform is normally continually being updated using data, it can slowly evolve in a way that looks like a time shift that is separate from the temporal progression of the phase. In other words, it should be possible to change the waveform parameters, as well as the current phase in the cycle, so as to leave the described position unchanged. Some constraint should be included to inhibit this normally unmeasurable combination of parameters from diverging.

Based on these considerations, each coordinate can be modeled as $$x(t) = c_{x0}(t) + \sum_{n=1}^{N} c_{xn}(t)\cos n\phi(t) + s_{xn}(t)\sin n\phi(t), \quad (1a)$$

with $$\phi(t) = \int_0^t 2\pi f(t')\,dt', \text{ where} \quad (2)$$

$f$ = frequency (Hz), $\phi$ = phase (rad), $c_{x0}$ = mean (non-periodic) component of $x$ (mm), $c_{xn}$ = $n^{th}$ coefficient of the cosine series for $x$ (mm), $s_{xn}$ = $n^{th}$ coefficient of the sine series for $x$ (mm).

The treatment of y and z is normally similar, with the same number of terms in the trigonometric series for each coordinate. Except for $\phi$, all these parameters are normally considered to be slowly varying.

The constraint typically used to eliminate the ambiguity described above is to let $c_{x1}=0$. However $c_{y1}$ and $Cc_{z1}$ are not normally restricted since the trigonometric series for all three coordinates use the same phase. Define the following vectors: $s_x \triangleq [s_{x1}\ s_{x2}\ \ldots\ s_{xN}]^T$, and similarly for y and z, as well as $c_y \triangleq [c_{y1}\ c_{y2}\ \ldots\ c_{yN}]^T$, and similarly for z, while $c_x \triangleq [c_{x2}\ \ldots\ c_{xN}]^T$. That is $c_x$ excludes the $c_{x1}$ component. The Kalman state vector is then:

$$x=[f\phi c_{x0}c_x^T s_x^T c_{y0}c_y^T s_y^T c_{z0}c_z^T s_z^T]^T \quad (3)$$

Note that the state vector, x, is different from the coordinate, x. Its length is typically 6N+4. In practice it may be easier to write the computer code to include $c_{x1}$, simply carrying around a zero in the fourth component of x, and expanding all the associated matrices with an appropriate row or column of zeros.

Accordingly, the only thing that normally changes predictably in time is the phase:

$$\phi(t+\Delta t)=\phi(t)+2\pi\Delta t f(t).$$

All other components of the state vector are normally constant save for unpredictable variations. Thus in the Kalman dynamical equation, $$X(t+\Delta t)=\Phi(t)x(t)+\Gamma(t)w(t), \quad (4)$$

The transition matrix, $\Phi$, normally differs from the identity matrix only in that $\Phi_{21}=2\pi\Delta t$. $\Phi$ is variable in time, only to the extent that $\Delta t$ changes, as would happen if one had to skip a frame due to real time processing limitations, for example. The term $\Gamma w$ represents the process noise.

Random noise sources normally drive the frequency, phase, and amplitude scaling of the periodic waveform, which are normally the same among the three coordinates, as well as the mean position and the waveform shape, which are normally independent. These are taken to be random walk noise processes. However, because the phase is normally the integral of the frequency, the phase variation is the sum of a random walk and an integrated random walk.

The noise vector, w, is given by:

$$w=[w_f w_{100}\ w_a w_s^T]^T$$

Where $w_f$=frequency noise (Hz) with variance $q_f \Delta t$, $w_{100}$ =phase noise (rad), with variance $q_{100}\Delta t$, $w_a$=amplitude noise (dimensionless), with variance $q_a\Delta t$, $w_s$=waveform shape noise (mm), with variance $q_s\Delta t$.

The q values are typically referenced to a one-second integration of the random walk; the scaling with $\Delta t$ normally assumes the process is stationary over that interval. These noise processes are taken to be independent, so their covariance can be given by:

$$Q = E\{ww^T\} = \Delta t \begin{bmatrix} q_f & 0 & 0 & \\ 0 & q_\phi & 0 & 0 \\ 0 & 0 & q_a & \\ & 0 & & q_s I_{6N+2} \end{bmatrix}$$

The process noise coupling matrix is then:

$$\Gamma = \begin{bmatrix} 1 & 0 & 0 & 0 \\ \pi\Delta t & 1 & & \\ & & 0 & \\ & & c_x & \\ & & s_x & \\ & 0 & 0 & I_{6N+2} \\ & & c_y & \\ & & s_y & \\ & & 0 & \\ & & c_z & \\ & & s_z & \end{bmatrix}$$

There are several points that can be noted. The noise parameter $w_a$ typically provides a proportional scaling of all the parameters that determine the waveform and therefore normally does not affect the shape, while the components of $w_s$ normally affect each of the coefficients in the trigonometric series, as well as the mean values, independently; thus they can affect the waveform shape. Since $w_a$ normally represents a proportional scaling, elements of the state vector enter $\Gamma$. The implications of this will now be discussed.

Following the Kalman formalism, both the estimated state vector and the state covariance matrix can be extrapolated from the time of the last data update to the time of the current data. For the state, this can be the deterministic part of the equation indicated at (4):

$$\hat{x}(t+\Delta t)=\Phi(t)\hat{x}(t) \qquad (5)$$

The phase, φ, is normally taken modulo 2π to inhibit it from growing so large as to limit numerical accuracy. The extrapolation of the state covariance, P, is $$P(t+\Delta t)=\Phi(t)P(t)\Phi(t)^T+\Gamma(t)Q(t)\Gamma(t)^T \qquad (6)$$

In implementing (6) the sparseness of Φ, Γ, and Q should be used. Relatively few computations are thus normally involved.

Because Γ contains elements of the state vector, it can have some uncertainty and the covariance of Γw includes more than just the $\Gamma Q \Gamma^T$ term in (6). However the other terms are usually small and can be neglected for simplicity.

The distortion correction process typically converts measured pixel coordinates ($\xi_0$, $\eta_0$) to a set of Cartesian image coordinates (ξ, η, ζ), measured in millimeters, with origin at the lens center and oriented anti-parallel to (x, y, z). The third coordinate, ζ, is typically nominally constant and equal to the focal distance of the lens, but in reality it may vary because the CCD chip may not be perfectly normal to the z-axis. However, it is typically considered to be free of measurement error. The relationships between the distortion-corrected image coordinates and marker location are:

$$\xi = \varsigma \frac{(x-x_c)}{(z-z_c)} \qquad (7)$$

$$\eta = \varsigma \frac{(y-y_c)}{(z-z_c)} \qquad (8)$$

where ($x_c$, $y_c$, $z_c$) location of the lens center. Subscripts L and R are added to (ξ, η, ζ) and ($x_c$, $y_c$, $z_c$) when it is necessary to distinguish between the left and right cameras.

Because the measurements depend nonlinearly on the parameters in the state vector, it is desirable to linearize the measurement model about the current estimate of the state vector, $\hat{x}$. As a result of this linearization, the filter is typically called an extended Kalman filter. Thus:

$$\xi(x)-\xi(\hat{x})=H_\xi(x-\hat{x}) \qquad (9)$$

$$\eta(x)-\eta(\hat{x})=H_\eta(x-\hat{x}) \qquad (10)$$

In this linearized measurement model, the measurement sensitivity is given by:

$$\left(H_\xi = \left[\frac{\delta\xi}{\delta x}\bigg|_{\hat{x}}\right]\right)^T = \left[\frac{\varsigma}{(z-z_c)}\left\{\frac{\delta x}{\delta x} - \frac{(x-x_c)\delta z}{(z-z_c)\delta x}\right\}\right]^T \qquad (11)$$

$$\left(H_\eta = \left[\frac{\delta\eta}{\delta x}\bigg|_{\hat{x}}\right]\right)^T = \left[\frac{\varsigma}{(z-z_c)}\left\{\frac{\delta x}{\delta x} - \frac{(x-x_c)\delta z}{(z-z_c)\delta x}\right\}\right]^T \qquad (12)$$

The various derivatives are readily found from equation (1) above. For example:

$$\frac{\delta x}{\delta f} = 0 \qquad (13)$$

$$\frac{\delta x}{\delta \phi} = \sum_{n=1}^{N} -nc_{xn}\sin n\phi + ns_{xn}\cos n\phi \qquad (14)$$

-continued $$\frac{\delta x}{\delta c_{xn}} = \cos n\phi \qquad (15)$$

$$\frac{\delta x}{\delta s_{xn}} = \sin n\phi \qquad (16)$$

$$\frac{\delta x}{\delta c_{yn}} = \frac{\delta x}{\delta s_{yn}} = \frac{\delta x}{\delta c_{zn}} = \frac{\delta x}{\delta s_{zn}} = 0 \qquad (17)$$

The derivatives of y and z are typically similar.

The four measurements at each time, ($\xi_L$, $\eta_L$, $\xi_R$, $\eta_R$), are treated as having independent measurement noise. This typically means that one can perform four scalar updates to the state vector and state covariance matrix, rather than a matrix update. Not only does this typically avoid a matrix inverse (or solving simultaneous linear equations), but if any of the four data samples is missing (for example, if the marker were not detected in one of the images) then it is a generally simple matter to perform the update only for the data available, without changing the dimensions of the variables entering the equations. Because the measurements are taken at the same time, there is normally no extrapolation between updates. For the lth update (l=1:4) the equations are:

$$K_l = \frac{P_{l-1}H_l^T}{H_l P_{l-1} H_l^T + r_l}$$

$$\hat{x}_l = \hat{x}_{l-1} + K_l[d_l - \hat{d}_l]$$

$$P_l = (I - K_l H_l) P_{l-1}$$

where K=Kalman gain,
H=measurement sensitivity vector, (11) or (12),
r=measurement noise variance,
$d_l$=$l^{th}$ measurement (ξ or η),
$\hat{d}_l$=prediction of the $l^{th}$ measurement from (7) or (8) using $\hat{x}_{l-1}$. When l=1 the quantities with subscript l−1 are normally predicted values at the current time from (5) and (6).

Because of the normally nonlinear character of the measurement model, starting the filter can be awkward. Before one has reasonably well established estimates of the state, the linearization in the vicinity of the current state estimate may be so far off that additional data may not lead to a convergent result. Starting normally requires performing a batch nonlinear iterative least squares solution using at least a full cycle of data. The resulting state vector and state covariance can then be used to start the Kalman filter.

The batch least squares can involve linearization similar to (9) and (10). It can differ from the recursive Kalman least squares estimator in using a fixed reference point (the previous iteration's solution for the state vector) for all the data, rather than letting the reference point change for each data sample. Iteration typically continues until the solution vector is essentially unchanged from the reference vector. Typically, five iterations are sufficient for convergence.

The state vector determined during start-up, $x_s$, can differ slightly from the one used in the Kalman filter (3):

$$x_s = [f\ c_{x0} c_{x1} c_x{}^T s_x{}^T c_{y0} c_y{}^T s_y{}^T c_{z0} c_z{}^T s_z{}^T]^T$$

The phase may not be included, while the parameter $c_{x1}$ is. Since the frequency is assumed to be constant for the batch of data, (2) can imply that the phase is simply linear in time:

$$\phi(t)=2\pi f(t-t_0)$$

where $t_0$ is a reference time chosen initially to be the midpoint of the batch of data. The derivatives (15)–(17) are typically unchanged, while (13) is typically replaced by the equivalent of (14):

$$\frac{\delta x}{\delta f} = \sum_{n=1}^{N} -2\pi n(t-t_0)c_{xn}\sin 2\pi nf(t-t_0) + 2\pi n(t-t_0)s_{xn}\cos 2\pi nf(t-t_0),$$

and similarly for y and z.

The least squares problem is typically of the form: $A\Delta x_s = b$, where b typically contains the difference between the measured positions and those predicted by the previous estimate of $\hat{x}_s$. The matrix A contains the derivatives of the predicted data with respect to the unknowns. A standard least squares technique (such as QR decomposition of A) may be used to solve for $\Delta x_s$. This is then added to the starting value of $\hat{x}_s$.

In each iteration, after finding the least-squares solution for $x_s$, $t_0$ is typically changed and all the (c, s) pairs are typically rotated to make $c_{x1}$ zero. Thus:

$$\theta = \tan^{-1}(c_{x1}/s_{x1})$$

$$t_0 \leftarrow t_0 - \theta/2\pi f$$

$$c_{xn} \leftarrow c_{xn} \cos n\theta - s_{xn} \sin n\theta$$

$$s_{xn} \leftarrow c_{xn} \sin n\theta + s_{xn} \cos n\theta$$

They and z coefficients typically mix using the same $\theta$.

For the first iteration one can let all the parameters start at 0 except for f and $c_{z0}$. Typically one could use f=1 Hz, but there can be a danger of converging to half the true value. This should be indicated by having very small values for all the trigonometric coefficients with n odd, implying a doubly periodic waveform. For $c_{z0}$ a typical value of 40 mm should be adequate. During the first iteration the frequency is typically not estimated, but is held at its starting value.

After convergence, the starting Kalman state vector is obtained by typically deleting $c_{x1}$ from $\hat{x}_s$ and inserting zero for $\phi$. The covariance of $\hat{x}_s$ is then:

$$P_s = r(A^T A)^{-1}$$

assuming all measurements have the same variance r. The Kalman covariance is typically obtained by deleting the row and column corresponding to $c_{x1}$ and inserting a row and column of zeros corresponding to $\phi$. The first extrapolation step of the Kalman filter should advance from to the time of the next observation, which can involve a nonstandard $\Delta t$.

This filter has been found to perform adequately so long as the components of Q are chosen suitably. However, if Q becomes too large, telling the filter that there is significant change of the waveform during one cycle, the filter may try to estimate the state using less than a full cycle of recent data. This can give rise to an unstable situation; typically the frequency may go to zero, the phase may oscillate rather than progressing monotonically, and the trigonometric coefficients may become quite large. The predicted positions may not be terribly outrageous, but the filter may not be working properly. Thus, care should be exercised in setting the process noise parameters.

Another parameter that may require user input is N, the number of terms in the trigonometric series. Adaptive estimation of this parameter should also be useful. One could keep track of the magnitude of the motion in the highest mode; if it became larger than some tolerance (say 0.1 mm) N can be increased. Conversely, if both of the two highest modes fell below the threshold, N can be decreased.

WARPING

The description immediately below describes the warping on a single image. Aspects of a stereo application will be described thereafter.

The reference image for the warping may be the "key frame". A keyfield is typically used. This is normally an image that is chosen by the surgeon, or otherwise, as already described herein above. The image is typically selected based on its "goodness" with respect to aspects like look angle, marker identification, area covered, residual motion (sharpness) and the like. Subsequent images are then typically warped, or distorted, to the marker locations in this image. The $(\xi, \eta)$ values of the markers are typically used as reference vertices for the warping.

The markers identified are typically numbered and sorted for association with markers in subsequent images, as already described herein above. Warping performance is typically enhanced by supplying marker $(\xi, \eta)$ information during possible periods of blocked markers. The marker locations in subsequent images are typically related to the key image by a sorting algorithm that normally takes into account marker array rotation and obscured markers. Once the markers in subsequent images are associated with the key image, the warping for those images can be achieved.

The warping algorithm typically used can require a minimum of three markers, such as for an affine transformation, or the like. Advantageously, five markers are used in a single solution, implying that the warping parameters calculated normally involve an optimal simultaneous fit of all five markers in the subsequent frame to the key frame. This approach may result in a small amount of residual motion in the warped image. Options in the warping code can provide a perspective transformation that may require a minimum of four markers. A more complex approach can involve dividing the marker array into collections of triangles, or other shapes, or the like. The markers may then define vertices. Three triangles may typically be used for five markers. Some of the markers can be used for more than one triangle. When this approach is used, the marker locations in the warped image are normally placed where the markers are in the key image. The output of the initial warping can provide warped data at real value indices, rather than integer locations. A bilinear transformation can be applied to the data to obtain the integer pixel locations. This can typically be achieved in most, or all, color planes. (The mathematics can be accomplished in RGB (Red, Green and Blue space) using nearest neighbor values, so that the warped image can have a correct color representation).

It is to be appreciated, that the image can be warped without distortion correction. Under such conditions, normally all stilled images can look like an original "fish eye" image. If distortion correction is applied to correct for endoscope lens distortion, it should be done prior to the selection of the key frame, and typically prior to the warping calculations being made, as well. The distortion correction is typically also a warping of the image, but is normally constant for all the images. It can be performed in a pipeline process prior to warping. When employed in the proper sequence, the distortion correction should preserve the stereo effect, as will now be described.

As mentioned, the warping calculations are normally performed on a key frame, typically used to provide a reference image for subsequent warping. The warping is typically performed in $(\xi, \eta)$ space rather than xyz space. When stereo warping is performed, the left and right key frames, from generally the same instant in time, are typically used. The relationship between the left and right images typically contains data with proper Xi relationship based on the distance to the markers (and other objects). Accordingly, the proper stereo distance relationship is typically preserved in the key frame images. Since all subsequent data are warped to match each key frame marker position, the stereo distance relationship in the data is normally preserved for all subsequent warped images. Since the warping desired to achieve the distortion correction preserves the proper Xi relationship between the left and right images, a correct stereo relationship is normally maintained.

Several techniques can be used to display the stereo warped image. For example, use can be made of two monitors and a mirror train to direct the stereo images to the surgeon, or a relatively high speed (120 Hz, for example) monitor with left-right switching can be used instead. Whatever technique is used, use is typically made of real-time dedicated hardware warping circuitry. Several options are available for the SGI 02 based system, which can be used. For example, a 120 Hz display (CrystalEyes with additional software) could be used, or small images (320 by 240 pixels for each image, for example) can be placed side by side in a single frame for use with a mirror system, or the like. Since in the case where SGI 02s is used, dual video streams can normally not be output, a relatively large computer can be used with a (genlocked) dual channel video board synchronously to drive two monitors in a mirror system. It will be appreciated that dedicated hardware can be used in addition to, or instead, where appropriate.

ALTERNATIVE APPROACHES

Instead of the methods described above, it will be appreciated that several alternative approaches can be used to still an image. Some of these approaches are listed below.

1) Rapid Shuttering of the Camera. Current endoscope CCD chips are normally not shuttered and thus integrate the observed image for typically $\frac{1}{60}^{th}$ second. When motion is present, blurring or the image can occur. By shuttering the camera, a "frozen" image can be produced, thus reducing the blurring caused by motion. The image then still moves from field to field in response to the heart motion and thus image warping can be applied, in addition, to still the image.

2) Strobe Lighting. As an alternative to shuttering, strobe lighting can be used to achieve the same "freezing" of motion as shuttering. The image then still moves from field to field in response to the heart motion and thus image warping can be applied, in addition, to still the image.

3) Pharmacological Control of the Heart. Heart motion can be controlled to some degree by drugs. These drugs can establish target heart rates, maximum velocity (impulsiveness), and maximum motion extent. The image then still moves from field to field in response to the heart motion and thus image warping can be applied, in addition, to still the image.

4) Electrical Control of the Heart. The heart rate can be controlled by electrical stimulus. Electrical stimulus may also control the velocity and extent of motion. The image still moves from field to field in response to the heart motion and thus image warping can be applied, in addition, to still the image.

5) Physical Constraint of the Heart Motion. Some sort of physical device can be used to limit the heart motion. This approach can reduce or eliminate motion in a small area, depending on the techniques used. If there is residual heart motion, image warping can be used, in addition, to still the motion.

6) Camera motion. The camera can be moved in synchronism with the observed heart motion. This approach can reduce or eliminate the apparent motion in the area where the reference motion is measured, depending on the number of degrees of freedom for the camera motion. If there is residual heart motion, image warping can be used, in addition, to still the motion.

7) Dynamic Lens Control. The camera optics can be dynamically controlled in synchronism with the observed heart motion while the camera CCD remains fixed. This approach can reduce or eliminate motion in a small area, depending on the number of degrees of freedom for the camera optics. If there is residual heart motion, image warping can be used, in addition, to still the motion.

The first four options can improve the sharpness of the image but may require either warping or a moving camera/lens assembly to provide a steady image of the heart. The fifth through to the seventh options can reduce, but may not eliminate the motion and thus may require warping to provide a steady image of the heart. Some key factors in evaluating the image quality will now be described.

A key to successful image stilling typically involves image sharpness, consistent high resolution, steady lighting, a steady and consistent area of interest, and control of the motion outside the area of interest or surgical site.

Image sharpness is typically based on "freezing" the image as well as maintaining a sharp focus. All of the above approaches can attempt to reduce the effects of heart motion. Combinations of these approaches can be used to reduce blurring effects of motion. It has been found that motions as low as 1 cm/sec can cause blurring in an unshuttered CCD for the camera used, namely the camera available from Welch Allyn and having the following part number Model 2002, and at the observation distance of about 30 mm as mentioned above. Although an endoscope is typically made to have a large depth of focus, the sharpness of the image can be enhanced by keeping the distance between the heart and the endoscope at an optimal distance.

High resolution can be achieved by maintaining a close distance from the heart surface as well as utilizing a resolution as high as possible in the camera CCD. In addition, several factors can affect the resolution achieved with the camera. These factors include the modulation transfer function of the CCD, the type or output format used, and the bandwidth of the display device. The modulation transfer function typically describes the response of the camera to spatially high-frequency (close together), high contrast (light to dark) images. A strong response to high spatial frequencies is desired in the modulation transfer function. The CCD output should advantageously be utilized directly, without any intervening conversion to a standard video format such as NTSC, PAL, or S-Video. This can mean that the output should either be RGB or digital directly out of the CCD. Using these direct outputs should decrease bandwidth restrictions (and therefore spatial resolution limitations) that may be inherent in standard video formats. The apparent resolution can change as the distance to the heart changes. This could be caused by heart motion relative to a fixed camera. The image warping for maintaining a constant size image can expand and contract the image, causing changes in the resolution.

Under some conditions when the camera is held stationary relative to a moving heart, the average lighting level may change as the heart moves closer and further from the camera. If warping is then used to provide image stilling, the changing lighting conditions may be distracting to the viewer. Therefore, intensity normalization could be utilized when the warping is applied. This normalization should typically only be applied to the area of interest and not the entire image since the outlying areas of the image are typically of less interest and may be dark enough to alter the intensity normalization process.

Although shuttering and/or strobe lighting should provide a sharp image, the image should be presented to the viewer with a constant position, orientation, and size. This may require relatively precise image warping. Any residual motion caused by imperfect warping of the marker control points may be more noticeable in a stilled image.

The areas outside the area of interest should preferably be eliminated from the image since those areas can have motions unrelated to the area of interest and lighting variations. Warping can have these artifacts and they should advantageously be eliminated from the final image by an image expansion and image cropping process, for example, to remove the distracting areas.

EVALUATION OF TECHNOLOGIES

Listed below are some alternative technologies that may be usable for measuring the surface position of the heart. Typical advantages and disadvantages of each technology are also provided.

OPTICS

Stereo Optics Using Endoscope Cameras and Colored Markers

This typically involves analyzing existing image data from the stereo endoscope camera on a field by field basis. To reduce the computational load, readily identifiable, colored markers can be used rather than the heart surface or surface patterns. The $(\xi, \eta)$ locations of the various markers in the two camera images can be used to determine the 3D location of the surface at the marker locations. This approach (and most other approaches) can require the calibration of the optics, sensors, and other parameters. Sub-millimeter resolutions can be achieved at close viewing distances (less than 50 mm, for example) and relatively small stereo angles (10°, for example).

Typical advantages of this technology may include:
  Can use existing video data stream thus requiring minimal additional hardware. The markers can provide specific information on rotation as well as 3D surface information. The data collected can also be used to "warp" the user video image. Markers can be small and could be made to fluoresce or to be moderately retro-reflective.

Typical disadvantages of this technology may include:
  Can require multiple markers. Accurate tracking of motion only at the marker locations may be involved due to elasticity of the heart during heartbeat.

Stereo Optics Using Crossed Line-Scan Endoscope Cameras and Colored Markers

This is a variation on the technique described above and can typically use line-scan cameras and cylindrical lenses in addition to area scan cameras. Two color line-scan cameras can be positioned at right angles relative to each other and can be coupled with cylindrical lenses to view the whole surface. Color (or brightness) markers can show up in the data if they are sufficiently bright. Typically, the line scan arrays can be read out faster than the area scan CCD's. The line scan arrays may also be made with higher resolutions than the area scan CCD's. This technique may only work with markers and may not work on low contrast pattern matching (feature recognition) approaches.

Typical advantages of this technology may include:
  Data processing load to locate the markers may be reduced. The cameras may provide high data rate (several kHz line scan rates, for example) and very high resolution (6000 pixels, for example).

Typical disadvantages of this technology may include:
  May require a beam splitter in the optical path (re-designed endoscope head). This may reduce the user's image intensity. Precise orientation of crossed (90 deg) line-scan sensors may be required. Signal (marker) to background (all other objects) ratio should be high so as to identify the marker location when using cylindrical lenses. The cylindrical lens approach may have ambiguities in marker position. These may be only resolved using scanning optics (which can increase data rate). High resolution devices can require physically large optics or may be diffraction limited.

Stereo Optics Using Feature Recognition

This technique can use stereo video images and can perform a 3D calculation on surface features by matching specific surface features in each image. This approach can use optics and may rely on identifiable features in the image. This approach an potentially track the entire surface. This approach is typically computationally intensive. Sub-millimeter resolutions may be achieved at close viewing distances (less than 50 mm, for example) and reasonable stereo angles (10°, for example).

Typical advantages of this technology may include:
  Can provide great detail on all surface position characteristics. May track elastic surfaces in greater detail than with markers. May follow rotations well.

Typical disadvantages of this technology may include:
  Can be computationally intensive. This approach may require identifiable features in both images. Manual intervention may be required to initiate the feature recognition and matching process.

IR

Stereo IR Using Endoscope Optics and IR Sources

This technique is similar to the stereo optics method using markers. In this approach, IR emitting sources can be placed at various locations on the heart. An IR sensitive camera can then track the positions of these high contrast IR points to compute the 3D positions. The IR camera optics path could be included in the visible camera optics path, or an additional optical path (second endoscope) could be used. The visible cameras should have IR blocking filters. Sub-millimeter resolutions should be achievable at close viewing distances (less than 50 mm, for example) and reasonable stereo angles (10°, for example).

Typical advantages of this technology may include:
  High contrast data may make the marker location process easier.

The data bandwidth may be lower than that required for the color marker approach.

Typical disadvantages of this technology may include:
  Many wires may be required to set up the multiple IR sources. The illumination source for the visual camera should have low IR content. May require a beam splitter to provide an optics path to the IR CCDs when using a single endoscope. IR sources can be relatively large (2 mm by 3 mm plus wires, for example) and could be cumbersome when attaching to the surface of the heart.

Stereo IR Using Endoscope Optics and IR Reflectors

This technique is similar to the IR method described above except that passive IR reflectors are used instead of IR sources. In this approach, IR retro-reflectors are used at various locations on the heart while IR light is sent through a fiber-optics bundle to illuminate the area (in addition to, or as part of the visible light illumination). An IR sensitive camera can track the position of the high contrast IR points to compute the 3D positions.

Typical advantages of this technology may include:

High contrast points should make the reflector location process easier. The data bandwidth is typically lower than that for the color marker process. The IR reflectors can be small (1 mm dia., for example). The reflectors typically do not require wires. IR reflectors can have a wide angular response characteristic.

Typical disadvantages of this technology may include:

Wet surfaces can be strong reflectors of IR. The heart surface and surrounding area should have low IR reflectivity. A polarization filter to reduce the wet surface reflectivity may also reduce the visible image intensity. The IR reflectors should include filters to decrease their reflectivity in the visible region. May require a beam splitter to provide an optics path to the IR CCDs (re-designed endoscope head), or a second endoscope.

X-RAY

Stereo X-Ray (bi-plane cineradiography)

This method is similar to the optical stereo approach. Opaque markers (tantalum, steel spheres, for example) can be used for both calibration and as surface position markers. The approach and mathematics are similar to the stereo optics approach, except that additional information on the illumination source position should be obtained.

Typical advantages of this technology may include:

This method should provide high accuracy data on the surface and other structures because of the wavelengths involved. The hardware is typically positioned outside of the body (source and receivers). Applied markers (opaque materials such as tantalum, or steel spheres, for example) can aid in finding and tracking the surface. The markers may be identified as a dark spot on an otherwise bright background.

Typical disadvantages of this technology may include:

Possible long term exposure risk. Instruments may cause shadowing of markers and surface characteristics. Uniform "illumination" may be needed to see all markers.

Compton Backscatter

This approach can use an input fan of X-rays and a line of detectors to monitor the 2D surface profiles in real time. The measurement system may be scanned along an axis perpendicular to the source and detector plane to build up a 3D surface.

Typical advantages of this technology may include:

A high 2D data rate may be achieved (in the order of 200 Hz, for example). Good accuracy of up to 0.1 mm may be obtained for the surface position.

Typical disadvantages of this technology may include:

Good contrast may be required to find the surface. Rotation may be determinable only through feature tracking. Possible long term exposure risk. Scattering from the instruments may cause problems. This approach may only be suitable for tracking dynamics at the epicardial-lung interface when not using markers. May not be able to do 3D in real time. May require source-sensor repositioning and post processing.

Stereo Angiography

This method is similar to the stereo X-ray approach. Opaque materials can be injected into the blood to highlight the blood vessels on the heart. An image of the heart blood vessel can then be seen in a fluoroscope which can be viewed by a high resolution camera. The approach and mathematics to locate 3D surface features may be similar to the stereo optics with pattern identification approach.

Typical advantages of this technology may include:

This method may provide high accuracy data on larger blood vessels. All of the hardware can typically be positioned outside of the body (source and receivers). The vessels may be identified as dark areas on an otherwise bright background.

Typical disadvantages of this technology may include:

Possible long term exposure risk. May be computationally relatively intensive. Instruments may cause shadowing of the image. Uniform "illumination" may be required to see all vessels. Smaller vessels may not be determinable.

LASER

Laser Interferometer

The surface is typically illuminated with a scanning laser and the scattered return is typically optically processed to extract the interferometric fringe pattern generated with the change in surface distance. Relative distance accuracies of about one-half wavelength may be achievable. Scanning in two dimensions may be required to cover a surface. Broad illumination may also be used in place of scanning. However, the return data should be either imaged or scanned to count the fringes.

Typical advantages of this technology may include:

Typically highly accurate surface definition. Due to high accuracy, this method may work well to locate small surface features undergoing a rotation. Should be able to provide a high data rate if the scanners are fast. Two-frequency laser approaches can be used to provide a more reasonable and useful resolution.

Typical disadvantages of this technology may include:

Too accurate of a surface definition may be created. May provide too much data. Scanner and sensor may need to be defined. May require insertion and extraction of scanning beam and return data in optical path. Invisible (IR or UV) laser may be required to decrease interference with the visual image. Accurate fringe counting may be required to track positions over several centimeters. An absolute reference measurement may be made with a different approach.

Laser Ranging

This approach can use a single pulsed light source and may measure the time of the return to determine range. A coherent (laser) source may be required to achieve reasonable accuracy. A scanning system may be required to gather 3D information.

Typical advantages of this technology may include:

Typically moderately accurate surface definition (resolutions to the order of 1 cm to 1 mm, for example). Can provide a moderate data rate if the scanners are fast.

Typical disadvantages of this technology may include:

Not typically intended for high accuracy due to the precise timings (~pico seconds) normally required. A two angle scanner is normally required. May require insertion and extraction by scanning beam and return data in optical path. Object rotation could be determined by identifying and tracking unique features.

Stereo Optics Using Structured Light

This method is similar to the laser ranging technique except that the surface is illuminated with a pattern such as a rectangular grid, or array, of dots. The video return is typically analyzed in the stereo images to follow the contours that result when the structured light impacts on the 3D object. Stereo data processing can extract the surface coordinates. The high timing accuracies that may be required in laser ranging may not be required in this approach. Reasonably accurate surface definition (resolution to 500 µm, for example) may be achievable.

Typical advantages of this technology may include:

Typically a reduced data rate compared to laser ranging. Should be able to map a large number of points on the surface.

Typical disadvantages of this technology may include:

Typically requires a "structured" light source to be injected into the optical path. Visible light implementation may detract from the image quality. Invisible light implementation (IR or UV) may require that the optical signal be extracted from the visible light path (separate CCD or second endoscope). May provide surface information only. Object rotation cold be determined by identifying and tracking unique features. Low reflectivity of the object may reduce effectiveness.

TACTILE

Tactile Sensing Using LVDTs. Angle Encoders. etc.

This method can use electromechanical devices attached to the surface to track position. By knowing the angle of various joints and the position of various sliders (LVDTs), the 3D position of a probe tip can be computed. Angle resolutions of better than ±15 arc seconds, for example, and LDVT resolutions of better than 0.0001 in. (0.0025 mm), for example, are typically achievable. A single LVDT device could provide an emergency backup to other 3D measurement methods.

Typical advantages of this technology may include:

May provide quick and accurate measurement of a specific surface point. May be able to sense position in three dimensions. Typically tracks the actual point attachment.

Typical disadvantages of this technology may include:

May require lots of sensors to map the dynamic surface. May get in the way of optics and tools. May be hard to use in closed spaces when using many sensors. The inertial mass of the measurement device may affect local surface motion.

ULTRASONIC

Low Frequency Ultrasonic

This method can involve using either pulsed or chirped ultrasonic sound waves (at a frequency of less than 100 kHz, for example) to determine the distance to a surface. Resolutions of 1 inch at a range of several feet may be achievable.

Typical advantages of this technology may include:

This may be a relatively simple system to implement. Propagation through air is typically effective at low frequencies.

Typical disadvantages of this technology may include:

The low frequencies that propagate through air may yield low position resolution. May require a two angle scanner or two dimensional steered array of transducers to find the characteristics of a complex surface. Object rotation should be determined by identifying and tracking unique features. Tool reflections may cause problems.

High Frequency Ultrasonic

This is the same approach as above except that higher frequencies are typically used. Frequencies in the order of 1 MHz, for example, are normally required to achieve resolutions in the order of 1 mm, for example. Such a system may require either a two angle scanner or a two dimensional steered array of transducers to locate the surface.

Typical advantages of this technology may include:

May provide a reasonably high resolution surface map. May also image beyond the surface to interior areas of the heart.

Typical disadvantages of this technology may include:

High frequencies that provide high resolution may not readily propagate through air. May require a two angle scanner or two dimensional steered array of transducers to find the characteristics of a complex surface. Object rotation may be determinable by identifying and tracking unique features. Tool reflections could be problematic.

RADAR

Radar Ranging

This method may use either impulses or chirps to provide ranging information in a standard radar approach. High frequencies and bandwidths may be required to achieve sub-millimeter resolutions in the desired range. Additional beam-forming and scanning techniques may be required to achieve cross-range resolution.

Typical advantages of this technology may include:

May be used outside the body. May not interfere with the video data collection path.

Typical disadvantages of this technology are:

May require high frequencies and short pulses (~pico seconds, for example) or wide bandwidths (~300 GHz, for example) to achieve the desired accuracy. May require two angle scanner with narrow beam to find surface, or two dimensional steered array. Reflections from tools could be problematic.

RF Interferometry

This approach is similar to laser interferometry except that the wavelengths are normally greater and the resultant resolution is normally more reasonable than with single frequency laser interferometry. This approach may use a two angle scanner with narrow beam or two dimensional steered array to locate the surface.

Typical advantages of this technology may include:

The resolutions may be achievable with a 30 GHz signal, for example, and 10°, for example. Phase resolution may be consistent with requirements.

Typical disadvantages of this technology may include:

Reflections from tools may be problematic. Non-homogeneous structure may result in varied propagation velocities, thus degrading accuracy. Direct path feedthrough may overload the receiver. Very high angular resolutions may be required to extract the cross range information desired to calculate the 3D surface information.

MAGNETIC

MRI Tagging SPAMM

The SPAMM (spatial modulation of magnetization) process is a NMR based image technique. The region to be imaged is typically "tagged" with planes of magnetization, themselves typically created by a pre-imaging pulse sequence, and the motion of the magnetization planes may be monitored. The magnetization planes typically remain fixed to the material and thus reveal the material motion. Two orthogonal planes may be used which may mean that only the motion within the image plane is measured. Two sets of images can be used to reconstruct the 3D motion of an object; i.e. heart motion.

There are typically 3 steps to prepare the material prior to normal NMR imaging (the so-called pre-imaging pulse sequence): 1) an initial RF pulse which produces typically transverse magnetization 2) a magnetic field gradient pulse which typically wraps the phase along the direction of the gradient, and 3) an RF pulse to mix the transverse and longitudinal magnetizations.

Typical advantages of this technology may include:

It may be used to image the motion of a volume of material, not just the surface. Sub millimeter accuracies may be obtained.

Typical disadvantages of this technology may include:

Only motion parallel to the image plane is typically measured. A special pulse structure may be required to tag the material. The tags are typically transitory, lasting only a few 0.1's of a second, for example, after which they could be recreated with special pulses. A NMR machine may be required. The measurements may not be continuous in time, that is, there may be a gap of time required in which the material is prepped for measurement and during which the motion of the material may not be measurable. Processing the data to extract the 3D surface position may be computationally intensive and generally done off-line.

CLOSING STATEMENT

While the present invention has been described, with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular aspect, situation or material to the teachings of the invention without departing from the essential scope and spirit of the present invention. It is intended that the invention not be limited to the particular embodiments disclosed but that the invention will include all embodiments and equivalents falling within the scope of the appended claims.

What is claimed is:

1. A method of performing a surgical procedure on a beating heart of a patient, the method including:

positioning an end effector in close proximity to a surgical site on the heart at which site a surgical procedure is to be performed, the end effector being mounted on a robotically controlled arm;

providing a brace member mounted on another robotically controlled arm;

forwarding command signals to actuators operatively associated with the another robotically controlled arm to cause the arm to move the brace member from a position clear of the heart to a position in contact with the heart;

bracing the beating heart with a brace member to at least reduce motion of the surgical site;

inputting an end effector movement command signal; and forwarding the end effector movement command signal to actuators operatively associated with the robotically controlled arm to cause the end effector to move relative to the surgical site so as to perform at least part of the surgical procedure at the surgical site.

2. A method as claimed in claim 1, in which the another robotically controlled arm is connected to a stationary base positioned outside the patient, bracing the beating heart including contacting the heart with the brace member.

3. A method as claimed in claim 2, in which the brace member is arranged to operate under suction, the method including displacing air relative to the brace member to cause the brace member to attach itself to the heart by suction.

4. A method as claimed in claim 2, which includes maintaining the brace member in a stationary condition relative to the base when in contact with the beating heart so as to inhibit heart motion by at least one degree of freedom of movement.

5. A method as claimed in claim 2, which includes permitting the brace member to move in sympathy with the heart whilst in contact therewith and restraining motion of the brace member so as to restrain motion of the surgical site.

6. A method as claimed in claim 1, wherein the surgical procedure is to be performed in a minimally invasive manner, positioning the end effector in close proximity to the surgical site on the heart then including the prior step of passing the end effector through a relatively small aperture in the patient.

7. A method as claimed in claim 6, which comprises the prior step of forming an incision in the chest region of the patient to define the aperture.

8. A method as claimed in claim 1, which further includes capturing an image of the surgical site by means of an image capture device.

9. A method as claimed in claim 8, which further includes forwarding the image of the surgical site captured by the image capture device to a remote image display.

10. A method as claimed in claim 9, wherein the image capture device is arranged to capture an image of the surgical site from each of two different vantage points, the method then including forwarding the images to the remote image display so as to display a stereo image of the surgical site.

11. A method as claimed in claim 8, in which the surgical procedure is to be performed in a minimally invasive manner, capturing an image of the surgical site by means of the image capture device then including the prior step of passing the image capture device through a relatively small aperture in the patient.

12. A method as claimed in claim 11, which comprises the prior step of forming an incision in the chest region of the patient to define the aperture.

13. A method as claimed in claim 1, in which the motion of the surgical site is reduced, the method further including:

monitoring the reduced motion of the surgical site;

computing end effector tracking command signals in response to the reduced monitored motion of the surgical site; and forwarding the tracking command signals to the actuators to cause the arm to move the end effector generally to track motion of the surgical site.

14. A method as claimed in claim 13, in which monitoring motion of the surgical site includes contacting the surgical site with a motion detector, permitting the motion detector to move in sympathy with the surgical site and monitoring movement of the motion detector so as to monitor motion of the surgical site.

15. A method of performing a surgical procedure on a beating heart of a patient, the method including:

positioning an end effector in close proximity to a surgical site on the heart at which site a surgical procedure is to be performed, the end effector being mounted on a robotically controlled arm;

bracing the beating heart with a brace member to at least reduce motion of the surgical site;

monitoring the reduced motion of the surgical site by securing at least one target marker on the surgical site and monitoring movement of the target marker so as to monitor motion of the surgical site;

computing end effector tracking command signals in response to the reduced monitored motion of the surgical site; and forwarding the tracking command signals to actuators to cause the arm to move the end effector generally to track motion of the surgical site.

16. A method as claimed in claim 15, wherein securing at least one target marker includes securing a plurality of target markers at spaced apart positions on the surgical site and monitoring movement of the target markers so as to monitor motion of the surgical site.

17. A method as claimed in claim 16, in which the movement of the target markers differ, monitoring motion of the surgical site then including monitoring a computed motion derived from the motions of at least some of the target markers.

18. A method as claimed in claim 16, in which the target markers are arranged to cooperate with a sensor, the method further including positioning a sensor at an appropriate position to detect motion of the target markers.

19. A method as claimed in claim 18, in which the sensor is arranged cooperate with the markers so as to sense their movement electromagnetically.

20. A method of performing a surgical procedure on a beating heart of a patient, the method including:

positioning an end effector in close proximity to a surgical site on the heart at which site a surgical procedure is to be performed, the end effector being mounted on a robotically controlled arm;

bracing the beating heart with a brace member to at least reduce motion of the surgical site;

directing an image capture device at the surgical site to capture an image of the surgical site;

displaying the image of the surgical site on an image display operatively connected to the image capture device; and compensating for motion of the surgical site to cause the image of the surgical site to be displayed on the image display as if the surgical site were generally stationary relative to the image capture device.

21. A method as claimed in claim 20, wherein the image capture device is mounted on a robotically controlled arm, compensating for motion of the surgical site to cause the image of the surgical site to be displayed on the image display as if the surgical site were generally stationary relative to the image capture device including:

computing tracking command signals in response to monitored motion of the surgical site; and forwarding the tracking command signals to actuators operatively associated with the robotically controlled arm to cause the arm to move the image capture device generally to track motion of the surgical site.

22. A method as claimed in claim 20, wherein the image capture device is arranged to capture at least two images of the surgical site from two different vantage points, compensating for motion of the surgical site to cause the image of the surgical site to be displayed on the image display as if the surgical site were generally stationary relative to the image capture device including processing information related to the two images so as to cause the image of the surgical site displayed on the image display to be displayed as if the surgical site were generally stationary relative to the image capture device.

23. A method as claimed in claim 22, in which processing the information related to the two images includes transforming optical information related to the two images into digital information and processing the digital information so as to cause the surgical site to be displayed on the image display as if the surgical site were generally stationary relative to the image capture device.

24. A method as claimed in claim 22, in which monitoring motion of the surgical site includes the processing of the information related to the two images.

25. A method as claimed in claim 24, in which computing tracking command signals in response to monitored motion of the surgical site includes computing tracking command signals in the form of vectors derived from monitored information corresponding to the two images.

26. A method as claimed in claim 24, in which processing the two images includes defining a plurality of discrete locations on the surgical site and monitoring the motion of the discrete locations by means of information derived from the two images.

27. A method as claimed in claim 24, which includes securing markers on the surgical site at the discrete locations.

28. A method as claimed in claim 27, in which the markers are distinctively colored, monitoring the motion of the discrete locations then including monitoring motion of the distinctively colored markers.

29. A method as claimed in claim 20, in which the image capture device is in the form of a stereo endoscope, directing the image capture device at the surgical site then including passing a viewing end of the endoscope through a relatively small aperture in the chest region of the patient.

30. A method as claimed in claim 20, which includes analyzing information corresponding to monitored motion history of the surgical site to predict motion of the surgical site.

31. A method as claimed in claim 30, in which computing tracking command signals in response to monitored motion of the surgical site includes computing the tracking command signals from predicted motion of the surgical site.

32. A method as claimed in claim 30, in which predicting motion of the surgical site includes comparing the information corresponding to monitored motion of the surgical site with an ECG signal.

33. A robotically controlled surgical system for performing a surgical procedure on a beating heart of a patient body, the system comprising:

a robotically controlled arm;

a brace member operatively mounted on the robotically controlled arm, the brace member being arranged to brace, or stabilize, a beating heart so as at least to reduce motion of a surgical site on the beating heart, at which site a surgical procedure is to be performed;

at least one other robotically controlled arm;

a surgical end effector operatively mounted on the other robotically controlled arm, the surgical end effector being arranged to perform at least part of the surgical procedure on the surgical site;

at least one master control input device; and a control system in which the robotically controlled arms, the brace member, the end effector and the master control input device are operatively connected, so as to enable movement of the robotically controlled arms, the brace member, and the end effector to be remotely controlled in response to input through the master control input device.

34. A robotically controlled surgical system as claimed in claim 33, wherein the end effector is mounted on an elongate shaft operatively connected to its associated robotically controlled arm so as to permit the end effector to be positioned at the surgical site by passing it through a relatively small aperture in the patient body.

35. A robotically controlled system as claimed in claim 34, wherein the brace member is mounted on an elongate shaft operatively connected to its associated robotically controlled arm so as to permit the brace member to be positioned at the surgical site by passing it through a relatively small aperture in the patient body.

36. A robotically controlled system as claimed in claim 35, wherein the brace member comprises at least two members moveable relative to each other between a collapsed condition, in which the brace member has a relatively small outermost lateral dimension, to permit it to be passed through the aperture, and a deployed condition, in which the brace member is arranged to brace the heart and in which it has a relatively large outermost lateral dimension.

37. A robotically controlled system as claimed in claim 35, wherein the robotically controlled arms are mounted on a common base.

38. A robotically controlled system as claimed in claim 37, wherein the base is defined on a mobile cart or trolley.

39. A robotically controlled system as claimed in claim 35, wherein the brace member defines at least one aperture through which air is to be displaced to cause the brace member to attach itself to the heart by suction.

40. A surgical system as claimed in claim 35, which comprises a pivotal connection between the brace member and the shaft and a drive system operatively associated with the brace member to enable the brace member to be moved about the pivotal connection and relative to the shaft by means of the drive system.

41. A surgical system as claimed in claim 40, wherein the drive system is operatively connected in the control system to enable the brace member to be moved about the pivotal connection in response to master control device input.

42. A surgical system as claimed in claim 40, further comprising a wrist assembly coupling the brace member to the shaft, the wrist assembly providing the brace member with first and second degrees of freedom of movement relative to the shaft.

43. A surgical system as claimed in claim 42, wherein the wrist assembly defines a first pivotal axis extending laterally relative to the shaft and a second pivotal axis extending laterally relative to the shaft and angularly relative the first pivotal axis.

44. A surgical system as claimed in claim 42, wherein the drive system comprises actuators and first and second drive elements moveable relative to the shaft by means of the actuators to cause movement of the brace member about the pivotal axes.

45. A surgical system as claimed in claim 42, in which the brace member defines a stabilizing surface arranged to engage the heart so as at least to reduce movement of the surgical site.

46. A surgical system as claimed in claim 34, which comprises an end effector pivotal connection between the end effector and the shaft and a drive system operatively associated with the end effector to enable the end effector to be moved about the pivotal connection and relative to the shaft by means of the drive system.

47. A surgical system as claimed in claim 46, wherein the drive system is operatively connected in the control system to enable the end effector to be moved about the pivotal connection in response to master control device input.

48. A surgical system as claimed in claim 47, further comprising an end effector wrist assembly coupling the end effector to the shaft, the wrist assembly providing the end effector with first and second degrees of freedom of movement relative to the shaft.

49. A surgical system as claimed in claim 48, wherein the end effector wrist assembly defines a first pivotal axis extending laterally relative to the shaft and a second pivotal axis extending laterally relative to the shaft and angularly relative to the first pivotal axis.

50. A surgical system as claimed in claim 49, wherein the drive system comprises actuators and first and second drive elements movable relative to the shaft by the actuators to cause movement of the end effector about the pivotal axes.

51. A robotically controlled surgical system for performing a surgical procedure on a beating heart of a patient body, the system comprising:
   a robotically controlled arm;
   a brace member operatively mounted on the robotically controlled arm, the brace member comprising two elongate members each defining a stabilizing surface arranged to engage the heart so as at least to reduce movement of a surgical site on the beating heart;
   at least one other robotically controlled arm;
   a surgical end effector operatively mounted on the other robotically controlled arm, the surgical end effector being arranged to perform at least part of the surgical procedure on the surgical site;
   at least one master control input device;
   a control system in which the robotically controlled arms, the brace member, the and effector and the master control input device are operatively connected, so as to enable movement of the robotically controlled arms, the brace member, and the end effector to be remotely controlled in response to input through the master control input device; and
   a drive system operatively connected to the control system to enable the brace member to be moved in response to the master control device input, the drive system also being operatively associated with the elongate members to selectively spread the elongate members apart.

52. A surgical system as claimed in claim 51, wherein the stabilizing surfaces of the elongate members remain aligned when the drive system moves the elongate members relative to each other.

53. A surgical system as claimed in claim 52, further comprising a flexible element extending from one elongate member to the other elongate member, the flexible element being arranged to urge the members toward each other when the one member is moved away relative to the other member.

54. A surgical system as claimed in claim 52, wherein the elongate members each have an anchor formation on which an elongate flexible tension member is anchorable so as to enable tissue to be engaged by looping the tension member around the tissue to form a loop around the tissue, anchoring opposed portions of the tension member on the anchor formations and spreading the elongate members to cause the loop to tighten thereby to engage the tissue.

55. A surgical system as claimed in claim 54, wherein the elongate members each have at least two spaced-apart anchor formations on which elongate flexible tension members are anchorable to enable tissue to be engaged at opposed positions by looping the tension members around the tissue to form spaced loops around the tissue, anchoring opposed portions of the tension members on the anchor formations and spreading the elongate members apart to cause the loops to tighten thereby to engage the tissue at the opposed positions.

56. A surgical system as claimed in claim 54 or 55, wherein each anchor formation comprises a channel, or slit, in which the flexible member or members are receivable.

57. A surgical system as claimed in claims 54 or 55, wherein the anchor formations stand proud of the elongate members at positions opposed from the tissue engaging surfaces.

58. A surgical system as claimed in claim 51, wherein the elongate members are displaceable relative to each other between a collapsed condition, in which the elongate members overlap each other, and a deployed condition, in which the elongate members are spread apart relative to each other.

59. A surgical system as claimed in claim 58, wherein each elongate member is in the form of an elongate flat finger.

60. A surgical system as claimed in claim 59, wherein each finger has at least one bend.

61. A robotically controlled surgical system for performing a surgical procedure on a beating heart of a patient body, the system comprising:
- a robotically controlled arm;
- a brace member operatively mounted on the robotically controlled arm, the brace member being arranged to brace, or stabilize, a beating heart so as at least to reduce motion of a surgical site on the beating heart, at which site a surgical procedure is to be performed;
- at least one other robotically controlled arm;
- a surgical end effector operatively mounted on the other robotically controlled arm, the surgical end effector being arranged to perform at least part of the surgical procedure on the surgical site;
- at least one master control input device;
- a control system in which the robotically controlled arms, the brace member, the end effector and the master control input device are operatively connected, so as to enable movement of the robotically controlled arms, the brace member, and the end effector to be remotely controlled in response to input through the master control input device; and
- an image capture device for capturing an image of the surgical site and remote display for displaying the captured image at a position outside the patient body.

62. A surgical system as claimed in claim 61, wherein the image capture device comprises an elongate shaft having a surgical site viewing end, the shaft being insertable into the patient body through a relatively small aperture so as to introduce the object viewing end to the surgical site thereby to enable an image of the surgical site to be captured.

63. A surgical system as claimed in claim 62, wherein the image capture device is arranged to capture a stereo image of the surgical site.

64. A surgical system as claimed in claim 63, which further comprises monitoring means for monitoring reduced motion of the surgical site, and computing means for computing end effector tracking command signals in response to the monitored reduced motion of the surgical site.

65. A surgical system as claimed in claim 64, in which the monitoring means comprises a motion detector arranged to contact the surgical site and to move in sympathy with the surgical site thereby to monitor movement of the surgical site.

66. A surgical system as claimed in claim 64, in which the monitoring means comprises an image processor for monitoring motion of at least one target marker secured on the surgical site so as to monitor movement of the target marker thereby to monitor motion of the surgical site.

67. A surgical system as claimed in claim 66, further comprising computing means arranged to compute a computed motion derived from the motion of a plurality of target markers secured on the surgical site.

68. A surgical system as claimed in claim 67, in which the image processing means is arranged to compensate for reduced motion of the surgical site thereby to cause the image of the surgical site to be displayed on the image display as if the surgical site were generally stationary relative to the image capture device.

69. A surgical system as claimed in claim 67, further comprising an image capture device robotically controlled arm the image capture device being mounted on the image capture device robotically controlled arm, and in which the computing means is arranged to compute image capture device tracking command signals to be forwarded to the image capture device robotically controlled arm to cause the image capture device robotically controlled arm to move the image capture device generally to track motion of the surgical site.

70. A method of performing a surgical procedure on a beating heart of a patient, the method including:
- positioning an end effector in close proximity to a surgical site on the heart at which site a surgical procedure is to be performed, the end effector being mounted on a robotically controlled arm;
- bracing the beating heart with a brace member to at least reduce motion of the surgical site;
- inputting an end effector movement command signal;
- forwarding the end effector movement command signal to actuators operatively associated with the robotically controlled arm to cause the end effector to move relative to the surgical site so as to perform at least part of the surgical procedure at the surgical site;
- monitoring the reduced motion of the surgical site;
- computing end effector tracking command signals in response to the reduced monitored motion of the surgical site;
- forwarding the tracking command signals to the actuators to cause the arm to move the end effector generally to track motion of the surgical site; and
- analyzing information corresponding to monitored motion history of the surgical site to predict motion of the surgical site.

71. A method as claimed in claim 70, in which computing tracking command signals in response to monitored motion of the surgical site includes computing the tracking command signals from predicted motion of the surgical site.

72. A method as claimed in claim 70, in which predicting motion of the surgical site includes comparing the information corresponding to monitored motion of the surgical site with an ECG signal.

73. A method of performing a surgical procedure on a beating heart of a patient, the method including:
- positioning an end effector in close proximity to a surgical site on the heart at which site a surgical procedure is to be performed, the end effector being mounted on a robotically controlled arm;

bracing the beating heart with a brace member to at least reduce motion of the surgical site;

inputting an end effector movement command signal;

forwarding the end effector movement command signal to actuators operatively associated with the robotically controlled arm to cause the end effector to move relative to the surgical site so as to perform at least part of the surgical procedure at the surgical site;

monitoring the reduced motion of the surgical site;

computing end effector tracking command signals in response to the reduced monitored motion of the surgical site;

forwarding the tracking command signals to the actuators to cause the arm to move the end effector generally to track motion of the surgical site;

directing an image capture device at the surgical site to capture an image of the surgical site;

displaying the image of the surgical site on an image display operatively connected to the image capture device;

compensating for motion of the surgical site to cause the image of the surgical site to be displayed on the image display as if the surgical site were generally stationary relative to the image capture device; and analyzing information corresponding to monitored motion history of the surgical site to predict motion of the surgical site.

74. A method as claimed in claim 73, in which computing tracking command signals in response to monitored motion of the surgical site includes computing the tracking command signals from predicted motion of the surgical site.

75. A method as claimed in claim 73, in which predicting motion of the surgical site includes comparing the information corresponding to monitored motion of the surgical site with an ECG signal.

* * * * *